United States Patent
Zhao

(10) Patent No.: US 11,766,453 B2
(45) Date of Patent: Sep. 26, 2023

(54) COMPOSITIONS AND METHODS COMPRISING PROSTATE STEM CELL ANTIGEN (PSCA) CHIMERIC ANTIGEN RECEPTORS (CARS)

(71) Applicant: The Trustees of the University of Pennsylvania, Philadelphia, PA (US)

(72) Inventor: Yangbing Zhao, Lumberton, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 273 days.

(21) Appl. No.: 17/017,238

(22) Filed: Sep. 10, 2020

(65) Prior Publication Data

US 2021/0069239 A1 Mar. 11, 2021

Related U.S. Application Data

(60) Provisional application No. 62/985,808, filed on Mar. 5, 2020, provisional application No. 62/898,896, filed on Sep. 11, 2019.

(51) Int. Cl.

| | | |
|---|---|---|
| *A61K 35/14* | (2015.01) | |
| *C07K 16/30* | (2006.01) | |
| *C12N 15/85* | (2006.01) | |
| *A61P 35/00* | (2006.01) | |
| *C07K 14/705* | (2006.01) | |
| *C07K 14/725* | (2006.01) | |

(52) U.S. Cl.
CPC .............. *A61K 35/14* (2013.01); *A61P 35/00* (2018.01); *C07K 14/7051* (2013.01); *C07K 14/70517* (2013.01); *C07K 14/70521* (2013.01); *C07K 16/3069* (2013.01); *C12N 15/85* (2013.01)

(58) Field of Classification Search
CPC .......... C07K 14/7051; C07K 14/70517; C07K 14/70521; C07K 16/3069; A61K 35/14; A61K 39/001195; A61K 39/001193; A61P 35/00; C12N 15/85
See application file for complete search history.

(56) References Cited

U.S. PATENT DOCUMENTS

| | | |
|---|---|---|
| 2012/0034228 A1 | 2/2012 | Kufer |
| 2015/0322169 A1 | 11/2015 | June |
| 2017/0335281 A1 | 11/2017 | Loew |

FOREIGN PATENT DOCUMENTS

| | | |
|---|---|---|
| CN | 108395480 | 8/2018 |
| CN | 109593726 | 4/2019 |
| WO | 2006089230 | 8/2006 |
| WO | 2016070061 A1 | 5/2016 |
| WO | 2017212250 A1 | 12/2017 |
| WO | 2018033749 A1 | 2/2018 |

OTHER PUBLICATIONS

International Search Report and Written Opinion issued in App. No PCT/US20/50090, dated Dec. 17, 2020, 17 pages.

*Primary Examiner* — Ruixiang Li
(74) *Attorney, Agent, or Firm* — Saul Ewing LLP; Kathryn Doyle

(57) ABSTRACT

The present disclosure provides modified immune cells or precursors thereof (e.g. T cells) comprising a chimeric antigen receptor (CAR) capable of binding human PSCA. CARs capable of binding human PSCA, and nucleic acids encoding the same are also provided. Provided herein are bispecific CARs capable of binding human PSCA and human PSMA, nucleic acids encoding the same, and modified immune cells comprising the same. Modified immune cells comprising a PSMA CAR and a PSCA CAR are also provided. Compositions and methods of treatment are also provided.

16 Claims, 17 Drawing Sheets

Specification includes a Sequence Listing.

2B3 (p-2B3) scFv: (a humanized anti-PSCA Ab with affinity at 5.4nM.)
DIQLTQSPSSLSASVGDRVTITCSASSSVRFIHWYQQKPGKAPKRLIYDTSKLASGVPSR
FSGSGSGTDFTLTISSLQPEDFATYYCQQWSSSPFTFGQGTKVEIKGSTSGGGSGGGSGG
GGSSEVQLVESGGGLVQPGGSLRLSCAASGFNIKDYYIHWVRQAPGKGLEWVAWIDPENGDTEFVPKFQG
RATISADTSKNTAYLQMNSLRAEDTAVYYCKTGGFWGQGTLVTVSSAAG (SEQ ID NO:148)

Upgene generated primers and 2B3-BBZ CAR was PCR assembled

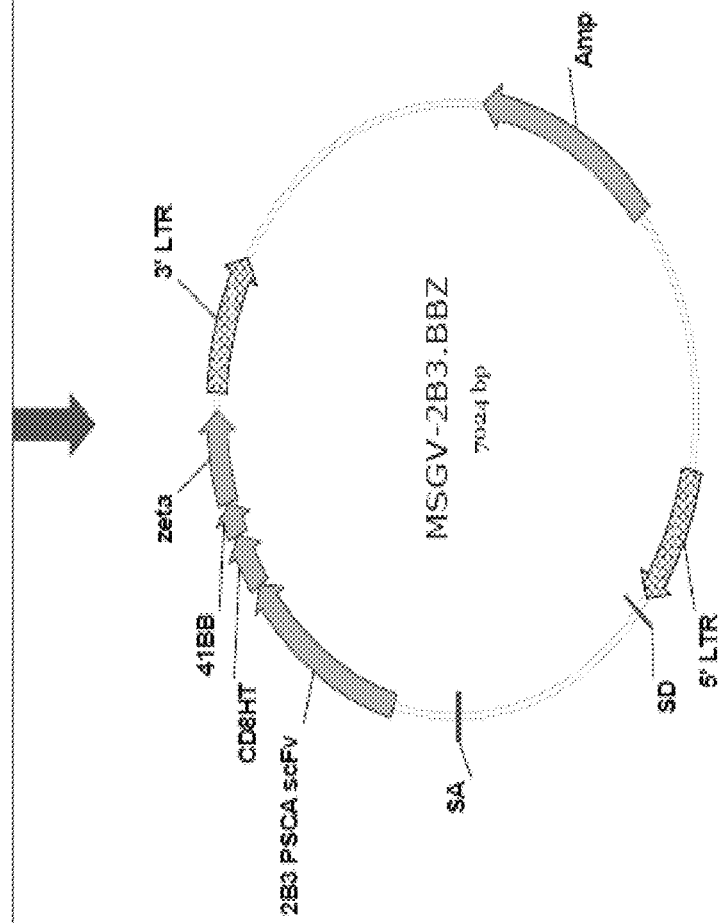

FIG. 1

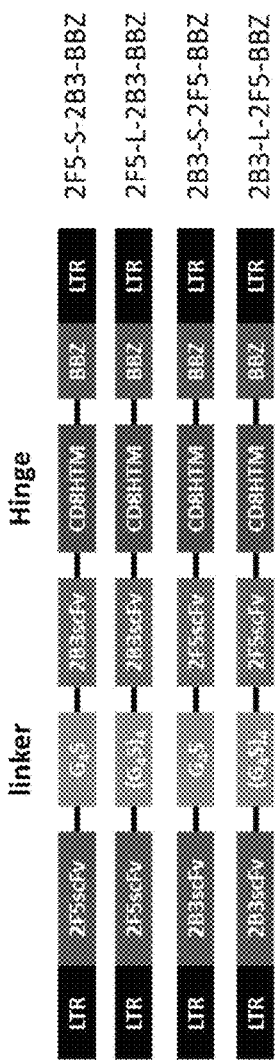
FIG. 9A
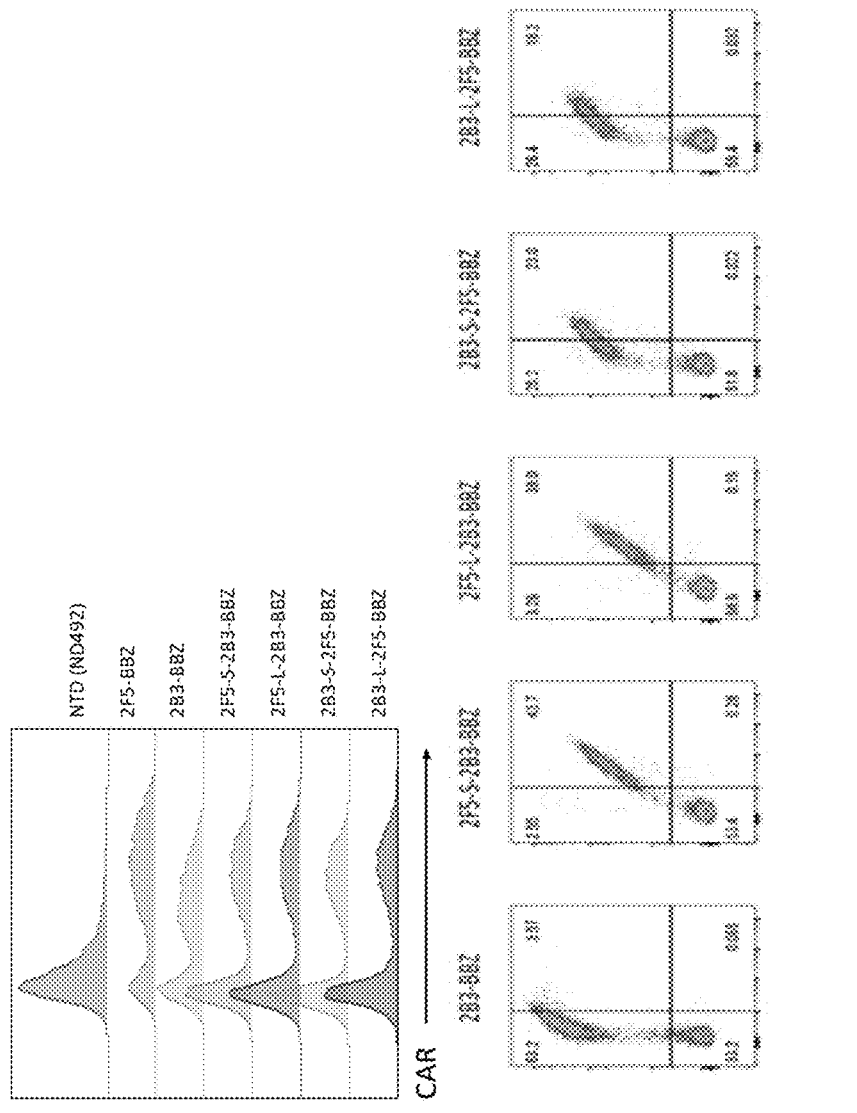
FIG. 9B
FIG. 9C

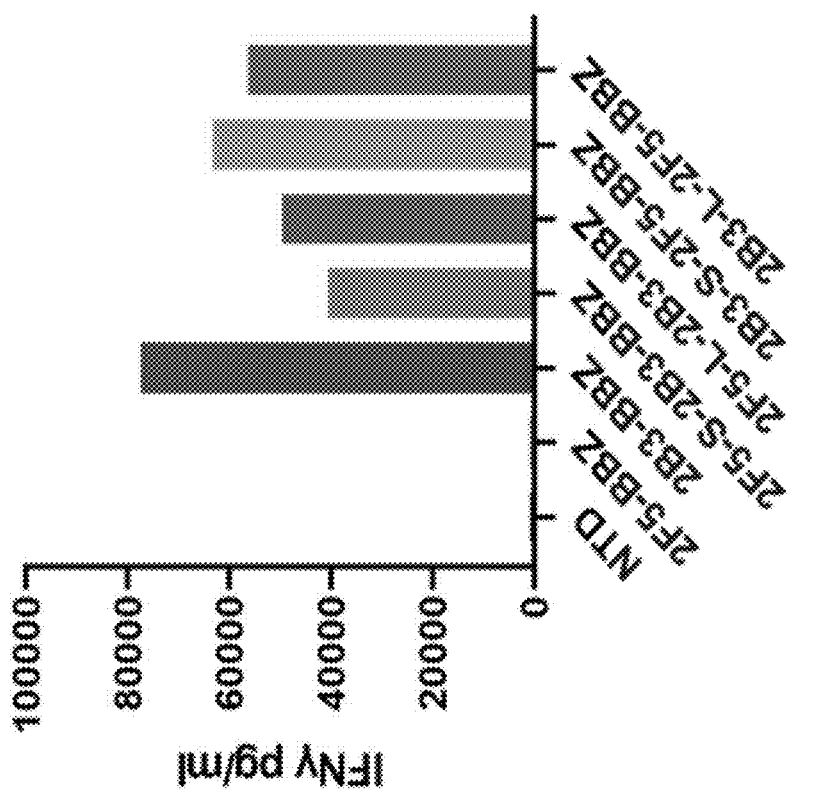
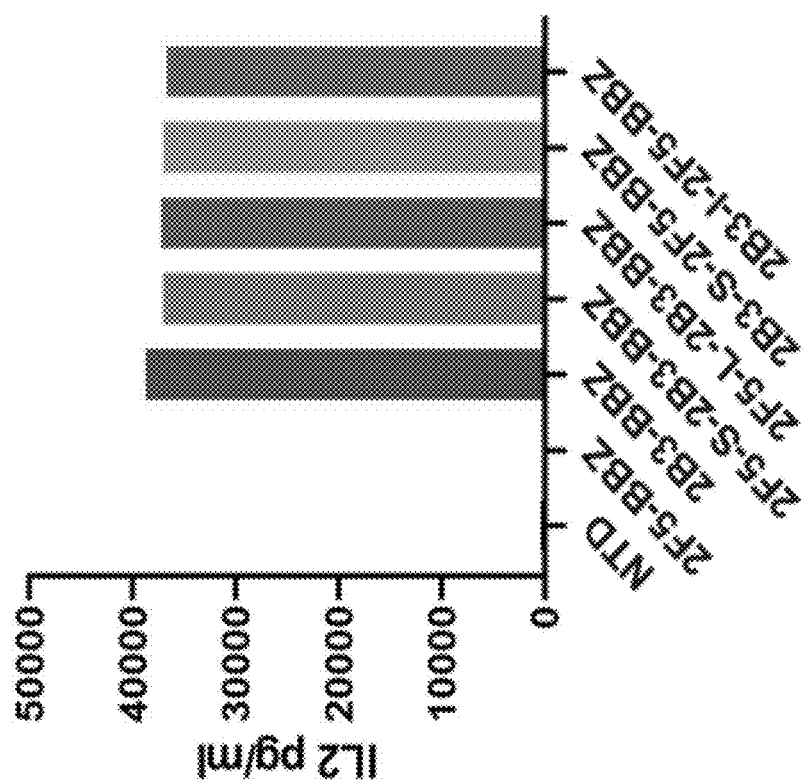
FIG. 10A

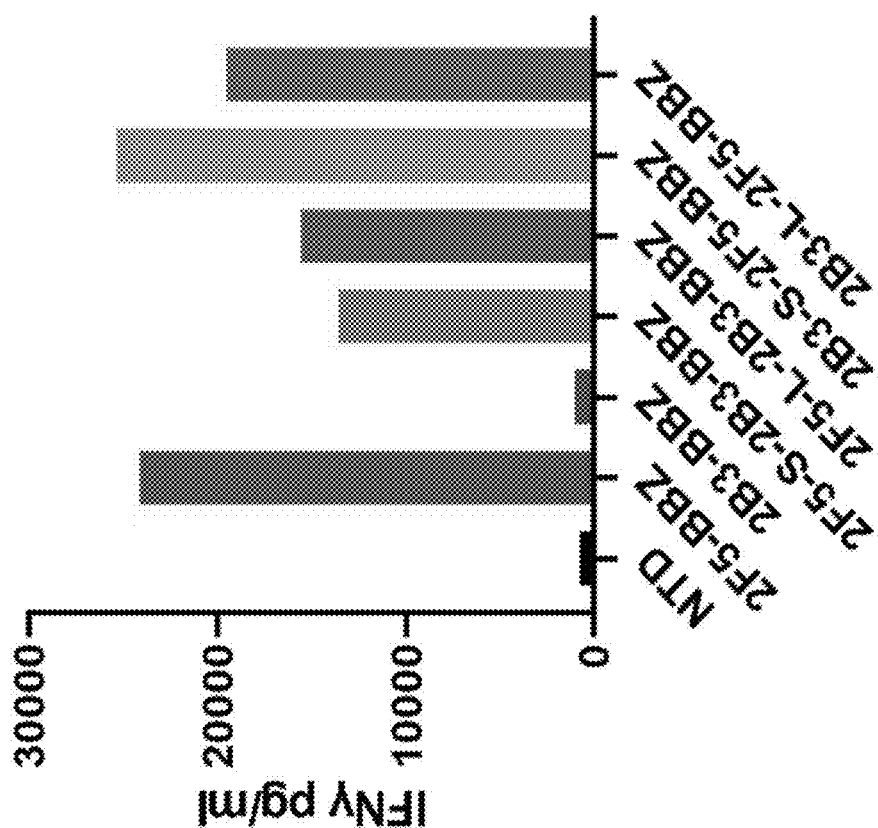
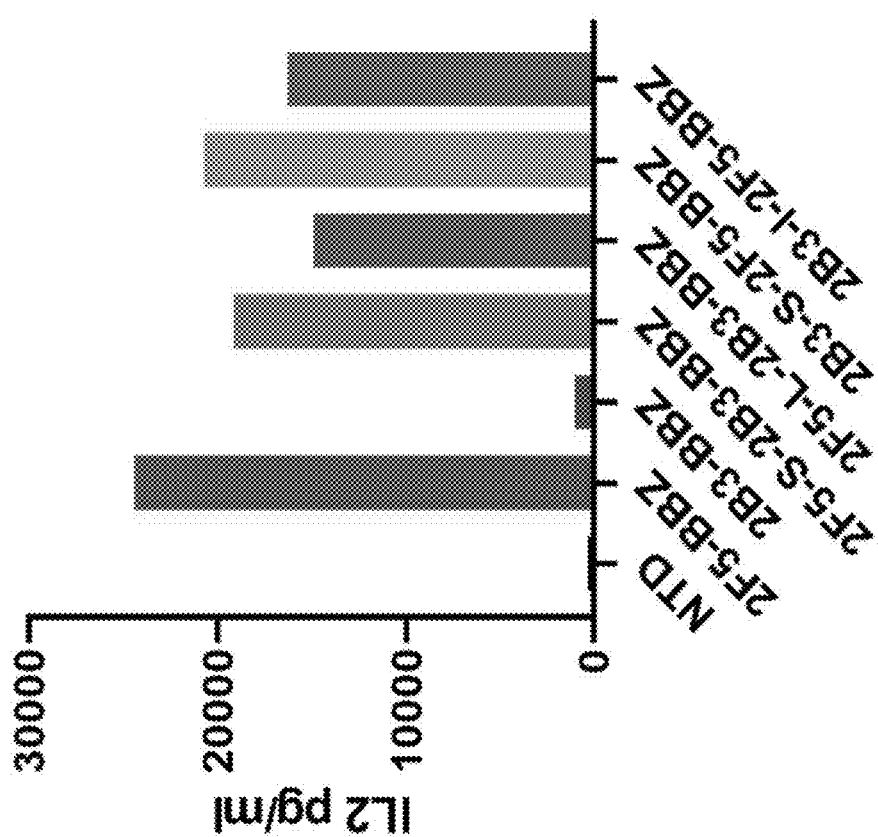
FIG. 10D

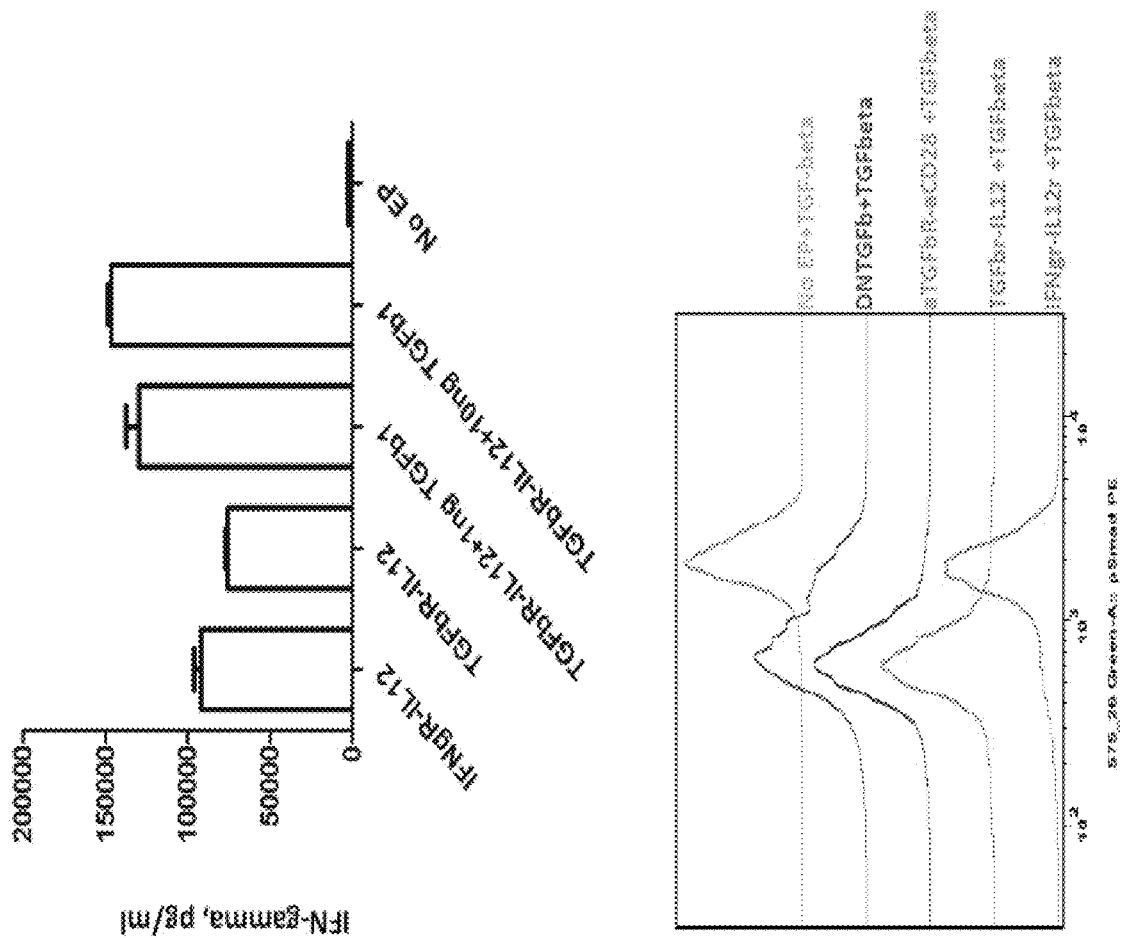
FIG. 11A
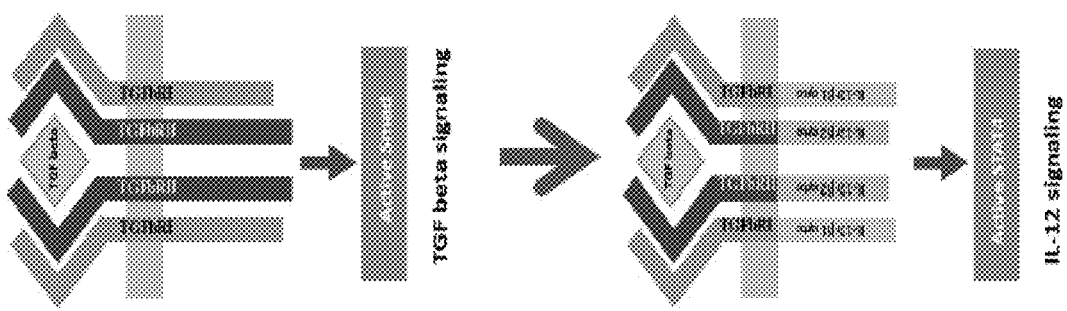

SEQUENCE LISTING

```
<160> NUMBER OF SEQ ID NOS: 148

<210> SEQ ID NO 1
<211> LENGTH: 5
<212> TYPE: PRT
<213> ORGANISM: Artificial Sequence
<220> FEATURE:
<223> OTHER INFORMATION: PSCA 2B3 HCDR1
```

<400> SEQUENCE: 1

Asp Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: PSCA 2B3 HCDR2

<400> SEQUENCE: 2

Trp Ile Asp Pro Glu Asn Gly Asp Thr Glu Phe Val Pro Lys Phe Gln
1               5                   10                  15

Gly

<210> SEQ ID NO 3
<211> LENGTH: 4
<212> TYPE: PRT
<213> ORGANISM: Artificial Sequence
<220> FEATURE:
<223> OTHER INFORMATION: PSCA 2B3 HCDR3

<400> SEQUENCE: 3

Thr Gly Gly Phe
1

<210> SEQ ID NO 4
<211> LENGTH: 11
<212> TYPE: PRT
<213> ORGANISM: Artificial Sequence
<220> FEATURE:
<223> OTHER INFORMATION: PSCA 2B3 LCDR1

<400> SEQUENCE: 4

Ser Ala Ser Ser Ser Val Arg Phe Ile His Trp
1               5                   10

<210> SEQ ID NO 5
<211> LENGTH: 7
<212> TYPE: PRT
<213> ORGANISM: Artificial Sequence
<220> FEATURE:
<223> OTHER INFORMATION: PSCA 2B3 LCDR2

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: PSCA 2B3 LCDR3

<400> SEQUENCE: 6

Gln Gln Trp Ser Ser Ser Pro Phe Thr
1               5

<210> SEQ ID NO 7
<211> LENGTH: 112
<212> TYPE: PRT
<213> ORGANISM: Artificial Sequence
<220> FEATURE:

<223> OTHER INFORMATION: PSCA 2B3 VH

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Ile His Trp Val Arg Gln Ala Pro Gly Lys Gly Leu Glu Trp Val
        35                  40                  45

Ala Trp Ile Asp Pro Glu Asn Gly Asp Thr Glu Phe Val Pro Lys Phe
    50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Lys Thr Gly Gly Phe Trp Gly Gln Gly Thr Leu Val Thr Val Ser Ser
            100                 105                 110

<210> SEQ ID NO 8
<211> LENGTH: 106
<212> TYPE: PRT
<213> ORGANISM: Artificial Sequence
<220> FEATURE:
<223> OTHER INFORMATION: PSCA 2B3 VL

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys
            100                 105

<210> SEQ ID NO 9
<211> LENGTH: 236
<212> TYPE: PRT
<213> ORGANISM: Artificial Sequence
<220> FEATURE:
<223> OTHER INFORMATION: PSCA 2B3 scFv

<400> SEQUENCE: 9

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu

```
                    65                  70                  75                  80
Asp Phe Ala Thr Tyr Tyr Cys Gln Gln Trp Ser Ser Ser Pro Phe Thr
                    85                  90                  95

Phe Gly Gln Gly Thr Lys Val Glu Ile Lys Gly Ser Thr Ser Gly Gly
                100                 105                 110

Gly Ser Gly Gly Ser Gly Gly Gly Ser Ser Glu Val Gln Leu
            115                 120                 125

Val Glu Ser Gly Gly Gly Leu Val Gln Pro Gly Gly Ser Leu Arg Leu
        130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser
225                 230                 235

<210> SEQ ID NO 10
<211> LENGTH: 45
<212> TYPE: PRT
<213> ORGANISM: Artificial Sequence
<220> FEATURE:
<223> OTHER INFORMATION: CD8 alpha hinge

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 11
<211> LENGTH: 23
<212> TYPE: PRT
<213> ORGANISM: Artificial Sequence
<220> FEATURE:
<223> OTHER INFORMATION: CD8 alpha transmembrane domain

<400> SEQUENCE: 11

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 12
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 12

Phe Trp Val Leu Val Val Val Gly Gly Val Leu Ala Cys Tyr Ser Leu
1               5                   10                  15
```

```
Leu Val Thr Val Ala Phe Ile Ile Phe Trp Val
        20                  25

<210> SEQ ID NO 13
<211> LENGTH: 21
<212> TYPE: PRT
<213> ORGANISM: Artificial Sequence
<220> FEATURE:
<223> OTHER INFORMATION: ICOS transmembrane domain

<400> SEQUENCE: 13

Phe Trp Leu Pro Ile Gly Cys Ala Ala Phe Val Val Cys Ile Leu
1               5                   10                  15

Gly Cys Ile Leu Ile
            20

<210> SEQ ID NO 14
<211> LENGTH: 41
<212> TYPE: PRT
<213> ORGANISM: Artificial Sequence
<220> FEATURE:
<223> OTHER INFORMATION: CD28 ICD

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
        35                  40

<210> SEQ ID NO 15
<211> LENGTH: 41
<212> TYPE: PRT
<213> ORGANISM: Artificial Sequence
<220> FEATURE:
<223> OTHER INFORMATION: CD28 ICD

<400> SEQUENCE: 15

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 16
<211> LENGTH: 38
<212> TYPE: PRT
<213> ORGANISM: Artificial Sequence
<220> FEATURE:
<223> OTHER INFORMATION: ICOS ICD

<400> SEQUENCE: 16

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 17
```

```
<211> LENGTH: 38
<212> TYPE: PRT
<213> ORGANISM: Artificial Sequence
<220> FEATURE:
<223> OTHER INFORMATION: ICOS YMNM ICD

<400> SEQUENCE: 17

Cys Trp Leu Thr Lys Lys Lys Tyr Ser Ser Ser Val His Asp Pro Asn
1               5                   10                  15

Gly Glu Tyr Met Asn Met Arg Ala Val Asn Thr Ala Lys Lys Ser Arg
            20                  25                  30

Leu Thr Asp Val Thr Leu
        35

<210> SEQ ID NO 18
<211> LENGTH: 113
<212> TYPE: PRT
<213> ORGANISM: Artificial Sequence
<220> FEATURE:
<223> OTHER INFORMATION: CD3 zeta ICD

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 19
<211> LENGTH: 112
<212> TYPE: PRT
<213> ORGANISM: Artificial Sequence
<220> FEATURE:
<223> OTHER INFORMATION: CD3 zeta Q14K ICD

<400> SEQUENCE: 19

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

<210> SEQ ID NO 20
<211> LENGTH: 1452
<212> TYPE: DNA
<213> ORGANISM: Artificial Sequence
<220> FEATURE:
<223> OTHER INFORMATION: PSCA CAR 2B3.BBZ

<400> SEQUENCE: 20

```
atggcgctac cggtgaccgc actcctgctg ccactcgccc tcctgctcca cgccgcccgc      60
cccgatatcc agctgaccca atcaccgtcg tccctgtctg cctccgtggg cgaccgggtg     120
acgatcacct gtagtgcctc gagcagtgta cggttcatcc actggtacca acagaagccc     180
ggcaaggcac caaagcggct gatctacgac accagcaagc tggcgtctgg ggtgcccagc     240
aggttctcgg gaagtggtag tggcacagac ttcactctca ccatcagttc actccagccg     300
gaggactttg ccacctacta ttgccagcag tggtcctcgt cccccttttac cttcggccag     360
ggaacaaagg tggaaattaa gggttcgacc tccggggggg gctccggtgg gggctccggc     420
ggggggggct catcggaggt tcagctggtg gagagcggcg gcggcctggt gcagcccggc     480
gggagtctgc ggctgtcctg tgccgccagc ggcttcaaca tcaaggacta ctacattcac     540
tgggtgcggc aagccccagg caagggtctg gagtgggtgg cttggattga ccctgaaaac     600
ggcgacactg agttcgtgcc aaaattccag gggcgggcga ccatctccgc cgacacctcc     660
aagaatacgg cctacctgca gatgaactcc ctgcgcgccg aagacacagc ggtctactac     720
tgcaagacag ggggtttctg ggggccaggggc accctcgtga ccgtttcgag tgccgccggc     780
accacgacgc cagcgccgcg accaccaaca ccggcgccca ccatcgcgtc gcagcccctg     840
tccctgcgcc cagaggcgtg ccggccagcg cggggggggcg cagtgcacac gaggggggctg     900
gacttcgcct gtgatatcta catctgggcg cccttggccg ggacttgtgg ggtccttctc     960
ctgtcactgg ttatcaccct ttactgcaaa cggggcagaa agaaactcct gtatatattc    1020
aaacaaccat ttatgagacc agtacaaact actcaagagg aagatggctg tagctgccga    1080
tttccagaag aagaagaagg aggatgtgaa ctgagagtga agttcagcag gagcgcagac    1140
gcccccgcgt acaagcaggg ccagaaccag ctctataacg agctcaatct aggacgaaga    1200
gaggagtacg acgttttgga caagagacgt ggccgggacc ctgagatggg gggaaagccg    1260
agaaggaaga accctcagga aggcctgtac aatgaactgc agaaagataa gatggcggag    1320
gcctacagtg agattgggat gaaaggcgag cgccggaggg gcaaggggca cgatggcctt    1380
taccagggtc tcagtacagc caccaaggac acctacgacg cccttcacat gcaggccctg    1440
cccccctcgct aa                                                       1452
```

<210> SEQ ID NO 21
<211> LENGTH: 483
<212> TYPE: PRT
<213> ORGANISM: Artificial Sequence
<220> FEATURE:
<223> OTHER INFORMATION: PSCA CAR 2B3.BBZ

<400> SEQUENCE: 21

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser

```
                35                  40                  45
Ser Val Arg Phe Ile His Trp Tyr Gln Gln Lys Pro Gly Lys Ala Pro
 50                  55                  60

Lys Arg Leu Ile Tyr Asp Thr Ser Lys Leu Ala Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460
```

Ser Thr Ala Thr Lys Asp Thr Tyr Asp Ala Leu His Met Gln Ala Leu
465                 470                 475                 480

Pro Pro Arg

<210> SEQ ID NO 22
<211> LENGTH: 1461
<212> TYPE: DNA
<213> ORGANISM: Artificial Sequence
<220> FEATURE:
<223> OTHER INFORMATION: PSCA CAR 2B3.28Z

<400> SEQUENCE: 22

| | | |
|---|---|---|
| atggcgctac cggtgaccgc actcctgctg ccactcgccc tcctgctcca cgccgcccgc | 60 |
| cccgatatcc agctgaccca atcaccgtcg tccctgtctg cctccgtggg cgaccgggtg | 120 |
| acgatcacct gtagtgcctc gagcagtgta cggttcatcc actggtacca acagaagccc | 180 |
| ggcaaggcac caaagcggct gatctacgac accagcaagc tggcgtctgg ggtgcccagc | 240 |
| aggttctcgg gaagtggtag tggcacagac ttcactctca ccatcagttc actccagccg | 300 |
| gaggactttg ccacctacta ttgccagcag tggtcctcgt cccccttttac cttcggccag | 360 |
| ggaacaaagg tggaaattaa gggttcgacc tccggggggg gctccggtgg gggctccggc | 420 |
| ggggggggct catcggaggt tcagctggtg gagagcggcg gcggcctggt gcagcccggc | 480 |
| gggagtctgc ggctgtcctg tgccgccagc ggcttcaaca tcaaggacta ctacattcac | 540 |
| tgggtgcggc aagccccagg caagggtctg gagtgggtgg cttggattga ccctgaaaac | 600 |
| ggcgacactg agttcgtgcc aaaattccag gggcgggcga ccatctccgc cgacacctcc | 660 |
| aagaatacgg cctacctgca gatgaactcc ctgcgcgccg aagacacagc ggtctactac | 720 |
| tgcaagacag ggggtttctg ggggcagggc accctcgtga ccgtttcgag tgccgccggc | 780 |
| accacgacgc cagcgccgcg accaccaaca ccggcgccca ccatcgcgtc gcagcccctg | 840 |
| tccctgcgcc cagaggcgtg ccggccagcg gcggggggcg cagtgcacac gagggggctg | 900 |
| gacttcgcct gtgattttg ggtgctggtg gtggttggtg gagtcctggc ttgctatagc | 960 |
| ttgctagtaa cagtggcctt tattattttc tgggtgagga gtaagaggag caggctcctg | 1020 |
| cacagtgact acatgaacat gactccccgc cgccccgggc ccacccgcaa gcattaccag | 1080 |
| ccctatgccc caccacgcga cttcgcagcc tatcgctcca gagtgaagtt cagcaggagc | 1140 |
| gcagacgccc ccgcgtacca gcagggccag aaccagctct ataacgagct caatctagga | 1200 |
| cgaagagagg agtacgatgt tttggacaag agacgtggcc gggaccctga tggggggga | 1260 |
| aagccgcaga gaaggaagaa ccctcaggaa ggcctgtaca tgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc cccctcgcta a | 1461 |

<210> SEQ ID NO 23
<211> LENGTH: 486
<212> TYPE: PRT
<213> ORGANISM: Artificial Sequence
<220> FEATURE:
<223> OTHER INFORMATION: PSCA CAR 2B3.28Z

<400> SEQUENCE: 23

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Arg Phe Ile His Trp Tyr Gln Gln Lys Pro Gly Lys Ala Pro
    50                  55                  60

Lys Arg Leu Ile Tyr Asp Thr Ser Lys Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Val Leu Val Val Gly Gly Val Leu Ala Cys Tyr Ser
305                 310                 315                 320

Leu Leu Val Thr Val Ala Phe Ile Ile Phe Trp Val Arg Ser Lys Arg
                325                 330                 335

Ser Arg Leu Leu His Ser Asp Tyr Met Asn Met Thr Pro Arg Arg Pro
            340                 345                 350

Gly Pro Thr Arg Lys His Tyr Gln Pro Tyr Ala Pro Pro Arg Asp Phe
        355                 360                 365

Ala Ala Tyr Arg Ser Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Gly Arg Asp Pro
                405                 410                 415

Glu Met Gly Gly Lys Pro Gln Arg Arg Lys Asn Pro Gln Glu Gly Leu
            420                 425                 430

Tyr Asn Glu Leu Gln Lys Asp Lys Met Ala Glu Ala Tyr Ser Glu Ile

Gly Met Lys Gly Glu Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 24
<211> LENGTH: 1434
<212> TYPE: DNA
<213> ORGANISM: Artificial Sequence
<220> FEATURE:
<223> OTHER INFORMATION: PSCA CAR 2B3.ICOSZ

<400> SEQUENCE: 24

```
atggcgctac cggtgaccgc actcctgctg ccactcgccc tcctgctcca cgccgcccgc      60
cccgatatcc agctgaccca atcaccgtcg tccctgtctg cctccgtggg cgaccgggtg     120
acgatcacct gtagtgcctc gagcagtgta cggttcatcc actggtacca acagaagccc     180
ggcaaggcac caaagcggct gatctacgac accagcaagc tggcgtctgg ggtgcccagc     240
aggttctcgg gaagtggtag tggcacagac ttcactctca ccatcagttc actccagccg     300
gaggactttg ccacctacta ttgccagcag tggtcctcgt cccccttac cttcggccag     360
ggaacaaagg tggaaattaa gggttcgacc tccggggggg gctccggtgg gggctccggc     420
gggggggct catcggaggt tcagctggtg gagagcggcg gcggcctggt gcagcccggc     480
gggagtctgc ggctgtcctg tgccgccagc ggcttcaaca tcaaggacta ctacattcac     540
tgggtgcggc aagccccagg caagggtctg gagtgggtgg cttggattga ccctgaaaac     600
ggcgacactg agttcgtgcc aaaattccag gggcgggcga ccatctccgc cgacacctcc     660
aagaatacgg cctacctgca gatgaactcc ctgcgcgccg aagacacagc ggtctactac     720
tgcaagacag ggggttttctg gggccagggc accctcgtga ccgtttcgag tgccgccggc     780
accacgacgc cagcgccgcg accaccaaca ccggcgccca ccatcgcgtc gcagcccctg     840
tccctgcgcc cagaggcgtg ccggccagcg gcggggggcg cagtgcacac gagggggctg     900
gacttcgcct gtgatttctg gttacccata ggatgtgcag cctttgttgt agtctgcatt     960
ttgggatgca tacttatttg ttggcttaca aaaagaagt attcatccag tgtgcacgac    1020
cctaacggtg aatacatgtt catgagagca gtgaacacag ccaaaaaatc cagactcaca    1080
gatgtgaccc taagagtgaa gttcagcagg agcgcagacg cccccgcgta ccagcagggc    1140
cagaaccagc tctataacga gctcaatcta ggacgaagag aggagtacga tgttttggac    1200
aagagacgtg gccggaccc tgagatgggg ggaaagccgc agagaaggaa gaaccctcag    1260
gaaggcctgt acaatgaact gcagaaagat aagatggcgg aggcctacag tgagattggg    1320
atgaaaggcg agcgccggag gggcaagggg cacgatggcc tttaccaggg tctcagtaca    1380
gccaccaagg acacctacga cgcccttcac atgcaggccc tgccccctcg ctaa          1434
```

<210> SEQ ID NO 25
<211> LENGTH: 477
<212> TYPE: PRT
<213> ORGANISM: Artificial Sequence
<220> FEATURE:
<223> OTHER INFORMATION: PSCA CAR 2B3.ICOSZ

<400> SEQUENCE: 25

-continued

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Arg Phe Ile His Trp Tyr Gln Gln Lys Pro Gly Lys Ala Pro
    50                  55                  60

Lys Arg Leu Ile Tyr Asp Thr Ser Lys Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Leu Pro Ile Gly Cys Ala Ala Phe Val Val Val Cys Ile
305                 310                 315                 320

Leu Gly Cys Ile Leu Ile Cys Trp Leu Thr Lys Lys Lys Tyr Ser Ser
                325                 330                 335

Ser Val His Asp Pro Asn Gly Glu Tyr Met Phe Met Arg Ala Val Asn
            340                 345                 350

Thr Ala Lys Lys Ser Arg Leu Thr Asp Val Thr Leu Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Gln Arg Arg
                405                 410                 415

Lys Asn Pro Gln Glu Gly Leu Tyr Asn Glu Leu Gln Lys Asp Lys Met
```

Ala Glu Ala Tyr Ser Glu Ile Gly Met Lys Gly Glu Arg Arg Gly
        420                 425                 430

Lys Gly His Asp Gly Leu Tyr Gln Gly Leu Ser Thr Ala Thr Lys Asp
435                 440                 445

Thr Tyr Asp Ala Leu His Met Gln Ala Leu Pro Pro Arg
465                 470                 475

<210> SEQ ID NO 26
<211> LENGTH: 1434
<212> TYPE: DNA
<213> ORGANISM: Artificial Sequence
<220> FEATURE:
<223> OTHER INFORMATION: PSCA CAR 2B3.ICOS.YMNM.Z

<400> SEQUENCE: 26

```
atggcgctac cggtgaccgc actcctgctg ccactcgccc tcctgctcca cgccgcccgc    60
cccgatatcc agctgaccca atcaccgtcg tccctgtctg cctccgtggg cgaccgggtg   120
acgatcacct gtagtgcctc gagcagtgta cggttcatcc actggtacca acagaagccc   180
ggcaaggcac caaagcggct gatctacgac accagcaagc tggcgtctgg ggtgcccagc   240
aggttctcgg gaagtggtag tggcacagac ttcactctca ccatcagttc actccagccg   300
gaggactttg ccacctacta ttgccagcag tggtcctcgt ccccctttac cttcggccag   360
ggaacaaagg tggaaattaa gggttcgacc tccggggggg gctccggtgg gggctccggc   420
gggggggggct catcggaggt tcagctggtg gagagcggcg gcggcctggt gcagcccggc   480
gggagtctgc ggctgtcctg tgccgccagc ggcttcaaca tcaaggacta ctacattcac   540
tgggtgcggc aagccccagg caagggtctg gagtgggtgg cttggattga ccctgaaaac   600
ggcgacactg agttcgtgcc aaaattccag gggcgggcga ccatctccgc cgacacctcc   660
aagaatacgg cctacctgca gatgaactcc ctgcgcgccg aagacacagc ggtctactac   720
tgcaagacag gggtttctg gggccagggc accctcgtga ccgtttcgag tgccgccggc   780
accacgacgc cagcgccgcg accaccaaca ccggcgccca ccatcgcgtc gcagcccctg   840
tccctgcgcc cagaggcgtg ccggccagcg gcggggggcg cagtgcacac gagggggctg   900
gacttcgcct gtgatttctg gttacccata ggatgtgcag cctttgttgt agtctgcatt   960
ttgggatgca tacttatttg ttggcttaca aaaagaagt attcatccag tgtgcacgac  1020
cctaacggtg aatacatgaa catgagagca gtgaacacag ccaaaaaatc cagactcaca  1080
gatgtgaccc taagagtgaa gttcagcagg agcgcagacg cccccgcgta ccagcagggc  1140
cagaaccagc tctataacga gctcaatcta ggacgaagag aggagtacga tgttttggac  1200
aagagacgtg gccgggaccc tgagatgggg ggaaagccgc agagaaggaa gaaccctcag  1260
gaaggcctgt acaatgaact gcagaaagat aagatggcgg aggcctacag tgagattggg  1320
atgaaaggcg agcgccggag gggcaagggg cacgatggcc tttaccaggg tctcagtaca  1380
gccaccaagg acacctacga cgcccttcac atgcaggccc tgccccctcg ctaa         1434
```

<210> SEQ ID NO 27
<211> LENGTH: 477
<212> TYPE: PRT
<213> ORGANISM: Artificial Sequence
<220> FEATURE:
<223> OTHER INFORMATION: PSCA CAR 2B3.ICOS.YMNM.Z

<400> SEQUENCE: 27

-continued

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Arg Phe Ile His Trp Tyr Gln Gln Lys Pro Gly Lys Ala Pro
    50                  55                  60

Lys Arg Leu Ile Tyr Asp Thr Ser Lys Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Phe Trp Leu Pro Ile Gly Cys Ala Ala Phe Val Val Val Cys Ile
305                 310                 315                 320

Leu Gly Cys Ile Leu Ile Cys Trp Leu Thr Lys Lys Lys Tyr Ser Ser
                325                 330                 335

Ser Val His Asp Pro Asn Gly Glu Tyr Met Asn Met Arg Ala Val Asn
            340                 345                 350

Thr Ala Lys Lys Ser Arg Leu Thr Asp Val Thr Leu Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Gln Arg Arg
                405                 410                 415

Lys Asn Pro Gln Glu Gly Leu Tyr Asn Glu Leu Gln Lys Asp Lys Met
```

```
              420                 425                 430
Ala Glu Ala Tyr Ser Glu Ile Gly Met Lys Gly Glu Arg Arg Arg Gly
            435                 440                 445

Lys Gly His Asp Gly Leu Tyr Gln Gly Leu Ser Thr Ala Thr Lys Asp
        450                 455                 460

Thr Tyr Asp Ala Leu His Met Gln Ala Leu Pro Pro Arg
465                 470                 475

<210> SEQ ID NO 28
<211> LENGTH: 5
<212> TYPE: PRT
<213> ORGANISM: Artificial Sequence
<220> FEATURE:
<223> OTHER INFORMATION: PSMA 2F5 HCDR1

<400> SEQUENCE: 28

Ser Asn Trp Ile Gly
1               5

<210> SEQ ID NO 29
<211> LENGTH: 17
<212> TYPE: PRT
<213> ORGANISM: Artificial Sequence
<220> FEATURE:
<223> OTHER INFORMATION: PSMA 2F5 HCDR2

<400> SEQUENCE: 29

Ile Ile Tyr Pro Gly Asp Ser Asp Thr Arg Tyr Ser Pro Ser Phe Gln
1               5                   10                  15
Gly

<210> SEQ ID NO 30
<211> LENGTH: 10
<212> TYPE: PRT
<213> ORGANISM: Artificial Sequence
<220> FEATURE:
<223> OTHER INFORMATION: PSMA 2F5 HCDR3

<400> SEQUENCE: 30

Gln Thr Gly Phe Leu Trp Ser Phe Asp Leu
1               5                   10

<210> SEQ ID NO 31
<211> LENGTH: 11
<212> TYPE: PRT
<213> ORGANISM: Artificial Sequence
<220> FEATURE:
<223> OTHER INFORMATION: PSMA 2F5 LCDR1

<400> SEQUENCE: 31

Arg Ala Ser Gln Asp Ile Ser Ser Ala Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: PSMA 2F5 LCDR2

<400> SEQUENCE: 32

Asp Ala Ser Ser Leu Glu Ser
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: PSMA 2F5 LCDR3

<400> SEQUENCE: 33

Gln Gln Phe Asn Ser Tyr Pro Leu Thr
1               5

<210> SEQ ID NO 34
<211> LENGTH: 119
<212> TYPE: PRT
<213> ORGANISM: Artificial Sequence
<220> FEATURE:
<223> OTHER INFORMATION: PSMA 2F5 VH

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Thr Gly Phe Leu Trp Ser Phe Asp Leu Trp Gly Arg Gly
            100                 105                 110

Thr Leu Val Thr Val Ser Ser
        115

<210> SEQ ID NO 35
<211> LENGTH: 109
<212> TYPE: PRT
<213> ORGANISM: Artificial Sequence
<220> FEATURE:
<223> OTHER INFORMATION: PSMA 2F5 VL

<400> SEQUENCE: 35

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Ile Lys
            100                 105

<210> SEQ ID NO 36
```

<211> LENGTH: 243
<212> TYPE: PRT
<213> ORGANISM: Artificial Sequence
<220> FEATURE:
<223> OTHER INFORMATION: PSMA 2F5 scFv

<400> SEQUENCE: 36

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Asn
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Asn Ser Leu Lys Ala Ser Asp Thr Ala Met Tyr Tyr Cys
                85                  90                  95
Ala Arg Gln Thr Gly Phe Leu Trp Ser Phe Asp Leu Trp Gly Arg Gly
            100                 105                 110
Thr Leu Val Thr Val Ser Ser Gly Gly Gly Ser Gly Gly Gly Gly
        115                 120                 125
Ser Gly Gly Gly Ser Ala Ile Gln Leu Thr Gln Ser Pro Ser Ser
    130                 135                 140
Leu Ser Ala Ser Val Gly Asp Arg Val Thr Ile Thr Cys Arg Ala Ser
145                 150                 155                 160
Gln Asp Ile Ser Ser Ala Leu Ala Trp Tyr Gln Lys Pro Gly Lys
                165                 170                 175
Ala Pro Lys Leu Leu Ile Tyr Asp Ala Ser Ser Leu Glu Ser Gly Val
            180                 185                 190
Pro Ser Arg Phe Ser Gly Ser Gly Ser Gly Thr Asp Phe Thr Leu Thr
        195                 200                 205
Ile Ser Ser Leu Gln Pro Glu Asp Phe Ala Thr Tyr Tyr Cys Gln Gln
    210                 215                 220
Phe Asn Ser Tyr Pro Leu Thr Phe Gly Gly Gly Thr Lys Val Glu Ile
225                 230                 235                 240
Lys Ile Lys

<210> SEQ ID NO 37
<211> LENGTH: 5
<212> TYPE: PRT
<213> ORGANISM: Artificial Sequence
<220> FEATURE:
<223> OTHER INFORMATION: Linker

<400> SEQUENCE: 37

Gly Gly Gly Gly Ser
1               5

<210> SEQ ID NO 38
<211> LENGTH: 21
<212> TYPE: PRT
<213> ORGANISM: Artificial Sequence
<220> FEATURE:
<223> OTHER INFORMATION: Linker

<400> SEQUENCE: 38

Gly Gly Gly Gly Gly Ser Gly Gly Gly Gly Ser Gly Gly Gly Gly Ser

```
            1               5              10              15
Gly Gly Gly Gly Ser
            20

<210> SEQ ID NO 39
<211> LENGTH: 2241
<212> TYPE: DNA
<213> ORGANISM: Artificial Sequence
<220> FEATURE:
<223> OTHER INFORMATION: 2B3L2F5.BBZ CAR

<400> SEQUENCE: 39
atggcgctac cggtgaccgc actcctgctg ccactcgccc tcctgctcca cgccgcccgc      60
cccgatatcc agctgaccca atcaccgtcg tccctgtctg cctccgtggg cgaccgggtg     120
acgatcacct gtagtgcctc gagcagtgta cggttcatcc actggtacca acagaagccc     180
ggcaaggcac aaagcggct gatctacgac accagcaagc tggcgtctgg ggtgcccagc      240
aggttctcgg gaagtggtag tggcacagac ttcactctca ccatcagttc actccagccg     300
gaggactttg ccacctacta ttgccagcag tggtcctcgt cccccttttac cttcggccag    360 ggaacaaagg tggaaattaa gggttcgacc tccggggggg gctccggtgg gggctccggc     420
ggggggggct catcggaggt tcagctggtg gagagcggcg gcggcctggt gcagcccggc     480
gggagtctgc ggctgtcctg tgccgccagc ggcttcaaca tcaaggacta ctacattcac     540
tgggtgcggc aagccccagg caagggtctg gagtgggtgg cttggattga ccctgaaaac     600
ggcgacactg agttcgtgcc aaaattccag gggcgggcga ccatctccgc cgacacctcc     660
aagaatacgg cctacctgca gatgaactcc ctgcgcgccg aagacacagc ggtctactac     720
tgcaagacag ggggtttctg gggccagggc accctcgtga ccgtttcgag tgccgccggc     780
ggaggtggtg gatccggcgg aggggggaagt ggcggggtg gtccggcgg cggcggctcg     840 gaggtgcagc tggtgcagtc tggagcagag gtgaaaaagc ccggggagtc tctgaagatc     900
tcctgtaagg gttctggata cagttttacc agcaactgga tcggctgggt gcgccagatg     960
cccgggaaag gcctggagtg gatgggggat cctcatcctg tgactctga taccagatac    1020 agcccgtcct tccaaggcca ggtcaccatc tcagccgaca gtccatcag caccgcctac    1080 ctgcagtgga acagcctgaa ggcctcggac accgccatgt attactgtgc gagacaaact    1140
ggtttcctct ggtccttcga tctctgggc cgtggcaccc tggtcactgt ctcctcaggt    1200
ggcggtgggt cgggcggtgg tgggtcgggt ggcggcggat ctgccatcca gttgacccag    1260
tctccatcct ccctgtctgc atctgtagga cagagtca ccatcacttg ccgggcaagt    1320
caggacatta gcagtgcttt agcctggtat cagcagaaac cggggaaagc tcctaagctc    1380
ctgatctatg atgcctccag tttgaaagt ggggtcccat caaggttcag cggcagtgga    1440
tctgggacag atttcactct caccatcagc agcctgcagc tgaagatttt gcaacttat    1500 tactgtcaac agtttaatag ttacccgctc actttcggcg agggaccaa ggtggagatc    1560 aaaatcaaaa ccacgacgcc agcgccgcga ccaccaacac cggcgcccac catcgcgtcg    1620
cagcccctgt ccctgcgccc agaggcgtgc cggccagcg cggggggcgc agtgcacacg    1680 aggggctgg acttcgcctg tgatatctac atctgggcgc ccttggccgg acttgtgggg    1740
gtccttctcc tgtcactggt tatcaccctt tactgcaaac ggggcagaaa gaaactcctg    1800
tatatattca acaaccattt tatgagacca gtacaaacta ctcaagagga gatggctgt    1860 agctgccgat tccagaaga agaagaagga ggatgtgaac tgagagtgaa gttcagcagg    1920
```

```
agcgcagacg ccccccgcgta caagcagggc cagaaccagc tctataacga gctcaatcta    1980
ggacgaagag aggagtacga tgttttggac aagagacgtg gccgggaccc tgagatgggg     2040
ggaaagccga gaaggaagaa ccctcaggaa ggcctgtaca atgaactgca gaaagataag     2100
atggcggagg cctacagtga gattgggatg aaaggcgagc gccggagggg caaggggcac     2160
gatggccttt accagggtct cagtacagcc accaaggaca cctacgacgc ccttcacatg     2220
caggccctgc cccctcgcta a                                               2241
```

<210> SEQ ID NO 40
<211> LENGTH: 746
<212> TYPE: PRT
<213> ORGANISM: Artificial Sequence
<220> FEATURE:
<223> OTHER INFORMATION: 2B3L2F5.BBZ CAR

<400> SEQUENCE: 40

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Arg Phe Ile His Trp Tyr Gln Gln Lys Pro Gly Lys Ala Pro
    50                  55                  60

Lys Arg Leu Ile Tyr Asp Thr Ser Lys Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Gly Gly Gly Ser Gly Gly Gly Gly Ser Gly Gly
            260                 265                 270

Gly Gly Ser Gly Gly Gly Gly Ser Glu Val Gln Leu Val Gln Ser Gly
        275                 280                 285

Ala Glu Val Lys Lys Pro Gly Glu Ser Leu Lys Ile Ser Cys Lys Gly
    290                 295                 300
```

```
Ser Gly Tyr Ser Phe Thr Ser Asn Trp Ile Gly Trp Val Arg Gln Met
305                 310                 315                 320

Pro Gly Lys Gly Leu Glu Trp Met Gly Ile Ile Tyr Pro Gly Asp Ser
                325                 330                 335

Asp Thr Arg Tyr Ser Pro Ser Phe Gln Gly Gln Val Thr Ile Ser Ala
            340                 345                 350

Asp Lys Ser Ile Ser Thr Ala Tyr Leu Gln Trp Asn Ser Leu Lys Ala
        355                 360                 365

Ser Asp Thr Ala Met Tyr Tyr Cys Ala Arg Gln Thr Gly Phe Leu Trp
370                 375                 380

Ser Phe Asp Leu Trp Gly Arg Gly Thr Leu Val Thr Val Ser Ser Gly
385                 390                 395                 400

Gly Gly Gly Ser Gly Gly Gly Ser Gly Gly Gly Ser Ala Ile
                405                 410                 415

Gln Leu Thr Gln Ser Pro Ser Ser Leu Ser Ala Ser Val Gly Asp Arg
                420                 425                 430

Val Thr Ile Thr Cys Arg Ala Ser Gln Asp Ile Ser Ser Ala Leu Ala
            435                 440                 445

Trp Tyr Gln Gln Lys Pro Gly Lys Ala Pro Lys Leu Leu Ile Tyr Asp
        450                 455                 460

Ala Ser Ser Leu Glu Ser Gly Val Pro Ser Arg Phe Ser Gly Ser Gly
465                 470                 475                 480

Ser Gly Thr Asp Phe Thr Leu Thr Ile Ser Ser Leu Gln Pro Glu Asp
                485                 490                 495

Phe Ala Thr Tyr Tyr Cys Gln Gln Phe Asn Ser Tyr Pro Leu Thr Phe
            500                 505                 510

Gly Gly Gly Thr Lys Val Glu Ile Lys Ile Lys Thr Thr Pro Ala
        515                 520                 525

Pro Arg Pro Pro Thr Pro Ala Pro Thr Ile Ala Ser Gln Pro Leu Ser
530                 535                 540

Leu Arg Pro Glu Ala Cys Arg Pro Ala Ala Gly Gly Ala Val His Thr
545                 550                 555                 560

Arg Gly Leu Asp Phe Ala Cys Asp Ile Tyr Ile Trp Ala Pro Leu Ala
                565                 570                 575

Gly Thr Cys Gly Val Leu Leu Leu Ser Leu Val Ile Thr Leu Tyr Cys
            580                 585                 590

Lys Arg Gly Arg Lys Lys Leu Leu Tyr Ile Phe Lys Gln Pro Phe Met
        595                 600                 605

Arg Pro Val Gln Thr Thr Gln Glu Glu Asp Gly Cys Ser Cys Arg Phe
610                 615                 620

Pro Glu Glu Glu Glu Gly Gly Cys Glu Leu Arg Val Lys Phe Ser Arg
625                 630                 635                 640

Ser Ala Asp Ala Pro Ala Tyr Lys Gln Gly Gln Asn Gln Leu Tyr Asn
                645                 650                 655

Glu Leu Asn Leu Gly Arg Arg Glu Glu Tyr Asp Val Leu Asp Lys Arg
            660                 665                 670

Arg Gly Arg Asp Pro Glu Met Gly Gly Lys Pro Arg Arg Lys Asn Pro
        675                 680                 685

Gln Glu Gly Leu Tyr Asn Glu Leu Gln Lys Asp Lys Met Ala Glu Ala
        690                 695                 700

Tyr Ser Glu Ile Gly Met Lys Gly Glu Arg Arg Arg Gly Lys Gly His
705                 710                 715                 720

Asp Gly Leu Tyr Gln Gly Leu Ser Thr Ala Thr Lys Asp Thr Tyr Asp
```

725                 730                 735
Ala Leu His Met Gln Ala Leu Pro Pro Arg
            740                 745

<210> SEQ ID NO 41
<211> LENGTH: 2196
<212> TYPE: DNA
<213> ORGANISM: Artificial Sequence
<220> FEATURE:
<223> OTHER INFORMATION: 2B3S2F5.BBZ CAR

<400> SEQUENCE: 41

| | | | | |
|---|---|---|---|---|
| atggcgctac | cggtgaccgc | actcctgctg | ccactcgccc | tcctgctcca | cgccgcccgc | 60 |
| cccgatatcc | agctgaccca | atcaccgtcg | tccctgtctg | cctccgtggg | cgaccgggtg | 120 |
| acgatcacct | gtagtgcctc | gagcagtgta | cggttcatcc | actggtacca | acagaagccc | 180 |
| ggcaaggcac | caaagcggct | gatctacgac | accagcaagc | tggcgtctgg | ggtgcccagc | 240 |
| aggttctcgg | gaagtggtag | tggcacagac | ttcactctca | ccatcagttc | actccagccg | 300 |
| gaggactttg | ccacctacta | ttgccagcag | tggtcctcgt | ccccctttac | cttcggccag | 360 |
| ggaacaaagg | tggaaattaa | gggttcgacc | tccgggggg | gctccggtgg | gggctccggc | 420 |
| ggggggggct | catcggaggt | tcagctggtg | gagagcggcg | gcggcctggt | gcagcccggc | 480 |
| gggagtctgc | ggctgtcctg | tgccgccagc | ggcttcaaca | tcaaggacta | ctacattcac | 540 |
| tgggtgcggc | aagccccagg | caagggtctg | gagtgggtgg | cttggattga | ccctgaaaac | 600 |
| ggcgacactg | agttcgtgcc | aaaattccag | gggcgggcga | ccatctccgc | cgacacctcc | 660 |
| aagaatacgg | cctacctgca | gatgaactcc | ctgcgcgccg | aagacacagc | ggtctactac | 720 |
| tgcaagacag | ggggtttctg | gggccagggc | accctcgtga | ccgtttcgag | tgccgccggc | 780 |
| ggaggtggtg | gatccgaggt | gcagctggtg | cagtctggag | cagaggtgaa | aaagcccggg | 840 |
| gagtctctga | gatctcctg | taagggttct | ggatacagtt | ttaccagcaa | ctggatcggc | 900 |
| tgggtgcgcc | agatgcccgg | gaaaggcctg | gagtggatgg | ggatcatcta | tcctggtgac | 960 |
| tctgatacca | gatacagccc | gtccttccaa | ggccaggtca | ccatctcagc | cgacaagtcc | 1020 |
| atcagcaccg | cctacctgca | gtggaacagc | ctgaaggcct | cggacaccgc | catgtattac | 1080 |
| tgtgcgagac | aaactggttt | cctctggtcc | ttcgatctct | ggggccgtgg | caccctggtc | 1140 |
| actgtctcct | caggtggcgg | tggctcgggc | ggtggtgggt | cgggtggcgg | cggatctgcc | 1200 |
| atccagttga | cccagtctcc | atcctccctg | tctgcatctg | taggagacag | agtcaccatc | 1260 |
| acttgccggg | caagtcagga | cattagcagt | gcttttagcct | ggtatcagca | gaaaccgggg | 1320 |
| aaagctccta | agctcctgat | ctatgatgcc | tccagtttgg | aaagtggggt | cccatcaagg | 1380 |
| ttcagcggca | gtggatctgg | gacagatttc | actctcacca | tcagcagcct | gcagcctgaa | 1440 |
| gattttgcaa | cttattactg | tcaacagttt | aatagttacc | cgctcacttt | cggcggaggg | 1500 |
| accaaggtgg | agatcaaaat | caaaaccacg | acgccagcgc | cgcgaccacc | aacaccggcg | 1560 |
| cccaccatcg | cgtcgcagcc | cctgtccctg | cgcccagagg | cgtgccggcc | agcggcgggg | 1620 |
| ggcgcagtgc | acacgagggg | gctggacttc | gcctgtgata | tctacatctg | ggcgcccttg | 1680 |
| gccgggactt | gtgggtcct | tctcctgtca | ctggttatca | cccttactg | caaacgggc | 1740 |
| agaaagaaac | tcctgtatat | attcaaacaa | ccatttatga | gaccagtaca | aactactcaa | 1800 |
| gaggaagatg | gctgtagctg | ccgatttcca | gaagaagaag | aaggaggatg | tgaactgaga | 1860 |
| gtgaagttca | gcaggagcgc | agacgccccc | gcgtacaagc | agggccagaa | ccagctctat | 1920 |

```
aacgagctca atctaggacg aagagaggag tacgatgttt tggacaagag acgtggccgg      1980
gaccctgaga tggggggaaa gccgagaagg aagaaccctc aggaaggcct gtacaatgaa      2040
ctgcagaaag ataagatggc ggaggcctac agtgagattg ggatgaaagg cgagcgccgg      2100
aggggcaagg ggcacgatgg cctttaccag ggtctcagta cagccaccaa ggacacctac      2160
gacgcccttc acatgcaggc cctgccccct cgctaa                               2196
```

<210> SEQ ID NO 42
<211> LENGTH: 731
<212> TYPE: PRT
<213> ORGANISM: Artificial Sequence
<220> FEATURE:
<223> OTHER INFORMATION: 2B3S2F5.BBZ CAR

<400> SEQUENCE: 42

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Thr Ile Thr Cys Ser Ala Ser Ser
        35                  40                  45

Ser Val Arg Phe Ile His Trp Tyr Gln Gln Lys Pro Gly Lys Ala Pro
    50                  55                  60

Lys Arg Leu Ile Tyr Asp Thr Ser Lys Leu Ala Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Trp Ser
            100                 105                 110

Ser Ser Pro Phe Thr Phe Gly Gln Gly Thr Lys Val Glu Ile Lys Gly
        115                 120                 125

Ser Thr Ser Gly Gly Gly Ser Gly Gly Gly Ser Gly Gly Gly Gly Ser
    130                 135                 140

Ser Glu Val Gln Leu Val Glu Ser Gly Gly Gly Leu Val Gln Pro Gly
145                 150                 155                 160

Gly Ser Leu Arg Leu Ser Cys Ala Ala Ser Gly Phe Asn Ile Lys Asp
                165                 170                 175

Tyr Tyr Ile His Trp Val Arg Gln Ala Pro Gly Lys Gly Leu Glu Trp
            180                 185                 190

Val Ala Trp Ile Asp Pro Glu Asn Gly Asp Thr Glu Phe Val Pro Lys
        195                 200                 205

Phe Gln Gly Arg Ala Thr Ile Ser Ala Asp Thr Ser Lys Asn Thr Ala
    210                 215                 220

Tyr Leu Gln Met Asn Ser Leu Arg Ala Glu Asp Thr Ala Val Tyr Tyr
225                 230                 235                 240

Cys Lys Thr Gly Gly Phe Trp Gly Gln Gly Thr Leu Val Thr Val Ser
                245                 250                 255

Ser Ala Ala Gly Gly Gly Gly Ser Glu Val Gln Leu Val Gln Ser
            260                 265                 270

Gly Ala Glu Val Lys Lys Pro Gly Glu Ser Leu Lys Ile Ser Cys Lys
        275                 280                 285

Gly Ser Gly Tyr Ser Phe Thr Ser Asn Trp Ile Gly Trp Val Arg Gln
    290                 295                 300

Met Pro Gly Lys Gly Leu Glu Trp Met Gly Ile Ile Tyr Pro Gly Asp
305                 310                 315                 320
```

```
Ser Asp Thr Arg Tyr Ser Pro Ser Phe Gln Gly Gln Val Thr Ile Ser
                325                 330                 335

Ala Asp Lys Ser Ile Ser Thr Ala Tyr Leu Gln Trp Asn Ser Leu Lys
            340                 345                 350

Ala Ser Asp Thr Ala Met Tyr Tyr Cys Ala Arg Gln Thr Gly Phe Leu
            355                 360                 365

Trp Ser Phe Asp Leu Trp Gly Arg Gly Thr Leu Val Thr Val Ser Ser
370                 375                 380

Gly Gly Gly Gly Ser Gly Gly Gly Ser Gly Gly Gly Gly Ser Gly Ala
385                 390                 395                 400

Ile Gln Leu Thr Gln Ser Pro Ser Ser Leu Ser Ala Ser Val Gly Asp
            405                 410                 415

Arg Val Thr Ile Thr Cys Arg Ala Ser Gln Asp Ile Ser Ser Ala Leu
            420                 425                 430

Ala Trp Tyr Gln Gln Lys Pro Gly Lys Ala Pro Lys Leu Leu Ile Tyr
            435                 440                 445

Asp Ala Ser Ser Leu Glu Ser Gly Val Pro Ser Arg Phe Ser Gly Ser
            450                 455                 460

Gly Ser Gly Thr Asp Phe Thr Leu Thr Ile Ser Ser Leu Gln Pro Glu
465                 470                 475                 480

Asp Phe Ala Thr Tyr Tyr Cys Gln Gln Phe Asn Ser Tyr Pro Leu Thr
            485                 490                 495

Phe Gly Gly Gly Thr Lys Val Glu Ile Lys Ile Lys Thr Thr Thr Pro
            500                 505                 510

Ala Pro Arg Pro Pro Thr Pro Ala Pro Thr Ile Ala Ser Gln Pro Leu
            515                 520                 525

Ser Leu Arg Pro Glu Ala Cys Arg Pro Ala Ala Gly Gly Ala Val His
530                 535                 540

Thr Arg Gly Leu Asp Phe Ala Cys Asp Ile Tyr Ile Trp Ala Pro Leu
545                 550                 555                 560

Ala Gly Thr Cys Gly Val Leu Leu Leu Ser Leu Val Ile Thr Leu Tyr
            565                 570                 575

Cys Lys Arg Gly Arg Lys Lys Leu Leu Tyr Ile Phe Lys Gln Pro Phe
            580                 585                 590

Met Arg Pro Val Gln Thr Thr Gln Glu Glu Asp Gly Cys Ser Cys Arg
            595                 600                 605

Phe Pro Glu Glu Glu Glu Gly Gly Cys Glu Leu Arg Val Lys Phe Ser
            610                 615                 620

Arg Ser Ala Asp Ala Pro Ala Tyr Lys Gln Gly Gln Asn Gln Leu Tyr
625                 630                 635                 640

Asn Glu Leu Asn Leu Gly Arg Arg Glu Glu Tyr Asp Val Leu Asp Lys
            645                 650                 655

Arg Arg Gly Arg Asp Pro Glu Met Gly Gly Lys Pro Arg Arg Lys Asn
            660                 665                 670

Pro Gln Glu Gly Leu Tyr Asn Glu Leu Gln Lys Asp Lys Met Ala Glu
            675                 680                 685

Ala Tyr Ser Glu Ile Gly Met Lys Gly Glu Arg Arg Arg Gly Lys Gly
            690                 695                 700

His Asp Gly Leu Tyr Gln Gly Leu Ser Thr Ala Thr Lys Asp Thr Tyr
705                 710                 715                 720

Asp Ala Leu His Met Gln Ala Leu Pro Pro Arg
            725                 730
```

<210> SEQ ID NO 43
<211> LENGTH: 336
<212> TYPE: DNA
<213> ORGANISM: Artificial Sequence
<220> FEATURE:
<223> OTHER INFORMATION: PSCA 2B3 VH

<400> SEQUENCE: 43

```
gaggttcagc tggtggagag cggcggcggc ctggtgcagc ccggcgggag tctgcggctg      60
tcctgtgccg ccagcggctt caacatcaag gactactaca ttcactgggt gcggcaagcc     120
ccaggcaagg gtctggagtg gtggcttgg attgaccctg aaaacggcga cactgagttc      180
gtgccaaaat tccaggggcg ggcgaccatc tccgccgaca cctccaagaa tacggcctac     240
ctgcagatga actccctgcg cgccgaagac acagcggtct actactgcaa gacagggggt     300
ttctggggcc agggcaccct cgtgaccgtt tcgagt                               336
```

<210> SEQ ID NO 44
<211> LENGTH: 318
<212> TYPE: DNA
<213> ORGANISM: Artificial Sequence
<220> FEATURE:
<223> OTHER INFORMATION: PSCA 2B3 VL

<400> SEQUENCE: 44

```
gatatccagc tgacccaatc accgtcgtcc ctgtctgcct ccgtgggcga ccgggtgacg      60
atcacctgta gtgcctcgag cagtgtacgg ttcatccact ggtaccaaca gaagcccggc     120
aaggcaccaa agcggctgat ctacgacacc agcaagctgg cgtctggggt gcccagcagg     180
ttctcgggaa gtggtagtgg cacagacttc actctcacca tcagttcact ccagccggag     240
gactttgcca cctactattg ccagcagtgg tcctcgtccc cctttacctt cggccaggga     300
acaaaggtgg aaattaag                                                   318
```

<210> SEQ ID NO 45
<211> LENGTH: 708
<212> TYPE: DNA
<213> ORGANISM: Artificial Sequence
<220> FEATURE:
<223> OTHER INFORMATION: PSCA 2B3 scFv

<400> SEQUENCE: 45

```
gatatccagc tgacccaatc accgtcgtcc ctgtctgcct ccgtgggcga ccgggtgacg      60
atcacctgta gtgcctcgag cagtgtacgg ttcatccact ggtaccaaca gaagcccggc     120
aaggcaccaa agcggctgat ctacgacacc agcaagctgg cgtctggggt gcccagcagg     180
ttctcgggaa gtggtagtgg cacagacttc actctcacca tcagttcact ccagccggag     240
gactttgcca cctactattg ccagcagtgg tcctcgtccc cctttacctt cggccaggga     300
acaaaggtgg aaattaaggg ttcgacctcc gggggggggct ccggtggggg ctccggcggg     360
gggggctcat cggaggttca gctggtggag agcggcggcg gcctggtgca gcccggcggg     420
agtctgcggc tgtcctgtgc cgccagcggc ttcaacatca aggactacta cattcactgg     480
gtgcggcaag ccccaggcaa gggtctggag tggtggcctt ggattgaccc tgaaaacggc     540
gacactgagt tcgtgccaaa attccagggg cgggcgacca tctccgccga cacctccaag     600
aatacggcct acctgcagat gaactccctg cgcgccgaag acacagcggt ctactactgc     660
aagacagggg gttttctgggg ccagggcacc ctcgtgaccg tttcgagt                  708
```

```
<210> SEQ ID NO 46
<211> LENGTH: 357
<212> TYPE: DNA
<213> ORGANISM: Artificial Sequence
<220> FEATURE:
<223> OTHER INFORMATION: PSMA 2F5 VH

<400> SEQUENCE: 46
gaggtgcagc tggtgcagtc tggagcagag gtgaaaaagc ccggggagtc tctgaagatc      60
tcctgtaagg gttctggata cagttttacc agcaactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga acagcctgaa ggcctcggac accgccatgt attactgtgc gagacaaact     300
ggtttcctct ggtccttcga tctctggggc cgtggcaccc tggtcactgt ctcctca       357

<210> SEQ ID NO 47
<211> LENGTH: 328
<212> TYPE: DNA
<213> ORGANISM: Artificial Sequence
<220> FEATURE:
<223> OTHER INFORMATION: PSMA 2F5 VL

<400> SEQUENCE: 47
gccatccagt tgacccagtc tccatcctcc ctgtctgcat ctgtaggaga cagagtcacc      60
atcacttgcc gggcaagtca ggacattagc agtgctttag cctggtatca gcagaaaccg     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt acccgctcac tttcggcgga     300
gggaccaagg tggagatcaa aatcaaaa                                        328

<210> SEQ ID NO 48
<211> LENGTH: 730
<212> TYPE: DNA
<213> ORGANISM: Artificial Sequence
<220> FEATURE:
<223> OTHER INFORMATION: PSMA 2F5 scFv

<400> SEQUENCE: 48
gaggtgcagc tggtgcagtc tggagcagag gtgaaaaagc ccggggagtc tctgaagatc      60
tcctgtaagg gttctggata cagttttacc agcaactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga acagcctgaa ggcctcggac accgccatgt attactgtgc gagacaaact     300
ggtttcctct ggtccttcga tctctggggc cgtggcaccc tggtcactgt ctcctcaggt     360
ggcggtggct cggcggtgg tggtcgggt ggcggcggat ctgccatcca gttgacccag       420
tctccatcct ccctgtctgc atctgtagga cagagtca ccatcacttg ccgggcaagt       480
caggacatta gcagtgcttt agcctggtat cagcagaaac cggggaaagc tcctaagctc     540
ctgatctatg atgcctccag tttgaaaagt ggggtcccat caaggttcag cggcagtgga     600
tctgggacag atttcactct caccatcagc agcctgcagc tgaagatttt gcaacttat     660 tactgtcaac agtttaatag ttacccgctc actttcggcg gagggaccaa ggtggagatc     720
aaaatcaaaa                                                             730
```

<210> SEQ ID NO 49
<211> LENGTH: 1507
<212> TYPE: DNA
<213> ORGANISM: Artificial Sequence
<220> FEATURE:
<223> OTHER INFORMATION: 2B3L2F5 Extracellular domain

<400> SEQUENCE: 49

```
gatatccagc tgacccaatc accgtcgtcc ctgtctgcct ccgtgggcga ccgggtgacg      60
atcacctgta gtgcctcgag cagtgtacgg ttcatccact ggtaccaaca gaagcccggc     120
aaggcaccaa agcggctgat ctacgacacc agcaagctgg cgtctggggt gcccagcagg     180
ttctcgggaa gtggtagtgg cacagacttc actctcacca tcagttcact ccagccggag     240
gactttgcca cctactattg ccagcagtgg tcctcgtccc cctttacctt cggccaggga     300
acaaaggtgg aaattaaggg ttcgacctcc ggggggggct ccggtggggg ctccggcggg     360
ggggctcat cggaggttca gctggtggag agcggcggcg gcctggtgca gcccggcggg      420
agtctgcggc tgtcctgtgc cgccagcggc ttcaacatca aggactacta cattcactgg     480
gtgcggcaag ccccaggcaa gggtctggag tgggtggctt ggattgaccc tgaaaacggc     540
gacactgagt tcgtgccaaa attccagggg cgggcgacca tctccgccga cacctccaag     600
aatacggcct acctgcagat gaactccctg cgcgccgaag acacagcggt ctactactgc     660
aagacagggg gtttctgggg ccagggcacc ctcgtgaccg tttcgagtgc cgccggcgga     720
ggtggtggat ccggcggagg gggaagtggc gggggtgggt ccggcggcgg cggctcggag     780
gtgcagctgg tgcagtctgg agcagaggtg aaaaagcccg gggagtctct gaagatctcc     840
tgtaagggtt ctggatacag ttttaccagc aactggatcg gctgggtgcg ccagatgccc     900
gggaaggcc tggagtggat ggggatcatc tatcctggtg actctgatac agatacagc      960
ccgtccttcc aaggccaggt caccatctca gccgacaagt ccatcagcac cgcctacctg    1020
cagtggaaca gcctgaaggc ctcggacacc gccatgtatt actgtgcgag acaaactggt    1080
ttcctctggt ccttcgatct ctggggccgt ggcaccctgg tcactgtctc ctcaggtggc    1140
ggtggctcgg gcggtggtgg gtcggtggc ggcggatctg ccatccagtt gacccagtct    1200
ccatcctccc tgtctgcatc tgtaggagac agagtcacca tcacttgccg ggcaagtcag    1260
gacattagca gtgctttagc ctggtatcag cagaaaccgg ggaaagctcc taagctcctg    1320
atctatgatg cctccagttt ggaaagtggg gtcccatcaa ggttcagcgg cagtggatct    1380
gggacagatt tcactctcac catcagcagc ctgcagcctg aagattttgc aacttattac    1440
tgtcaacagt ttaatagtta cccgctcact ttcggcggag ggaccaaggt ggagatcaaa    1500
atcaaaa                                                              1507
```

<210> SEQ ID NO 50
<211> LENGTH: 502
<212> TYPE: PRT
<213> ORGANISM: Artificial Sequence
<220> FEATURE:
<223> OTHER INFORMATION: 2B3L2F5 Extracellular domain

<400> SEQUENCE: 50

```
Asp Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
```

```
                35                  40                  45
Asp Thr Ser Lys Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Pro Phe Thr
                 85                  90                  95

Phe Gly Gln Gly Thr Lys Val Glu Ile Lys Gly Ser Thr Ser Gly Gly
                100                 105                 110

Gly Ser Gly Gly Ser Gly Gly Gly Ser Ser Glu Val Gln Leu
                115                 120                 125

Val Glu Ser Gly Gly Gly Leu Val Gln Pro Gly Gly Ser Leu Arg Leu
                130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
                180                 185                 190

Thr Ile Ser Ala Asp Thr Ser Lys Asn Thr Ala Tyr Leu Gln Met Asn
                195                 200                 205

Ser Leu Arg Ala Glu Asp Thr Ala Val Tyr Tyr Cys Lys Thr Gly Gly
210                 215                 220

Phe Trp Gly Gln Gly Thr Leu Val Thr Val Ser Ser Ala Ala Gly Gly
225                 230                 235                 240

Gly Gly Gly Ser Gly Gly Gly Ser Gly Gly Gly Ser Gly Gly
                245                 250                 255

Gly Gly Ser Glu Val Gln Leu Val Gln Ser Gly Ala Glu Val Lys Lys
                260                 265                 270

Pro Gly Glu Ser Leu Lys Ile Ser Cys Lys Gly Ser Gly Tyr Ser Phe
                275                 280                 285

Thr Ser Asn Trp Ile Gly Trp Val Arg Gln Met Pro Gly Lys Gly Leu
290                 295                 300

Glu Trp Met Gly Ile Ile Tyr Pro Gly Asp Ser Asp Thr Arg Tyr Ser
305                 310                 315                 320

Pro Ser Phe Gln Gly Gln Val Thr Ile Ser Ala Asp Lys Ser Ile Ser
                325                 330                 335

Thr Ala Tyr Leu Gln Trp Asn Ser Leu Lys Ala Ser Asp Thr Ala Met
                340                 345                 350

Tyr Tyr Cys Ala Arg Gln Thr Gly Phe Leu Trp Ser Phe Asp Leu Trp
                355                 360                 365

Gly Arg Gly Thr Leu Val Thr Val Ser Ser Gly Gly Gly Gly Ser Gly
                370                 375                 380

Gly Gly Ser Gly Gly Gly Ser Ala Ile Gln Leu Thr Gln Ser
385                 390                 395                 400

Pro Ser Ser Leu Ser Ala Ser Val Gly Asp Arg Val Thr Ile Thr Cys
                405                 410                 415

Arg Ala Ser Gln Asp Ile Ser Ser Ala Leu Ala Trp Tyr Gln Gln Lys
                420                 425                 430

Pro Gly Lys Ala Pro Lys Leu Leu Ile Tyr Asp Ala Ser Ser Leu Glu
                435                 440                 445

Ser Gly Val Pro Ser Arg Phe Ser Gly Ser Gly Ser Gly Thr Asp Phe
                450                 455                 460
```

Thr Leu Thr Ile Ser Ser Leu Gln Pro Glu Asp Phe Ala Thr Tyr Tyr
465                 470                 475                 480

Cys Gln Gln Phe Asn Ser Tyr Pro Leu Thr Phe Gly Gly Gly Thr Lys
                485                 490                 495

Val Glu Ile Lys Ile Lys
            500

<210> SEQ ID NO 51
<211> LENGTH: 1462
<212> TYPE: DNA
<213> ORGANISM: Artificial Sequence
<220> FEATURE:
<223> OTHER INFORMATION: 2B3S2F5 Extracellular domain

<400> SEQUENCE: 51

| | | |
|---|---|---|
| gatatccagc tgacccaatc accgtcgtcc ctgtctgcct ccgtgggcga ccgggtgacg | 60 |
| atcacctgta gtgcctcgag cagtgtacgg ttcatccact ggtaccaaca gaagcccggc | 120 |
| aaggcaccaa agcggctgat ctacgacacc agcaagctgg cgtctggggt gcccagcagg | 180 |
| ttctcgggaa gtggtagtgg cacagacttc actctcacca tcagttcact ccagccggag | 240 |
| gactttgcca cctactattg ccagcagtgg tcctcgtccc cctttacctt cggccaggga | 300 |
| acaaaggtgg aaattaaggg ttcgacctcc ggggggggct ccggtggggg ctccggcggg | 360 |
| gggggctcat cggaggttca gctggtggag agcggcggcg gcctggtgca gcccggcggg | 420 |
| agtctgcggc tgtcctgtgc cgccagcggc ttcaacatca aggactacta cattcactgg | 480 |
| gtgcggcaag ccccaggcaa gggtctggag tgggtggctt ggattgaccc tgaaaacggc | 540 |
| gacactgagt tcgtgccaaa attccagggg cgggcgacca tctccgccga cacctccaag | 600 |
| aatacgccct acctgcagat gaactccctg cgcgccgaag acacagcggt ctactactgc | 660 |
| aagacagggg gtttctgggg ccagggcacc ctcgtgaccg tttcgagtgc cgccggcgga | 720 |
| ggtggtggat ccgaggtgca gctggtgcag tctggagcag aggtgaaaaa gcccggggag | 780 |
| tctctgaaga tctcctgtaa gggttctgga tacagtttta ccagcaactg gatcggctgg | 840 |
| gtgcgccaga tgcccgggaa aggcctggag tggatgggga tcatctatcc tggtgactct | 900 |
| gataccagat acagcccgtc cttccaaggc caggtcacca tctcagccga caagtccatc | 960 |
| agcaccgcct acctgcagtg gaacagcctg aaggcctcgg acaccgccat gtattactgt | 1020 |
| gcgagacaaa ctggttttcct ctggtccttc gatctctggg gccgtggcac cctggtcact | 1080 |
| gtctcctcag gtggcggtgg ctcggccggt ggtgggtcgg gtggcggcgg atctgccatc | 1140 |
| cagttgaccc agtctccatc ctccctgtct gcatctgtag gagacagagt caccatcact | 1200 |
| tgccgggcaa gtcaggacat tagcagtgct ttagcctggt atcagcagaa accggggaaa | 1260 |
| gctcctaagc tcctgatcta tgatgcctcc agtttggaaa gtggggtccc atcaaggttc | 1320 |
| agcggcagtg gatctgggac agatttcact ctcaccatca gcagcctgca gcctgaagat | 1380 |
| tttgcaactt attactgtca acagtttaat agttacccgc tcactttcgg cggagggacc | 1440 |
| aaggtggaga tcaaaatcaa aa | 1462 |

<210> SEQ ID NO 52
<211> LENGTH: 487
<212> TYPE: PRT
<213> ORGANISM: Artificial Sequence
<220> FEATURE:
<223> OTHER INFORMATION: 2B3S2F5 Extracellular domain

<400> SEQUENCE: 52

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65              70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Gly
                100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
                180                 185                 190

Thr Ile Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Ala Ala Gly Gly
225                 230                 235                 240

Gly Gly Gly Ser Glu Val Gln Leu Val Gln Ser Gly Ala Glu Val Lys
            245                 250                 255

Lys Pro Gly Glu Ser Leu Lys Ile Ser Cys Lys Gly Ser Gly Tyr Ser
                260                 265                 270

Phe Thr Ser Asn Trp Ile Gly Trp Val Arg Gln Met Pro Gly Lys Gly
            275                 280                 285

Leu Glu Trp Met Gly Ile Ile Tyr Pro Gly Asp Ser Asp Thr Arg Tyr
    290                 295                 300

Ser Pro Ser Phe Gln Gly Gln Val Thr Ile Ser Ala Asp Lys Ser Ile
305                 310                 315                 320

Ser Thr Ala Tyr Leu Gln Trp Asn Ser Leu Lys Ala Ser Asp Thr Ala
                325                 330                 335

Met Tyr Tyr Cys Ala Arg Gln Thr Gly Phe Leu Trp Ser Phe Asp Leu
                340                 345                 350

Trp Gly Arg Gly Thr Leu Val Thr Val Ser Ser Gly Gly Gly Gly Ser
            355                 360                 365

Gly Gly Gly Gly Ser Gly Gly Gly Ser Ala Ile Gln Leu Thr Gln
    370                 375                 380

Ser Pro Ser Ser Leu Ser Ala Ser Val Gly Asp Arg Val Thr Ile Thr
385                 390                 395                 400

Cys Arg Ala Ser Gln Asp Ile Ser Ser Ala Leu Ala Trp Tyr Gln Gln
                405                 410                 415
```

-continued

```
Lys Pro Gly Lys Ala Pro Lys Leu Leu Ile Tyr Asp Ala Ser Ser Leu
                420                 425                 430

Glu Ser Gly Val Pro Ser Arg Phe Ser Gly Ser Gly Ser Gly Thr Asp
            435                 440                 445

Phe Thr Leu Thr Ile Ser Ser Leu Gln Pro Glu Asp Phe Ala Thr Tyr
        450                 455                 460

Tyr Cys Gln Gln Phe Asn Ser Tyr Pro Leu Thr Phe Gly Gly Gly Thr
465                 470                 475                 480

Lys Val Glu Ile Lys Ile Lys
                485

<210> SEQ ID NO 53
<211> LENGTH: 15
<212> TYPE: DNA
<213> ORGANISM: Artificial Sequence
<220> FEATURE:
<223> OTHER INFORMATION: Linker

<400> SEQUENCE: 53
ggcggcggcg gcagc                                                         15

<210> SEQ ID NO 54
<211> LENGTH: 63
<212> TYPE: DNA
<213> ORGANISM: Artificial Sequence
<220> FEATURE:
<223> OTHER INFORMATION: Linker

<400> SEQUENCE: 54
ggcggcggcg gcggcagcgg cggcggcggc agcggcggcg gcggcagcgg cggcggcggc        60
agc                                                                      63

<210> SEQ ID NO 55
<211> LENGTH: 603
<212> TYPE: DNA
<213> ORGANISM: Artificial Sequence
<220> FEATURE:
<223> OTHER INFORMATION: TGFBRII.dn

<400> SEQUENCE: 55
atgggtcggg ggctgctcag gggcctgtgg ccgctgcaca tcgtcctgtg gacgcgtatc        60
gccagcacga tcccaccgca cgttcagaag tcggttaata cgacatgat agtcactgac       120 aacaacggtg cagtcaagtt tccacaactg tgtaattttt gtgatgtgag attttccacc      180
tgtgacaacc agaaatcctg catgagcaac tgcagcatca cctccatctg tgagaagcca      240
caggaagtct gtgtggctgt atggagaaag aatgacgaga acataacact agagacagtt      300
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata caccagcaa tcctgacttg       480 ttgctagtca tatttcaagt gacaggcatc agcctcctgc caccactggg agttgccata      540
tctgtcatca tcatcttcta ctgctaccgc gttaaccggc agcagaagct gagttcatcc      600
gga                                                                    603

<210> SEQ ID NO 56
<211> LENGTH: 201
<212> TYPE: PRT
<213> ORGANISM: Artificial Sequence
<220> FEATURE:
```

<223> OTHER INFORMATION: TGFBRII.dn

<400> SEQUENCE: 56

```
Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys
                115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Ser Gly
            195                 200
```

<210> SEQ ID NO 57
<211> LENGTH: 714
<212> TYPE: DNA
<213> ORGANISM: Artificial Sequence
<220> FEATURE:
<223> OTHER INFORMATION: PD1CTMCD28 switch

<400> SEQUENCE: 57

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg ggccatctc cctggccccc aaggcgcaga tcaaagagag cctgcgggca     420
gagctcaggg tgacagagag aagggcagaa gtgcccacag cccaccccag cccctcaccc     480
aggccagccg ccagttccaa accctggtg ttttgggtgc tggtggtggt tggtggagtc     540
ctggcttgct atagcttgct agtaacagtg gcctttatta ttttctgggt gaggagtaag     600
aggagcaggc tcctgcacag tgactacatg aacatgactc ccgccgccc gggcccacc     660
cgcaagcatt accagcccta tgccccacca cgcgacttcg cagcctatcg ctcc          714
```

<210> SEQ ID NO 58

```
<211> LENGTH: 238
<212> TYPE: PRT
<213> ORGANISM: Artificial Sequence
<220> FEATURE:
<223> OTHER INFORMATION: PD1CTMCD28 switch

<400> SEQUENCE: 58

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
                165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Leu Leu His Ser Asp
        195                 200                 205

Tyr Met Asn Met Thr Pro Arg Arg Pro Gly Pro Thr Arg Lys His Tyr
210                 215                 220

Gln Pro Tyr Ala Pro Pro Arg Asp Phe Ala Ala Tyr Arg Ser
225                 230                 235

<210> SEQ ID NO 59
<211> LENGTH: 1074
<212> TYPE: DNA
<213> ORGANISM: Artificial Sequence
<220> FEATURE:
<223> OTHER INFORMATION: hIFNgRIL12rb1 switch

<400> SEQUENCE: 59
atggctctcc tctttctcct accccttgtc atgcagggtg tgagcagggc tgagatgggc      60
accgcggatc tggggccgtc ctcagtgcct acaccaacta atgttacaat tgaatcctat     120
aacatgaacc ctatcgtata ttgggagtac cagatcatgc acaggtccc  tgttttacc     180 gtagaggtaa agaactatgg tgttaagaat tcagaatgga ttgatgcctg catcaatatt    240
tctcatcatt attgtaatat ttctgatcat gttggtgatc catcaaattc tctttgggtc    300
agagttaaag ccagggttgg acaaaaagaa tctgcctatg caaagtcaga agaatttgct    360
gtatgccgag atggaaaaat tggaccacct aaactggata tcagaaagga ggagaagcaa    420
atcatgattg acatatttca cccttcagtt tttgtaaatg gagacgagca ggaagtcgat    480
```

| | | |
|---|---|---|
| tatgatcccg aaactacctg ttacattagg gtgtacaatg tgtatgtgag aatgaacgga | 540 | |
| agtgagatcc agtataaaat actcacgcag aaggaagatg attgtgacga gattcagtgc | 600 | |
| cagttagcga ttccagtatc ctcactgaat tctcagtact gtgtttcagc agaaggagtc | 660 | |
| ttacatgtgt ggggtgttac aactgaaaag tcaaaagaag tttgtattac cattttcaat | 720 | |
| agcagtataa aaggttctct ttggattcca gttgttgctg ctttactact ctttctagtg | 780 | |
| cttagcctgg tattcatcag ggccgcacgg cacctgtgcc cgccgctgcc cacaccctgt | 840 | |
| gccagctccg ccattgagtt ccctggaggg aaggagactt ggcagtggat caacccagtg | 900 | |
| gacttccagg aagaggcatc cctgcaggag gccctggtgg tagagatgtc ctgggacaaa | 960 | |
| ggcgagagga ctgagcctct cgagaagaca gagctacctg agggtgcccc tgagctggcc | 1020 | |
| ctggatacag agttgtcctt ggaggatgga gacaggtgca aggccaagat gtga | 1074 | |

```
<210> SEQ ID NO 60
<211> LENGTH: 357
<212> TYPE: PRT
<213> ORGANISM: Artificial Sequence
<220> FEATURE:
<223> OTHER INFORMATION: hIFNgRIL12rb1 switch

<400> SEQUENCE: 60
```

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser Leu Trp Ile Pro Val Val Ala Ala Leu Leu
                245                 250                 255

Leu Phe Leu Val Leu Ser Leu Val Phe Ile Arg Ala Ala Arg His Leu

```
                260              265              270
Cys Pro Pro Leu Pro Thr Pro Cys Ala Ser Ser Ala Ile Glu Phe Pro
            275              280              285

Gly Gly Lys Glu Thr Trp Gln Trp Ile Asn Pro Val Asp Phe Gln Glu
        290              295              300

Glu Ala Ser Leu Gln Glu Ala Leu Val Val Glu Met Ser Trp Asp Lys
305              310              315              320

Gly Glu Arg Thr Glu Pro Leu Glu Lys Thr Glu Leu Pro Glu Gly Ala
            325              330              335

Pro Glu Leu Ala Leu Asp Thr Glu Leu Ser Leu Glu Asp Gly Asp Arg
            340              345              350

Cys Lys Ala Lys Met
        355

<210> SEQ ID NO 61
<211> LENGTH: 1470
<212> TYPE: DNA
<213> ORGANISM: Artificial Sequence
<220> FEATURE:
<223> OTHER INFORMATION: hIFNgbIL12rb2 switch

<400> SEQUENCE: 61
```

| | | | | | |
|---|---|---|---|---|---|
| atgcgaccga | cgctgctgtg | gtcgctgctg | ctgctgctcg | gagtcttcgc | cgccgccgcc | 60 |
| gcggccccgc | cagaccctct | ttcccagctg | cccgctcctc | agcacccgaa | gattcgcctg | 120 |
| tacaacgcag | agcaggtcct | gagttgggag | ccagtggccc | tgagcaatag | cacgaggcct | 180 |
| gttgtctacc | aagtgcagtt | taaatacacc | gacagtaaat | ggttcacggc | cgacatcatg | 240 |
| tccataggg | tgaattgtac | acagatcaca | gcaacagagt | gtgacttcac | tgccgccagt | 300 |
| ccctcagcag | gcttcccaat | ggatttcaat | gtcactctac | gccttcgagc | tgagctggga | 360 |
| gcactccatt | ctgcctgggt | gacaatgcct | tggtttcaac | actatcggaa | tgtgactgtc | 420 |
| gggcctccag | aaaacattga | ggtgaccca | ggagaaggct | ccctcatcat | caggttctcc | 480 |
| tctcccttg | acatcgctga | tacctccacg | gccttttttt | gttattatgt | ccattactgg | 540 |
| gaaaaaggag | gaatccaaca | ggtcaaaggc | cctttcagaa | gcaactccat | tcattggat | 600 |
| aacttaaaac | cctccagagt | gtactgttta | caagtccagg | cacaactgct | ttggaacaaa | 660 |
| agtaacatct | ttagagtcgg | gcatttaagc | aacatatctt | gctacgaaac | aatggcagat | 720 |
| gcctccactg | agcttcagca | agtcatcctg | atctccgtgg | aacatttttc | gttgctgtcg | 780 |
| gtgctggcag | gagcctgttt | cttcctggtc | ctgaaatatc | agcaaaaggt | gtttgttctc | 840 |
| ctagcagccc | tcagacctca | gtggtgtagc | agagaaattc | cagatccagc | aaatagcact | 900 |
| tgcgctaaga | aatatcccat | tgcagaggag | aagacacagc | tgcccttgga | caggctcctg | 960 |
| atagactggc | ccacgcctga | agatcctgaa | ccgctggtca | tcagtgaagt | ccttcatcaa | 1020 |
| gtgaccccag | ttttcagaca | tcccccctgc | tccaactggc | cacaaaggga | aaaggaatc | 1080 |
| caaggtcatc | aggcctctga | aaagacatg | atgcacagtg | cctcaagccc | accacctcca | 1140 |
| agagctctcc | aagctgagag | cagacaactg | gtggatctgt | acaaggtgct | ggagagcagg | 1200 |
| ggctccgacc | caaagccaga | aaacccagcc | tgtccctgga | cggtgctccc | agcaggtgac | 1260 |
| cttcccaccc | atgatggcta | cttaccctcc | aacatagatg | acctccccta | catgaggca | 1320 |
| cctctcgctg | actctctgga | agaactggag | cctcagcaca | tctcccttc | tgttttcccc | 1380 |
| tcaagttctc | ttcaccccact | caccttctcc | tgtggtgata | agctgactct | ggatcagtta | 1440 |
| aagatgaggt | gtgactccct | catgctctga | | | | 1470 |

<210> SEQ ID NO 62
<211> LENGTH: 489
<212> TYPE: PRT
<213> ORGANISM: Artificial Sequence
<220> FEATURE:
<223> OTHER INFORMATION: hIFNgbIL12rb2 switch

<400> SEQUENCE: 62

```
Met Arg Pro Thr Leu Leu Trp Ser Leu Leu Leu Leu Leu Gly Val Phe
1               5                   10                  15

Ala Ala Ala Ala Ala Ala Pro Pro Asp Pro Leu Ser Gln Leu Pro Ala
            20                  25                  30

Pro Gln His Pro Lys Ile Arg Leu Tyr Asn Ala Glu Gln Val Leu Ser
        35                  40                  45

Trp Glu Pro Val Ala Leu Ser Asn Ser Thr Arg Pro Val Val Tyr Gln
    50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
            100                 105                 110

Leu Arg Leu Arg Ala Glu Leu Gly Ala Leu His Ser Ala Trp Val Thr
        115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
            180                 185                 190

Arg Ser Asn Ser Ile Ser Leu Asp Asn Leu Lys Pro Ser Arg Val Tyr
        195                 200                 205

Cys Leu Gln Val Gln Ala Gln Leu Leu Trp Asn Lys Ser Asn Ile Phe
    210                 215                 220

Arg Val Gly His Leu Ser Asn Ile Ser Cys Tyr Glu Thr Met Ala Asp
225                 230                 235                 240

Ala Ser Thr Glu Leu Gln Gln Val Ile Leu Ile Ser Val Gly Thr Phe
                245                 250                 255

Ser Leu Leu Ser Val Leu Ala Gly Ala Cys Phe Phe Leu Val Leu Lys
            260                 265                 270

Tyr Gln Gln Lys Val Phe Val Leu Leu Ala Ala Leu Arg Pro Gln Trp
        275                 280                 285

Cys Ser Arg Glu Ile Pro Asp Pro Ala Asn Ser Thr Cys Ala Lys Lys
    290                 295                 300

Tyr Pro Ile Ala Glu Glu Lys Thr Gln Leu Pro Leu Asp Arg Leu Leu
305                 310                 315                 320

Ile Asp Trp Pro Thr Pro Glu Asp Pro Glu Pro Leu Val Ile Ser Glu
                325                 330                 335

Val Leu His Gln Val Thr Pro Val Phe Arg His Pro Pro Cys Ser Asn
            340                 345                 350

Trp Pro Gln Arg Glu Lys Gly Ile Gln Gly His Gln Ala Ser Glu Lys
        355                 360                 365
```

```
Asp Met Met His Ser Ala Ser Ser Pro Pro Pro Arg Ala Leu Gln
        370                 375                 380

Ala Glu Ser Arg Gln Leu Val Asp Leu Tyr Lys Val Leu Glu Ser Arg
385                 390                 395                 400

Gly Ser Asp Pro Lys Pro Glu Asn Pro Ala Cys Pro Trp Thr Val Leu
                405                 410                 415

Pro Ala Gly Asp Leu Pro Thr His Asp Gly Tyr Leu Pro Ser Asn Ile
                420                 425                 430

Asp Asp Leu Pro Ser His Glu Ala Pro Leu Ala Asp Ser Leu Glu Glu
            435                 440                 445

Leu Glu Pro Gln His Ile Ser Leu Ser Val Phe Pro Ser Ser Ser Leu
    450                 455                 460

His Pro Leu Thr Phe Ser Cys Gly Asp Lys Leu Thr Leu Asp Gln Leu
465                 470                 475                 480

Lys Met Arg Cys Asp Ser Leu Met Leu
                485
```

<210> SEQ ID NO 63
<211> LENGTH: 1503
<212> TYPE: DNA
<213> ORGANISM: Artificial Sequence
<220> FEATURE:
<223> OTHER INFORMATION: 10A5 1412 aPDL1 aCd28 bispecific Ab

<400> SEQUENCE: 63

```
atgggctgga gttgcatcat tctcttcctc gtggcgaccg caacagggt gcactccgac      60
atccagatga cccagtcccc gagttccctg tctgcttccg tgggagatcg cgtgactatc    120
acctgccggg cttcccaggg catctcttcc tggctggcgt ggtaccagca gaaaccagaa    180
aaggctccta agtccctgat ctacgcagct tcgtccctcc aatccggcgt ccctctcgc    240
ttctccggct ccggatccgg caccgacttc acgctgacaa tctcgagttt gcagcccgag    300
gacttcgcca cctactactg ccagcagtac aactcctacc cttacacctt cggccagggc    360
acaaagctcg aaatcaagtc gggggggggc gggtcgcagg tccagctggt gcagtccggc    420
gccgaagtca agaagcccgg agcaagtgtg aaagtgtcgt gcaaggcaag tgggtatacc    480
ttcacctcat acgacgtaca ctgggtgcgc caggcgcccg tcagcgcct tgagtggatg    540
ggctggctcc acgccgacac cggcattacc aagttctctc agaagttcca gggaagagtg    600
accataacac gcgacaccag tgcttccaca gcttacatgg aactttcgag tctgagatcc    660
gaggacacag ccgtgtatta ctgtgcccgt gagcgcatcc agctgtggtt cgactactgg    720
gggcagggca ccctcgtgac ggtgtcgtcg gggggcgggg ggagtcaggt gcagctggtg    780
cagtccggag ccgaggtaaa gaagccaggc gcttccgtca aggtgtcatg caaggcctca    840
ggctacacct tcacaagcta ttacatccac tgggtgcgcc aagctcccgg tcagggcttg    900
gagtggatcg ggtgcattta cccagggaac gtcaacacaa actacaacga agttcaag    960
gatcgggcaa ccctgaccgt ggacacatcc atctctaccg cctacatgga gctgtcacgc   1020
ctgcgctctg atgacaccgc agtgtacttc tgtaccagga gtcactacgg cctggactgg   1080
aactttgatg tctggggcca gggaaccacc gtgacggtgt ccagtgtgga gggcggtagt   1140
ggcggctctg gtgggtccgg aggctcaggc ggcgtgatgg atgacattca gatgacccag   1200
agtccctcct ccctctccgc ttccgtcgga gaccgcgtga ccatcacttg tcacgcctca   1260
cagaatatct acgtgtggct gaactggtac caacagaagc ccggcaaggc cccaagctg   1320
```

```
cttatctata aagcgtccaa cctccacacg ggagtcccctt cccgcttctc cggatccggc      1380
agtgggacgg acttcacact cacaatctcg tcgctgcagc cagaggactt tgcgacgtac      1440
tactgccagc agggccagac ctacccatat actttcggcg gcgggaccaa ggtggagatt      1500
aag                                                                    1503

<210> SEQ ID NO 64
<211> LENGTH: 501
<212> TYPE: PRT
<213> ORGANISM: Artificial Sequence
<220> FEATURE:
<223> OTHER INFORMATION: 10A5 1412 aPDL1 aCd28 bispecific Ab

<400> SEQUENCE: 64

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Ser Trp Leu Ala Trp Tyr Gln Gln Lys Pro Glu Lys Ala Pro Lys
    50                  55                  60

Ser Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Asn Ser
            100                 105                 110

Tyr Pro Tyr Thr Phe Gly Gln Gly Thr Lys Leu Glu Ile Lys Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Asp Val His Trp Val Arg Gln Ala Pro Gly Gln Arg
                165                 170                 175

Leu Glu Trp Met Gly Trp Leu His Ala Asp Thr Gly Ile Thr Lys Phe
            180                 185                 190

Ser Gln Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Glu Arg Ile Gln Leu Trp Phe Asp Tyr Trp
225                 230                 235                 240

Gly Gln Gly Thr Leu Val Thr Val Ser Ser Gly Gly Gly Gly Ser Gln
                245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Ser Tyr Tyr
        275                 280                 285

Ile His Trp Val Arg Gln Ala Pro Gly Gln Gly Leu Glu Trp Ile Gly
    290                 295                 300

Cys Ile Tyr Pro Gly Asn Val Asn Thr Asn Tyr Asn Glu Lys Phe Lys
305                 310                 315                 320

Asp Arg Ala Thr Leu Thr Val Asp Thr Ser Ile Ser Thr Ala Tyr Met
```

```
                325                 330                 335
Glu Leu Ser Arg Leu Arg Ser Asp Asp Thr Ala Val Tyr Phe Cys Thr
        340                 345                 350

Arg Ser His Tyr Gly Leu Asp Trp Asn Phe Asp Val Trp Gly Gln Gly
        355                 360                 365

Thr Thr Val Thr Val Ser Ser Val Glu Gly Gly Ser Gly Gly Ser Gly
        370                 375                 380

Gly Ser Gly Gly Ser Gly Val Met Asp Asp Ile Gln Met Thr Gln
385                 390                 395                 400

Ser Pro Ser Ser Leu Ser Ala Ser Val Gly Asp Arg Val Thr Ile Thr
                405                 410                 415

Cys His Ala Ser Gln Asn Ile Tyr Val Trp Leu Asn Trp Tyr Gln Gln
                420                 425                 430

Lys Pro Gly Lys Ala Pro Lys Leu Leu Ile Tyr Lys Ala Ser Asn Leu
            435                 440                 445

His Thr Gly Val Pro Ser Arg Phe Ser Gly Ser Gly Ser Gly Thr Asp
            450                 455                 460

Phe Thr Leu Thr Ile Ser Ser Leu Gln Pro Glu Asp Phe Ala Thr Tyr
465                 470                 475                 480

Tyr Cys Gln Gln Gly Gln Thr Tyr Pro Tyr Thr Phe Gly Gly Gly Thr
                485                 490                 495

Lys Val Glu Ile Lys
            500

<210> SEQ ID NO 65
<211> LENGTH: 744
<212> TYPE: DNA
<213> ORGANISM: Artificial Sequence
<220> FEATURE:
<223> OTHER INFORMATION: TGFB 1412 aTGFbRII aCd28 bispecific Ab

<400> SEQUENCE: 65
atgggttggt cctgcatcat cctgtttctc gtggccaccg ccaccggcgt gcactccgaa      60
attgtgttga cacagtctcc agccaccctg tctttgtctc aggggaaag agccaccctc     120 tcctgcaggg ccagtcagag tgttagaagt ttcttagcct ggtaccaaca gaaacctggc    180
caggctccca ggctcctcat ctatgatgca tccaacaggg ccactggcat cccagccagg    240
ttcagtggca gtgggtctgg gacagacttc actctcacca tcagcagcct agagcctgaa    300
gattttgcag tttattactg tcagcagcgt agcaactggc ctccgacgtt cggccaaggg    360
accaaggtgg aaatcaaaag tggaggggc ggttcacagc tacagctgca ggagtcgggc     420
ccaggactgg tgaagccttc ggagaccctg tccctcacct gcactgtctc tggtggctcc    480
atcagcagta gtagttactc ctggggctgg atccgccagc ccccagggaa gggcctggag    540
tggattggga gtttctatta cagtgggatc acctactaca gcccgtccct caagagtcga    600
attatcatat ccgaagacac gtccaagaac cagttctccc tgaagctgag ttctgtgacc    660
gccgcagaca cggctgtgta ttactgtgcg agcgggttta ctatgattcg gggagccctt    720
gactactggg gccagggaac cctg                                            744

<210> SEQ ID NO 66
<211> LENGTH: 248
<212> TYPE: PRT
<213> ORGANISM: Artificial Sequence
<220> FEATURE:
<223> OTHER INFORMATION: TGFB 1412 aTGFbRII aCd28 bispecific Ab
```

<400> SEQUENCE: 66

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Arg Ser Phe Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Ser Gly
        115                 120                 125

Gly Gly Gly Ser Gln Leu Gln Leu Gln Glu Ser Gly Pro Gly Leu Val
    130                 135                 140

Lys Pro Ser Glu Thr Leu Ser Leu Thr Cys Thr Val Ser Gly Gly Ser
145                 150                 155                 160

Ile Ser Ser Ser Ser Tyr Ser Trp Gly Trp Ile Arg Gln Pro Pro Gly
                165                 170                 175

Lys Gly Leu Glu Trp Ile Gly Ser Phe Tyr Tyr Ser Gly Ile Thr Tyr
            180                 185                 190

Tyr Ser Pro Ser Leu Lys Ser Arg Ile Ile Ile Ser Glu Asp Thr Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Ser Gly Phe Thr Met Ile Arg Gly Ala Leu
225                 230                 235                 240

Asp Tyr Trp Gly Gln Gly Thr Leu
                245

<210> SEQ ID NO 67
<211> LENGTH: 487
<212> TYPE: PRT
<213> ORGANISM: Artificial Sequence
<220> FEATURE:
<223> OTHER INFORMATION: PSMA 2F5BBZ CAR

<400> SEQUENCE: 67

Met Ala Leu Pro Val Thr Ala Leu Leu Leu Pro Leu Ala Leu Leu Leu
1               5                   10                  15

His Ala Ala Arg Pro Glu Val Gln Leu Val Gln Ser Gly Ala Glu Val
            20                  25                  30

Lys Lys Pro Gly Glu Ser Leu Lys Ile Ser Cys Lys Gly Ser Gly Tyr
        35                  40                  45

Ser Phe Thr Ser Asn Trp Ile Gly Trp Val Arg Gln Met Pro Gly Lys
    50                  55                  60

Gly Leu Glu Trp Met Gly Ile Ile Tyr Pro Gly Asp Ser Asp Thr Arg
65                  70                  75                  80

Tyr Ser Pro Ser Phe Gln Gly Gln Val Thr Ile Ser Ala Asp Lys Ser
                85                  90                  95

Ile Ser Thr Ala Tyr Leu Gln Trp Asn Ser Leu Lys Ala Ser Asp Thr

```
                    100                 105                 110
Ala Met Tyr Tyr Cys Ala Arg Gln Thr Gly Phe Leu Trp Ser Phe Asp
                115                 120                 125

Leu Trp Gly Arg Gly Thr Leu Val Thr Val Ser Ser Gly Gly Gly Gly
        130                 135                 140

Ser Gly Gly Gly Gly Ser Gly Gly Gly Ser Ala Ile Gln Leu Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Ile Ser Ser Ala Leu Ala Trp Tyr Gln
                180                 185                 190

Gln Lys Pro Gly Lys Ala Pro Lys Leu Leu Ile Tyr Asp Ala Ser Ser
                195                 200                 205

Leu Glu Ser Gly Val Pro Ser Arg Phe Ser Gly Ser Gly Ser Gly Thr
                210                 215                 220

Asp Phe Thr Leu Thr Ile Ser Ser Leu Gln Pro Glu Asp Phe Ala Thr
225                 230                 235                 240

Tyr Tyr Cys Gln Gln Phe Asn Ser Tyr Pro Leu Thr Phe Gly Gly Gly
                245                 250                 255

Thr Lys Val Glu Ile Lys Ile Lys Thr Thr Pro Ala Pro Arg Pro
                260                 265                 270

Pro Thr Pro Ala Pro Thr Ile Ala Ser Gln Pro Leu Ser Leu Arg Pro
                275                 280                 285

Glu Ala Cys Arg Pro Ala Ala Gly Gly Ala Val His Thr Arg Gly Leu
                290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
                370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
                450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 68
<211> LENGTH: 5
<212> TYPE: PRT
<213> ORGANISM: Artificial Sequence
```

```
<220> FEATURE:
<223> OTHER INFORMATION: hJ591 HCDR1

<400> SEQUENCE: 68

Glu Tyr Thr Ile His
1               5

<210> SEQ ID NO 69
<211> LENGTH: 17
<212> TYPE: PRT
<213> ORGANISM: Artificial Sequence
<220> FEATURE:
<223> OTHER INFORMATION: hJ591 HCDR2

<400> SEQUENCE: 69

Asn Ile Asn Pro Asn Asn Gly Gly Thr Thr Tyr Asn Gln Lys Phe Glu
1               5                   10                  15
Asp

<210> SEQ ID NO 70
<211> LENGTH: 6
<212> TYPE: PRT
<213> ORGANISM: Artificial Sequence
<220> FEATURE:
<223> OTHER INFORMATION: hJ591 HCDR3

<400> SEQUENCE: 70

Gly Trp Asn Phe Asp Tyr
1               5

<210> SEQ ID NO 71
<211> LENGTH: 11
<212> TYPE: PRT
<213> ORGANISM: Artificial Sequence
<220> FEATURE:
<223> OTHER INFORMATION: hJ591 LCDR1

<400> SEQUENCE: 71

Lys Ala Ser Gln Asp Val Gly Thr Ala Val Asp
1               5                   10

<210> SEQ ID NO 72
<211> LENGTH: 7
<212> TYPE: PRT
<213> ORGANISM: Artificial Sequence
<220> FEATURE:
<223> OTHER INFORMATION: hJ591 LCDR2

<400> SEQUENCE: 72

Trp Ala Ser Thr Arg His Thr
1               5

<210> SEQ ID NO 73
<211> LENGTH: 9
<212> TYPE: PRT
<213> ORGANISM: Artificial Sequence
<220> FEATURE:
<223> OTHER INFORMATION: hJ591 LCDR3

<400> SEQUENCE: 73

Gln Gln Tyr Asn Ser Tyr Pro Leu Thr
1               5

<210> SEQ ID NO 74
<211> LENGTH: 345
<212> TYPE: DNA
```

<213> ORGANISM: Artificial Sequence
<220> FEATURE:
<223> OTHER INFORMATION: hJ591 VH

<400> SEQUENCE: 74

```
gaggtccagc tggtgcagtc tggagctgag gtgaagaagc ctggggcctc agtgaaggtc      60
tcctgcaagg cttctggata cacattcact gaatacacca tccactgggt gaggcaggcc     120
cctggaaagg gccttgagtg gattggaaac attaatccta acaatggtgg tactacctac     180
aaccagaagt tcgaggacag agtcacaatc actgtagaca gtccaccag cacagcctac      240
atggagctca gcagcctgag atctgaggat actgcagtct attactgtgc agctggttgg     300
aactttgact actggggcca aggcaccacg gtcaccgtct cctca                    345
```

<210> SEQ ID NO 75
<211> LENGTH: 115
<212> TYPE: PRT
<213> ORGANISM: Artificial Sequence
<220> FEATURE:
<223> OTHER INFORMATION: hJ591 VH

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 76
<211> LENGTH: 321
<212> TYPE: DNA
<213> ORGANISM: Artificial Sequence
<220> FEATURE:
<223> OTHER INFORMATION: hJ591 VL

<400> SEQUENCE: 76

```
gacattcaga tgacccagtc tccagcacc ctgtccgcat cagtaggaga cagggtcacc        60
atcacttgca aggccagtca ggatgtgggt actgctgtag actggtatca acagaaacca     120
gggcaagctc ctaaactact gatttactgg gcatccaccc ggcacactgg agtccctgat     180
cgcttcagcg gcagtggatc tgggacagat ttcactctca ccatcagcag actgcagcct     240
gaagactttg cagtttatta ctgtcagcaa tataacagct atcctctcac gttcggccag     300
gggaccaagg tggatatcaa a                                                321
```

<210> SEQ ID NO 77
<211> LENGTH: 107
<212> TYPE: PRT
<213> ORGANISM: Artificial Sequence
<220> FEATURE:
<223> OTHER INFORMATION: hJ591 VL

<400> SEQUENCE: 77

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
            100                 105

<210> SEQ ID NO 78
<211> LENGTH: 237
<212> TYPE: PRT
<213> ORGANISM: Artificial Sequence
<220> FEATURE:
<223> OTHER INFORMATION: hJ591 scFv VLVH

<400> SEQUENCE: 78

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys Gly Gly Gly Gly Ser
            100                 105                 110

Gly Gly Gly Gly Ser Gly Gly Ser Glu Val Gln Leu Val Gln
        115                 120                 125

Ser Gly Ala Glu Val Lys Lys Pro Gly Ala Ser Val Lys Val Ser Cys
130                 135                 140

Lys Ala Ser Gly Tyr Thr Phe Thr Glu Tyr Thr Ile His Trp Val Arg
145                 150                 155                 160

Gln Ala Pro Gly Lys Gly Leu Glu Trp Ile Gly Asn Ile Asn Pro Asn
                165                 170                 175

Asn Gly Gly Thr Thr Tyr Asn Gln Lys Phe Glu Asp Arg Val Thr Ile
            180                 185                 190

Thr Val Asp Lys Ser Thr Ser Thr Ala Tyr Met Glu Leu Ser Ser Leu
        195                 200                 205

Arg Ser Glu Asp Thr Ala Val Tyr Tyr Cys Ala Ala Gly Trp Asn Phe
210                 215                 220

Asp Tyr Trp Gly Gln Gly Thr Thr Val Thr Val Ser Ser 225            230            235

<210> SEQ ID NO 79
<211> LENGTH: 2247
<212> TYPE: DNA
<213> ORGANISM: Artificial Sequence
<220> FEATURE:
<223> OTHER INFORMATION: 2B3hJ591.BBZ bispecific CAR

<400> SEQUENCE: 79

| | | | | | |
|---|---|---|---|---|---|
| atggccctgc | tgtgacagc | cctgctgctg | cctctggctc | tgctgctgca | cgccgccaga | 60 |
| cctggagcca | ccatggcgct | accggtgacc | gcactcctgc | tgccactcgc | cctcctgctc | 120 |
| cacgccgccc | gccccgatat | ccagctgacc | caatcaccgt | cgtccctgtc | tgcctccgtg | 180 |
| ggcgaccggg | tgacgatcac | ctgtagtgcc | tcgagcagtg | tacggttcat | ccactggtac | 240 |
| caacagaagc | ccggcaaggc | accaaagcgg | ctgatctacg | acaccagcaa | gctggcgtct | 300 |
| ggggtgccca | gcaggttctc | gggaagtggt | agtggcacag | acttcactct | caccatcagt | 360 |
| tcactccagc | cggaggactt | tgccacctac | tattgccagc | agtggtcctc | gtcccccttt | 420 |
| accttcggcc | agggaacaaa | ggtggaaatt | aagggttcga | cctccggggg | gggctccggt | 480 |
| gggggctccg | gcgggggggg | ctcatcggag | gttcagctgg | tggagagcgg | cggcggcctg | 540 |
| gtgcagcccg | gcggagtctc | gcggctgtcc | tgtgccgcca | gcggcttcaa | catcaaggac | 600 |
| tactacattc | actgggtgcg | gcaagcccca | ggcaagggtc | tggagtgggt | ggcttggatt | 660 |
| gaccctgaaa | acggcgacac | tgagttcgtg | ccaaaattcc | aggggcgggc | gaccatctcc | 720 |
| gccgacacct | ccaagaatac | ggcctacctg | cagatgaact | ccctgcgcgc | cgaagacaca | 780 |
| gcggtctact | actgcaagac | aggggttttc | tggggccagg | gcaccctcgt | gaccgtttcg | 840 |
| agtgccgccg | gcggaggtgg | tggatccgac | attcagatga | cccagtctcc | cagcaccctg | 900 |
| tccgcatcag | taggagacag | ggtcaccatc | acttgcaagg | ccagtcagga | tgtgggtact | 960 |
| gctgtagact | ggtatcaaca | gaaaccaggg | caagctccta | aactactgat | ttactgggca | 1020 |
| tccacccggc | acactggagt | ccctgatcgc | ttcagcggca | gtggatctgg | gacagatttc | 1080 |
| actctcacca | tcagcagact | gcagcctgaa | gactttgcag | tttattactg | tcagcaatat | 1140 |
| aacagctatc | ctctcacgtt | cggccagggg | accaaggtgg | atatcaaagg | aggcggagga | 1200 |
| tctggcggcg | gaggaagttc | tggcggaggc | agcgaggtcc | agctggtgca | gtctggagct | 1260 |
| gaggtgaaga | agcctggggc | ctcagtgaag | gtctcctgca | aggcttctgg | atacacattc | 1320 |
| actgaataca | ccatccactg | ggtgaggcag | gcccctggaa | agggccttga | gtggattgga | 1380 |
| aacattaatc | ctaacaatgg | tggtactacc | tacaaccaga | agttcgagga | cagagtcaca | 1440 |
| atcactgtag | acaagtccac | cagcacagcc | tacatggagc | tcagcagcct | gagatctgag | 1500 |
| gatactgcag | tctattactg | tgcagctggt | tggaactttg | actactgggg | ccaaggcacc | 1560 |
| acggtcaccg | tctcctcaaa | ccacgacgcc | agcgccgcga | ccaccaacac | cggcgcccac | 1620 |
| catgcgtcgc | agcccctgtc | cctgcgccca | gaggcgtgcc | ggccagcggc | gggggcgca | 1680 |
| gtgcacacga | gggggctgga | cttcgcctgt | gatatctaca | tctgggcgcc | cttggccggg | 1740 |
| acttgtgggg | tccttctcct | gtcactggtt | atcacccttt | actgcaaacg | gggcagaaag | 1800 |
| aaactcctgt | atatattcaa | acaaccattt | atgagaccag | tacaaactac | tcaagaggaa | 1860 |
| gacggctgta | gctgccgatt | tccagaagaa | gaagaaggag | gatgtgaact | gagagtgaag | 1920 |
| ttcagcagga | gcgcagacgc | ccccgcgtac | aagcagggcc | agaaccagct | ctataacgag | 1980 |
| ctcaatctag | gacgaagaga | ggagtacgac | gttttggaca | agagacgtgg | ccgggaccct | 2040 |

```
gagatggggg gaaagccgag aaggaagaac cctcaggaag gcctgtacaa cgaactgcag    2100
aaagataaga tggcggaggc ctacagtgag attgggatga aagcgagcg ccggaggggc    2160 aaggggcacg acggccttta ccagggtctc agtacagcca ccaaggacac ctacgacgcc    2220
cttcacatgc aggccctgcc ccctcgc                                        2247

<210> SEQ ID NO 80
<211> LENGTH: 749
<212> TYPE: PRT
<213> ORGANISM: Artificial Sequence
<220> FEATURE:
<223> OTHER INFORMATION: 2B3hJ591.BBZ bispecific CAR

<400> SEQUENCE: 80

Met Ala Leu Pro Val Thr Ala Leu Leu Leu Pro Leu Ala Leu Leu Leu
1               5                   10                  15

His Ala Ala Arg Pro Gly Ala Thr Met Ala Leu Pro Val Thr Ala Leu
                20                  25                  30

Leu Leu Pro Leu Ala Leu Leu Leu His Ala Ala Arg Pro Asp Ile Gln
            35                  40                  45

Leu Thr Gln Ser Pro Ser Ser Leu Ser Ala Ser Val Gly Asp Arg Val
        50                  55                  60

Thr Ile Thr Cys Ser Ala Ser Ser Ser Val Arg Phe Ile His Trp Tyr
65                  70                  75                  80

Gln Gln Lys Pro Gly Lys Ala Pro Lys Arg Leu Ile Tyr Asp Thr Ser
                85                  90                  95

Lys Leu Ala Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Trp Ser Ser Ser Pro Phe Thr Phe Gly Gln
    130                 135                 140

Gly Thr Lys Val Glu Ile Lys Gly Ser Thr Ser Gly Gly Gly Ser Gly
145                 150                 155                 160

Gly Gly Ser Gly Gly Gly Ser Ser Glu Val Gln Leu Val Glu Ser
                165                 170                 175

Gly Gly Gly Leu Val Gln Pro Gly Gly Ser Leu Arg Leu Ser Cys Ala
            180                 185                 190

Ala Ser Gly Phe Asn Ile Lys Asp Tyr Tyr Ile His Trp Val Arg Gln
        195                 200                 205

Ala Pro Gly Lys Gly Leu Glu Trp Val Ala Trp Ile Asp Pro Glu Asn
    210                 215                 220

Gly Asp Thr Glu Phe Val Pro Lys Phe Gln Gly Arg Ala Thr Ile Ser
225                 230                 235                 240

Ala Asp Thr Ser Lys Asn Thr Ala Tyr Leu Gln Met Asn Ser Leu Arg
                245                 250                 255

Ala Glu Asp Thr Ala Val Tyr Tyr Cys Lys Thr Gly Gly Phe Trp Gly
            260                 265                 270

Gln Gly Thr Leu Val Thr Val Ser Ser Ala Ala Gly Gly Gly Gly
        275                 280                 285

Ser Asp Ile Gln Met Thr Gln Ser Pro Ser Thr Leu Ser Ala Ser Val
    290                 295                 300

Gly Asp Arg Val Thr Ile Thr Cys Lys Ala Ser Gln Asp Val Gly Thr
305                 310                 315                 320
```

```
Ala Val Asp Trp Tyr Gln Gln Lys Pro Gly Gln Ala Pro Lys Leu Leu
            325                 330                 335

Ile Tyr Trp Ala Ser Thr Arg His Thr Gly Val Pro Ala Arg Phe Ser
            340                 345                 350

Gly Ser Gly Ser Gly Thr Asp Phe Thr Leu Thr Ile Ser Arg Leu Gln
            355                 360                 365

Pro Glu Asp Phe Ala Val Tyr Tyr Cys Gln Gln Tyr Asn Ser Tyr Pro
        370                 375                 380

Leu Thr Phe Gly Gln Gly Thr Lys Val Asp Ile Lys Gly Gly Gly Gly
385                 390                 395                 400

Ser Gly Gly Gly Gly Ser Ser Gly Gly Gly Ser Glu Val Gln Leu Val
            405                 410                 415

Gln Ser Gly Ala Glu Val Lys Lys Pro Gly Ala Ser Val Lys Val Ser
            420                 425                 430

Cys Lys Ala Ser Gly Tyr Thr Phe Thr Glu Tyr Thr Ile His Trp Val
        435                 440                 445

Arg Gln Ala Pro Gly Lys Gly Leu Glu Trp Ile Gly Asn Ile Asn Pro
        450                 455                 460

Asn Asn Gly Gly Thr Thr Tyr Asn Gln Lys Phe Glu Asp Arg Val Thr
465                 470                 475                 480

Ile Thr Val Asp Lys Ser Thr Ser Thr Ala Tyr Met Glu Leu Ser Ser
            485                 490                 495

Leu Arg Ser Glu Asp Thr Ala Val Tyr Tyr Cys Ala Ala Gly Trp Asn
            500                 505                 510

Phe Asp Tyr Trp Gly Gln Gly Thr Thr Val Thr Val Ser Ser Asn His
        515                 520                 525

Asp Ala Ser Ala Ala Thr Thr Asn Thr Gly Ala His His Ala Ser Gln
        530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
            565                 570                 575

Pro Leu Ala Gly Thr Cys Gly Val Leu Leu Leu Ser Leu Val Ile Thr
            580                 585                 590

Leu Tyr Cys Lys Arg Gly Arg Lys Lys Leu Leu Tyr Ile Phe Lys Gln
        595                 600                 605

Pro Phe Met Arg Pro Val Gln Thr Thr Gln Glu Glu Asp Gly Cys Ser
        610                 615                 620

Cys Arg Phe Pro Glu Glu Glu Glu Gly Gly Cys Glu Leu Arg Val Lys
625                 630                 635                 640

Phe Ser Arg Ser Ala Asp Ala Pro Ala Tyr Lys Gln Gly Gln Asn Gln
            645                 650                 655

Leu Tyr Asn Glu Leu Asn Leu Gly Arg Arg Glu Glu Tyr Asp Val Leu
            660                 665                 670

Asp Lys Arg Arg Gly Arg Asp Pro Glu Met Gly Gly Lys Pro Arg Arg
        675                 680                 685

Lys Asn Pro Gln Glu Gly Leu Tyr Asn Glu Leu Gln Lys Asp Lys Met
        690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
            725                 730                 735

Thr Tyr Asp Ala Leu His Met Gln Ala Leu Pro Pro Arg
```

-continued

<210> SEQ ID NO 81
<211> LENGTH: 749
<212> TYPE: PRT
<213> ORGANISM: Artificial Sequence
<220> FEATURE:
<223> OTHER INFORMATION: 2B3hJ591.BBZ bispecific CAR

<400> SEQUENCE: 81

Met Ala Leu Pro Val Thr Ala Leu Leu Leu Pro Leu Ala Leu Leu Leu
1               5                   10                  15

His Ala Ala Arg Pro Gly Ala Thr Met Ala Leu Pro Val Thr Ala Leu
            20                  25                  30

Leu Leu Pro Leu Ala Leu Leu Leu His Ala Ala Arg Pro Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Ser Ser Val Arg Phe Ile His Trp Tyr
65                  70                  75                  80

Gln Gln Lys Pro Gly Lys Ala Pro Lys Arg Leu Ile Tyr Asp Thr Ser
                85                  90                  95

Lys Leu Ala Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Trp Ser Ser Ser Pro Phe Thr Phe Gly Gln
    130                 135                 140

Gly Thr Lys Val Glu Ile Lys Gly Ser Thr Ser Gly Gly Gly Ser Gly
145                 150                 155                 160

Gly Gly Ser Gly Gly Gly Ser Ser Glu Val Gln Leu Val Glu Ser
                165                 170                 175

Gly Gly Gly Leu Val Gln Pro Gly Gly Ser Leu Arg Leu Ser Cys Ala
            180                 185                 190

Ala Ser Gly Phe Asn Ile Lys Asp Tyr Tyr Ile His Trp Val Arg Gln
        195                 200                 205

Ala Pro Gly Lys Gly Leu Glu Trp Val Ala Trp Ile Asp Pro Glu Asn
    210                 215                 220

Gly Asp Thr Glu Phe Val Pro Lys Phe Gln Gly Arg Ala Thr Ile Ser
225                 230                 235                 240

Ala Asp Thr Ser Lys Asn Thr Ala Tyr Leu Gln Met Asn Ser Leu Arg
                245                 250                 255

Ala Glu Asp Thr Ala Val Tyr Tyr Cys Lys Thr Gly Gly Phe Trp Gly
            260                 265                 270

Gln Gly Thr Leu Val Thr Val Ser Ser Ala Ala Gly Gly Gly Gly
        275                 280                 285

Ser Asp Ile Gln Met Thr Gln Ser Pro Ser Thr Leu Ser Ala Ser Val
    290                 295                 300

Gly Asp Arg Val Thr Ile Thr Cys Lys Ala Ser Gln Asp Val Gly Thr
305                 310                 315                 320

Ala Val Asp Trp Tyr Gln Gln Lys Pro Gly Gln Ala Pro Lys Leu Leu
                325                 330                 335

Ile Tyr Trp Ala Ser Thr Arg His Thr Gly Val Pro Asp Arg Phe Ser
            340                 345                 350

Gly Ser Gly Ser Gly Thr Asp Phe Thr Leu Thr Ile Ser Arg Leu Gln

```
                355                 360                 365
Pro Glu Asp Phe Ala Val Tyr Tyr Cys Gln Gln Tyr Asn Ser Tyr Pro
370                 375                 380

Leu Thr Phe Gly Gln Gly Thr Lys Val Asp Ile Lys Gly Gly Gly Gly
385                 390                 395                 400

Ser Gly Gly Gly Gly Ser Ser Gly Gly Gly Ser Glu Val Gln Leu Val
            405                 410                 415

Gln Ser Gly Ala Glu Val Lys Lys Pro Gly Ala Ser Val Lys Val Ser
        420                 425                 430

Cys Lys Ala Ser Gly Tyr Thr Phe Thr Glu Tyr Thr Ile His Trp Val
    435                 440                 445

Arg Gln Ala Pro Gly Lys Gly Leu Glu Trp Ile Gly Asn Ile Asn Pro
450                 455                 460

Asn Asn Gly Gly Thr Thr Tyr Asn Gln Lys Phe Glu Asp Arg Val Thr
465                 470                 475                 480

Ile Thr Val Asp Lys Ser Thr Ser Thr Ala Tyr Met Glu Leu Ser Ser
            485                 490                 495

Leu Arg Ser Glu Asp Thr Ala Val Tyr Tyr Cys Ala Ala Gly Trp Asn
        500                 505                 510

Phe Asp Tyr Trp Gly Gln Gly Thr Thr Val Thr Val Ser Ser His Thr
    515                 520                 525

Thr Pro Ala Pro Arg Pro Pro Thr Pro Ala Pro Thr Ile Ala Ser Gln
530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
            565                 570                 575

Pro Leu Ala Gly Thr Cys Gly Val Leu Leu Leu Ser Leu Val Ile Thr
        580                 585                 590

Leu Tyr Cys Lys Arg Gly Arg Lys Lys Leu Leu Tyr Ile Phe Lys Gln
    595                 600                 605

Pro Phe Met Arg Pro Val Gln Thr Thr Gln Glu Glu Asp Gly Cys Ser
610                 615                 620

Cys Arg Phe Pro Glu Glu Glu Glu Gly Gly Cys Glu Leu Arg Val Lys
625                 630                 635                 640

Phe Ser Arg Ser Ala Asp Ala Pro Ala Tyr Lys Gln Gly Gln Asn Gln
            645                 650                 655

Leu Tyr Asn Glu Leu Asn Leu Gly Arg Arg Glu Glu Tyr Asp Val Leu
        660                 665                 670

Asp Lys Arg Arg Gly Arg Asp Pro Glu Met Gly Gly Lys Pro Arg Arg
    675                 680                 685

Lys Asn Pro Gln Glu Gly Leu Tyr Asn Glu Leu Gln Lys Asp Lys Met
690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
            725                 730                 735

Thr Tyr Asp Ala Leu His Met Gln Ala Leu Pro Pro Arg
        740                 745

<210> SEQ ID NO 82
<211> LENGTH: 749
<212> TYPE: PRT
<213> ORGANISM: Artificial Sequence
```

<220> FEATURE:
<223> OTHER INFORMATION: 2B3hJ591.BBZ bispecific CAR

<400> SEQUENCE: 82

```
Met Ala Leu Pro Val Thr Ala Leu Leu Leu Pro Leu Ala Leu Leu
1               5                   10                  15

His Ala Ala Arg Pro Gly Ala Thr Met Ala Leu Pro Val Thr Ala Leu
            20                  25                  30

Leu Leu Pro Leu Ala Leu Leu Leu His Ala Ala Arg Pro Asp Ile Gln
            35                  40                  45

Leu Thr Gln Ser Pro Ser Ser Leu Ser Ala Ser Val Gly Asp Arg Val
        50                  55                  60

Thr Ile Thr Cys Ser Ala Ser Ser Ser Val Arg Phe Ile His Trp Tyr
65                  70                  75                  80

Gln Gln Lys Pro Gly Lys Ala Pro Lys Arg Leu Ile Tyr Asp Thr Ser
                85                  90                  95

Lys Leu Ala Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Trp Ser Ser Ser Pro Phe Thr Phe Gly Gln
130                 135                 140

Gly Thr Lys Val Glu Ile Lys Gly Ser Thr Ser Gly Gly Gly Ser Gly
145                 150                 155                 160

Gly Gly Ser Gly Gly Gly Ser Ser Glu Val Gln Leu Val Glu Ser
                165                 170                 175

Gly Gly Gly Leu Val Gln Pro Gly Gly Ser Leu Arg Leu Ser Cys Ala
            180                 185                 190

Ala Ser Gly Phe Asn Ile Lys Asp Tyr Tyr Ile His Trp Val Arg Gln
            195                 200                 205

Ala Pro Gly Lys Gly Leu Glu Trp Val Ala Trp Ile Asp Pro Glu Asn
        210                 215                 220

Gly Asp Thr Glu Phe Val Pro Lys Phe Gln Gly Arg Ala Thr Ile Ser
225                 230                 235                 240

Ala Asp Thr Ser Lys Asn Thr Ala Tyr Leu Gln Met Asn Ser Leu Arg
                245                 250                 255

Ala Glu Asp Thr Ala Val Tyr Tyr Cys Lys Thr Gly Gly Phe Trp Gly
            260                 265                 270

Gln Gly Thr Leu Val Thr Val Ser Ser Ala Ala Gly Gly Gly Gly
        275                 280                 285

Ser Asp Ile Gln Met Thr Gln Ser Pro Ser Thr Leu Ser Ala Ser Val
        290                 295                 300

Gly Asp Arg Val Thr Ile Thr Cys Lys Ala Ser Gln Asp Val Gly Thr
305                 310                 315                 320

Ala Val Asp Trp Tyr Gln Gln Lys Pro Gly Gln Ala Pro Lys Leu Leu
                325                 330                 335

Ile Tyr Trp Ala Ser Thr Arg His Thr Gly Val Pro Asp Arg Phe Ser
            340                 345                 350

Gly Ser Gly Ser Gly Thr Asp Phe Thr Leu Thr Ile Ser Arg Leu Gln
        355                 360                 365

Pro Glu Asp Phe Ala Val Tyr Tyr Cys Gln Gln Tyr Asn Ser Tyr Pro
        370                 375                 380

Leu Thr Phe Gly Gln Gly Thr Lys Val Asp Ile Lys Gly Gly Gly Gly
385                 390                 395                 400
```

| | | | | | | | | | | | |
|---|---|---|---|---|---|---|---|---|---|---|---|
|Ser|Gly|Gly|Gly|Ser|Ser|Gly|Gly|Ser|Glu|Val|Gln|Leu|Val|
| | | |405| | | |410| | | |415|

Gln Ser Gly Ala Glu Val Lys Lys Pro Gly Ala Ser Val Lys Val Ser
                420                 425                 430

Cys Lys Ala Ser Gly Tyr Thr Phe Thr Glu Tyr Thr Ile His Trp Val
            435                 440                 445

Arg Gln Ala Pro Gly Lys Gly Leu Glu Trp Ile Gly Asn Ile Asn Pro
450                 455                 460

Asn Asn Gly Gly Thr Thr Tyr Asn Gln Lys Phe Glu Asp Arg Val Thr
465                 470                 475                 480

Ile Thr Val Asp Lys Ser Thr Ser Thr Ala Tyr Met Glu Leu Ser Ser
                485                 490                 495

Leu Arg Ser Glu Asp Thr Ala Val Tyr Tyr Cys Ala Ala Gly Trp Asn
            500                 505                 510

Phe Asp Tyr Trp Gly Gln Gly Thr Thr Val Thr Val Ser Ser Thr Thr
        515                 520                 525

Thr Pro Ala Pro Arg Pro Pro Thr Pro Ala Pro Thr Ile Ala Ser Gln
    530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
                565                 570                 575

Pro Leu Ala Gly Thr Cys Gly Val Leu Leu Leu Ser Leu Val Ile Thr
            580                 585                 590

Leu Tyr Cys Lys Arg Gly Arg Lys Lys Leu Leu Tyr Ile Phe Lys Gln
        595                 600                 605

Pro Phe Met Arg Pro Val Gln Thr Thr Gln Glu Glu Asp Gly Cys Ser
    610                 615                 620

Cys Arg Phe Pro Glu Glu Glu Glu Gly Gly Cys Glu Leu Arg Val Lys
625                 630                 635                 640

Phe Ser Arg Ser Ala Asp Ala Pro Ala Tyr Lys Gln Gly Gln Asn Gln
                645                 650                 655

Leu Tyr Asn Glu Leu Asn Leu Gly Arg Arg Glu Glu Tyr Asp Val Leu
            660                 665                 670

Asp Lys Arg Arg Gly Arg Asp Pro Glu Met Gly Gly Lys Pro Arg Arg
        675                 680                 685

Lys Asn Pro Gln Glu Gly Leu Tyr Asn Glu Leu Gln Lys Asp Lys Met
    690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
                725                 730                 735

Thr Tyr Asp Ala Leu His Met Gln Ala Leu Pro Pro Arg
            740                 745

<210> SEQ ID NO 83
<211> LENGTH: 711
<212> TYPE: DNA
<213> ORGANISM: Artificial Sequence
<220> FEATURE:
<223> OTHER INFORMATION: hJ591 scFv VLVH

<400> SEQUENCE: 83
gacattcaga tgacccagtc tcccagcacc ctgtccgcat cagtaggaga cagggtcacc        60

```
atcacttgca aggccagtca ggatgtgggt actgctgtag actggtatca acagaaacca      120
gggcaagctc ctaaactact gatttactgg gcatccaccc ggcacactgg agtccctgat      180
cgcttcagcg gcagtggatc tgggacagat ttcactctca ccatcagcag actgcagcct      240
gaagactttg cagtttatta ctgtcagcaa tataacagct atcctctcac gttcggccag      300
gggaccaagg tggatatcaa aggaggcgga ggatctggcg gcggaggaag ttctggcgga      360
ggcagcgagt ccagctggt gcagtctgga gctgaggtga agaagcctgg ggcctcagtg       420
aaggtctcct gcaaggcttc tggatacaca ttcactgaat acaccatcca ctgggtgagg      480
caggcccctg gaaagggcct tgagtggatt ggaaacatta atcctaacaa tggtggtact      540
acctacaacc agaagttcga ggacagagtc acaatcactg tagacaagtc caccagcaca      600
gcctacatgg agctcagcag cctgagatct gaggatactg cagtctatta ctgtgcagct      660
ggttggaact ttgactactg gggccaaggc accacggtca ccgtctcctc a               711
```

<210> SEQ ID NO 84
<211> LENGTH: 222
<212> TYPE: PRT
<213> ORGANISM: Artificial Sequence
<220> FEATURE:
<223> OTHER INFORMATION: hJ591 scFv VLVH no linker

<400> SEQUENCE: 84

```
Asp Ile Gln Met Thr Gln Ser Pro Ser Thr Leu Ser Ala Ser Val Gly
  1               5                  10                  15

Asp Arg Val Thr Ile Thr Cys Lys Ala Ser Gln Asp Val Gly Thr Ala
             20                  25                  30

Val Asp Trp Tyr Gln Gln Lys Pro Gly Gln Ala Pro Lys Leu Leu Ile
         35                  40                  45

Tyr Trp Ala Ser Thr Arg His Thr Gly Val Pro Asp Arg Phe Ser Gly
     50                  55                  60

Ser Gly Ser Gly Thr Asp Phe Thr Leu Thr Ile Ser Arg Leu Gln Pro
 65                  70                  75                  80

Glu Asp Phe Ala Val Tyr Tyr Cys Gln Gln Tyr Asn Ser Tyr Pro Leu
                 85                  90                  95

Thr Phe Gly Gln Gly Thr Lys Val Asp Ile Lys Glu Val Gln Leu Val
            100                 105                 110

Gln Ser Gly Ala Glu Val Lys Lys Pro Gly Ala Ser Val Lys Val Ser
        115                 120                 125

Cys Lys Ala Ser Gly Tyr Thr Phe Thr Glu Tyr Thr Ile His Trp Val
    130                 135                 140

Arg Gln Ala Pro Gly Lys Gly Leu Glu Trp Ile Gly Asn Ile Asn Pro
145                 150                 155                 160

Asn Asn Gly Gly Thr Thr Tyr Asn Gln Lys Phe Glu Asp Arg Val Thr
                165                 170                 175

Ile Thr Val Asp Lys Ser Thr Ser Thr Ala Tyr Met Glu Leu Ser Ser
            180                 185                 190

Leu Arg Ser Glu Asp Thr Ala Val Tyr Tyr Cys Ala Ala Gly Trp Asn
        195                 200                 205

Phe Asp Tyr Trp Gly Gln Gly Thr Thr Val Thr Val Ser Ser
    210                 215                 220
```

<210> SEQ ID NO 85
<211> LENGTH: 237
<212> TYPE: PRT
<213> ORGANISM: Artificial Sequence
<220> FEATURE:
<223> OTHER INFORMATION: hJ591 scFv VHVL

<400> SEQUENCE: 85

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser Gly Gly Gly Gly Ser Gly Gly Gly Gly Ser Ser Gly Gly
        115                 120                 125

Gly Ser Asp Ile Gln Met Thr Gln Ser Pro Ser Thr Leu Ser Ala Ser
    130                 135                 140

Val Gly Asp Arg Val Thr Ile Thr Cys Lys Ala Ser Gln Asp Val Gly
145                 150                 155                 160

Thr Ala Val Asp Trp Tyr Gln Gln Lys Pro Gly Gln Ala Pro Lys Leu
                165                 170                 175

Leu Ile Tyr Trp Ala Ser Thr Arg His Thr Gly Val Pro Asp Arg Phe
            180                 185                 190

Ser Gly Ser Gly Ser Gly Thr Asp Phe Thr Leu Thr Ile Ser Arg Leu
        195                 200                 205

Gln Pro Glu Asp Phe Ala Val Tyr Tyr Cys Gln Gln Tyr Asn Ser Tyr
    210                 215                 220

Pro Leu Thr Phe Gly Gln Gly Thr Lys Val Asp Ile Lys
225                 230                 235

<210> SEQ ID NO 86
<211> LENGTH: 711
<212> TYPE: DNA
<213> ORGANISM: Artificial Sequence
<220> FEATURE:
<223> OTHER INFORMATION: hJ591 scFv VHVL

<400> SEQUENCE: 86

```
gaggtccagc tggtgcagtc tggagctgag gtgaagaagc ctggggcctc agtgaaggtc      60
tcctgcaagg cttctggata cacattcact gaatacacca tccactgggt gaggcaggcc     120
cctggaaagg gccttgagtg gattggaaac attaatccta caatggtgg tactacctac      180
aaccagaagt tcgaggacag agtcacaatc actgtagaca gtccaccag cacagcctac     240
atggagctca gcagcctgag atctgaggat actgcagtct attactgtgc agctggttgg     300
aactttgact actggggcca aggcaccacg gtcaccgtct cctcaggagg cggaggatct     360
ggcggcggag gaagttctgg cggaggcagc gacattcaga tgacccagtc tccagcacc     420
ctgtccgcat cagtaggaga cagggtcacc atcacttgca aggccagtca ggatgtgggt     480
actgctgtag actggtatca acagaaacca gggcaagctc ctaaactact gatttactgg     540
gcatccaccc ggcacactgg agtccctgat cgcttcagcg gcagtggatc tgggacagat     600
```

```
ttcactctca ccatcagcag actgcagcct gaagactttg cagtttatta ctgtcagcaa    660
tataacagct atcctctcac gttcggccag gggaccaagg tggatatcaa a             711
```

<210> SEQ ID NO 87
<211> LENGTH: 482
<212> TYPE: PRT
<213> ORGANISM: Artificial Sequence
<220> FEATURE:
<223> OTHER INFORMATION: hJ591VHVK.BBZ

<400> SEQUENCE: 87

```
Met Ala Leu Pro Val Thr Ala Leu Leu Leu Pro Leu Ala Leu Leu Leu
1               5                   10                  15

His Ala Ala Arg Pro Gly Glu Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Glu Tyr Thr Ile His Trp Val Arg Gln Ala Pro Gly
    50                  55                  60

Lys Gly Leu Glu Trp Ile Gly Asn Ile Asn Pro Asn Asn Gly Gly Thr
65                  70                  75                  80

Thr Tyr Asn Gln Lys Phe Glu Asp Arg Val Thr Ile Thr Val Asp Lys
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Ala Gly Trp Asn Phe Asp Tyr Trp Gly
        115                 120                 125

Gln Gly Thr Thr Val Thr Val Ser Ser Gly Gly Gly Ser Gly Gly
    130                 135                 140

Gly Gly Ser Ser Gly Gly Ser Asp Ile Gln Met Thr Gln Ser Pro
145                 150                 155                 160

Ser Thr Leu Ser Ala Ser Val Gly Asp Arg Val Thr Ile Thr Cys Lys
                165                 170                 175

Ala Ser Gln Asp Val Gly Thr Ala Val Asp Trp Tyr Gln Gln Lys Pro
            180                 185                 190

Gly Gln Ala Pro Lys Leu Leu Ile Tyr Trp Ala Ser Thr Arg His Thr
        195                 200                 205

Gly Val Pro Asp Arg Phe Ser Gly Ser Gly Ser Gly Thr Asp Phe Thr
    210                 215                 220

Leu Thr Ile Ser Arg Leu Gln Pro Glu Asp Phe Ala Val Tyr Tyr Cys
225                 230                 235                 240

Gln Gln Tyr Asn Ser Tyr Pro Leu Thr Phe Gly Gln Gly Thr Lys Val
                245                 250                 255

Asp Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
```

```
            340                 345                 350
Glu Asp Gly Cys Ser Cys Arg Phe Pro Glu Glu Glu Gly Gly Cys
            355                 360                 365
Glu Leu Arg Val Lys Phe Ser Arg Ser Ala Asp Ala Pro Ala Tyr Lys
            370                 375                 380
Gln Gly Gln Asn Gln Leu Tyr Asn Glu Leu Asn Leu Gly Arg Arg Glu
385                 390                 395                 400
Glu Tyr Asp Val Leu Asp Lys Arg Arg Gly Arg Asp Pro Glu Met Gly
                405                 410                 415
Gly Lys Pro Arg Arg Lys Asn Pro Gln Glu Gly Leu Tyr Asn Glu Leu
            420                 425                 430
Gln Lys Asp Lys Met Ala Glu Ala Tyr Ser Glu Ile Gly Met Lys Gly
            435                 440                 445
Glu Arg Arg Arg Gly Lys Gly His Asp Gly Leu Tyr Gln Gly Leu Ser
            450                 455                 460
Thr Ala Thr Lys Asp Thr Tyr Asp Ala Leu His Met Gln Ala Leu Pro
465                 470                 475                 480
Pro Arg
```

<210> SEQ ID NO 88
<211> LENGTH: 1446
<212> TYPE: DNA
<213> ORGANISM: Artificial Sequence
<220> FEATURE:
<223> OTHER INFORMATION: hJ591VHVK.BBZ

<400> SEQUENCE: 88

```
atggccctgc ctgtgacagc cctgctgctg cctctggctc tgctgctgca cgccgccaga      60
cctggagagg tccagctggt gcagtctgga gctgaggtga agaagcctgg ggcctcagtg     120
aaggtctcct gcaaggcttc tggatacaca ttcactgaat acaccatcca ctgggtgagg     180
caggcccctg gaaagggcct tgagtggatt ggaaacatta tcctaacaa tggtggtact     240
acctacaacc agaagttcga ggacagagtc acaatcactg tagacaagtc caccagcaca     300
gcctacatgg agctcagcag cctgagatct gaggatactg cagtctatta ctgtgcagct     360
ggttggaact ttgactactg gggccaaggc accacggtca ccgtctcctc aggaggcgga     420
ggatctggcg gcggaggaag ttctggcgga ggcagcgaca ttcagatgac ccagtctccc     480
agcaccctgt ccgcatcagt aggagacagg gtcaccatca cttgcaaggc cagtcaggat     540
gtgggtactg ctgtagactg gtatcaacag aaaccagggc aagctcctaa actactgatt     600
tactgggcat ccacccggca cactggagtc cctgatcgct tcagcggcag tggatctggg     660
acagatttca ctctcaccat cagcagactg cagcctgaag actttgcagt ttattactgt     720
cagcaatata cagctatcc tctcacgttc ggccagggga ccaaggtgga tatcaaaacc     780
acgacgccag cgccgcgacc accaacaccg gcgcccacca tcgcgtcgca gcccctgtcc     840
ctgcgcccag aggcgtgccg gccagcggcg ggggcgcag tgcacacgag ggggctggac     900
ttcgcctgtg atatctacat ctgggcgccc ttggccggga cttgtggggt ccttctcctg     960
tcactggtta tcacccttta ctgcaaacgg ggcagaaaga aactcctgta tatattcaaa    1020
caaccattta tgagaccagt acaaactact caagaggaag acggctgtag ctgccgattt    1080
ccagaagaag aagaaggagg atgtgaactg agagtgaagt tcagcaggag cgcagacgcc    1140
cccgcgtaca gcagggcca gaaccagctc tataacgagc tcaatctagg acgaagagag    1200
gagtacgacg ttttggacaa gagacgtggc cgggaccctg agatgggggg aaagccgaga    1260
```

```
aggaagaacc ctcaggaagg cctgtacaac gaactgcaga aagataagat ggcggaggcc    1320
tacagtgaga ttgggatgaa aggcgagcgc cggaggggca aggggcacga cggcctttac    1380
cagggtctca gtacagccac caaggacacc tacgacgccc ttcacatgca ggccctgccc    1440
cctcgc                                                                1446
```

```
<210> SEQ ID NO 89
<211> LENGTH: 482
<212> TYPE: PRT
<213> ORGANISM: Artificial Sequence
<220> FEATURE:
<223> OTHER INFORMATION: hJ591VKVH.BBZ

<400> SEQUENCE: 89
```

Met Ala Leu Pro Val Thr Ala Leu Leu Leu Pro Leu Ala Leu Leu Leu
1               5                   10                  15

His Ala Ala Arg Pro Gly Asp Ile Gln Met Thr Gln Ser Pro Ser Thr
            20                  25                  30

Leu Ser Ala Ser Val Gly Asp Arg Val Thr Ile Thr Cys Lys Ala Ser
        35                  40                  45

Gln Asp Val Gly Thr Ala Val Asp Trp Tyr Gln Gln Lys Pro Gly Gln
    50                  55                  60

Ala Pro Lys Leu Leu Ile Tyr Trp Ala Ser Thr Arg His Thr Gly Val
65                  70                  75                  80

Pro Asp Arg Phe Ser Gly Ser Gly Ser Gly Thr Asp Phe Thr Leu Thr
                85                  90                  95

Ile Ser Arg Leu Gln Pro Glu Asp Phe Ala Val Tyr Tyr Cys Gln Gln
            100                 105                 110

Tyr Asn Ser Tyr Pro Leu Thr Phe Gly Gln Gly Thr Lys Val Asp Ile
        115                 120                 125

Lys Gly Gly Gly Gly Ser Gly Gly Gly Gly Ser Ser Gly Gly Gly Ser
    130                 135                 140

Glu Val Gln Leu Val Gln Ser Gly Ala Glu Val Lys Lys Pro Gly Ala
145                 150                 155                 160

Ser Val Lys Val Ser Cys Lys Ala Ser Gly Tyr Thr Phe Thr Glu Tyr
                165                 170                 175

Thr Ile His Trp Val Arg Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
        195                 200                 205

Glu Asp Arg Val Thr Ile Thr Val Asp Lys Ser Thr Ser Thr Ala Tyr
    210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Thr Val Thr
                245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
            325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Lys
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 90
<211> LENGTH: 1446
<212> TYPE: DNA
<213> ORGANISM: Artificial Sequence
<220> FEATURE:
<223> OTHER INFORMATION: hJ591VKVH.BBZ

<400> SEQUENCE: 90

```
atggccctgc ctgtgacagc cctgctgctg cctctggctc tgctgctgca cgccgccaga      60
cctggagaca ttcagatgac ccagtctccc agcaccctgt ccgcatcagt aggagacagg     120
gtcaccatca cttgcaaggc cagtcaggat gtgggtactg ctgtagactg gtatcaacag     180
aaaccagggc aagctcctaa actactgatt tactgggcat ccacccggca cactggagtc     240
cctgatcgct tcagcggcag tggatctggg acagatttca ctctcaccat cagcagactg     300
cagcctgaag actttgcagt ttattactgt cagcaatata cagctatccc tctcacgttc     360
ggccagggga ccaaggtgga tatcaaagga ggcggaggat ctggcggcgg aggaagttct     420
ggcggaggca gcgaggtcca gctggtgcag tctggagctg aggtgaagaa gcctggggcc     480
tcagtgaagg tctcctgcaa ggcttctgga tacacattca ctgaatacac catccactgg     540
gtgaggcagg cccctggaaa gggccttgag tggattggaa acattaatcc taacaatggt     600
ggtactacct acaaccagaa gttcgaggac agagtcacaa tcactgtaga caagtccacc     660
agcacagcct acatggagct cagcagcctg agatctgagg atactgcagt ctattactgt     720
gcagctggtt ggaactttga ctactggggc caaggcacca cggtcaccgt ctcctcaacc     780
acgacgccag cgccgcgacc accaacaccg gcgcccacca tcgcgtcgca gcccctgtcc     840
ctgcgcccag aggcgtgccg gccagcggcg ggggcgcag tgcacacgag ggggctggac     900
ttcgcctgtg atatctacat ctgggcgccc ttggccggga cttgtggggt ccttctcctg     960
tcactggtta tcaccttta ctgcaaacgg ggcagaaaga aactcctgta tatattcaaa    1020
caaccattta tgagaccagt acaaactact caagaggaag acggctgtag ctgccgattt    1080
ccagaagaag aagaaggagg atgtgaactg agagtgaagt tcagcaggag cgcagacgcc    1140
```

-continued

```
cccgcgtaca agcagggcca gaaccagctc tataacgagc tcaatctagg acgaagagag      1200
gagtacgacg tttggacaa gagacgtggc cgggaccctg agatggggg aaagccgaga        1260 aggaagaacc ctcaggaagg cctgtacaac gaactgcaga agataagat ggcggaggcc       1320 tacagtgaga ttgggatgaa aggcgagcgc cggaggggca aggggcacga cggcctttac     1380
cagggtctca gtacagccac caaggacacc tacgacgccc ttcacatgca ggccctgccc     1440
cctcgc                                                                 1446
```

<210> SEQ ID NO 91
<211> LENGTH: 517
<212> TYPE: PRT
<213> ORGANISM: Artificial Sequence
<220> FEATURE:
<223> OTHER INFORMATION: hJ591VKVH.ICOSBBZ

<400> SEQUENCE: 91

```
Met Ala Leu Pro Val Thr Ala Leu Leu Leu Pro Leu Ala Leu Leu Leu
1               5                   10                  15

His Ala Ala Arg Pro Gly Asp Ile Gln Met Thr Gln Ser Pro Ser Thr
            20                  25                  30

Leu Ser Ala Ser Val Gly Asp Arg Val Thr Ile Thr Cys Lys Ala Ser
        35                  40                  45

Gln Asp Val Gly Thr Ala Val Asp Trp Tyr Gln Gln Lys Pro Gly Gln
    50                  55                  60

Ala Pro Lys Leu Leu Ile Tyr Trp Ala Ser Thr Arg His Thr Gly Val
65                  70                  75                  80

Pro Asp Arg Phe Ser Gly Ser Gly Ser Gly Thr Asp Phe Thr Leu Thr
                85                  90                  95

Ile Ser Arg Leu Gln Pro Glu Asp Phe Ala Val Tyr Tyr Cys Gln Gln
            100                 105                 110

Tyr Asn Ser Tyr Pro Leu Thr Phe Gly Gln Gly Thr Lys Val Asp Ile
        115                 120                 125

Lys Gly Gly Gly Gly Ser Gly Gly Gly Gly Ser Ser Gly Gly Gly Ser
    130                 135                 140

Glu Val Gln Leu Val Gln Ser Gly Ala Glu Val Lys Lys Pro Gly Ala
145                 150                 155                 160

Ser Val Lys Val Ser Cys Lys Ala Ser Gly Tyr Thr Phe Thr Glu Tyr
                165                 170                 175

Thr Ile His Trp Val Arg Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
        195                 200                 205

Glu Asp Arg Val Thr Ile Thr Val Asp Lys Ser Thr Ser Thr Ala Tyr
    210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Thr Val Thr
                245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300
```

| Phe | Trp | Leu | Pro | Ile | Gly | Cys | Ala | Ala | Phe | Val | Val | Cys | Ile | Leu |
| --- | --- | --- | --- | --- | --- | --- | --- | --- | --- | --- | --- | --- | --- | --- |
| 305 | | | | 310 | | | | 315 | | | | | | 320 |

| Gly | Cys | Ile | Leu | Ile | Cys | Trp | Leu | Thr | Lys | Lys | Tyr | Ser | Ser | Ser |
| --- | --- | --- | --- | --- | --- | --- | --- | --- | --- | --- | --- | --- | --- | --- |
| | | | | 325 | | | | | 330 | | | | | 335 |

| Val | His | Asp | Pro | Asn | Gly | Glu | Tyr | Met | Phe | Met | Arg | Ala | Val | Asn | Thr |
| --- | --- | --- | --- | --- | --- | --- | --- | --- | --- | --- | --- | --- | --- | --- | --- |
| | | | 340 | | | | | 345 | | | | | 350 | | |

| Ala | Lys | Lys | Ser | Arg | Leu | Thr | Asp | Val | Thr | Leu | Lys | Arg | Gly | Arg | Lys |
| --- | --- | --- | --- | --- | --- | --- | --- | --- | --- | --- | --- | --- | --- | --- | --- |
| | | | 355 | | | | | 360 | | | | | 365 | | |

| Lys | Leu | Leu | Tyr | Ile | Phe | Lys | Gln | Pro | Phe | Met | Arg | Pro | Val | Gln | Thr |
| --- | --- | --- | --- | --- | --- | --- | --- | --- | --- | --- | --- | --- | --- | --- | --- |
| | 370 | | | | | 375 | | | | | 380 | | | | |

| Thr | Gln | Glu | Glu | Asp | Gly | Cys | Ser | Cys | Arg | Phe | Pro | Glu | Glu | Glu |
| --- | --- | --- | --- | --- | --- | --- | --- | --- | --- | --- | --- | --- | --- | --- |
| 385 | | | | 390 | | | | 395 | | | | | | 400 |

| Gly | Gly | Cys | Glu | Leu | Arg | Val | Lys | Phe | Ser | Arg | Ser | Ala | Asp | Ala | Pro |
| --- | --- | --- | --- | --- | --- | --- | --- | --- | --- | --- | --- | --- | --- | --- | --- |
| | | | | 405 | | | | | 410 | | | | | 415 | |

| Ala | Tyr | Lys | Gln | Gly | Gln | Asn | Gln | Leu | Tyr | Asn | Glu | Leu | Asn | Leu | Gly |
| --- | --- | --- | --- | --- | --- | --- | --- | --- | --- | --- | --- | --- | --- | --- | --- |
| | | | 420 | | | | | 425 | | | | | 430 | | |

| Arg | Arg | Glu | Glu | Tyr | Asp | Val | Leu | Asp | Lys | Arg | Arg | Gly | Arg | Asp | Pro |
| --- | --- | --- | --- | --- | --- | --- | --- | --- | --- | --- | --- | --- | --- | --- | --- |
| | | | 435 | | | | | 440 | | | | | 445 | | |

| Glu | Met | Gly | Gly | Lys | Pro | Arg | Arg | Lys | Asn | Pro | Gln | Glu | Gly | Leu | Tyr |
| --- | --- | --- | --- | --- | --- | --- | --- | --- | --- | --- | --- | --- | --- | --- | --- |
| | 450 | | | | | 455 | | | | | 460 | | | | |

| Asn | Glu | Leu | Gln | Lys | Asp | Lys | Met | Ala | Glu | Ala | Tyr | Ser | Glu | Ile | Gly |
| --- | --- | --- | --- | --- | --- | --- | --- | --- | --- | --- | --- | --- | --- | --- | --- |
| 465 | | | | | 470 | | | | | 475 | | | | | 480 |

| Met | Lys | Gly | Glu | Arg | Arg | Arg | Gly | Lys | Gly | His | Asp | Gly | Leu | Tyr | Gln |
| --- | --- | --- | --- | --- | --- | --- | --- | --- | --- | --- | --- | --- | --- | --- | --- |
| | | | | 485 | | | | | 490 | | | | | 495 | |

| Gly | Leu | Ser | Thr | Ala | Thr | Lys | Asp | Thr | Tyr | Asp | Ala | Leu | His | Met | Gln |
| --- | --- | --- | --- | --- | --- | --- | --- | --- | --- | --- | --- | --- | --- | --- | --- |
| | | | 500 | | | | | 505 | | | | | 510 | | |

| Ala | Leu | Pro | Pro | Arg |
| --- | --- | --- | --- | --- |
| | | 515 | | |

<210> SEQ ID NO 92
<211> LENGTH: 1551
<212> TYPE: DNA
<213> ORGANISM: Artificial Sequence
<220> FEATURE:
<223> OTHER INFORMATION: hJ591VKVH.ICOSBBZ

<400> SEQUENCE: 92

| | | |
| --- | --- | --- |
| atggccctgc ctgtgacagc cctgctgctg cctctggctc tgctgctgca cgccgccaga | 60 |
| cctggagaca ttcagatgac ccagtctccc agcaccctgt ccgcatcagt aggagacagg | 120 |
| gtcaccatca cttgcaaggc cagtcaggat gtgggtactg ctgtagactg gtatcaacag | 180 |
| aaaccagggc aagctcctaa actactgatt tactgggcat ccacccggca cactggagtc | 240 |
| cctgatcgct tcagcggcag tggatctggg acagatttca ctctcaccat cagcagactg | 300 |
| cagcctgaag actttgcagt ttattactgt cagcaatata cagctatcc tctcacgttc | 360 |
| ggccagggga ccaaggtgga tatcaaagga ggcggaggat ctggcggcgg aggaagttct | 420 |
| ggcggaggca gcgaggtcca gctggtgcag tctggagctg aggtgaagaa gcctggggcc | 480 |
| tcagtgaagg tctcctgcaa ggcttctgga tacacattca ctgaatacac catccactgg | 540 |
| gtgaggcagg cccctggaaa gggccttgag tggattggaa acattaatcc taacaatggt | 600 |
| ggtactacct acaaccagaa gttcgaggac agagtcacaa tcactgtaga caagtccacc | 660 |
| agcacagcct acatggagct cagcagcctg agatctgagg atactgcagt ctattactgt | 720 |
| gcagctggtt ggaactttga ctactggggc caaggcacca cggtcaccgt ctcctcaacc | 780 |

-continued

| | |
|---|---|
| acgacgccag cgccgcgacc accaacaccg gcgcccacca tcgcgtcgca gcccctgtcc | 840 |
| ctgcgcccag aggcgtgccg gccagcggcg gggggcgcag tgcacacgag ggggctggac | 900 |
| ttcgcctgtg atttctggtt acccatagga tgtgcagcct ttgttgtagt ctgcattttg | 960 |
| ggatgcatac ttatttgttg gcttacaaaa aagaagtatt catccagtgt gcacgaccct | 1020 |
| aacggtgaat acatgttcat gagagcagtg aacacagcca aaaatccag actcacagat | 1080 |
| gtgaccctaa acggggcag aaagaaactc ctgtatatat tcaaacaacc atttatgaga | 1140 |
| ccagtacaaa ctactcaaga ggaagatggc tgtagctgcc gatttccaga agaagaagaa | 1200 |
| ggaggatgtg aactgagagt gaagttcagc aggagcgcag acgccccgc gtacaagcag | 1260 |
| ggccagaacc agctctataa cgagctcaat ctaggacgaa gagaggagta cgacgttttg | 1320 |
| gacaagagac gtggccggga ccctgagatg gggggaaagc cgagaaggaa gaaccctcag | 1380 |
| gaaggcctgt acaacgaact gcagaaagat aagatggcgg aggcctacag tgagattggg | 1440 |
| atgaaaggcg agcgcggag gggcaagggg cacgacggcc tttaccaggg tctcagtaca | 1500 |
| gccaccaagg acacctacga cgcccttcac atgcaggccc tgccccctcg c | 1551 |

<210> SEQ ID NO 93
<211> LENGTH: 517
<212> TYPE: PRT
<213> ORGANISM: Artificial Sequence
<220> FEATURE:
<223> OTHER INFORMATION: hJ591VKVH.ICOSBBZYMNM

<400> SEQUENCE: 93

Met Ala Leu Pro Val Thr Ala Leu Leu Leu Pro Leu Ala Leu Leu Leu
1               5                   10                  15

His Ala Ala Arg Pro Gly Asp Ile Gln Met Thr Gln Ser Pro Ser Thr
            20                  25                  30

Leu Ser Ala Ser Val Gly Asp Arg Val Thr Ile Thr Cys Lys Ala Ser
        35                  40                  45

Gln Asp Val Gly Thr Ala Val Asp Trp Tyr Gln Lys Pro Gly Gln
    50                  55                  60

Ala Pro Lys Leu Leu Ile Tyr Trp Ala Ser Thr Arg His Thr Gly Val
65                  70                  75                  80

Pro Asp Arg Phe Ser Gly Ser Gly Ser Gly Thr Asp Phe Thr Leu Thr
                85                  90                  95

Ile Ser Arg Leu Gln Pro Glu Asp Phe Ala Val Tyr Tyr Cys Gln Gln
            100                 105                 110

Tyr Asn Ser Tyr Pro Leu Thr Phe Gly Gln Gly Thr Lys Val Asp Ile
        115                 120                 125

Lys Gly Gly Gly Ser Gly Gly Gly Ser Ser Gly Gly Gly Ser
    130                 135                 140

Glu Val Gln Leu Val Gln Ser Gly Ala Glu Val Lys Lys Pro Gly Ala
145                 150                 155                 160

Ser Val Lys Val Ser Cys Lys Ala Ser Gly Tyr Thr Phe Thr Glu Tyr
                165                 170                 175

Thr Ile His Trp Val Arg Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
        195                 200                 205

Glu Asp Arg Val Thr Ile Thr Val Asp Lys Ser Thr Ser Thr Ala Tyr
    210                 215                 220

Met Glu Leu Ser Ser Leu Arg Ser Glu Asp Thr Ala Val Tyr Tyr Cys 225                 230                 235                 240
Ala Ala Gly Trp Asn Phe Asp Tyr Trp Gly Gln Gly Thr Thr Val Thr
                    245                 250                 255

Val Ser Ser Thr Thr Thr Pro Ala Pro Arg Pro Pro Thr Pro Ala Pro
                    260                 265                 270

Thr Ile Ala Ser Gln Pro Leu Ser Leu Arg Pro Glu Ala Cys Arg Pro
                    275                 280                 285

Ala Ala Gly Gly Ala Val His Thr Arg Gly Leu Asp Phe Ala Cys Asp
                    290                 295                 300

Phe Trp Leu Pro Ile Gly Cys Ala Ala Phe Val Val Cys Ile Leu
305                 310                 315                 320

Gly Cys Ile Leu Ile Cys Trp Leu Thr Lys Lys Lys Tyr Ser Ser Ser
                    325                 330                 335

Val His Asp Pro Asn Gly Glu Tyr Met Asn Met Arg Ala Val Asn Thr
                    340                 345                 350

Ala Lys Lys Ser Arg Leu Thr Asp Val Thr Leu Lys Arg Gly Arg Lys
                    355                 360                 365

Lys Leu Leu Tyr Ile Phe Lys Gln Pro Phe Met Arg Pro Val Gln Thr
370                 375                 380

Thr Gln Glu Glu Asp Gly Cys Ser Cys Arg Phe Pro Glu Glu Glu Glu
385                 390                 395                 400

Gly Gly Cys Glu Leu Arg Val Lys Phe Ser Arg Ser Ala Asp Ala Pro
                    405                 410                 415

Ala Tyr Lys Gln Gly Gln Asn Gln Leu Tyr Asn Glu Leu Asn Leu Gly
                    420                 425                 430

Arg Arg Glu Glu Tyr Asp Val Leu Asp Lys Arg Arg Gly Arg Asp Pro
                    435                 440                 445

Glu Met Gly Gly Lys Pro Arg Arg Lys Asn Pro Gln Glu Gly Leu Tyr
                    450                 455                 460

Asn Glu Leu Gln Lys Asp Lys Met Ala Glu Ala Tyr Ser Glu Ile Gly
465                 470                 475                 480

Met Lys Gly Glu Arg Arg Arg Gly Lys Gly His Asp Gly Leu Tyr Gln
                    485                 490                 495

Gly Leu Ser Thr Ala Thr Lys Asp Thr Tyr Asp Ala Leu His Met Gln
                    500                 505                 510

Ala Leu Pro Pro Arg
                    515

<210> SEQ ID NO 94
<211> LENGTH: 1551
<212> TYPE: DNA
<213> ORGANISM: Artificial Sequence
<220> FEATURE:
<223> OTHER INFORMATION: hJ591VKVH.ICOSBBZYMNM

<400> SEQUENCE: 94
atggccctgc ctgtgacagc cctgctgctg cctctggctc tgctgctgca cgccgccaga     60
cctggagaca ttcagatgac ccagtctccc agcaccctgt ccgcatcagt aggagacagg    120
gtcaccatca cttgcaaggc cagtcaggat gtgggtactg ctgtagactg gtatcaacag    180
aaaccagggc aagctcctaa actactgatt tactgggcat ccacccggca cactggagtc    240
cctgatcgct tcagcggcag tggatctggg acagatttca ctctcaccat cagcagactg    300
cagcctgaag actttgcagt ttattactgt cagcaatata acagtatcc tctcacgttc     360 ggccagggga ccaaggtgga tatcaaagga ggcggaggat ctggcggcgg aggaagttct    420

-continued

```
ggcggaggca gcgaggtcca gctggtgcag tctggagctg aggtgaagaa gcctggggcc      480
tcagtgaagg tctcctgcaa ggcttctgga tacacattca ctgaatacac catccactgg      540
gtgaggcagg cccctggaaa gggccttgag tggattggaa acattaatcc taacaatggt      600
ggtactacct acaaccagaa gttcgaggac agagtcacaa tcactgtaga caagtccacc      660
agcacagcct acatggagct cagcagcctg agatctgagg atactgcagt ctattactgt      720
gcagctggtt ggaactttga ctactggggc caaggcacca cggtcaccgt ctcctcaacc      780
acgacgccag cgccgcgacc accaacaccg gcgcccacca tcgcgtcgca gcccctgtcc      840
ctgcgcccag aggcgtgccg gccagcggcg ggggcgcag tgcacacgag ggggctggac       900
ttcgcctgtg atttctggtt acccatagga tgtgcagcct tgttgtagt ctgcattttg       960 ggatgcatac ttatttgttg gcttacaaaa aagaagtatt catccagtgt gcacgaccct     1020
aacggtgaat acatgaacat gagagcagtg aacacagcca aaaaatccag actcacagat     1080
gtgaccctaa acggggcag aaagaaactc ctgtatatat tcaaacaacc atttatgaga       1140
ccagtacaaa ctactcaaga ggaagatggc tgtagctgcc gatttccaga agaagaagaa     1200
ggaggatgtg aactgagagt gaagttcagc aggagcgcag acgccccgc gtacaagcag       1260 ggccagaacc agctctataa cgagctcaat ctaggacgaa gagaggagta cgacgttttg     1320
gacaagagac gtggccggga ccctgagatg ggggaaaagc cgagaaggaa gaaccctcag     1380
gaaggcctgt acaacgaact gcagaaagat aagatggcgg aggcctacag tgagattggg     1440
atgaaaggcg agcgccggag gggcaagggg cacgacggcc tttaccaggg tctcagtaca     1500
gccaccaagg acacctacga cgcccttcac atgcaggccc tgccccctcg c              1551
```

<210> SEQ ID NO 95
<211> LENGTH: 475
<212> TYPE: PRT
<213> ORGANISM: Artificial Sequence
<220> FEATURE:
<223> OTHER INFORMATION: hJ591VKVH.ICOSZ

<400> SEQUENCE: 95

```
Met Ala Leu Pro Val Thr Ala Leu Leu Leu Pro Leu Ala Leu Leu Leu
1               5                   10                  15

His Ala Ala Arg Pro Gly Asp Ile Gln Met Thr Gln Ser Pro Ser Thr
            20                  25                  30

Leu Ser Ala Ser Val Gly Asp Arg Val Thr Ile Thr Cys Lys Ala Ser
        35                  40                  45

Gln Asp Val Gly Thr Ala Val Asp Trp Tyr Gln Gln Lys Pro Gly Gln
    50                  55                  60

Ala Pro Lys Leu Leu Ile Tyr Trp Ala Ser Thr Arg His Thr Gly Val
65                  70                  75                  80

Pro Asp Arg Phe Ser Gly Ser Gly Ser Gly Thr Asp Phe Thr Leu Thr
                85                  90                  95

Ile Ser Arg Leu Gln Pro Glu Asp Phe Ala Val Tyr Tyr Cys Gln Gln
            100                 105                 110

Tyr Asn Ser Tyr Pro Leu Thr Phe Gly Gln Gly Thr Lys Val Asp Ile
        115                 120                 125

Lys Gly Gly Gly Gly Ser Gly Gly Gly Gly Ser Gly Gly Gly Gly Ser
    130                 135                 140

Glu Val Gln Leu Val Gln Ser Gly Ala Glu Val Lys Lys Pro Gly Ala
145                 150                 155                 160
```

Ser Val Lys Val Ser Cys Lys Ala Ser Gly Tyr Thr Phe Thr Glu Tyr
165                 170                 175

Thr Ile His Trp Val Arg Gln Ala Pro Gly Lys Gly Leu Glu Trp Ile
        180                 185                 190

Gly Asn Ile Asn Pro Asn Asn Gly Gly Thr Thr Tyr Asn Gln Lys Phe
            195                 200                 205

Glu Asp Arg Val Thr Ile Thr Val Asp Lys Ser Thr Ser Thr Ala Tyr
210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Thr Val Thr
                245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
290                 295                 300

Phe Trp Leu Pro Ile Gly Cys Ala Ala Phe Val Val Val Cys Ile Leu
305                 310                 315                 320

Gly Cys Ile Leu Ile Cys Trp Leu Thr Lys Lys Lys Tyr Ser Ser Ser
                325                 330                 335

Val His Asp Pro Asn Gly Glu Tyr Met Phe Met Arg Ala Val Asn Thr
            340                 345                 350

Ala Lys Lys Ser Arg Leu Thr Asp Val Thr Leu Arg Val Lys Phe Ser
        355                 360                 365

Arg Ser Ala Asp Ala Pro Ala Tyr Lys Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
450                 455                 460

Asp Ala Leu His Met Gln Ala Leu Pro Pro Arg
465                 470                 475

<210> SEQ ID NO 96
<211> LENGTH: 1425
<212> TYPE: DNA
<213> ORGANISM: Artificial Sequence
<220> FEATURE:
<223> OTHER INFORMATION: hJ591VKVH.ICOSZ

<400> SEQUENCE: 96
atggccctgc ctgtgacagc cctgctgctg cctctggctc tgctgctgca cgccgccaga      60
cctggagaca ttcagatgac ccagtctccc agcaccctgt ccgcatcagt aggagacagg     120
gtcaccatca cttgcaaggc cagtcaggat gtgggtactg ctgtagactg gtatcaacag     180
aaaccagggc aagctcctaa actactgatt tactgggcat ccacccggca cactggagtc     240
cctgatcgct tcagcggcag tggatctggg acagatttca ctctcaccat cagcagactg     300

-continued

```
cagcctgaag actttgcagt ttattactgt cagcaatata acagctatcc tctcacgttc      360
ggccagggga ccaaggtgga tatcaaagga ggcggaggat ctggcggcgg aggaagttct      420
ggcggaggca gcgaggtcca gctggtgcag tctggagctg aggtgaagaa gcctggggcc      480
tcagtgaagg tctcctgcaa ggcttctgga tacacattca ctgaatacac catccactgg      540
gtgaggcagg cccctggaaa gggccttgag tggattggaa acattaatcc taacaatggt      600
ggtactacct acaaccagaa gttcgaggac agagtcacaa tcactgtaga caagtccacc      660
agcacagcct acatggagct cagcagcctg agatctgagg atactgcagt ctattactgt      720
gcagctggtt ggaactttga ctactggggc caaggcacca cggtcaccgt ctcctcaacc      780
acgacgccag cgccgcgacc accaacaccg gcgcccacca tcgcgtcgca gcccctgtcc      840
ctgcgcccag aggcgtgccg gccagcggcg ggggcgcag tgcacacgag ggggctggac       900
ttcgcctgtg atttctggtt acccatagga tgtgcagcct tgttgtagt ctgcattttg        960 ggatgcatac ttatttgttg gcttacaaaa aagaagtatt catccagtgt gcacgaccct     1020
aacggtgaat acatgttcat gagagcagtg aacacagcca aaaaatccag actcacagat     1080 gtgacccta gagtgaagtt cagcaggagc gcagacgccc ccgcgtacaa gcagggccag      1140
aaccagctct ataacgagct caatctagga cgaagagagg agtacgacgt tttggacaag     1200
agacgtggcc gggaccctga gatgggggga agccgagaa ggaagaaccc tcaggaaggc      1260
ctgtacaacg aactgcagaa agataagatg gcggaggcct acagtgagat tgggatgaaa    1320
ggcgagcgcc ggaggggcaa ggggcacgac ggcctttacc agggtctcag tacagccacc    1380
aaggacacct acgacgccct tcacatgcag gccctgcccc ctcgc                      1425
```

<210> SEQ ID NO 97
<211> LENGTH: 475
<212> TYPE: PRT
<213> ORGANISM: Artificial Sequence
<220> FEATURE:
<223> OTHER INFORMATION: hJ591VKVH.ICOSZYMNM

<400> SEQUENCE: 97

Met Ala Leu Pro Val Thr Ala Leu Leu Leu Pro Leu Ala Leu Leu Leu
1               5                   10                  15

His Ala Ala Arg Pro Gly Asp Ile Gln Met Thr Gln Ser Pro Ser Thr
            20                  25                  30

Leu Ser Ala Ser Val Gly Asp Arg Val Thr Ile Thr Cys Lys Ala Ser
        35                  40                  45

Gln Asp Val Gly Thr Ala Val Asp Trp Tyr Gln Gln Lys Pro Gly Gln
    50                  55                  60

Ala Pro Lys Leu Leu Ile Tyr Trp Ala Ser Thr Arg His Thr Gly Val
65                  70                  75                  80

Pro Asp Arg Phe Ser Gly Ser Gly Ser Gly Thr Asp Phe Thr Leu Thr
                85                  90                  95

Ile Ser Arg Leu Gln Pro Glu Asp Phe Ala Val Tyr Tyr Cys Gln Gln
            100                 105                 110

Tyr Asn Ser Tyr Pro Leu Thr Phe Gly Gln Gly Thr Lys Val Asp Ile
        115                 120                 125

Lys Gly Gly Gly Gly Ser Gly Gly Gly Gly Ser Gly Gly Gly Gly Ser
    130                 135                 140

Glu Val Gln Leu Val Gln Ser Gly Ala Glu Val Lys Lys Pro Gly Ala
145                 150                 155                 160

| | | | | | | | | | | | |
|---|---|---|---|---|---|---|---|---|---|---|---|
|Ser|Val|Lys|Val|Ser|Cys|Lys|Ala|Ser|Gly|Tyr|Thr|Phe|Thr|Glu|Tyr|
| | | | |165| | | |170| | | |175| | | |

Ser Val Lys Val Ser Cys Lys Ala Ser Gly Tyr Thr Phe Thr Glu Tyr
            165                 170                 175

Thr Ile His Trp Val Arg Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
            195                 200                 205

Glu Asp Arg Val Thr Ile Thr Val Asp Lys Ser Thr Ser Thr Ala Tyr
210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Thr Val Thr
            245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
            290                 295                 300

Phe Trp Leu Pro Ile Gly Cys Ala Ala Phe Val Val Val Cys Ile Leu
305                 310                 315                 320

Gly Cys Ile Leu Ile Cys Trp Leu Thr Lys Lys Lys Tyr Ser Ser Ser
            325                 330                 335

Val His Asp Pro Asn Gly Glu Tyr Met Asn Met Arg Ala Val Asn Thr
            340                 345                 350

Ala Lys Lys Ser Arg Leu Thr Asp Val Thr Leu Arg Val Lys Phe Ser
            355                 360                 365

Arg Ser Ala Asp Ala Pro Ala Tyr Lys Gln Gly Gln Asn Gln Leu Tyr
            370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
            405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
            450                 455                 460

Asp Ala Leu His Met Gln Ala Leu Pro Pro Arg
465                 470                 475

<210> SEQ ID NO 98
<211> LENGTH: 1425
<212> TYPE: DNA
<213> ORGANISM: Artificial Sequence
<220> FEATURE:
<223> OTHER INFORMATION: hJ591VKVH.ICOSZYMNM

<400> SEQUENCE: 98
atggccctgc ctgtgacagc cctgctgctg cctctggctc tgctgctgca cgccgccaga      60
cctggagaca ttcagatgac ccagtctccc agcaccctgt ccgcatcagt aggagacagg     120
gtcaccatca cttgcaaggc cagtcaggat gtgggtactg ctgtagactg gtatcaacag     180
aaaccagggc aagctcctaa actactgatt tactgggcat ccaccccggca cactggagtc     240 cctgatcgct tcagcggcag tggatctggg acagatttca ctctcaccat cagcagactg     300

```
cagcctgaag actttgcagt ttattactgt cagcaatata acagctatcc tctcacgttc    360
ggccagggga ccaaggtgga tatcaaagga ggcggaggat ctggcggcgg aggaagttct    420
ggcggaggca gcgaggtcca gctggtgcag tctggagctg aggtgaagaa gcctggggcc    480
tcagtgaagg tctcctgcaa ggcttctgga tacacattca ctgaatacac catccactgg    540
gtgaggcagg cccctggaaa gggccttgag tggattggaa acattaatcc taacaatggt    600
ggtactacct acaaccagaa gttcgaggac agagtcacaa tcactgtaga caagtccacc    660
agcacagcct acatggagct cagcagcctg agatctgagg atactgcagt ctattactgt    720
gcagctggtt ggaactttga ctactggggc caaggcacca cggtcaccgt ctcctcaacc    780
acgacgccag cgccgcgacc accaacaccg gcgcccacca tcgcgtcgca gcccctgtcc    840
ctgcgcccag aggcgtgccg gccagcggcg ggggcgcag tgcacacgag ggggctggac    900
ttcgcctgtg atttctggtt acccatagga tgtgcagcct ttgttgtagt ctgcattttg    960
ggatgcatac ttatttgttg gcttacaaaa aagaagtatt catccagtgt gcacgacct   1020 aacggtgaat acatgaacat gagagcagtg aacacagcca aaaaatccag actcacagat   1080
gtgaccctaa gagtgaagtt cagcaggagc gcagacgccc ccgcgtacaa gcagggccag   1140
aaccagctct ataacgagct caatctagga cgaagagagg agtacgacgt tttggacaag   1200
agacgtggcc gggaccctga gatgggggga aagccgagaa ggaagaaccc tcaggaaggc   1260
ctgtacaacg aactgcagaa agataagatg gcggaggcct acagtgagat tgggatgaaa   1320
ggcgagcgcc ggaggggcaa ggggcacgac ggcctttacc agggtctcag tacagccacc   1380
aaggacacct acgacgccct tcacatgcag gccctgcccc ctcgc              1425

<210> SEQ ID NO 99
<211> LENGTH: 45
<212> TYPE: PRT
<213> ORGANISM: Artificial Sequence
<220> FEATURE:
<223> OTHER INFORMATION: Hinge

<400> SEQUENCE: 99

Asn His Asp Ala Ser Ala Ala Thr Thr Asn Thr Gly Ala His His Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 100
<211> LENGTH: 45
<212> TYPE: PRT
<213> ORGANISM: Artificial Sequence
<220> FEATURE:
<223> OTHER INFORMATION: Hinge

<400> SEQUENCE: 100

His Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 101
```

```
<211> LENGTH: 115
<212> TYPE: PRT
<213> ORGANISM: Artificial Sequence
<220> FEATURE:
<223> OTHER INFORMATION: PSMA VH Consensus Sequence
<220> FEATURE:
<221> NAME/KEY: misc_feature
<222> LOCATION: (9)..(9)
<223> OTHER INFORMATION: Xaa is A or P
<220> FEATURE:
<221> NAME/KEY: misc_feature
<222> LOCATION: (11)..(11)
<223> OTHER INFORMATION: Xaa is V or L
<220> FEATURE:
<221> NAME/KEY: misc_feature
<222> LOCATION: (24)..(24)
<223> OTHER INFORMATION: Xaa is A or T
<220> FEATURE:
<221> NAME/KEY: misc_feature
<222> LOCATION: (38)..(38)
<223> OTHER INFORMATION: Xaa is R or K
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa is N or Q
<220> FEATURE:
<221> NAME/KEY: misc_feature
<222> LOCATION: (68)..(68)
<223> OTHER INFORMATION: Xaa is V or A
<220> FEATURE:
<221> NAME/KEY: misc_feature
<222> LOCATION: (70)..(70)
<223> OTHER INFORMATION: Xaa is I or L

<400> SEQUENCE: 101

Glu Val Gln Leu Val Gln Ser Gly Xaa Glu Xaa Lys Lys Pro Gly Ala
1               5                   10                  15

Ser Val Lys Val Ser Cys Lys Xaa Ser Gly Tyr Thr Phe Thr Glu Tyr
            20                  25                  30

Thr Ile His Trp Val Xaa Gln Ala Xaa Gly Lys Gly Leu Glu Trp Ile
        35                  40                  45

Gly Asn Ile Asn Pro Asn Xaa Gly Gly Thr Thr Tyr Asn Gln Lys Phe
    50                  55                  60

Glu Asp Arg Xaa Thr Xaa Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 102
<211> LENGTH: 107
<212> TYPE: PRT
<213> ORGANISM: Artificial Sequence
<220> FEATURE:
<223> OTHER INFORMATION: PSMA VL Consensus Sequence
<220> FEATURE:
<221> NAME/KEY: misc_feature
<222> LOCATION: (3)..(3)
<223> OTHER INFORMATION: Xaa is Q or V
<220> FEATURE:
<221> NAME/KEY: misc_feature
<222> LOCATION: (10)..(10)
<223> OTHER INFORMATION: Xaa is T or F
```

```
<220> FEATURE:
<221> NAME/KEY: misc_feature
<222> LOCATION: (63)..(63)
<223> OTHER INFORMATION: Xaa is S or T
<220> FEATURE:
<221> NAME/KEY: misc_feature
<222> LOCATION: (80)..(80)
<223> OTHER INFORMATION: Xaa is P or S
<220> FEATURE:
<221> NAME/KEY: misc_feature
<222> LOCATION: (85)..(85)
<223> OTHER INFORMATION: Xaa is V or D
<220> FEATURE:
<221> NAME/KEY: misc_feature
<222> LOCATION: (87)..(87)
<223> OTHER INFORMATION: Xaa is Y or F
<220> FEATURE:
<221> NAME/KEY: misc_feature
<222> LOCATION: (103)..(103)
<223> OTHER INFORMATION: Xaa is K or M

<400> SEQUENCE: 102

Asp Ile Xaa Met Thr Gln Ser Pro Ser Xaa Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Xaa Gly
50                  55                  60

Ser Gly Ser Gly Thr Asp Phe Thr Leu Thr Ile Ser Arg Leu Gln Xaa
65                  70                  75                  80

Glu Asp Phe Ala Xaa Tyr Xaa Cys Gln Gln Tyr Asn Ser Tyr Pro Leu
                85                  90                  95

Thr Phe Gly Gln Gly Thr Xaa Val Asp Ile Lys
            100                 105

<210> SEQ ID NO 103
<211> LENGTH: 115
<212> TYPE: PRT
<213> ORGANISM: Artificial Sequence
<220> FEATURE:
<223> OTHER INFORMATION: PSMA VH

<400> SEQUENCE: 103

Glu Val Gln Leu Val Gln Ser Gly Pro Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Lys Gln Ala His Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115
```

```
<210> SEQ ID NO 104
<211> LENGTH: 107
<212> TYPE: PRT
<213> ORGANISM: Artificial Sequence
<220> FEATURE:
<223> OTHER INFORMATION: PSMA VL

<400> SEQUENCE: 104

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Arg Leu Gln Ser
65                  70                  75                  80

Glu Asp Phe Ala Asp Tyr Phe Cys Gln Gln Tyr Asn Ser Tyr Pro Leu
                85                  90                  95

Thr Phe Gly Gln Gly Thr Met Val Asp Ile Lys
            100                 105

<210> SEQ ID NO 105
<211> LENGTH: 115
<212> TYPE: PRT
<213> ORGANISM: Artificial Sequence
<220> FEATURE:
<223> OTHER INFORMATION: PSMA VH

<400> SEQUENCE: 105

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Lys Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
50                  55                  60

Glu Asp Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 106
<211> LENGTH: 107
<212> TYPE: PRT
<213> ORGANISM: Artificial Sequence
<220> FEATURE:
<223> OTHER INFORMATION: PSMA VL

<400> SEQUENCE: 106

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30
```

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Arg Leu Gln Ser
65                  70                  75                  80

Glu Asp Phe Ala Asp Tyr Phe Cys Gln Gln Tyr Asn Ser Tyr Pro Leu
                85                  90                  95

Thr Phe Gly Gln Gly Thr Lys Val Asp Ile Lys
                100                 105

<210> SEQ ID NO 107
<211> LENGTH: 115
<212> TYPE: PRT
<213> ORGANISM: Artificial Sequence
<220> FEATURE:
<223> OTHER INFORMATION: PSMA VH

<400> SEQUENCE: 107

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
                20                  25                  30

Thr Ile His Trp Val Arg Gln Ala Pro Gly Lys Gly Leu Glu Trp Ile
            35                  40                  45

Gly Asn Ile Asn Pro Asn Asn Gly Gly Thr Thr Tyr Asn Gln Lys Phe
    50                  55                  60

Glu Asp Arg Ala Thr Ile Thr Val Asp Lys Ser Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
                100                 105                 110

Val Ser Ser
        115

<210> SEQ ID NO 108
<211> LENGTH: 107
<212> TYPE: PRT
<213> ORGANISM: Artificial Sequence
<220> FEATURE:
<223> OTHER INFORMATION: PSMA VL

<400> SEQUENCE: 108

Asp Ile Val Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
                20                  25                  30

Val Asp Trp Tyr Gln Gln Lys Pro Gly Gln Ala Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Asp Tyr Tyr Cys Gln Gln Tyr Asn Ser Tyr Pro Leu
                85                  90                  95

Thr Phe Gly Gln Gly Thr Lys Val Asp Ile Lys

<210> SEQ ID NO 109
<211> LENGTH: 115
<212> TYPE: PRT
<213> ORGANISM: Artificial Sequence
<220> FEATURE:
<223> OTHER INFORMATION: PSMA VH

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Gln Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 110
<211> LENGTH: 115
<212> TYPE: PRT
<213> ORGANISM: Artificial Sequence
<220> FEATURE:
<223> OTHER INFORMATION: PSMA VH Consensus Sequence
<220> FEATURE:
<221> NAME/KEY: misc_feature
<222> LOCATION: (9)..(9)
<223> OTHER INFORMATION: Xaa is A or P
<220> FEATURE:
<221> NAME/KEY: misc_feature
<222> LOCATION: (11)..(11)
<223> OTHER INFORMATION: Xaa is V or L
<220> FEATURE:
<221> NAME/KEY: misc_feature
<222> LOCATION: (24)..(24)
<223> OTHER INFORMATION: Xaa is A or T
<220> FEATURE:
<221> NAME/KEY: misc_feature
<222> LOCATION: (38)..(38)
<223> OTHER INFORMATION: Xaa is R or K
<220> FEATURE:
<221> NAME/KEY: misc_feature
<222> LOCATION: (41)..(41)
<223> OTHER INFORMATION: Xaa is P or H
<220> FEATURE:
<221> NAME/KEY: misc_feature
<222> LOCATION: (55)..(55)
<223> OTHER INFORMATION: Xaa is N or Q
<220> FEATURE:
<221> NAME/KEY: misc_feature
<222> LOCATION: (68)..(68)
<223> OTHER INFORMATION: Xaa is V or A
<220> FEATURE:
<221> NAME/KEY: misc_feature
<222> LOCATION: (70)..(70)
<223> OTHER INFORMATION: Xaa is I or L
<220> FEATURE:
<221> NAME/KEY: misc_feature
<222> LOCATION: (86)..(86)
<223> OTHER INFORMATION: Xaa is L or P

```
<220> FEATURE:
<221> NAME/KEY: misc_feature
<222> LOCATION: (98)..(102)
<223> OTHER INFORMATION: Xaa-Xaa is AYWLF, GGWTF, or GAWTM

<400> SEQUENCE: 110

Glu Val Gln Leu Val Gln Ser Gly Xaa Glu Xaa Lys Lys Pro Gly Ala
1               5                   10                  15

Ser Val Lys Val Ser Cys Lys Xaa Ser Gly Tyr Thr Phe Thr Glu Tyr
            20                  25                  30

Thr Ile His Trp Val Xaa Gln Ala Xaa Gly Lys Gly Leu Glu Trp Ile
        35                  40                  45

Gly Asn Ile Asn Pro Asn Xaa Gly Gly Thr Thr Tyr Asn Gln Lys Phe
    50                  55                  60

Glu Asp Arg Xaa Thr Xaa Thr Val Asp Lys Ser Thr Ser Thr Ala Tyr
65                  70                  75                  80

Met Glu Leu Ser Ser Xaa Arg Ser Glu Asp Thr Ala Val Tyr Tyr Cys
                85                  90                  95

Ala Xaa Xaa Xaa Xaa Xaa Asp Tyr Trp Gly Gln Gly Thr Thr Val Thr
            100                 105                 110

Val Ser Ser
        115

<210> SEQ ID NO 111
<211> LENGTH: 107
<212> TYPE: PRT
<213> ORGANISM: Artificial Sequence
<220> FEATURE:
<223> OTHER INFORMATION: PSMA VL Consensus Sequence
<220> FEATURE:
<221> NAME/KEY: misc_feature
<222> LOCATION: (3)..(3)
<223> OTHER INFORMATION: Xaa is Q or V
<220> FEATURE:
<221> NAME/KEY: misc_feature
<222> LOCATION: (10)..(10)
<223> OTHER INFORMATION: Xaa is T or F
<220> FEATURE:
<221> NAME/KEY: misc_feature
<222> LOCATION: (63)..(63)
<223> OTHER INFORMATION: Xaa is S or T
<220> FEATURE:
<221> NAME/KEY: misc_feature
<222> LOCATION: (80)..(80)
<223> OTHER INFORMATION: Xaa is P or S
<220> FEATURE:
<221> NAME/KEY: misc_feature
<222> LOCATION: (85)..(85)
<223> OTHER INFORMATION: Xaa is V or D
<220> FEATURE:
<221> NAME/KEY: misc_feature
<222> LOCATION: (87)..(87)
<223> OTHER INFORMATION: Xaa is Y or F
<220> FEATURE:
<221> NAME/KEY: misc_feature
<222> LOCATION: (91)..(95)
<223> OTHER INFORMATION: Xaa-Xaa is FTRYP or YNAYS
<220> FEATURE:
<221> NAME/KEY: misc_feature
<222> LOCATION: (103)..(103)
<223> OTHER INFORMATION: Xaa is K or M

<400> SEQUENCE: 111

Asp Ile Xaa Met Thr Gln Ser Pro Ser Xaa Leu Ser Ala Ser Val Gly
1               5                   10                  15

Asp Arg Val Thr Ile Thr Cys Lys Ala Ser Gln Asp Val Gly Thr Ala
            20                  25                  30
```

```
Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Xaa Gly
    50                  55                  60

Ser Gly Ser Gly Thr Asp Phe Thr Leu Thr Ile Ser Arg Leu Gln Xaa
65                  70                  75                  80

Glu Asp Phe Ala Xaa Tyr Xaa Cys Gln Gln Xaa Xaa Xaa Xaa Xaa Leu
                85                  90                  95

Thr Phe Gly Gln Gly Thr Xaa Val Asp Ile Lys
                100                 105
```

```
<210> SEQ ID NO 112
<211> LENGTH: 115
<212> TYPE: PRT
<213> ORGANISM: Artificial Sequence
<220> FEATURE:
<223> OTHER INFORMATION: PSMA VH

<400> SEQUENCE: 112

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Tyr Trp Leu Phe Asp Tyr Trp Gly Gln Gly Thr Thr Val Thr
                100                 105                 110

Val Ser Ser
        115
```

```
<210> SEQ ID NO 113
<211> LENGTH: 107
<212> TYPE: PRT
<213> ORGANISM: Artificial Sequence
<220> FEATURE:
<223> OTHER INFORMATION: PSMA VL

<400> SEQUENCE: 113

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ser Tyr Pro Leu
                85                  90                  95

Thr Phe Gly Gln Gly Thr Lys Val Asp Ile Lys
                100                 105
```

<210> SEQ ID NO 114
<211> LENGTH: 115
<212> TYPE: PRT
<213> ORGANISM: Artificial Sequence
<220> FEATURE:
<223> OTHER INFORMATION: PSMA VH

<400> SEQUENCE: 114

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Trp Thr Phe Asp Tyr Trp Gly Gln Gly Thr Thr Val Thr
            100                 105                 110

Val Ser Ser
        115
```

<210> SEQ ID NO 115
<211> LENGTH: 107
<212> TYPE: PRT
<213> ORGANISM: Artificial Sequence
<220> FEATURE:
<223> OTHER INFORMATION: PSMA VL

<400> SEQUENCE: 115

```
Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Phe Thr Arg Tyr Pro Leu
                85                  90                  95

Thr Phe Gly Gln Gly Thr Lys Val Asp Ile Lys
            100                 105
```

<210> SEQ ID NO 116
<211> LENGTH: 115
<212> TYPE: PRT
<213> ORGANISM: Artificial Sequence
<220> FEATURE:
<223> OTHER INFORMATION: PSMA VH

<400> SEQUENCE: 116

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
 50                  55                  60

Glu Asp Arg Val Thr Ile Thr Val Asp Lys Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Gly Ala Trp Thr Met Asp Tyr Trp Gly Gln Gly Thr Thr Val Thr
            100                 105                 110

Val Ser Ser
        115

<210> SEQ ID NO 117
<211> LENGTH: 107
<212> TYPE: PRT
<213> ORGANISM: Artificial Sequence
<220> FEATURE:
<223> OTHER INFORMATION: PSMA VL

<400> SEQUENCE: 117

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Gln Ala Pro Lys Leu Leu Ile
        35                  40                  45

Tyr Trp Ala Ser Thr Arg His Thr Gly Val Pro Asp Arg Phe Ser Gly
 50                  55                  60

Ser Gly Ser Gly Thr Asp Phe Thr Leu Thr Ile Ser Arg Leu Gln Pro
65                  70                  75                  80

Glu Asp Phe Ala Val Tyr Tyr Cys Gln Gln Tyr Asn Ala Tyr Ser Leu
            85                  90                  95

Thr Phe Gly Gln Gly Thr Lys Val Asp Ile Lys
            100                 105

<210> SEQ ID NO 118
<211> LENGTH: 115
<212> TYPE: PRT
<213> ORGANISM: Artificial Sequence
<220> FEATURE:
<223> OTHER INFORMATION: PSMA VH

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Lys Gly Leu Glu Trp Ile
        35                  40                  45

Gly Asn Ile Asn Pro Asn Asn Gly Gly Thr Thr Tyr Asn Gln Lys Phe
 50                  55                  60

Glu Asp Arg Val Thr Ile Thr Val Asp Lys Ser Thr Ser Thr Ala Tyr
65                  70                  75                  80

Met Glu Leu Ser Ser Pro Arg Ser Glu Asp Thr Ala Val Tyr Tyr Cys
            85                  90                  95
```

```
Ala Ala Gly Trp Asn Phe Asp Tyr Trp Gly Gln Gly Thr Thr Val Thr
            100                 105                 110

Val Ser Ser
        115

<210> SEQ ID NO 119
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 119

Gly Ser Gly Gly Ser
1               5

<210> SEQ ID NO 120
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(4)
<223> OTHER INFORMATION: repeat n times, where n represents an integer
      of at least 1

<400> SEQUENCE: 120

Gly Gly Gly Ser
1

<210> SEQ ID NO 121
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 121

Gly Gly Gly Gly Ser
1               5

<210> SEQ ID NO 122
<211> LENGTH: 4
<212> TYPE: PRT
<213> ORGANISM: Artificial Sequence
<220> FEATURE:
<223> OTHER INFORMATION: Linker

<400> SEQUENCE: 122

Gly Gly Ser Gly
1

<210> SEQ ID NO 123
<211> LENGTH: 5
<212> TYPE: PRT
<213> ORGANISM: Artificial Sequence
```

```
<220> FEATURE:
<223> OTHER INFORMATION: Linker

<400> SEQUENCE: 123

Gly Gly Ser Gly Gly
1               5

<210> SEQ ID NO 124
<211> LENGTH: 5
<212> TYPE: PRT
<213> ORGANISM: Artificial Sequence
<220> FEATURE:
<223> OTHER INFORMATION: Linker

<400> SEQUENCE: 124

Gly Ser Gly Ser Gly
1               5

<210> SEQ ID NO 125
<211> LENGTH: 5
<212> TYPE: PRT
<213> ORGANISM: Artificial Sequence
<220> FEATURE:
<223> OTHER INFORMATION: Linker

<400> SEQUENCE: 125

Gly Ser Gly Gly Gly
1               5

<210> SEQ ID NO 126
<211> LENGTH: 5
<212> TYPE: PRT
<213> ORGANISM: Artificial Sequence
<220> FEATURE:
<223> OTHER INFORMATION: Linker

<400> SEQUENCE: 126

Gly Gly Gly Ser Gly
1               5

<210> SEQ ID NO 127
<211> LENGTH: 5
<212> TYPE: PRT
<213> ORGANISM: Artificial Sequence
<220> FEATURE:
<223> OTHER INFORMATION: Linker

<400> SEQUENCE: 127

Gly Ser Ser Ser Gly
1               5

<210> SEQ ID NO 128
<211> LENGTH: 5
<212> TYPE: PRT
<213> ORGANISM: Artificial Sequence
<220> FEATURE:
<223> OTHER INFORMATION: Linker

<400> SEQUENCE: 128

Gly Gly Gly Gly Ser
1               5

<210> SEQ ID NO 129
<211> LENGTH: 15
<212> TYPE: PRT
<213> ORGANISM: Artificial Sequence
<220> FEATURE:
```

<223> OTHER INFORMATION: Linker

<400> SEQUENCE: 129

Gly Gly Gly Gly Ser Gly Gly Gly Gly Ser Gly Gly Gly Gly Ser
1               5                   10                  15

<210> SEQ ID NO 130
<211> LENGTH: 45
<212> TYPE: DNA
<213> ORGANISM: Artificial Sequence
<220> FEATURE:
<223> OTHER INFORMATION: Linker

<400> SEQUENCE: 130
ggtggcggtg gctcgggcgg tggtgggtcg ggtggcggcg gatct          45

<210> SEQ ID NO 131
<211> LENGTH: 5
<212> TYPE: PRT
<213> ORGANISM: Artificial Sequence
<220> FEATURE:
<223> OTHER INFORMATION: Hinge

<400> SEQUENCE: 131

Asp Lys Thr His Thr
1               5

<210> SEQ ID NO 132
<211> LENGTH: 4
<212> TYPE: PRT
<213> ORGANISM: Artificial Sequence
<220> FEATURE:
<223> OTHER INFORMATION: Hinge

<400> SEQUENCE: 132

Cys Pro Pro Cys
1

<210> SEQ ID NO 133
<211> LENGTH: 15
<212> TYPE: PRT
<213> ORGANISM: Artificial Sequence
<220> FEATURE:
<223> OTHER INFORMATION: Hinge

<400> SEQUENCE: 133

Cys Pro Glu Pro Lys Ser Cys Asp Thr Pro Pro Pro Cys Pro Arg
1               5                   10                  15

<210> SEQ ID NO 134
<211> LENGTH: 12
<212> TYPE: PRT
<213> ORGANISM: Artificial Sequence
<220> FEATURE:
<223> OTHER INFORMATION: Hinge

<400> SEQUENCE: 134

Glu Leu Lys Thr Pro Leu Gly Asp Thr Thr His Thr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Hinge

```
<400> SEQUENCE: 135

Lys Ser Cys Asp Lys Thr His Thr Cys Pro
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Hinge

<400> SEQUENCE: 136

Lys Cys Cys Val Asp Cys Pro
1               5

<210> SEQ ID NO 137
<211> LENGTH: 7
<212> TYPE: PRT
<213> ORGANISM: Artificial Sequence
<220> FEATURE:
<223> OTHER INFORMATION: Hinge

<400> SEQUENCE: 137

Lys Tyr Gly Pro Pro Cys Pro
1               5

<210> SEQ ID NO 138
<211> LENGTH: 15
<212> TYPE: PRT
<213> ORGANISM: Artificial Sequence
<220> FEATURE:
<223> OTHER INFORMATION: Hinge

<400> SEQUENCE: 138

Glu Pro Lys Ser Cys Asp Lys Thr His Thr Cys Pro Pro Cys Pro
1               5                   10                  15

<210> SEQ ID NO 139
<211> LENGTH: 12
<212> TYPE: PRT
<213> ORGANISM: Artificial Sequence
<220> FEATURE:
<223> OTHER INFORMATION: Hinge

<400> SEQUENCE: 139

Glu Arg Lys Cys Cys Val Glu Cys Pro Pro Cys Pro
1               5                   10

<210> SEQ ID NO 140
<211> LENGTH: 17
<212> TYPE: PRT
<213> ORGANISM: Artificial Sequence
<220> FEATURE:
<223> OTHER INFORMATION: Hinge

<400> SEQUENCE: 140

Glu Leu Lys Thr Pro Leu Gly Asp Thr Thr His Thr Cys Pro Arg Cys
1               5                   10                  15
Pro

<210> SEQ ID NO 141
<211> LENGTH: 12
<212> TYPE: PRT
<213> ORGANISM: Artificial Sequence
<220> FEATURE:
<223> OTHER INFORMATION: Hinge
```

```
<400> SEQUENCE: 141

Ser Pro Asn Met Val Pro His Ala His His Ala Gln
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Hinge

<400> SEQUENCE: 142

Glu Pro Lys Ser Cys Asp Lys Thr Tyr Thr Cys Pro Pro Cys Pro
1               5                   10                  15

<210> SEQ ID NO 143
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 143

Arg Xaa Lys Arg
1

<210> SEQ ID NO 144
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 144

Arg Xaa Arg Arg
1

<210> SEQ ID NO 145
<211> LENGTH: 5
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (1)..(1)
<223> OTHER INFORMATION: Xaa is K or R
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is K or R

<400> SEQUENCE: 145

Xaa Arg Xaa Xaa Arg
1               5
```

```
<210> SEQ ID NO 146
<211> LENGTH: 4
<212> TYPE: PRT
<213> ORGANISM: Artificial Sequence
<220> FEATURE:
<223> OTHER INFORMATION: Furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 146

Arg Xaa Xaa Arg
1

<210> SEQ ID NO 147
<211> LENGTH: 4
<212> TYPE: PRT
<213> ORGANISM: Artificial Sequence
<220> FEATURE:
<223> OTHER INFORMATION: Furin cleavage site

<400> SEQUENCE: 147

Arg Gln Lys Arg
1

<210> SEQ ID NO 148
<211> LENGTH: 239
<212> TYPE: PRT
<213> ORGANISM: Artificial Sequence
<220> FEATURE:
<223> OTHER INFORMATION: 2B3 scFv

<400> SEQUENCE: 148

Asp Ile Gln Leu Thr Gln Ser Pro Ser Leu Ser Ala Ser Val Gly
1               5                   10                  15

Asp Arg Val Thr Ile Thr Cys Ser Ala Ser Ser Ser Val Arg Phe Ile
                20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
```

```
              210                 215                 220
Phe Trp Gly Gln Gly Thr Leu Val Thr Val Ser Ser Ala Ala Gly
225                 230                 235
```

COMPOSITIONS AND METHODS COMPRISING PROSTATE STEM CELL ANTIGEN (PSCA) CHIMERIC ANTIGEN RECEPTORS (CARS)

CROSS-REFERENCE TO RELATED APPLICATION

The present application is entitled to priority under 35 U.S.C. § 119(e) to U.S. Provisional Patent Application No. 62/985,808 filed Mar. 5, 2020, and U.S. Provisional Patent Application No. 62/898,896 filed Sep. 11, 2019, which are hereby incorporated by reference in their entirety herein.

BACKGROUND OF THE INVENTION

Prostate cancer is the most common cancer diagnosis and the second leading cause of cancer-related death in American men. Despite recent advances in the detection and treatment of localized disease, significant challenges remain in the management of this disease. Current diagnostic modalities are limited by a lack of specificity and an inability to predict which patients are at risk to develop metastatic disease. Prostate-specific antigen (PSA) is effective at identifying men who may have prostate cancer but is often elevated in men with benign prostatic hyperplasia, prostatitis, and other nonmalignant disorders. PSA and other current markers fail to discriminate accurately between indolent and aggressive cancers. There is no effective treatment for the 20-40% of patients who develop recurrent disease after surgery or radiation therapy or for those who have metastatic disease at the time of diagnosis. Although hormone ablation therapy can palliate these patients, the majority inevitably progress to develop incurable androgen-independent disease.

There is a need in the art for compositions and methods for treating prostate cancer. The present invention addresses this need.

SUMMARY OF THE INVENTION

The present invention is based on the finding that prostate stem cell antigen (PSCA) chimeric antigen receptor (CAR) T cells exhibit potent anti-tumor activity. The present invention is also based on the finding that bispecific CARs and dual CARs capable of binding PSCA and prostate specific membrane antigen (PSMA) exhibit significantly enhanced anti-tumor activity.

Accordingly, in certain aspects, the instant disclosure provides a chimeric antigen receptor (CAR) comprising an antigen binding domain capable of binding prostate stem cell antigen (PSCA), a transmembrane domain, and an intracellular domain.

In certain exemplary embodiments, the CAR is capable of binding prostate stem cell antigen (PSCA), and comprises an amino acid sequence at least 80%, 85%, 90%, 95%, 96%, 97%, 98%, 99%, or 100% identical to SEQ ID NO: 21, 23, 25, or 27.

In another aspect, the instant disclosure provides a bispecific chimeric antigen receptor (CAR) comprising an extracellular domain comprising an antigen-binding domain capable of binding prostate stem cell antigen (PSCA), and an antigen-binding domain capable of binding prostate specific membrane antigen (PSMA), a transmembrane domain, and an intracellular domain.

In certain exemplary embodiments, the CAR is capable of binding prostate stem cell antigen (PSCA) and prostate specific membrane antigen (PSMA), and comprises an amino acid sequence at least 80%, 85%, 90%, 95%, 96%, 97%, 98%, 99%, or 100% identical to SEQ ID NO: 40, 42, 80, 81, or 82.

In another aspect, the instant disclosure provides a nucleic acid comprising a polynucleotide sequence encoding a CAR, wherein the CAR is capable of binding prostate stem cell antigen (PSCA), and comprises an amino acid sequence at least 80%, 85%, 90%, 95%, 96%, 97%, 98%, 99%, or 100% identical to SEQ ID NO: 21, 23, 25, or 27.

In certain exemplary embodiments, the CAR is capable of binding prostate stem cell antigen (PSCA), and is encoded by a polynucleotide sequence at least 80%, 85%, 90%, 95%, 96%, 97%, 98%, 99%, or 100% identical to SEQ ID NO: 20, 22, 24, or 26.

In another aspect, the instant disclosure provides a nucleic acid comprising a polynucleotide sequence encoding a bispecific CAR, wherein the CAR is capable of binding prostate stem cell antigen (PSCA) and prostate specific membrane antigen (PSMA), and comprises an amino acid sequence at least 80%, 85%, 90%, 95%, 96%, 97%, 98%, 99%, or 100% identical to SEQ ID NO: 40, 42, 80, 81, or 82.

In certain exemplary embodiments, the bispecific CAR is encoded by a polynucleotide sequence at least 80%, 85%, 90%, 95%, 96%, 97%, 98%, 99%, or 100% identical to SEQ ID NO: 39 or 41 or 79.

In another aspect, the instant disclosure provides a vector comprising a nucleic acid comprising a polynucleotide sequence encoding a CAR, wherein the CAR is capable of binding prostate stem cell antigen (PSCA), and is encoded by a polynucleotide sequence at least 80%, 85%, 90%, 95%, 96%, 97%, 98%, 99%, or 100% identical to SEQ ID NO: 20, 22, 24, or 26.

In another aspect, the instant disclosure provides a vector comprising a nucleic acid comprising a polynucleotide sequence encoding a bispecific CAR, wherein the CAR is capable of binding prostate stem cell antigen (PSCA) and prostate specific membrane antigen (PSMA), and wherein the bispecific CAR is encoded by a polynucleotide sequence at least 80%, 85%, 90%, 95%, 96%, 97%, 98%, 99%, or 100% identical to SEQ ID NO: 39 or 41 or 79.

In certain exemplary embodiments, the vector is an expression vector.

In another aspect, the instant disclosure provides a modified immune cell or precursor cell thereof comprising a CAR, wherein the CAR is capable of binding prostate stem cell antigen (PSCA), and comprises an amino acid sequence at least 80%, 85%, 90%, 95%, 96%, 97%, 98%, 99%, or 100% identical to SEQ ID NO: 21, 23, 25, or 27.

In another aspect, the instant disclosure provides a modified immune cell or precursor cell thereof, comprising a bispecific CAR, wherein the bispecific CAR is capable of binding prostate stem cell antigen (PSCA) and prostate specific membrane antigen (PSMA), and comprises an amino acid sequence at least 80%, 85%, 90%, 95%, 96%, 97%, 98%, 99%, or 100% identical to SEQ ID NO: 40, 42, 80, 81, or 82.

In another aspect, the instant disclosure provides a modified immune cell or precursor cell thereof comprising a vector that comprises a nucleic acid comprising a polynucleotide sequence encoding a CAR, wherein the CAR is capable of binding prostate stem cell antigen (PSCA), and is encoded by a polynucleotide sequence at least 80%, 85%, 90%, 95%, 96%, 97%, 98%, 99%, or 100% identical to SEQ ID NO: 20, 22, 24, or 26.

In certain exemplary embodiments, the modified immune cell or precursor cell thereof further comprises a PSMA- CAR, wherein the PSMA-CAR comprises an antigen-binding domain, a transmembrane domain, and an intracellular domain.

In another aspect, the instant disclosure provides a pharmaceutical composition comprising a therapeutically effective amount of a modified immune cell or precursor cell thereof comprising a CAR, wherein the CAR is capable of binding prostate stem cell antigen (PSCA), and comprises an amino acid sequence at least 80%, 85%, 90%, 95%, 96%, 97%, 98%, 99%, or 100% identical to SEQ ID NO: 21, 23, 25, or 27.

In another aspect, the instant disclosure provides a method of treating a disease in a subject in need thereof, comprising administering to the subject an effective amount of a modified cell or precursor cell thereof comprising a CAR, wherein the CAR is capable of binding prostate stem cell antigen (PSCA), and comprises an amino acid sequence at least 80%, 85%, 90%, 95%, 96%, 97%, 98%, 99%, or 100% identical to SEQ ID NO: 21, 23, 25, or 27.

In certain exemplary embodiments, the disease is a cancer.

In certain exemplary embodiments, the disease is prostate cancer.

In certain exemplary embodiments, the subject is a human.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1 illustrates the generation of a prostate stem cell antigen (PSCA)-specific CAR. A PSCA CAR comprised of an scFv from a humanized anti-PSCA Ab (2B3) was constructed and cloned into retroviral vector MSGV.

FIG. 9A is a schematic of the bi-specific CAR vectors used for studies encoding the PSMA (with 2F5 scFv) and PSCA (with 2B3 scFv)-targeted CARs, linked with a Gly4Ser element. Abbreviations used in FIGS. 9A-9D: non-transduced (NTD); PSMA (2F5) CAR with 4-1BB and CD3z domains (2F5-BBZ); PSCA (2B3) CAR with 4-1BB and CD3z domains (2B3-BBZ); PSMA (2F5) and PSCA (2B3) bispecific CAR with 4-1BB and CD3z domains (2F5-S-2B3-BBZ; Gly4Ser linker); PSMA (2F5) and PSCA (2B3) bispecific CAR with 4-1BB and CD3z domains (2F5-S-2B3-BBZ; (Gly4Ser)4 linker); PSCA (2B3) and PSMA (2F5) bispecific CAR with 4-1BB and CD3z domains (2B3-S-2F5-BBZ; Gly4Ser linker); PSCA (2B3) and PSMA (2F5) bispecific CAR with 4-1BB and CD3z domains (2B3-L-2F5-BBZ; (Gly4Ser)4 linker).

FIG. 9B illustrates surface expression of the CARs on lentivirus transduced CAR T cells at the end of the primary expansion.

FIG. 9C illustrates the percentage of lentivirus transduced CAR T cells that express the PSMA or PSCA-CAR, or PSMA-PSCA bispecific CAR staining with human recombinant PSMA-Fc and PSCA-His protein, as measured through flow cytometry.

FIG. 10A illustrates results from CAR T cells co-cultured with PC3-PSCA cells (Effector:Target ratio=1:1). Supernatants were obtained 24 hours after co-culture, and cytokine production was analyzed by ELISA. Abbreviations used in FIGS. 10A-10D are the same as used in FIGS. 9A-9D.

FIG. 10D illustrates results from T cells tested for their cytolytic activity at indicated E:T ratios for 8 hours against PC3-PSMA cells.

FIGS. 11A-11B illustrate the finding that TGFbR-IL12R switch receptors can boost T cell function. FIG. 11A, upper right panel, shows IFN-gamma production of NK cells transferred with TGFbR-IL12R co-cultured with K562, with or without TGFb1 in the cutures. FIG. 11A, lower right panel, shows pSmad staining of T cells transferred with TGFbR-IL12R switch receptors after stimulation with TGF beta. FIG. 11B shows cytokine production of NY-ESO-1 positive tumors stimulated NY-ESO-1 TCR transduced T cells, co-transferred with TGFbR-IL12R switch receptors.

DETAILED DESCRIPTION

Figure 2:
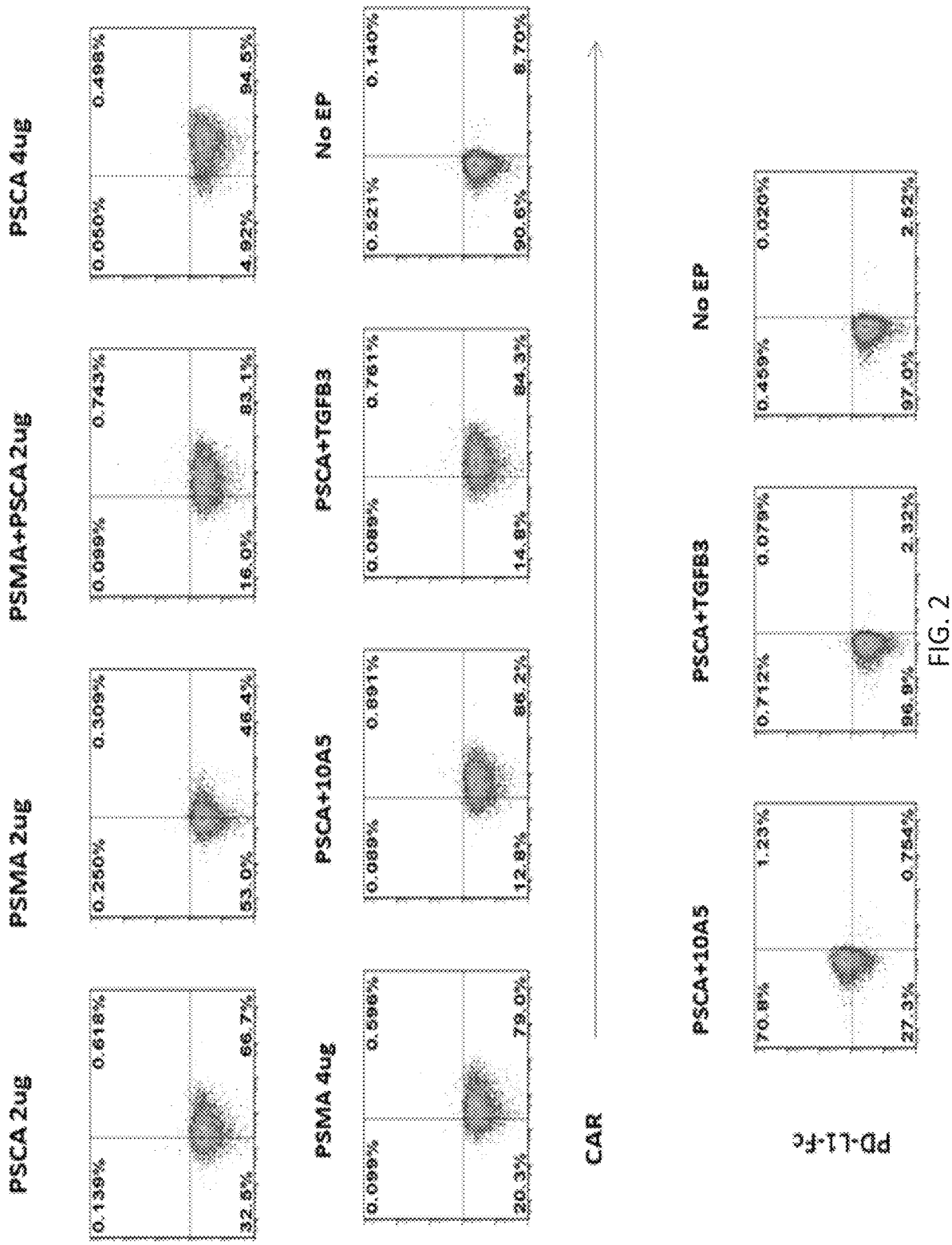
FIG. 2 illustrates CAR expression of T cells electroporated with in vitro transcribed RNA of a PSCA CAR with 4-1BB and CD3z domains (2B3.BBZ) and/or a PSMA CAR with 4-1BB and CD3z domains (J591.BBZ) (upper panel), and PD-L1-Fc staining of a PSCA CAR co-electroporated with bispecific antibody 10A5-1412 (an aPDL1-aCD28 bispecific Ab; indicated as 10A5) or TGFB3-1412 (an aTGFbRII-aCD28 bispecific Ab; indicated as TGFB3).

The present invention provides compositions and methods for modified immune cells or precursors thereof (e.g., modified T cells) comprising chimeric antigen receptors (CARs) capable of binding prostate stem cell antigen (PSCA). In certain embodiments, the invention provides compositions and methods for modified immune cells or precursors thereof comprising bispecific CARs (e.g PSCA & PSMA), PSCA CARs with a dominant negative receptor (e.g., TGFbRDN), PSCA CARs with a switch receptor (e.g., PD1/CD28 or TGFbR/IL12R), and PSCA CARs in combination with bispecific antibodies (e.g., PD-L1/CD28). The provided compositions and methods are useful for treating cancer (e.g. prostate cancer).

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or 10%, more preferably +5%, even more preferably 1%, and still more preferably 0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MIIC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Antigen Receptors

The present invention provides chimeric antigen receptors (CARs) capable of binding prostate stem cell antigen (PSCA). In certain embodiments, a subject CAR comprises an antigen binding domain capable of binding PSCA, a transmembrane domain, and an intracellular domain. In another aspect, the invention includes a bispecific CAR comprising an extracellular domain comprising an antigen-binding domain capable of binding prostate stem cell antigen (PSCA) and an antigen-binding domain capable of binding prostate specific membrane antigen (PSMA), a transmembrane domain, and an intracellular domain.

Also provided are compositions and methods for modified immune cells or precursors thereof, e.g., modified T cells, comprising the CAR. Thus, in some embodiments, the immune cell has been genetically modified to express the CAR. Nucleic acids encoding said CARs, vectors encoding said nucleic acids, and modified cells (e.g. modified T cells) comprising said CARs, vectors, or nucleic acids, are also provided.

A subject CAR of the invention comprises an antigen binding domain capable of binding PSCA, a transmembrane domain, and an intracellular domain. A subject CAR of the invention may optionally comprise a hinge domain. Accordingly, a subject CAR of the invention comprises an antigen binding domain capable of binding PSCA, a hinge domain, a transmembrane domain, and an intracellular domain. A subject bispecific CAR of the invention comprises an extracellular domain comprising an antigen-binding domain capable of binding prostate stem cell antigen (PSCA) and an antigen-binding domain capable of binding prostate specific membrane antigen (PSMA). In embodiments where the CAR is a bispecific CAR, the antigen-binding domain capable of binding PSCA is linked to the antigen-binding domain capable of binding PSMA. In some embodiments, the PSCA antigen-binding domain may be N-terminal to the PSMA antigen-binding domain. In some embodiments, the PSMA antigen-binding domain may be N-terminal the PSCA antigen-binding domain. The C-terminal antigen binding domain of a bispecific CAR of the invention may be operably linked to another domain of the CAR as described herein.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a hinge domain as described herein. A subject CAR of the present invention may also include a spacer domain as described herein. In some embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. A subject CAR of the invention comprises an antigen binding domain capable of binding prostate stem cell antigen (PSCA).

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

In some embodiments, the antigen binding domain is selected from the group consisting of an antibody, an antigen binding fragment (Fab), and a single-chain variable fragment (scFv). In some embodiments, a PSCA binding domain of the present invention is selected from the group consisting of a PSCA-specific antibody, a PSCA-specific Fab, and a PSCA-specific scFv. In one embodiment, a PSCA binding domain is a PSCA-specific antibody. In one embodiment, a PSCA binding domain is a PSCA-specific Fab. In one embodiment, a PSCA binding domain is a PSCA-specific scFv.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., PSCA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:119), $(GGGS)_n$ (SEQ ID NO:120), and $(GGGGS)_n$ (SEQ ID NO:121), where n represents an integer of at least 1. Exemplary linker sequences can comprise amino acid sequences including, without limitation, GGSG (SEQ ID NO:122), GGSGG (SEQ ID NO:123), GSGSG (SEQ ID NO:124), GSGGG (SEQ ID NO:125), GGGSG (SEQ ID NO:126), GSSSG (SEQ ID NO:127), GGGGS (SEQ ID NO:128), GGGGSGGGGSGGGGS (SEQ ID NO:129) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:129), which may be encoded by the nucleic acid sequence GGTGGCGGTGGCTCGGGCGGTGGTGGGTCGGGTG-GCGGCGGATCT (SEQ ID NO:130).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof.

In certain embodiments, the antigen binding domain capable of binding prostate stem cell antigen (PSCA) comprises a heavy chain variable region that comprises three heavy chain complementarity determining regions (HCDRs). HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3). The antigen binding domain capable of binding prostate stem cell antigen (PSCA) also comprises a light chain variable region that comprises three light chain complementarity determining regions (LCDRs). In certain embodiments, LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6).

In certain embodiments, the heavy chain variable region (VH) of the antigen binding domain capable of binding prostate stem cell antigen (PSCA) comprises an amino acid sequence at least 80%, 85%, 90%, 95%, 96%, 97%, 98%, 99%, or 100% identical to SEQ ID NO: 7 and/or the light chain variable region (VH) comprises an amino acid sequence at least 80%, 85%, 90%, 95%, 96%, 97%, 98%, 99%, or 100% identical to SEQ ID NO: 8.

In certain embodiments, the antigen binding domain capable of binding prostate stem cell antigen (PSCA) is selected from the group consisting of a full length antibody or antigen-binding fragment thereof, a Fab, a single-chain variable fragment (scFv), or a single-domain antibody. In certain embodiments, the antigen binding domain is a single-chain variable fragment (scFv) comprising an amino acid sequence at least 80%, 85%, 90%, 95%, 96%, 97%, 98%, 99%, or 100% identical to SEQ ID NO: 9.

Tolerable variations of the antigen binding domain sequences will be known to those of skill in the art. For example, in some embodiments the antigen-binding domain capable of binding prostate stem cell antigen (PSCA) comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 1, 2, 3, 4, 5, 6, 7, 8, or 9.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In certain aspects, the invention includes a bispecific CAR comprising an extracellular domain comprising an antigen-binding domain capable of binding prostate stem cell antigen (PSCA) and an antigen-binding domain capable of binding prostate specific membrane antigen (PSMA), a transmembrane domain, and an intracellular domain.

In certain embodiments, the antigen binding domain capable of binding PSCA comprises a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPE-NGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The antigen binding domain capable of binding PSMA comprises a second heavy chain variable region that comprises three heavy chain complementarity determining regions (HCDRs), wherein HCDR1 comprises the amino acid sequence SNWIG (SEQ ID NO: 28), HCDR2 comprises the amino acid sequence IIYPGDSDT-RYSPSFQG (SEQ ID NO: 29), and HCDR3 comprises the amino acid sequence QTGFLWSFDL (SEQ ID NO: 30); and a second light chain variable region that comprises three light chain complementarity determining regions (LCDRs), wherein LCDR1 comprises the amino acid sequence RASQ-DISSALA (SEQ ID NO: 31), LCDR2 comprises the amino acid sequence DASSLES (SEQ ID NO: 32), and LCDR3 comprises the amino acid sequence QQFNSYPLT (SEQ ID NO: 33).

In certain embodiments, the antigen binding domain capable of binding PSCA comprises a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6) and the antigen binding domain capable of binding PSMA comprises a second heavy chain variable region that comprises three heavy chain complementarity determining regions (HCDRs), wherein HCDR1 comprises the amino acid sequence EYTIH (SEQ ID NO: 68), HCDR2 comprises the amino acid sequence NINPNNGGT-TYNQKFED (SEQ ID NO: 69), HCDR3 comprises the amino acid sequence GWNFDY (SEQ ID NO: 70); and a second light chain variable region that comprises three light chain complementarity determining regions (LCDRs), wherein LCDR1 comprises the amino acid sequence KASQDVGTAVD (SEQ ID NO: 71), LCDR2 comprises the amino acid sequence WASTRHT (SEQ ID NO: 72), and LCDR3 comprises the amino acid sequence QQYNSYPLT (SEQ ID NO: 73).

In certain embodiments, the bispecific CAR comprises a first heavy chain variable region comprising an amino acid sequence at least 60%, 65%, 70%, 75%, 80%, 85%, 90%, 95%, 96%, 97%, 98%, 99%, or 100% identical to SEQ ID NO: 7 and a first light chain variable region comprising an amino acid sequence at least 60%, 65%, 70%, 75%, 80%, 85%, 90%, 95%, 96%, 97%, 98%, 99%, or 100% identical to SEQ ID NO: 8 and/or a second heavy chain variable region comprising an amino acid sequence at least 60%, 65%, 70%, 75%, 80%, 85%, 90%, 95%, 96%, 97%, 98%, 99%, or 100% identical to SEQ ID NO: 34 and a second light chain variable region comprising an amino acid sequence at least 60%, 65%, 70%, 75%, 80%, 85%, 90%, 95%, 96%, 97%, 98%, 99%, or 100% identical to SEQ ID NO: 35.

In certain embodiments, the bispecific CAR comprises a first heavy chain variable region comprising an amino acid sequence at least 60%, 65%, 70%, 75%, 80%, 85%, 90%, 95%, 96%, 97%, 98%, 99%, or 100% identical to SEQ ID NO: 7 and a first light chain variable region comprising an amino acid sequence at least 60%, 65%, 70%, 75%, 80%, 85%, 90%, 95%, 96%, 97%, 98%, 99%, or 100% identical to SEQ ID NO: 8 and/or a second heavy chain variable region comprising an amino acid sequence at least 60%, 65%, 70%, 75%, 80%, 85%, 90%, 95%, 96%, 97%, 98%, 99%, or 100% identical to SEQ ID NO: 75 and a second light chain variable region comprising an amino acid sequence at least 60%, 65%, 70%, 75%, 80%, 85%, 90%, 95%, 96%, 97%, 98%, 99%, or 100% identical to SEQ ID NO: 77.

In certain embodiments, the antigen binding domain capable of binding PSCA is a single-chain variable fragment (scFv) comprising an amino acid sequence at least 60%, 65%, 70%, 75%, 80%, 85%, 90%, 95%, 96%, 97%, 98%, 99%, or 100% identical to SEQ ID NO: 9 and/or the antigen-binding domain capable of binding PSMA is a single-chain variable fragment (scFv) comprising an amino acid sequence at least 60%, 65%, 70%, 75%, 80%, 85%, 90%, 95%, 96%, 97%, 98%, 99%, or 100% identical to SEQ ID NO: 36, 78, 84, or 85.

In certain embodiments, the bispecific CAR comprises an extracellular domain comprising an antigen-binding domain capable of binding PSCA and an antigen-binding domain capable of binding PSMA, wherein the extracellular domain comprises the amino acid sequence at least at least 60%, 65%, 70%, 75%, 80%, 85%, 90%, 95%, 96%, 97%, 98%, 99%, or 100% identical to identical to the amino acid sequence set forth in SEQ ID NO: 50 or 52.

In certain embodiments, the antigen binding domain capable of binding PSCA and the antigen-binding domain capable of binding PSMA are separated by a linker. Any linker known in the art may be used to separate the antigen-binding domain capable of binding PSCA and the antigen-binding domain capable of binding PSMA. In certain embodiments, the linker comprises the amino acid sequence set forth in SEQ ID NO: 37 or 38.

Additional PSMA binders and CARS are described in PCT/US2019/020729, contents of which are incorporated by reference in their entirety herein. In certain embodiments, the antigen binding domain capable of binding PSMA comprises a heavy chain variable region comprising an amino acid sequence at least 60%, 65%, 70%, 75%, 80%, 85%, 90%, 95%, 96%, 97%, 98%, 99%, or 100% identical to SEQ ID NO: 75. In certain embodiments, the antigen binding domain capable of binding PSMA comprises a light chain variable region comprising an amino acid sequence at least 60%, 65%, 70%, 75%, 80%, 85%, 90%, 95%, 96%, 97%, 98%, 99%, or 100% identical to SEQ ID NO: 77. In certain embodiments, the antigen-binding domain capable of binding PSMA is a single-chain variable fragment (scFv) comprising an amino acid sequence at least 60%, 65%, 70%, 75%, 80%, 85%, 90%, 95%, 96%, 97%, 98%, 99%, or 100% identical to SEQ ID NO: 36, 78, or 84.

In certain embodiments, the antigen binding domain capable of binding PSMA comprises any of the heavy and light chain variable regions disclosed in PCT Publication Nos. WO2017212250A1 and WO2018033749A1, the disclosures of which are hereby incorporated herein by reference in their entirety. For example, an antigen binding domain capable of binding PSMA can comprise an scFv comprising any of the heavy and light chain variable regions disclosed therein. Accordingly, a bispecific CAR or PSMA-CAR of the present invention comprises an antigen binding domain capable of binding PSMA can comprise any scFv and any heavy and light chain variable regions as disclosed in WO2017212250A1 and WO2018033749A1.

In certain embodiments, an antigen binding domain capable of binding PSMA can comprise a heavy chain variable region and a light chain variable region of any of those set forth in Table 1:

TABLE 1

| Heavy Chain Variable Region Sequences | Light Chain Variable Region Sequences |
|---|---|
| VH Consensus Sequence<br>SEQ ID NO: 101<br>EVQLVQSGX$_1$EX$_2$KKPGASVKVSCKX$_3$<br>SGYTFTEYTIHWVX$_4$QAX$_5$GKGLEWIG<br>NINPNX$_6$GGTTYNQKFEDRX$_7$TX$_8$TVD<br>KSTSTAYMELSSLRSEDTAVYYCAAG<br>WNFDYWGQGTTVTVSS<br>wherein:<br>X$_1$ is A or P;<br>X$_2$ is V or L;<br>X$_3$ is A or T;<br>X$_4$ is R or K;<br>X$_5$ is P or H;<br>X$_6$ is N or Q;<br>X$_7$ is V or A; and<br>X$_8$ is I or L. | VL Consensus Sequence<br>SEQ ID NO: 102<br>DIX$_1$MTQSPSX$_2$LSASVGDRVTITCKASQDV<br>GTAVDWYQQKPGQAPKLLIYWASTRHTG<br>VPDRFX$_3$GSGSGTDFTLTISRLQX$_4$EDFAX$_5$Y<br>X$_6$CQQYNSYPLTFGQGTX$_7$VDIK<br>wherein:<br>X$_1$ is Q or V;<br>X$_2$ is T or F;<br>X$_3$ iS S or T;<br>X$_4$ is P or S;<br>X$_5$ is V or D;<br>X$_6$ is Y or F; and<br>X$_7$ is K or M. |
| SEQ ID NO: 103<br>EVQLVQSGPELKKPGASVKVSCKTSG<br>YTFTEYTIHWVKQAHGKGLEWIGNIN<br>PNNGGTTYNQKFEDRATLTVDKSTST<br>AYMELSSLRSEDTAVYYCAAGWNFD<br>YWGQGTTVTVSS | SEQ ID NO: 104<br>DIVMTQSPSFLSASVGDRVTITCKASQDVG<br>TAVDWYQQKPGQAPKLLIYWASTRHTGV<br>PDRFTGSGSGTDFTLTISRLQSEDFADYFCQ<br>QYNSYPLTFGQGTMVDIK |
| SEQ ID NO: 105<br>EVQLVQSGAEVKKPGASVKVSCKTSG<br>YTFTEYTIHWVKQAPGKGLEWIGNIN<br>PNNGGTTYNQKFEDRATITVDKSTST<br>AYMELSSLRSEDTAVYYCAAGWNFD<br>YWGQGTTVTVSS | SEQ ID NO: 106<br>DIVMTQSPSTLSASVGDRVTITCKASQDVG<br>TAVDWYQQKPGQAPKLLIYWASTRHTGV<br>PDRFTGSGSGTDFTLTISRLQSEDFADYFCQ<br>QYNSYPLTFGQGTKVDIK |

TABLE 1-continued

| Heavy Chain Variable Region Sequences | Light Chain Variable Region Sequences |
|---|---|
| SEQ ID NO: 107<br>EVQLVQSGAEVKKPGASVKVSCKTSG<br>YTFTEYTIHWVRQAPGKGLEWIGNIN<br>PNNGGTTYNQKFEDRATITVDKSTST<br>AYMELSSLRSEDTAVYYCAAGWNFD<br>YWGQGTTVTVSS | SEQ ID NO: 108<br>DIVMTQSPSTLSASVGDRVTITCKASQDVG<br>TAVDWYQQKPGQAPKLLIYWASTRHTGV<br>PDRFSGSGSGTDFTLTISRLQPEDFADYYCQ<br>QYNSYPLTFGQGTKVDIK |
| SEQ ID NO: 75<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAAGWNF<br>DYWGQGTTVTVSS | SEQ ID NO: 77<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QYNSYPLTFGQGTKVDIK |
| SEQ ID NO: 109<br>EVQLVQSGAEVKKPGASVKVSCKAS<br>GYTFTEYTIHWVRQAPGKGLEWIGNI<br>NPNQGGTTYNQKFEDRVTITVDKSTS<br>TAYMELSSLRSEDTAVYYCAAGWNF<br>DYWGQGTTVTVSS | |
| VH Consensus Sequence<br>SEQ ID NO: 110<br>EVQLVQSGX$_1$EX$_2$KKPGASVKVSCKX$_3$<br>SGYTFTEYTIHWVX$_4$QAX$_5$GKGLEWIG<br>NINPNX$_6$GGTTYNQKFEDRX$_7$TX$_8$TVD<br>KSTSTAYMELSSX$_9$RSEDTAVYYCAX$_{10}$<br>X$_{11}$X$_{12}$X$_{13}$X$_{14}$DYWGQGTTVTVSS<br>wherein:<br>X$_1$ is A or P;<br>X$_2$ is V or L;<br>X$_3$ is A or T;<br>X$_4$ is R or K;<br>X$_5$ is P or H;<br>X$_6$ is N or Q;<br>X$_7$ is V or A;<br>X$_7$ is I or L;<br>X$_9$ is L or P; and<br>X$_{10}$-X$_{14}$ is AYWLF, GGWTF, or GAWTM. | VL Consensus Sequence<br>SEQ ID NO: 111<br>DIX$_1$MTQSPSX$_2$LSASVGDRVTITCKASQDV<br>GTAVDWYQQKPGQAPKLLIYWASTRHTG<br>VPDRFX$_3$GSGSGTDFTLTISRLQX$_4$EDFAX$_5$Y<br>X$_6$CQQX$_7$X$_8$X$_9$X$_{10}$X$_{11}$LTFGQGTX$_{12}$VDIK<br>wherein:<br>X$_1$ is Q or V;<br>X$_2$ is T or F;<br>X$_3$ is S or T;<br>X$_4$ is P or S;<br>X$_5$ is V or D;<br>X$_6$ is Y or F;<br>X$_7$-X$_{11}$ is FTRYP or YNAYS; and<br>X$_{12}$ is K or M. |
| SEQ ID NO: 112<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAAYWLF<br>DYWGQGTTVTVSS | SEQ ID NO: 113<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QYNSYPLTFGQGTKVDIK |
| SEQ ID NO: 114<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAGGWTF<br>DYWGQGTTVTVSS | SEQ ID NO: 115<br>DIQMTQSPSTLSASVGDRVTITCKASQDVG<br>TAVDWYQQKPGQAPKLLIYWASTRHTGV<br>PDRFSGSGSGTDFTLTISRLQPEDFAVYYCQ<br>QFTRYPLTFGQGTKVDIK |
| SEQ ID NO: 116<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSLRSEDTAVYYCAGAWTM<br>DYWGQGTTVTVSS | SEQ ID NO: 117<br>DIQMTQSPSTLSASVGDRVTITCKASQDVG<br>TAVDWYQQKPGQAPKLLD(WASTRHTGV<br>PDRFSGSGSGTDFTLTISRLQPEDFAVYYCQ<br>QYNAYSLTFGQGTKVDIK |
| SEQ ID NO: 118<br>EVQLVQSGAEVKKPGASVKVSCKAS<br>GYTFTEYTIHWVRQAPGKGLEWIGNI<br>NPNNGGTTYNQKFEDRVTITVDKSTS<br>TAYMELSSPRSEDTAVYYCAAGWNF<br>DYWGQGTTVTVSS | |

Transmembrane Domain

CARs of the present invention (including bispecific CARs) may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1B), CD154 (CD40L), ICOS (CD278), Toll-like receptor 1 (TLR1), TLR2, TLR3, TLR4, TLR5, TLR6, TLR7, TLR8, TLR9, or a transmembrane domain derived from a killer immunoglobulin-like receptor (KR).

In certain embodiments, the transmembrane domain comprises a transmembrane domain of CD8. In certain embodiments, the transmembrane domain of CD8 is a transmembrane domain of CD8 alpha. In certain embodiments, the transmembrane domain the transmembrane domain of CD8 comprises the amino acid sequence set forth in SEQ ID NO: 11. In certain embodiments, the transmembrane domain comprises a transmembrane domain of CD28. In certain embodiments, the transmembrane domain of CD28 comprises the amino acid sequence set forth in SEQ ID NO: 12. In certain embodiments, the transmembrane domain comprises a transmembrane domain of ICOS. In certain embodiments, the transmembrane domain of ICOS comprises the amino acid sequence set forth in SEQ ID NO: 13.

In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure (including a bispecific CAR) includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., Cancer Immunol. Res. (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:119) and $(GGGS)_n$ (SEQ ID NO:120), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, Rev. Computational. Chem. (1992) 2: 73-142). Exemplary hinge regions can comprise amino acid sequences including, but not limited to, GGSG (SEQ ID NO:122), GGSGG (SEQ ID NO:123), GSGSG (SEQ ID NO:124), GSGGG (SEQ ID NO:125), GGGSG (SEQ ID NO:126), GSSSG (SEQ ID NO:127), and the like.

In some embodiments, the hinge region is an immunoglobulin heavy chain hinge region.

Immunoglobulin hinge region amino acid sequences are known in the art; see, e.g., Tan et al., *Proc. Nat. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT (SEQ ID NO:131); CPPC (SEQ ID NO:132); CPEPKSCDTPPPCPR (SEQ ID NO:133) (see, e.g., Glaser et al., *J. Biol. Chem.* (2005) 280:41494-41503); ELKTPLGDTTHT (SEQ ID NO:134); KSCDKTHTCP (SEQ ID NO:135); KCCVDCP (SEQ ID NO:136); KYGPPCP (SEQ ID NO:137); EPKSCDKTHTCPPCP (SEQ ID NO:138) (human IgG1 hinge); ERKCCVECPPCP (SEQ ID NO:139) (human IgG2 hinge); ELKTPLGDTTHTCPRCP (SEQ ID NO:140) (human IgG3 hinge); SPNMVPHAHHAQ (SEQ ID NO:141) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:142); see, e.g., Yan et al., *J. Biol. Chem.* (2012) 287: 5891-5897.

In certain embodiments, the hinge region can comprise an amino acid sequence derived from human CD8, or a variant thereof. In certain embodiments, the CAR comprises a CD8 alpha hinge sequence comprising the amino acid sequence set forth in SEQ ID NO: 10. In certain embodiments, the CAR comprises a hinge sequence comprising the amino acid sequence set forth in SEQ ID NO: 99. In certain embodiments, the CAR comprises a hinge sequence comprising the amino acid sequence set forth in SEQ ID NO: 100.

Intracellular Domain

A subject CAR of the present invention (including a subject bispecific CAR) also includes an intracellular domain. In certain embodiments, the intracellular domain comprises a costimulatory signaling domain and an intracellular signaling domain. The intracellular domain of the CAR is responsible for activation of at least one of the effector functions of the cell in which the CAR is expressed (e.g., immune cell). The intracellular domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include, without limitation, the ζ chain of the T cell receptor complex or any of its homologs, e.g., η chain, FcsRIγ and β chains, MB 1 (Igα) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In certain embodiments, the intracellular domain of the CAR includes any portion of one or more co-stimulatory molecules, such as at least one signaling domain from CD2, CD3, CD8, CD27, CD28, ICOS (CD278), 4-1BB, PD-1, any derivative or variant thereof, any synthetic sequence thereof that has the same functional capability, and any combination thereof the intracellular domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR).

Further, variant intracellular signaling domains suitable for use in a subject CAR are known in the art. The YMFM motif is found in ICOS and is a SH2 binding motif that recruits both p85 and p50alpha subunits of PI3K, resulting in enhanced AKT signaling. See, e.g., Simpson et al. (2010) *Curr. Opin. Immunol.*, 22:326-332. In one embodiment, a CD28 intracellular domain variant may be generated to comprise a YMFM motif. The YMNM motif is found in the CD28 cytoplasmic domain and is a known binding site for phosphatidylinositol 3-kinase (PI3-K) and Grb2. See, Harada et al. (2003) *J. Exp. Med.*, 197(2):257-262. In one embodiment, an ICOS intracellular domain variant may be generated to comprise a YMNM motif.

In certain embodiments, the intracellular domain comprises a costimulatory domain of 4-1BB. In certain embodiments, the costimulatory domain of 4-1BB comprises the amino acid sequence set forth in SEQ ID NO: 14. In certain embodiments, the intracellular domain comprises a costimulatory domain of CD28. In certain embodiments, the costimulatory domain of CD28 comprises the amino acid sequence set forth in SEQ ID NO: 15. In certain embodiments, the intracellular domain comprises a costimulatory domain of ICOS. In certain embodiments, the costimulatory domain of ICOS comprises the amino acid sequence set forth in SEQ ID NO: 16. In certain embodiments, the intracellular domain comprises a costimulatory domain of ICOS(YMNM). In certain embodiments, the costimulatory domain of ICOS(YMNM) comprises the amino acid sequence set forth in SEQ ID NO: 17.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD1ib, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP12 (see, e.g., Topfer et al., J. Immunol. (2015) 194(7): 3201-3212), NKG2D, NKp44, NKp46, DAP10, and CD3z.

In certain embodiments, the intracellular domain comprises an intracellular signaling domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain embodiments, the intracellular domain comprises an intracellular domain of CD3ζ or a variant thereof. In certain embodiments, the intracellular domain of CD3ζ comprises the amino acid sequence set forth in 18 or 19.

Intracellular domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular domain includes at least one (e.g., one, two, three, four, five, six, etc.) ITAM motif as described below. In some embodiments, the intracellular domain includes DAP10/CD28 type signaling chains. In some embodiments, the intracellular domain is not covalently attached to the membrane bound CAR, but is instead diffused in the cytoplasm.

Intracellular domains suitable for use in a subject CAR of the present invention include immunoreceptor tyrosine-based activation motif (ITAM)-containing intracellular signaling polypeptides. In some embodiments, an ITAM motif is repeated twice in an intracellular domain, where the first and second instances of the ITAM motif are separated from one another by 6 to 8 amino acids. In one embodiment, the intracellular domain of a subject CAR comprises 3 ITAM motifs.

In some embodiments, intracellular domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular domain can be an ITAM motif-containing portion that is derived from a polypeptide that contains an ITAM motif. For example, a suitable intracellular domain can be an ITAM motif-containing domain from any ITAM motif-containing protein. Thus, a suitable intracellular domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). In one embodiment, the intracellular domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular domain suitable for use in an FN3 CAR of the present disclosure includes a DAP10/CD28 type signaling chain. In one embodiment, an intracellular domain suitable for use in an FN3 CAR of the present disclosure includes a ZAP70 polypeptide. In some embodiments, the intracellular domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular domain in the CAR includes a cytoplasmic signaling domain of human CD3 zeta.

While usually the entire intracellular domain can be employed, in many cases it is not necessary to use the entire chain. To the extent that a truncated portion of the intracellular domain is used, such truncated portion may be used in place of the intact chain as long as it transduces the effector function signal. The intracellular domain includes any truncated portion of the intracellular domain sufficient to transduce the effector function signal.

The intracellular domains described herein can be combined with any of the antigen binding domains described herein, any of the transmembrane domains described herein, or any of the other domains described herein that may be included in the CAR.

Tolerable variations of the individual CAR domain sequences (hinge, transmembrane, and intracellular domains) will be known to those of skill in the art. For example, in some embodiments the CAR domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 10, 11, 12, 13, 14, 15, 16, 17, 18, 19, 99, and 100.

In one aspect, the invention provides a chimeric antigen receptor (CAR) capable of binding prostate stem cell antigen (PSCA), comprising an antigen-binding domain, a transmembrane domain, and an intracellular domain, wherein the antigen-binding domain comprises a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 8.

In one aspect, the invention provides a chimeric antigen receptor (CAR) capable of binding prostate stem cell antigen (PSCA), comprising an amino acid sequence at least 80%, 85%, 90%, 95%, 96%, 97%, 98%, 99%, or 100% identical to SEQ ID NO: 9.

In one aspect, the invention provides a chimeric antigen receptor (CAR) capable of binding prostate stem cell antigen (PSCA), comprising an amino acid sequence at least 80%, 85%, 90%, 95%, 96%, 97%, 98%, 99%, or 100% identical to SEQ ID NO: 21, 23, 25, or 27. Tolerable variations of the CAR sequences will be known to those of skill in the art. For example, in some embodiments the CAR comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 21, 23, 25, or 27.

In one aspect, the invention provides a chimeric antigen receptor (CAR) capable of binding prostate specific membrane antigen (PSMA), comprising an amino acid sequence at least 80%, 85%, 90%, 95%, 96%, 97%, 98%, 99%, or 100% identical to SEQ ID NO: 67, 87, 89, 91, 93, 95, or 97. Tolerable variations of the CAR sequences will be known to those of skill in the art. For example, in some embodiments the CAR comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence set forth in SEQ ID NO: 67, 87, 89, 91, 93, 95, or 97.

In one aspect, the invention provides a bispecific chimeric antigen receptor (CAR) comprising an extracellular domain comprising an antigen-binding domain capable of binding prostate stem cell antigen (PSCA) and an antigen-binding domain capable of binding prostate specific membrane antigen (PSMA), a transmembrane domain, and an intracellular domain.

In one aspect, the invention provides a bispecific CAR, wherein the extracellular domain comprises an antigen-binding domain capable of binding PSCA and an antigen-binding domain capable of binding PSMA, wherein the bispecific CAR comprises the amino acid sequence set forth in SEQ ID NO: 40, 42, or 80-82. Tolerable variations of the CAR sequences will be known to those of skill in the art. For example, in some embodiments the CAR comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 40, 42, or 80-82.

In one aspect, the invention provides a bispecific chimeric antigen receptor (CAR) capable of binding prostate stem cell antigen (PSCA) and prostate specific membrane antigen (PSMA), wherein the antigen binding domain capable of binding PSMA is a single-chain variable fragment (scFv) comprising an amino acid sequence at least 80%, 85%, 90%, 95%, 96%, 97%, 98%, 99%, or 100% identical to SEQ ID NO: 78, 84, or 85 and/or the antigen-binding domain capable of binding PSCA and an antigen-binding domain capable of binding PSMA comprises the amino acid sequence set forth in SEQ ID NO: 50 or 52.

In one aspect, the invention provides a bispecific chimeric antigen receptor (CAR) capable of binding prostate stem cell antigen (PSCA) and prostate specific membrane antigen (PSMA), comprising extracellular domain comprising an antigen binding domain capable of PSCA and an antigen-binding domain capable of binding PSMA, a transmembrane domain, and an intracellular domain. The antigen binding domain capable of binding PSCA comprises a heavy chain variable region comprising an amino acid sequence at least 80%, 85%, 90%, 95%, 96%, 97%, 98%, 99%, or 100% identical to SEQ ID NO: 7, and/or a light chain variable region comprising an amino acid sequence at least 80%, 85%, 90%, 95%, 96%, 97%, 98%, 99%, or 100% identical to SEQ ID NO: 8. The antigen-binding domain capable of binding PSMA comprises a heavy chain variable region comprising an amino acid sequence at least 80%, 85%, 90%, 95%, 96%, 97%, 98%, 99%, or 100% identical to SEQ ID NO: 34, and/or a light chain variable region comprising an amino acid sequence at least 80%, 85%, 90%, 95%, 96%, 97%, 98%, 99%, or 100% identical to SEQ ID NO: 35.

In one aspect, the invention provides a bispecific chimeric antigen receptor (CAR) capable of binding prostate stem cell antigen (PSCA) and prostate specific membrane antigen (PSMA), wherein the antigen binding domain capable of binding PSCA is a single-chain variable fragment (scFv) comprising an amino acid sequence at least 80%, 85%, 90%, 95%, 96%, 97%, 98%, 99%, or 100% identical to SEQ ID NO: 9 and/or the antigen binding domain capable of binding PSMA is a single-chain variable fragment (scFv) comprising an amino acid sequence at least 80%, 85%, 90%, 95%, 96%, 97%, 98%, 99%, or 100% identical to SEQ ID NO: 36.

In one aspect, the invention provides a bispecific chimeric antigen receptor (CAR) capable of binding prostate stem cell antigen (PSCA) and prostate specific membrane antigen (PSMA), comprising an extracellular domain comprising an antigen binding domain capable of PSCA and an antigen-binding domain capable of binding PSMA, a transmembrane domain, and an intracellular domain. The antigen binding domain capable of binding PSCA comprises a heavy chain variable region comprising an amino acid sequence at least 80%, 85%, 90%, 95%, 96%, 97%, 98%, 99%, or 100% identical to SEQ ID NO: 7, and a light chain variable region comprising an amino acid sequence at least 80%, 85%, 90%, 95%, 96%, 97%, 98%, 99%, or 100% identical to SEQ ID NO: 8. The antigen-binding domain capable of binding PSMA comprises a heavy chain variable region comprising an amino acid sequence at least 80%, 85%, 90%, 95%, 96%, 97%, 98%, 99%, or 100% identical to SEQ ID NO: 75, and a light chain variable region comprising an amino acid sequence at least 80%, 85%, 90%, 95%, 96%, 97%, 98%, 99%, or 100% identical to SEQ ID NO: 77.

In one aspect, the invention provides a bispecific CAR, wherein the extracellular domain comprises an antigen binding domain capable of binding PSCA comprising a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and/or a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6); and an antigen binding domain capable of binding PSMA comprising a second heavy chain variable region that comprises three heavy chain complementarity determining regions (HCDRs), wherein HCDR1 comprises the amino acid sequence SNWIG (SEQ ID NO: 28), HCDR2 comprises the amino acid sequence IIYPGDSDTRYSPSFQG (SEQ ID NO: 29), and HCDR3 comprises the amino acid sequence QTGFLWSFDL (SEQ ID NO: 30); and/or a second light chain variable region that comprises three light chain complementarity determining regions (LCDRs), wherein LCDR1 comprises the amino acid sequence RASQDISSALA (SEQ ID NO: 31), LCDR2 comprises the amino acid sequence DASSLES (SEQ ID NO: 32), and LCDR3 comprises the amino acid sequence QQFNSYPLT (SEQ ID NO: 33).

In one aspect, the invention provides a bispecific CAR, wherein the extracellular domain comprises an antigen binding domain capable of binding PSCA comprising a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and/or a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6); and the antigen binding domain capable of binding PSMA comprises a second heavy chain variable region that comprises three heavy chain complementarity determining regions (HCDRs), wherein HCDR1 comprises the amino acid sequence EYTIH (SEQ ID NO: 68), HCDR2 comprises the amino acid sequence NINPNNGGTTYNQKFED (SEQ ID NO: 69), and HCDR3 comprises the amino acid sequence GWNFDY (SEQ ID NO: 70); and/or a second light chain variable region that comprises three light chain complementarity determining regions (LCDRs), wherein LCDR1 comprises the amino acid sequence KASQDVGTAVD (SEQ ID NO: 71), LCDR2 comprises the amino acid sequence WASTRHT (SEQ ID NO: 72), and LCDR3 comprises the amino acid sequence QQYNSYPLT (SEQ ID NO: 73).

TABLE 2

Sequences used in the invention

| SEQ ID NO: Name | | Amino Acid/Nucleotide Sequence |
|---|---|---|
| 1 | PSCA 2B3 HCDR1 | DYYIH |
| 2 | PSCA 2B3 HCDR2 | WIDPENGDTEFVPKFQG |
| 3 | PSCA 2B3 HCDR3 | TGGF |
| 4 | PSCA 2B3 LCDR1 | SASSSVRFIHW |
| 5 | PSCA 2B3 LCDR2 | DTSKLAS |
| 6 | PSCA 2B3 LCDR3 | QQWSSSPFT |
| 7 | PSCA 2B3 VH | EVQLVESGGGLVQPGGSLRLSCAASGFNIKDYYIHWVRQAPGKGL EWVAWIDPENGDTEFVPKFQGRATISADTSKNTAYLQMNSLRAED TAVYYCKTGFWGQGTLVTVSS |
| 8 | PSCA 2B3 VL | DIQLTQSPSSLSASVGDRVTITCSASSSVRFIHWYQQKPGKAPKRLI YDTSKLASGVPSRFSGSGSGTDFTLTISSLQPEDFATYYCQQWSSSP FTFGQGTKVEIK |
| 9 | PSCA 2B3 scFv | DIQLTQSPSSLSASVGDRVTITCSASSSVRFIHWYQQKPGKAPKRLI YDTSKLASGVPSRFSGSGSGTDFTLTISSLQPEDFATYYCQQWSSSP FTFGQGTKVEIKGSTSGGGSGGGSGGGGSSEVQLVESGGGLVQPG GSLRLSCAASGFNIKDYYIHWVRQAPGKGLEWVAWIDPENGDTEF VPKFQGRATISADTSKNTAYLQMNSLRAEDTAVYYCKTGFWGQ GTLVTVSS |
| 10 | CD8 alpha hinge | TTTPAPRPPTPAPTIASQPLSLRPEACRPAAGGAVHTRGLDFACD |
| 99 | Hinge | NHDASAATTNTGAHHASQPLSLRPEACRPAAGGAVHTRGLDFAC D |
| 100 | Hinge | HTTPAPRPPTPAPTIASQPLSLRPEACRPAAGGAVHTRGLDFACD |
| 11 | CD8 alpha transmembrane domain | IYIWAPLAGTCGVLLLSLVITLY |
| 12 | CD28 transmembrane domain | FWVLVVVGGVLACYSLLVTVAFIIFWV |

TABLE 2-continued

Sequences used in the invention

| SEQ ID NO: Name | Amino Acid/Nucleotide Sequence |
|---|---|
| 13 ICOS transmembrane domain | FWLPIGCAAFVVVCILGCILI |
| 14 4-1BB ICD | KRGRKKLLYIFKQPFMRPVQTTQEEDGCSCRYPEEEGGCE |
| 15 CD28 ICD | RSKRSRLLHSDYMNMTPRRPGPTRKHYQPYAPPDFAAYRS |
| 16 ICOS ICD | CWLTKKKYSSSVHDPNGEYMFMRAVNTAKKSRLTDVTL |
| 17 ICOS(YMNM) ICD | CWLTKKKYSSSVHDPNGEYMNMRAVNTAKKSRLTDVTL |
| 18 CD3 zeta ICD | RVKFSRSADAPAYQQGQNQLYNELNLGRREEYDVLDKRRGRDPE MGGKPQRRKNPQEGLYNELQKDKMAEAYSEIGMKGERRRGKGH DGLYQGLSTATKDTYDALHMQALPPR |
| 19 CD3 zeta (Q14K) ICD | RVKFSRSADAPAYKQGQNQLYNELNLGRREEYDVLDKRRGRDPE MGGKPRRKNPQEGLYNELQKDKMAEAYSEIGMKGERRRGKGFID GLYQGLSTATKDTYDALHMQALPPR |
| 20 PSCA CAR 2B3.BBZ | atggcgctaccggtgaccgcactcctgctgcctgtgtccactgctgcctcctgtcctgtcctgctgcgcccatatcc agctgaccccaatcaccgctgtccctgtctgcctcgtgggcgacgatcacctgtagtgcctc gagcagtgtacggttcatccactgcttcaacagaagccggcaaggcaccaaagcggctgatctacga gagcagtgtacggttcatccactggtaccaacagaagccccggcaaggcaaggcctgatctacga caccagcaagctggctcgtctgggtgcccagcaggttctcggaagtggtagtggacacagattcactctc accatcagttcactccagcgcggacactcattgccagcagtggtcctcgtccctttacct tcggccaggaaccaaagtggaaattaaggttcgacctccgggggtcgtgggggctccgg cggggggctcatcggaggttcagctggtgcgccagcggcttcaacatcaaggactactacattcactggttgcgcaaggcc caggcaaggtctgagttggtggcttgaactgcgacaactgagttcgtgccaaaatt ccagggggggcgaccatctccgcgacactccaagaatacggcctacctgcagatgaactccctgc gcgccgaagacacagccgccggcaccacagccgctactactgcacgacgcgcgcaaccggcgccaccatcgt gttccgagtgcgcaccgtcccctgcccagagcgccggggcccagcagggggcagtgcacgaggg gcgacccccgtcccctgcccagagcgccggggcccagcagggggcagtgcacgaggg ggctgacttcgcctgcgtgatatctcatatctgggccccttggccggacttgtgggtcttctccctgtcact gttatcaccctctactcaagagaagatgcctgagctgccgatttccagaagaagaaggaaggatcttataaccattatgagacca gtaaaactactcaagagaagatgcctgagctgccgatttccagaagaagaaggaaggctctataa ctgaggtgaagttcagcaggacgaagagagtacgactttggacagagagcgtgcccggagcctgaga cagtccaatctagagcgagaagaaggaaccctcaggaggcctgtacaatgaaactgcagaagataagat tggggggaaagcgagaagaccagagaagaaccctcaggaggcctgtacaatgaaactgcagaagataagat ggcgaggcctacagtgagattggatgaaaggcgagccgagggcacgatggcct taccagggtctcagtacagccaccaaggacacctacgacgcccttcactcatgcgaggcccctgccccctcgc taa |

TABLE 2-continued

Sequences used in the invention

| SEQ ID NO: Name | Amino Acid/Nucleotide Sequence |
|---|---|
| 21 PSCA CAR 2B3.BBZ | MALPVTALLLPLALLLHAARPDIQLTQSPSSLSASVGDRVTITCSAS SSVRFIHWYQQKPGKAPKRLIYDTSKLASGVPSRFSGSGSGTDFTL TISSLQPEDFATYYCQQWSSSPFTFGQGTKVEIKGSTSGGGSGGGS GGGGSSEVQLVESGGGLVQPGGSLRLSCAASGFNIKDYYIHWVRQ APGKGLEWVAMIDPENGDTEFVPKFQGRATISADTSKNTAYLQM NSLRAEDTAVYYCKTGGFWGQGTLVTVSSAAGTTTPAPRPPTPAP TIASQPLSLRPEACRPAAGGAVHTRGLDFACDIYIWAPLAGTCGVL LLSLVITLYCKRGRKKLLYIFKQPFMRPVQTTQEEDGCSCRFPEEEE GGCELRVKFSRSADAPAYKQGQNQLYNELNLGRREYDVLDKRR GRDPEMGGKPRRKNPQEGLYNELQKDKMAEAYSEIGMKGERRRG KGHDGLYQGLSTATKDTYDALHMQALPPR |
| 22 PSCA CAR 2B3.28Z | Atggctgctaccggtgaccgcactcctgctgccactcgctgctgcctccacgcgccccgatatc cagctgacccaatccaccggtctgcctgtcctgccctcccgtgggcgacggtgacgatcacctgtagtgcctc gagcagttacgttcatccactggtaccaacagaagcccggcaaggccaccaaagcggctgatctacga caccagcaagctggctcgtctgggcgtccagccagcaggtctcggaagtggtagtgcacagactcactctc accattcagttcactccagccgaggactttgccacttactattgccagcagtggtcctcgtccccccttacct tcggccagggaacaaaggtggaaattaaggtttcgacctcggggggctccgtggggctcggtgctcagccggcagag tctcggctgtcctgtgccgccaggtggttgcctcaactaacctggaattgaccctgaaaacgaccactgagttcgtgccaaaatt ccaggcggggcgaccatccgccgacacctccaagaatacggctacctgcagatgaactccctgc gcgcgaagacacagcggctactactgcaagacaggggtttctgggcaggcaggcacctgtgacc gttcgagtgccgcgcaccgtgccggctctacgacgccagctctatgcccaacacgcagggccagtgcacagggg ggctgacttcgcgtgatTttttggtgctgtggtgtctggctgctagtgctagt aacagtggcctttattattctggtgagagtaagagagcatccgctgcacagtgactacatgaacat gactcccccgccccgaaggtaccagcattaccgctaccgggccagagaaccccgagaacca cctatcgctcc agagtgaagttcagcaggagcgcagacgcccccgcttaccacggccaggcgcagaacca gctctataacgagctccaatctaggacgaagaaggagtacgatgtttttgacaagagacgtggcggga cctgagatggggggaagcgcagaaggaagaggaaatttggatgaaggccaccgcgaggcaagg aaagataagatggcggagcctaacagtgagtctcagtacgcaccagatgacaccctccactgagggcaagg cagatggcctttaccaggtctcagtacacgcgccctccctccacatgcaggccc tgcccctctcgctaa |
| 23 PSCA CAR 2B3.28Z | MALPVTALLLPLALLLHAARPDIQLTQSPSSLSASVGDRVTITCSAS SSVRFIHWYQQKPGKAPKRLIYDTSKLASGVPSRFSGSGSGTDFTL TISSLQPEDFATYYCQQWSSSPFTFGQGTKVEIKGSTSGGGSGGGS GGGGSSEVQLVESGGGLVQPGGSLRLSCAASGFNIKDYYIHWVRQ APGKGLEWVAMIDPENGDTEFVPKFQGRATISADTSKNTAYLQM NSLRAEDTAVYYCKTGGFWGQGTLVTVSSAAGTTTPAPRPPTPAP TIASQPLSLRPEACRPAAGGAVHTRGLDFACDFWVLVVVGGVLAC YSLLVTVAFIIFWVRSKRSRLLHSDYMNMTPRRPGPTRKHYQPYAP PRDFAAYRSRVKFSRSADAPAYQQGQNQLYNELNLGRREEYDVL DKRRGRDPEMGGKPQRRKNPQEGLYNELQKDKMAEAYSEIGMK GERRRGKGHDGLYQGLSTATKDTYDALHMQALPPR |

TABLE 2-continued

Sequences used in the invention

| SEQ ID NO: Name | Amino Acid/Nucleotide Sequence |
|---|---|
| 24 PSCA CAR 2B3.ICOSZ | atggcgctaccggtgaccgcactcctgctgccactccctgctccacgcgcccgccgatatcc<br>agctgacccaatcaccgtcctgtccctgtctgcctccgtgggcgaccggtgacgatcacctgtagtgcctc<br>gagcagtgtacggtcatccactggtaccaacagaagccggcaaggccaccaaagcggctgatctacga<br>caccagcaagctggcgtctgggtgtcccagcaggttgccactactactttgccacagcagtgtcacagactttcactctc<br>accatcagttcactccagccggaggactttgccactactattgccactactactttcctccccttcact<br>tcggccaggaacaaaagtggaaattaaggttcagctggtggagagcggcggcggcctggtgcagccggggag<br>tctggcctgtcctgtgccgccagcggcttcaacattaaggactactactactttcactgggtgcgccaagcc<br>caggccaaggtctggagtggtggctgagaattgaacctgaaaacgccgacctgagttcgtgccaaaatt<br>ccaggggcggcgaccatctccgcgacactccaagaataccggctacctgcagtgaactccctgc<br>gccgcgaagacacagcggctactactgcgacgcgcagcgcgccgaccaacacgggccccaccatgcgt<br>gttccgagtgcggcggcAccacgccagaggcgtccaagaagcaggcgggcgtgcacgaggg<br>ggctggacttcgcctgtgatTtcctgtaccacaaaaagaagtattcatccagtgcacctcaaccggtgaatcagcagg<br>atattattgttggcttacaaaaagaagtatcatcagatctgacctctataacgagctcaatctaggacgagg<br>gagagcagtgaacacagccaagcagcaaggccagactctcagcaggtctataaacgagctcaatctaggacgaag<br>agagacagccccccgtaccacagccggcccagaagcaggacctgcgatatggcgaggccagagacgcagaga<br>aggagtgtacgatgttttgacaagaagactggccggacctgagatgggggaaagccgcagag<br>gattggaatgaaggcgagccggagggcaaggcaacgactgaatggccaggtctcagtacga<br>ccaccaaggcactacgacgccttcactgcaggccctgccccctgctaa |
| 25 PSCA CAR 2B3.ICOSZ | MALPVTALLLPLALLLHAARPDIQLTQSPSSLSASVGDRVTITCSAS<br>SSVRFIHWYQQKPGKAPKRLIYDTSKLASGVPSRFSGSGSGTDFTL<br>TISLQPEDFATYYCQQWSSSPFTFGQGTKVEIKGSTSGGSGGS<br>GGGGSEVQLVESGGGLVQPGGSLRLSCAASGFNIKDYYIHWVRQ<br>APGKGLEWVAWIDPENGDTEFVPKFQGRATISADTSKNTAYLQM<br>NSLRAEDTAVYYCKTGGFWGQGTLVTVSSAAGTTTPAPRPPTPAP<br>TIASQPLSLRPEACRPAAGGAVHTRGLDFACDFWLPIGCAAFVVVC<br>ILGCILICWLTKKKYSSSVHDPNGEYMFMRAVNTAKKSRLTDVTL<br>RVKFSRSADAPAYQQGQNQLYNELNLGRREYDVLDKRRGRDPE<br>MGGKPQRRKNPQEGLYNELQKDKMAEAYSEIGMKGERRRGKGH<br>DGLYQGLSTATKDTYDALHMQALPPR |
| 26 PSCA CAR 2B3.ICOS.YMNM.Z | Atggcgctaccggtgaccgcactcctgctgccactccctgctccacgcgcccgccgatatc<br>cagtgacccaatcaccgtcctgtccctgtctgcctccgtgggcgaccggtgacgatcacctgtagtgcctc<br>gagcagtgtacggtcatccactggtaccaacagaagccggcaaggccaccaaagcggctgatctacga<br>caccagcaagctggcgtctgggtgtcccagcaggttgccactactactttgccacagcagtgtcacagacttcactctc<br>accatcagttcactccagccggaggactttgccactactattgccactactactttcctccccttcact<br>tcggccaggaacaaaagtggaaattaaggttcagctggtggagagcggcggcggcctggtgcagccggggag<br>tctggcctgtcctgtgccgccagcggcttcaacattaaggactactactactttcactgggtgcgccaagcc<br>caggccaaggtctggagtggtggctgagaattgaacctgaaaacgccgacctgagttcgtgccaaaatt<br>ccaggggcggcgaccatctccgcgacactccaagaataccggctacctgcagtgaactccctgc<br>gccgcgaagacacagcggctactactgcgacgcgcagcgcgccgaccaacacgggccccaccatgcgt<br>gttccgagtgcggcggcAccacgccagaggcgtccaagaagcaggcgggcgtgcacgaggg |

TABLE 2-continued

Sequences used in the invention

| SEQ ID NO: Name | Amino Acid/Nucleotide Sequence |
|---|---|
| | ggctggacttcgcctgctgattctgttacccataggatgtgcagcctttgttgtagtctgcatttgggatgca |
| | tacttattgttgcttacaaaaagaagtattcatccagtgtcacgaccctaagagtgaagttcagcag |
| | atgagagcagtgaacacagccaacaaatcCagactcacagatgtgacccaagagtgaagttcagcag |
| | gagcgcagacgcccccgcgtaccagcagcccagaaccagctctataacgagctcaatctaggacgaa |
| | gagagagtacgatgttttgacaagagactgcccggaccctgagatggggccgaaagcccagag |
| | aaggagaacccctcaggaaggcctgtacaatgaactgcagaaagataaggtgggaggcctacagtg |
| | agattgggatgaaggcgagcgccgagggcgaaggggcacgatgccttaccagggtctccagtaca |
| | gccaccaaggaacacctgacgacgccctcacatgcaggccctgccccctcgctaa |
| 27 PSCA CAR 2B3.ICOS.YMNM.Z | MALPVTALLLPLALLLHAARPDIQLTQSPSSLSASVGDRVTITCSAS SSVRFIHWYQQKPGKAPKRLIYDTSKLASGVPSRFSGSGSGTDFTL TISSLQPEDFATYYCQQWSSSPFTFGQGTKVEIKGSTSGGGSGGGS GGGSSEVQLVESGGGLVQPGGSLRLSCAASGFNIKDYYIHWVRQ APGKGLEWVAWIDPENGDTRFVPKFQGRATISADTSKNTAYLQM NSLRAEDTAVYYCKTGGFWGQGTLVTVSSAAGTTTPAPRPPTPAP TIASQPLSLRPEACRPAAGGAVHTRGLDFACDFWLPIGCAAPVVVC ILGCILICWLTKKKYSSSVHDPNGEYMNMRAVNTAKKSRLTDVTL RVKFSRSADAPAYQQGQNQLYNELNLGRREYDVLDKRRGRDPE MGGKPQRRKNPQEGLYNELQKDKMAEAYSEIGMKGERRRGKGH DGLYQGLSTATKDTYDALHMQALPPR |
| 28 PSMA 2F5 HCDR1 | SNWIG |
| 29 PSMA 2F5 HCDR2 | IIYPGDSDTRYSPSFQG |
| 30 PSMA 2F5 HCDR3 | QTGFLWSFDL |
| 31 PSMA 2F5 LCDR1 | RASQDISSALA |
| 32 PSMA 2F5 LCDR2 | DASSLES |
| 33 PSMA 2F5 LCDR3 | QQFNSYPLT |
| 34 PSMA 2F5 VH | EVQLNQSGAEVKKPGESLKISCKGSGYSFTSNWIGWVRQMPGKGL EWMGIIYPGDSDTRYSPSFQGQVTISADKSISTAYLQWNSLKASDT AMYYCARQTGFLWSFDLWGRGTLVTVSS |
| 35 PSMA 2F5 VL | AIQLTQSPSSLSASVGDRVTITCRASQDISSALAWYQQKPGKAPKL LIYDASSLESGVPSRFSGSGSGTDFTLTISSLQPEDFATYYCQQFNSY PLTFGGGTKVEIKIK |
| 36 PSMA 2F5 scFv | EVQLVQSGAEVKKPGESLKISCKGSGYSFTSNWIGWVRQMPGKGL EWMGIIYPGDSDTRYSPSFQGQVTISADKSISTAYLQWNSLKASDT AMYYCARQTGFLWSFDLWGRGTLVTVSSGGGGSGGGGSGGGGS AIQLTQSPSSLSASVGDRVTITCRASQDISSALAWYQQKPGKAPKL LIYDASSLESGVPSRFSGSGSGTDFTLTISSLQPEDFATYYCQQFNSY PLTFGGGTKVEIKIK |

TABLE 2-continued

Sequences used in the invention

| SEQ ID NO: | Name | Amino Acid/Nucleotide Sequence |
|---|---|---|
| 37 | Linker | GGGGS |
| 38 | Linker | GGGGSGGGGSGGGGSGGGGS |
| 39 | 2B3-L-2F5.BBZ CAR | atggctaccgtgaccgactgctctgtgccactcctgctcctgcccactgcccgatatcc agctgacccaatcaccgtccctgtcctgtgcctcgtgggcgaccggtgacgatcactgtagtgcctc gagcagtgtacggttcatccactggtaccaacagaagcccggcaaggccaagcggctgatctacga cacccagcaagctggctgtcccagcaagctctcggagaagtgcctagtgcacagacttcactctc accatccagttcactccagccggaggaactttgccactactattgccagcagtggctcctcgtccccttacct tcggccaggaacaaaggtgaaattaaggttcgacctgcaggctggagagcgccagcagtccggtcagccggcgga tctgcggctcctgcctcgcccagcgactcaactcaaggactactactcactggtgcgcaagccc caggccaaggctcgagtgggtggttgacctgactgacgtccagaaacgcgacaactgagttcgtgccaaatt ccaggggtgggcgaccattccccgacaactccaagacaggggttctgggcaggtgcgggttggtctga gcccagaacacagcggctctgcatctggcgttgcagtctgggaagtgccccacctcgtgcggc gtttgagtcgcccagaggtgtgcagtgtgcactggatccggtgagcagtggcccccgggagtcctga agatcctctaaggttctggatacagtttaccagcaactgatccgtggtgcgccagatgccgg aaaaggcctcgaggtggatgggaaatcatcatccctggtgactcgatatccagatacagccccgtccttccaagg ccagtccaccattccacgacaagtccatcagacaaaaactggttctccctcgagtcctgatcctcgaggctc ggacaccgccatgtctactgcgagacaaaactggttcctccttggtcctcgatcctcgtgggcgtggcac cctgtcactgtctcctcagtggctgcctggccctgtgatctgtaggacagagtcaccatcactgccgggcaa gtcaggacattagcagtgctttagcctgatcagcagaaacgggaaagctcctaagctcgtgatctat gatgctccagttcgaaagtgggacttgaagagctggtgaacaggatcttcacttt caccatcagcagcctgcagcctgaagatttgcaacttattactgtcaacttatoaacagttaatagttaccgctcacttt cggcgaggacaaggccaagtgagatcaagaccgcgtcccgcacggccacagcgcagcgtccggccagcgggg cgcagtgcacgaggggctgcaatctgactctgtattacactgggcgcccttggccgcggacttgt gggtcctctcctgcactggtgtacacctttactgaacagggcagaaagaaacctctgcaagaagaa acacccatttatgaacgaggatgaactgagtgagttcagcagggcagagcagcagccccgtcaaagcgag gccgaaaccagctcctataacgagctcaatgagttggaaggggaaagccgagttgagatttggcaacaagagac gtgcggccggaccctgagatggggggaaaagccgaggcctacagtgagaccacaggaagaggccgagagggc actgcagaaataagatgcctgaggccttaccagggtccagtacagccagtagcaagacacctcacgacgcctcacatg caggccctgcccctcgctaa |
| 40 | 2B3-L-2F5.BRZ CAR | MALPVTALLLPLALLHAARPDIQLTQSPSSLSASVGDRVTITCSAS SSVRFIHWYQQKPGKAPKRLIYDTSKLASGVPSRFSGSGSGTDFTL TISSLQPEDFATYYCQQWSSSPFTFGQGTKVEIKGSTSGGGSGGGS GGGGSEVQLVESGGGLVQPGGSLRLSCAASGFNIKDYYIHWVRQ APGKGLEWVAWIDPENGDTEFVPKFQGRATISADTSKNTAYLQM NSLRAEDTAVYYCKTGGFWGQGTLVTVSSAAGGGGSGGGGSG GGGGSGGGGSEVQLVQSGAEVKKPGESLKISCKGSGYSFTSNWIGW VRQMPGKGLEWMGIIYPGDSDTRYSPSFQGQVTISADKSISTAYLQ |

TABLE 2-continued

Sequences used in the invention

| SEQ ID NO: Name | Amino Acid/Nucleotide Sequence |
|---|---|
| 41 2B3-S-2F5.BBZ CAR | WNSLKASDTAMYYCARQTGFLWSFDLWGRGTLVTVSSGGGGSG<br>GGGSGGGGSAIQLTQSPSSLSASVGDRVTITCRASQDISSALAWYQ<br>QKPGKAPKLLIYDASSLESGVPSRFSGSGSGTDFTLTISLQPEDFAT<br>YYCQQFNSYPLTFGGGTKVEIKIKTTTPAPRPPTPAPTIASQPLSLRP<br>EACRPAAGGAVHTRGLDFACDIYIWAPLAGTCGVLLLSLVITLYCK<br>RGRKKLLYIFKQPFMRPVQTTQEEDGCSCRFPEEEEGGCELRVKFS<br>RSADAPAYKQGQNQLYNELNLGRREEYDVLDKRRGRDPEMGGKP<br>RRKNPQEGLYNELQKDKMAEAYSEIGMKGERRRGKGHDGLYQG<br>LSTATKDTYDALHMQALPPR |
|  | atggctacggctgaccgctgctcctgcactgccctctgctccagcgcgcccgcgcccgatatcc<br>agctgacccaatcaccgtctgtccctgtctgcctcgtgggcgaccgggtgacgatcacctgtagtgcctc<br>gagcagtgtacggttcatccactgtataccaacaagagcccgcaaggcaccaaagcggctgatctacga<br>caccagcaagctggtctgtgggctgccccagcaggttctcggaaagttcctctactctcactctc<br>accatcagttcactccagccggaggactttgcaactctactattgccagcagtgtcctgtcccccattacct<br>tcggccaggggaacaaaggtggaattaaggttcgacctccggggggctctccgtgggggctccgg<br>cggggggggctcatcggaagttcagctggtgcctgtcaacaaggactactactctcactgggtgcggcaagccc<br>tctgcggctctctgtcccaggggtggtgcttgattgaccctgaaaacgggcacactgatgtcgtgccaaaatt<br>caggcaagggtctggagtggtggtggtcccgcgacacctccaagacaggggtttctgggcaggcaccctgacc<br>ccaggggcgggcgaccattccgcgaagtgtgccagcgtgtgtcgtgaacgaagacaaagtgggggcacccctgagctgaa<br>gttcgagtccgccgaggactgcggcgaggtggtggatccgagtgcgtcagtctgaagcagaggtgaa<br>aaagccgggagtctctgaagatctcctgaaggttctggatacagtttaccagcaactgatcggct<br>gggtgccagaccgcctccttccaaggccaggtcaccatccagcgaccagtcaccatcagcaccgcaccgctgca<br>gataacagccgctgagctccgacaccgccatgattactgcgagaacaaactggtttccctcggtcctt<br>gttgaacagccccgctgaccctctcagtggtcactgtcctcagtgggtgccggggtggttggtcg<br>ggtgcggcgcgatccgccatcggcaggtgacccagcaggcaccgccggagagctttgccctcagtgggaccctgctgaccccccctgctcgatctgatcagcgagatccccctgtctgagggaaacaagacagt<br>gctcctaagctcctctatgatcctccaagttcgaagtgggtccccatcaaggttcagcgcagtgg<br>atctggacagattcactctccaccatcagcagcctgcagcctgaagattttgcaacttattactgtcaacagt<br>taatagtacccgctcacttcggccggagggaccaaggtgcagccctgtccctgcgcccagccgc<br>cgccgacccaacaccggcgcccacccatcgcgtgcaccgggtccttccctgccactgttcgcctgtgatctacatctgggc<br>gccctggccggactgtgggtcctttccctgcactgttatcaccctttactgcaaacggggcagaaa<br>gaactcctgtatattcaaacaaccattatgagacagtacagtgaactgagagtgagttcagcaggggaagtggctgtag<br>ctgccgattccagaagaagaaggaatgggaactgagagtgaagttcagcaggcggaggcagacg<br>cccccgcttcacaaggccagaacccgtctataaacgacctcaatcagggaagaagaggagtac<br>gatgtttgacaagaggcggcgggacctggcgagatgggggaaagcgagaggaagaccctc<br>aggaaggcctgtacaatgaactgcagaaagataagatggcggaggcctacagtgagtggatgaaa<br>ggcagccggagggggcaaggggcacgatgccttaccaggtctcagtacagcccaccaagaca<br>cctacgaccccttcaatgcaggccctgccccctcgctaa |

TABLE 2-continued

Sequences used in the invention

| SEQ ID NO: Name | Amino Acid/Nucleotide Sequence |
|---|---|
| 42 2B3-S-2F5.BBZ CAR | MALPVTALLLPLALLLHAARPDIQLTQSPSLSASVGDRVTITCSAS SSVRFIHWYQQKPGKAPKRLIYDTSKLASGVPSRFSGSGSGTDFTL TISSLQPEDFATYYCQQWSSSPFTFGQGTKVEIKGSTSGSGSGGGS GGGGSSEVQLVESGGGLVQPGGSLRLSCAASGFNIKDYYIHWVRQ APGKGLEWVAMIDPENGDTEFVPKFQGRATISADTSKNTAYLQM NSLRAEDTAVYYCKTGGFWGQGTLVTVSSAAGGGGSEVQLVQS GAEVKKPGESLKISCKGSGYSFTSNWIGWVRQMPGKGLEWMGIIY PGDSDTRYSPSFQGQVTISADKSISTAYLQWNSLKASDTAMYYCA RQTGFLWSFDLWGRGTLVTVSSGGGSGGGGSAIQLTQSP SSLSASVGDRVTITCRASQDISSALAWYQQKPGKAPKLLIYDASSL ESGVPSRFSGSGSGTDFTLTISSLQPEDFATYYCQQFNSYPLTFGGG TKVEIKIKTTTPAPRPPTPAPTIASQPLSLRPEACRPAAGGAVHTRGL DFACDIYIWAPLAGTCGVLLLSLVITLYCKRGRKLLYIFKQPFMR PVQTTQEEDGCSCRFPEEEEGGCELRVKFSRSADAPAYKQGQNQL YNELNLGRREEYDVLDKRRGRDPEMGGKPRRKNPQEGLYNELQK DKMAEAYSEIGMKGERRRGKGHDGLYQGLSTATKDTYDALHMQ ALPPR |
| 43 PSCA 2133 VH | gaggttcagctggtggagagcggcggcctgttgcacccgggagtctgcggctgtcctgtgc cgcagcggcttcaactcaaggactactacattcactgggtgcgccaagcccaggctctgga gtgggtggcttgattgaccctgaaaacggcgacactgagttcgtgccaaaattccagggccgac catctccgcacactccagaatacgcagatgacctccaagaatactctgcgccgaagacacagc ggtctactgcaagacaggggttcttgggccagggcaccctgtgaccgtttcgagt |
| 44 PSCA 2B3 YL | gatatccagctgaccaatcaccgtcgtccctgctcctccgtggggcgaccggtgacgatcacctgtag tgcctcgagcagtgacgtcatccactggtatcaacaagaaccccaagcccaagacggctgat ctacgacaccagcaagtgcgtctgggtgccagtccggagactttgccacctactactgcagcagc cacctccaccatcagttcactcagccggagactttgccacctactactgcagcagc ctttacctccggccaggggaacaaggtggaaattaag |
| 45 PSCA 2B3 scFv | gatatccagctgacccaatcaccgtcgtccctgctcctccgtggggcgaccggtgacgatcacctgtag tgcctcgacagtgacgtcatccactggtatcaacaagagcccccaagcccaagacggctgat ctacgacaccagcaagtgcgtctgggtgccagtccggagactttgccacctactactgcagcagc cacctccaccatcagttcactcagccggagactttgccacctactactgcagcagc ctttacctccggccaggggaacaaggtggaaattaaggcttcctaccgcgtcggcggcgggg aggtccccaaggcaaggaagtccgggagtctgattgacctcaagatacgcctacctgcagtgaact caaattccagggggcgaccatctccgcgacactccaagaacagggggtcctgggcacgcctc gtgaccgtttcgagt |
| 46 PSMA 2F5 VH | GAGGTGCAGCTGGTGCAGTCTGGACCAGAGGTGAAAAAGCCCG GGGAGTCTCTGAAGATCTCCTGTAAGGGTTCTGATACAGTTTT ACCAGCAATTGGATCGGCTGGTGCGCCAGATGCCCGGGAAAG GCCTGGAGTGGATGGGGATCATCTATCCTGGTGACTCTGATACC AGATACAGCCCGTCCTTCCAAGGCCAGGTCACCATCTCAGCCGA |

TABLE 2-continued

Sequences used in the invention

| SEQ ID NO: Name | Amino Acid/Nucleotide Sequence |
|---|---|
| 47 PSMA 2F5 VL | CAAGTCCATCAGCACCGCCTACCTGCAGTGGAACAGCCTGAAG<br>GCCTCGGACACCGCCATGTATTACTGTGCGAGACAAACTGGTTT<br>CCTCTGGTCCTTCGATCTCTGGGCCGTGCACCCTGGTCACTG<br>TCTCCTCA |
| 47 PSMA 2F5 VL | GCCATCCAGTTGACCCAGTCTCCATCCTCCCTGTCTGCATCTGTA<br>GGAGACAGAGTCACCATCACTTGCCGGGCAAGTCAGGACATTA<br>GCAGTGCTTTAGCCTGGTATCAGCAGAAACCGGGAAAGCTCC<br>TAAGCTCCTGATCTATGATGCCTCCAGTTTGGAAAGTGGGGTCC<br>CATCAAGGTTCAGCGGCAGTGGATCTGGACAGATTTCACTCTC<br>ACCATCAGCAGCCTGCAGCCTGAAGATTTTGCAACTTATTACTG<br>TCAACAGTTTAATAGTTACCCGCTCACTTTCGGCGGAGGGACCA<br>AGGTGGAGATCAAAATCAAAA |
| 48 PSMA 2F5 scFv | GAGGTGCAGCTGGTGCAGTCTGGAGCAGAGGTGAAAAAGCCCG<br>GGGAGTCTCTGAAGATCTCCTGTAAGGGTTCTGGATACAGTTTT<br>ACCAGCAACTGGATCGGCTGGGTGCGCCAGATGCCCGGGAAAG<br>GCCTGGAGTGGATGGGGATCATCTATCCTGGTGACTCTGATACC<br>AGATACAGCCCGTCCTTCCAAGGCCAGTCACCATCTCAGCCGA<br>CAAGTCCATCAGCACCGCCTACCTGCAGTGGAACAGCCTGAAG<br>GCCTCGGACACCGCCATGTATTACTGTGCGAGACAAACTGGTTT<br>CCTCTGGTCCTTCGATCTCTGGGCCGTGCACCCTGGTCACTG<br>TCTCCTCAGGTGGCGGTGGCTCGGGCGGTGGTGGGTCGGGTGG<br>CGGCGGATCTGCCATCCAGTTGACCCAGTCTCCATCCTCCCTGT<br>CTGCATCTGTAGGAGACAGAGTCACCATCACTTGCCGGCAAG<br>TCAGGACATTAGCAGTGCTTTAGCCTGGTATCAGCAGAAACCG<br>GGGAAAGCTCCTAAGCTCCTGATCTATGATGCCTCCAGTTTGGA<br>AAGTGGGGTCCCATCAAGGTTCAGCGGCAGTGGATCTGGGACA<br>GATTTCACTCTCACCATCAGCAGCCTGCAGCCTGAAGATTTTGC<br>AACTTATTACTGTCAACAGTTTAATAGTTACCCGCTCACTTTCG<br>GCGGAGGGACCAAGGTGGAGATCAAAATCAAAA |
| 49 2B3-L-2F5 Extracellular domain | gatatccagctgaccaataccaccgtgtcctgtcgtcctgccgtcctgggcgaccggtgacgatcacctgtag<br>tgcctcgacagtgacgtgacgtagcctctcactcgccacagacgccggcaagtcaccaaagcggctgat<br>ctacgacaccaagcaagctgcgtctgggtgccagatggcacagagcagttgcagtcctcgtgggg<br>cactctcaccatcagttcactccagcccgaggacttttgccaactcactattgcagcagtgtcctcgtcccc<br>ctttacctcggccaggaacaaagtggaaattaaggtgcaacatcgggggccggtggcca<br>ctccggcccggggggctgcatcaggtgcagcgtggtggagggcgggcctggtgcagccggc<br>gggagtctggcgtctcctgtgccggccagtccctggcttcaactcaactcaacggggctacacattcactgggtgcggc<br>aagcccaggcaaggtggtcgatgggtgtgtggattgaccctgaagaataccgcctacctgcagatgaact<br>cctgcgccgaagacacagccgtctactactgtcagagacaggggtctctgggccagggaccctc<br>gtgaccgttcagtcgagtcgcggggaggagggtggtggctgggcccaaggggaaagcgggtgggt<br>cggcggcggcggctcgaagtgcaggtgtgcagtcgagtgcagcagaggtgaaaaagcccgggagt<br>ctctgaagatctcctgtaagggtgatgggaatacagttttaccagcaactggatcggctggtgcgccagatgc<br>ccgggaaaggcctggagtggatgggatcatctatcctggagatcgatactcgatacagcccgtcctc<br>caaggccaagtcactcagcaccgccaagtccatcagcaccgcctacctgcagtggaacagcctgaag |

TABLE 2-continued

Sequences used in the invention

| SEQ ID NO: Name | Amino Acid/Nucleotide Sequence |
|---|---|
| | gcctcggacaccgcctgatgtattactgtgcgagacaaactggttcctctggtcctcgatctcgtgggccgt |
| | ggcaccctgtcactgtctcccagtggcgtggtcgtcggcgtggtcggtgttcggtcggtgccggatct |
| | gccatccagttgacccagtccatcctccctgctgcactctgaggacagaaccgggaaagctcctaagctcctgat |
| | ctatgatgcctccagttgaaagggggtcccatcaagttcagcggcagtggatctgggacagattca |
| | ctctcaccatcagcagcctgcagcctgaagatttgcaacttactgtcaacagttcaactgtacccgctc |
| | actttcggccaaggaccaaggtcgaagatcaaaatcaaaa |
| 50 2B3-L-2F5 Extracellular domain | DIQLTQSPSSLSASVGDRVTITCSASSSVRFIHWYQQKPGKAPKRLI YDTSKLASGVPSRFSGSGSGTDFTLTISSLQPEDFATYYCQQWSSSP FTFGQGTKVEIKGSTSGGGSGGGSGGGSSEVQLVESGGGLVQPG GSLRLSCAASGFNIKDYYIHWVRQAPGKGLEWVAWIDPENGDTEF VPKFQGRATISADTSKNTAYLQMNSLRAEDTAVYYCKTGFWGQ GTLVTVSSAAGGGGSGGGGSGGGGSGGGGSEVQLVQSGAEVKK PGESLKISCKGSGYSFTSNWIGWVRQMPGKGLEWMGIIYPGDSDT RYSPSFQGQVTISADKSISTAYLQWNSLKASDTAMYYCARQTGFL WSFDLWGRGTLVTVSSGGGGSGGGGSGGGGSAIQLTQSPSSLSAS VGDRVTITCRASQDISSALAWYQQKPGKAPKLLIYDASSLESGVPS RFSGSGSGTDFTLTISSLQPEDFATYYCQQFNSYPLTFGGGTKVEIKI K |
| 51 2B3-S-2F5 Extracellular domain | gatatccagctgacccaatcaccgtcgtccctgtcgcctctgggcgacgggtgacgatcacctgtag tgcctcgagcagtgtacggtctccactggtaccaacagaagcccggcaaggcaccaagagcggctgat ctacgacacccagcagctgcgctggagtccccgagttcagcggcagtggatctggcacagagactt cactctcaccatccagtcagctgcactctgagatcatcatattgccagcagtggtctcgtcccc cttacctcggccagggaccaaaagtcgaaattaaggtcacctccggtggtggcggttctccggg ctccggggggggcggtctgcagtgtgaagagcggtctgtgcag ggagtctcgcgtcgcaaggttcggatgtggttcgggatcaaggctcaactgcactgagtcgctg aagccccagcaaggtcggagatgtggctggagtcggttgcactctgcctgatgacaactggtagc caaattccaggggcgggtcgacaccttccccgacacctgacgccacctgcagatgaact cccctgcgccgaaacaccgaggtctactactgcaagacaggggtctgggcggcagtctggagcaga ggtgcaacacagtcctcggggagctcctgtaggttcttggatacagtttaccagcagctga tcggctggaagcccaaggacccggagtccggaagagtcgtgtacaacaattgcagcagacttga accagatccaccatcagcggcaccggtcctccccaaggcgtgcatcatcttgctgagactctga taccgatacagccagtcctcggggcctcgggcctgtgcaccgcagaagctggacaatctcatcagcaccgcctac ctgagtgaacagctcactccaggagccctcagctcagctgattactgcgagacaaactggttcctcctg gtcctccggcagggctgaccagagctgcgtgcaccacctggcactgcaccttgtacctgcctgcctcatctgtggtg gtcggtggctgcggcaagtcctgctggcaccttgaccacattagcagtgcttagctgtatcagcagaaccgg agagtccacctcaccttcgcccggcagtcctgatctataaggtcctttccaagctctcagcgcgatcgagaactgc gggaaggctctaagctcctgatctatgatgcctccaagcttgaaagtgggggtcccatcagcctgaaagattgagcggc agtggatctggcacagataccgtccaccctctcactgctgccccatcagccgcagcgcagccccgaagattgcaacttatatcagctacctcgctggaggtgagatcaaaatcaaaa |
| 52 2B3-S-2F5 Extracellular domain | DIQLTQSPSSLSASVGDRVTITCSASSSVRFIHWYQQKPGKAPKRLI YDTSKLASGVPSRFSGSGSGTDFTLTISSLQPEDFATYYCQQWSSSP FTFGQGTKVEIKGSTSGGGSGGGSGGGSSEVQLVESGGGLVQPG GSLRLSCNASGFNIKDYIHWVRQAPGKGLEWVAWIDPENGDTEF |

TABLE 2-continued

Sequences used in the invention

| SEQ ID NO: Name | Amino Acid/Nucleotide Sequence |
|---|---|
| | VPKFQGRATISADTSKNTAYLQMNSLRAEDTAVYYCKTGFWGQ<br>GTLVTVSSAAGGGGSEVQLVQSGAEVKKPGESLKISCKGSGYSF<br>TSNWIGWVRQMPGKGLEWMGIIYPGDSDTRYSPSFQGQVTISADK<br>SISTAYLQWNSLKASDTAMYYCARQTGFLWSFDLWGRGTLVTVS<br>SGGGGSGGGGSGGGGSAIQLTQSPSSLSASVGDRVTITCRASQDISS<br>ALAWYQQKPGKAPKLLIYDASSLESGVPSRFSGSGSGTDFTLTISSL<br>QPEDFATYYCQQFNSYPLTFGGGTKVEIKIK |
| 53 linker | GGCGGCGGCGGCAGC |
| 54 linker | GGCGGCGGCGGCAGCGGCGGCGGCGGCAGCGGCGGCGGCGGCAGC |
| 55 TGFBRII.dn | atggtcgggggctctccagggcctgctgcccgtgcacatcgtcctgtggacgctatcgccagcacg<br>atcccaactgcacgttcagaagtcggttaataagcacatgatagttcactgacaacaacgtgcagtcaagtt<br>tccacaactgtgataatttgtgatgtgagatttccaactgtgacaaccagaatcctgcatgagcaactgc<br>agcatcacctccatctgtgagaagccacaggaagttctgtgtgatcagacctttattctgaagatgctgctctcc<br>taactagagacagttgccatgccaccaagctcgctgactccaagctgtgagactttcatgtcctgtagcttcagtgagtgc<br>aaagtgcattatgaaggaaaaaaaaagctgtgagactttcatgtcctgtagtcatatttcaagtgac<br>aatgcaaacatcatcttcagaagaataaccagcaatcctgactgtgctcatatttctactgtctactgtctacccgttaac<br>aggcatcagctcctgccaccactggagtgcatatctggaattgtatcacacatcctactccggga<br>cggcagcagaagctgagttcatccgga |
| 56 TGFBRII.dn | MGRGLLRGLWPLHIVLWTRIASTIPPHVQKSVNNDMIVTDNNGAV<br>KFPQLCKFCDVRFSTCDNQKSCMSNCSITSICEKRPQEVCVAVWRK<br>NDENITLETVCHDPKLPYHDFILEDAASPKCIMKEKKPGETFMC<br>SCSSDECNDNIIFSEYNTSNPDLLLVIFQVTGISLLPPLGVAISVIIIF<br>YCYRVNRQQKLSSSG |
| 57 PD1-CTM-CD28 switch | atgcagatccccaggccgcctggccagtcgtctggccggtgctacaactgggctggcgcaggatg<br>gtcttagactcccagacaggccctgagctctccaacatcgaagagttcgtctaaactgtaccgccat<br>gggacaacgcaacctcacctgcagctctcacaacatcgaagagttcgtctaaactgtaccgccat<br>gagcccagcaaccagcaagctggccgcctggcacaactgccgaggaccgcagccagccagga<br>ctgccgttccgtgccacacaacagcggcgtgacttccacatgagcgtgttcagggccggg<br>caatgacagcggcacctacctctgggggcatcctctgggcccaagcgcaatcaagagaggccct<br>gcgggcagagctcaggtgacagagaaggcaggaagtgcccaccagcccaccagcctacc<br>cagccagccggccagtccaaacctggttggttgggtctggtgggtgggtgggtctgcttgct<br>atagctgctagtaacagtgccttatattttctggtgaggtaagaggagcaggctctgcacagtg<br>actacatgaacatgactcccgccccgccccccaagcattaccagccctatgcccccccac<br>gcgacttcgcagcctatcgctcc |
| 58 PD1-CTM-CD28 switch | MQIPQAPWPVVWAVLQLGWRPGWFLDSPDRPWNPPTFSPALLVV<br>TEGDNATFTCSFSNTSESFVLNWYRMSPSNQTDKLAAFPEDRSQPG<br>QDCRFRVTQLPNGRDFHMSVVRARRNDSGTYLCGAISLAPKAQIK<br>ESLRAELRVTERRAEVPTAHPSPSPRPAGQFQTLVFWVLVVVGGV<br>LACYSLLVTVAFIIFWVRSKRSRLLHSDYMNMTPRRPGPTRKHYQP<br>YAPPRDFAAYRS |

TABLE 2-continued

Sequences used in the invention

| SEQ ID NO: Name | Amino Acid/Nucleotide Sequence |
|---|---|
| 59 hIFNgR-Il12rb1 switch | atggctctctcttttctcctacccctgtcatgcagggtgtgagcaggctgagatgggcacgcggatctg gggcgtcctcagtgcctacaccaactaatgttacaactgacatccctataacatgaacctatcgtatattggg agtaccagatcatgccaccaggtccctgttttaccgtagaggtaagaactaatggtgttaagaattcagaatg gattgatgctgcatcaatattctccatcattttgatcatgttggttgttcatcaaattctcttgg gtcagagtaaagccaggggtggacaaaagaatctgccatgcaaagtcagaagaattgctgtatgccg agatgaaaattgaccaccaaactggatacagaaaggagagaagcaaatcatgattgacatattc acccttcagtttttgtaaatggagcaggaggcagttatgatccgaaactacctgtacattaggt gtacatgtatcgtgagaagaacgagagagttccagtataaaatactcacgcagaagaagatgatt gtgacagattcagtgccagttagcgatctcccactgatctcctgagtctgttttcagcagaagg agtttacatgtgtgggtgttacaactgaaagtcaaaagagtttgattaccattctcaatagcagtataa aaggttctctttggattccagtgttgctgctttactactccttctagtgcttagcctggtattcatcagggccgc acggcaccctgcccgcccgccgaccccgagttccaggacgacacagacacacttgagtctggaagga gacttggccgtggaccaaaaggcgagaggactgagcctctcgagaagacagagcacctgagggtgtaga gatgtcctggacaaaagcgagaggactgagcctctcgagaagacagagcacctgagggtgccctg agctggcctggatacagagttgctcctggaggatggagactgagtccaaggccaaggcaccatga |
| 60 hIFNgR-Il12rb1 switch | MALLFLLPLVMQGVSRAEMGTADLGPSSVPTPTNVTIESYNMNPIV YWEYQIMPQVPVFTVEVKNYGVKNSEWIDACINISHHYCNISDHV GDPSNSLMVRVKARVGQKESSAYAKSEEFAVCRDGKIGPPKLDIRK EEKQIMIDIFHPSVFVNGDBEQEVDYDPETTCYIRVYNVVRMNGSE IQYKILTQKEDDCDEIQCQLAIPVSSLNSQYCVSAEGVLHVWGVTT EKSKEVCITIFNSSIKGSLWIPVVAALLFLVLSLVFIRAARHLCPPL PTPCASSAIEFPGGKETWQWINPVDFQERASLQEFALVVEMSWDKG ERTEPLEKTELPEGAPELALDTELSLEDGDRCKAKM |
| 61 hIFNgb-Il12rb2 switch | atgcaccgacgcgctgctggtcgctgctgctgctcggagtcttcgcgcgccgcgcggccccg ccagaccccttcccagctgccgcctcccagccagcacgaggcctgtctaccaagtgcagtttaaatacacc tgagttgggagccagtggcctgagcaatgacagaggcctgtgtctaccaagtgcagtttaaatacacc gacagtaaatggttcacggccgaccatcatgtccaagggtgaatgtacacagatcacgacaacagagt gtgacttcactgcgccagtccccagcaggcttccaatggacttccaatgtcactcagcctggagctga gctgggagaactccattctgcctggtgacccaggagaggctcccatcatcaggttctcctccctttgacatcgc tgaatcctccagcgccttttttttgtattgtccattactggagaagaggaataccaacaggtcaaaggc ccttcagaagcaacccattcattgataacttaaaaccctccagagtgactgtttacaagtccaggcac aactgcttggaacaaaatacactttagaagtcaggaatttaagcaacatatcttgctacaaaacaatggc agagcccactgcctccagcaagtcatccgtgaaatacagcaatacgaacttctcgtgggaacatttcgttgctgtcgggtgatcagagt ggagcgttttcttcctgcctgaaatatcagcagtggcccacccccgtctaagatatccattgcacaggagaa gacacaggcgccttggacaggccagtccctgaatagactggccacgctccaagcccaccacctccaag agtgaagtccttcatcaagtcaggcctgaccaagttcagacatcagcaaaagactttttgtaaaagagcc aggaatccaaggtcatcaagctccagaagacatgatgcacatagagaaagactggcttgaagagggaaa agctccaagagagaagacaactgggatcgtgtaccaagcaggtgagacaggggtccgacc aaagccagaaacccagcctgcctgacggtctccagcaggtgacctccacaccatgatggcta cttacccccaacatagatgacctccccaccagggcacccctcgtgactctcggaagaactgagc ctcagcacatccccttccgttccccaagtctcttcaccactccaagctctcctgtggtgataagctgac tctggatcagttaagatgaggtgactccctcatgctctga |

TABLE 2-continued

Sequences used in the invention

| SEQ ID NO: Name | Amino Acid/Nucleotide Sequence |
|---|---|
| 62 hIFNgb-Il12rb2 switch | MRPTLLWSLLLLLGVFAAAAAPPDPLSQLPAPQHPKIRLYNAEQ VLSWEPVALSNSTRPVVYQVQFKTYDSKNFTADIMSIGVNCTQIT ATECDFTAASPSAGFPMDFNVTLRLRAELGALHSAWVTMPWFQH YRNVTVGPPENIEVTPGEGSLIIRPSSPPFIADTSTAFFCYYVHYWE KGGIQQVKGPFRSNSISLDNLKPSRVYCLQVQAQLLWNKSNIFRVG HLSNISCYETMADASTELQQVILISVGTFSLLSVLAGACFFLVLKYQ QKVFVLLAALRPQWCSREIPDPANSTCAKKYPIAEEKTQLPLDRLLI DWPTPEDPEPLVISVLHQVTPVFRHPPCSNW TABLE 2-continued Sequences used in the invention

| SEQ ID NO: Name | Amino Acid/Nucleotide Sequence |
|---|---|
| | ASVGDRVTTCHASQNIYWLNWYQQKPGKAPKLLIYKASNLHTG<br>VPSRFSGSGSGTDFTLTISSLQPEDFATYYCQQGQTYPYTFGGGTK<br>VEIK |
| 65 TGFB-1412 (aTGFbRII-aCd28 bispecific Ab) | atgggttggtcctgcatcatcctgttctcgtggccaccggcgtgcactccgaaattgtgttgaca<br>cagttccagccaccctgtcttgtctccaggggaaagagccaccctcctgcagtgcagagtgt<br>tagaagttcttagcctggtaccaacagaaactggccaggctcccaggctcctcattcatgatgcatccaa<br>cagggccactggcatcccagccaggttcagtggcagtggtctggacagactcactctcaccatcagc<br>agcctgagcctgaagatttgcagttattactgtcagcagcgtacaactggcctccgacgtcggccaa<br>gggaccaaggtggaaatcaaaagtggagggggcggttcacagctacagctgcagagtcgggccag<br>gactgtgaagcttcggagaccatccctcacctgggaaggcctgagtggattgggagttctatacagtg<br>actcctgggctagatccgccagcccccagggaagggccctgagtggattgggagttctatacagtg<br>gatcacctactacagccccgtccctcaagagtcgaattatcatccaagaacactccaagaaccagtctc<br>cctgaagctgagtctgtgaccgcgcagacacgctgtgtattactgtgcgagcggggttactatgattcg<br>gggagccctgactactgggccagggaaccctg |
| 66 TGFB-1412 (aTGFbRII-aCd28 bispecific Ab) | MGWSCIILFLVATATGVHSEIVLTQSPATLSLSPGERATLSCRASQS<br>VRSFLAWYQQKPGQAPRLLIYDASNRATGIPARFSGSGSGTDFTLTI<br>SSLEPEDFAVYYCQQRSNWPPTFGQGTKVEIKSGGGSQLQES<br>GPGLVKPSETLSLTCTVSGGSISSSSYSNWIRQPPGKGLEWIGSFY<br>YSGITYYSPSLKSRIIISEDTSKNQFSLKLSSVTAADTAVYYCASGFT<br>MIRGALDYWGQGTL |
| 67 PSMA 2F5-BBZ CAR | MALPVTALLLPLALLLHAARPEVQLVQSGAEVKKPGESLKISCKGS<br>GYSFTSNWIGWVRQMPGKGLEWMGIIYPGDSDTRYSPSFQGQVTI<br>SADKSISTAYLQWNSLKASDTAMYYCARQTGFLWSFDLWGRGTL<br>VTVSSGGGGSGGGGSGGGGSAIQLTQSPSSLSASVGDRVTITCRAS<br>QDISSALAWYQQKPGKAPKLLIYDASSLESGVPSRFSGSGSGTDFT<br>LTISSLQPEDFATYYCQQFNSYPLTFGGGTKVEIKIKTTTPAPRPPTP<br>APTIASQPLSLRPEACRPAAGGAVHTRGLDFACDIYIWAPLAGTCG<br>VLLLSIVITLYCKRGRKKLLYIFKQPFMRPVQTTQEEDGCSCRFPEE<br>EEGGCELRVKFSRSADAPAYKQGQNQLYNELNLGRREEYDVLDK<br>RRGRDPEMGGKPRRKNPQEGLYNELQKDKMAEAYSEIGMKGERR<br>RGKGHDGLYQGLSTATKDTYDALHMQALPPR |
| 68 hJ591 HCDR1 | EYTIH |
| 69 hJ591 HCDR2 | NINPNNGGTTYNQKFED |
| 70 hJ591 HCDR3 | GWNFDY |
| 71 hJ591 LCDR1 | KASQDVGTAVD |
| 72 hJ591 LCDR2 | WASTRHT |
| 73 hJ591 LCDR3 | QQYNSYPLT |

TABLE 2-continued

Sequences used in the invention

| SEQ ID NO: Name | Amino Acid/Nucleotide Sequence |
|---|---|
| 74 hJ591 VH | GAGGTCCAGCTGGTCCAGTCTGGAGCTGAGGTGAAGAAGCCTG GGGCCTCAGTGAAGGTCTCCTGCAAGGCTTCTGGATACACATTC ACTGAATACACCATCCACTGGGTGAGGCAGGCCCCTGGAAAGG GCCTTGAGTGGATTGGAAACATTAATCCTAACAATGGTGTACT ACCTACAACCAGAAGTTCGAGGACAGAGTCACAATCACTGTAG ACAAGTCCACCAGCACCGCCTACATGGAGCTCAGCAGCCTGAG ATCTGAGGATACTGCAGTTTATTACTGTGCAGCTGGTTGAACT TTGACTACTGGGGCCAAGGCACCACGGTCACCGTCTCCTCA |
| 75 hJ591 VH | EVQLVQSGAEVKKPGASVKVSCKASGYTFTEYTIHWVRQAPGKG LEWIGNINPNNGGTTYNQKFEDRVTITVDKSTSTAYMELSSLRSED TAVYYCAAGWNFDYWGQGTTVTVSS |
| 76 hJ591 VL | GACATTCAGATGACCCAGTCTCCCAGCACCCTGTCCGCATCAGT AGGAGACAGGGTCACCATCACTTGCAAGGCCAGTCAGGATGTG GGTACTGCTGTAGACTGGTATCAACAGAAACCAGGGCAAGCTC CTAAACTACTGATTTACTGGGCATCCACCCGGCACACTGGTTC CCTGATCGCTTCAGCGGCAGTGGATCTGGGACAGATTTCACTCT CACCATCAGCAGACTGCAGCCTGAAGACTTTGCAGTTTATTACT GTCAGCAATATAACAGCTATCCTCTCACGTTCGGCCAGGGACC AAGGTGGATATCAAA |
| 77 hJ591 VL | DIQMTQSPSTLSASVGDRVTITCKASQDVGTAVDWYQQKPGQAPK LLIYWASTRHTGVPDRFSGSGSGTDFTLTISRLQPEDFAVYYCQQY NSYPLTFGQGTKVDIK |
| 78 hJ591 scFv (VL-VH) | DIQMTQSPSTLSASVGDRVTITCKASQDVGTAVDWYQQKPGQAPK LLIYWASTRHTGVPDRFSGSGSGTDFTLTISRLQPEDFAVYYCQQY NSYPLTFGQGTKVDIKGGGGSGGGGSGGGGSEVQLVQSGAEVKKP GASVKVSCKASGYTFTEYTIHWVRQAPGKGLEWIGNINPNNGGTT YNQKFEDRVTITVDKSTSTAYMELSSLRSEDTAVYYCAAGWNFDY WGQGTTVTVSS |
| 83 hJ591 scFv (VL-VH) | Gacattcagatgacccagtctcccagcaccctgtccgcatcagtaggagacagggtcaccatcacttgca aggccagtcaggatgtgggtactgctgtagactggtatcaacagaaaccagggcaagctcctaaactact gatttactgggcatccacccggcacactggagttccctgatcgcttcagcggcagtggatctggacagatt tcactctcaccatcagcagactgcagcctgaagactagcagttatactgtcagcaatataacagctatcct ctcacgttcggccagggaccaaggtggatatcaaaggaggcggttctggcggcggaggaagttc tggcggaggagcgaggtccagctggtccagtctggagctgaggtgaagaagcctgggcctcagtga agtctctgcaaggcttctggatatacatttactgaatacaccatccactgggtactacaccagaagttcgagga aagggcttgagtggattggaaacattaatcctaacaatgtgtactacctacaaccagaagttcgagga cagagtcacaatcactgtagacaagtccacagccctacatggagctgagcagcctgagatctga ggatactgcagtcttattactgtgcagctggttgaactactgactactgggccaaggcaccaccgtcaccg tctcctca |

TABLE 2-continued

Sequences used in the invention

| SEQ ID NO: Name | Amino Acid/Nucleotide Sequence |
|---|---|
| 84 hJ591 scFv (VL-VH) | DIQMTQSPSTLSASVGDRVTITCKASQDVGTAVDWYQQKPGQAPK LLIYWASTRHTGVPDRFSGSGSGTDFTLTISRLQPEDFAVYYCQQY NSYPLTFGQGTKVDIKEVQLVQSGAEVKKPGASVKVSCKASGYTF TEYTIHWVRQAPGKGLEWIGNINPNNGGTTYNQKFEDRVTITVDK STSTAYMELSSLRSEDTAVYYCAAGWNFDYWGQGTTVTVSS |
| 85 hJ591 scFv (VH-VL) | EVQLVQSGAEVKKPGASVKVSCKASGYTFTEYTIHWVRQAPGKG LEWIGNINPNNGGTTYNQKFEDRVTITVDKSTSTAYMELSSLRSED TAVYYCAAGWNFDYWGQGTTVTVSSGGGGSGGGGSGGGGSDIQ MTQSPSTLSASVGDRVTITCKASQDVGTAVDWYQQKPGQAPKLLI YWASTRHTGVPDRFSGSGSGTDFTLTISRLQPEDFAVYYCQQYNS YPLTFGQGTKVDIK |
| 86 hJ591 scFv (VH-VL) | Gaggtccagctggtgcagtctggagctgaagtgaagaagcctgggg cttctgtgataacaatttaatcctaacatgtggtactaccacagcgagctgagctgagctgatctgat...<br>(nucleotide sequence) |
| 87 hJ591VHWK.BBZ | MALPVTALLLPLALLLHAARPGEVQLVQSGAEVKKPGASVKVSCK ASGYTFTEYTIHWVRQAPGKGLEWIGNINPNNGGTTYNQKFEDRV TITVDKSTSTAYMELSSLRSEDTAVYYCAAGWNFDYWGQGTTVT VSSGGGGSGGGGSGGGGSDIQMTQSPSTLSASVGDRVTITCKASQD VGTAVDWYQQKPGQAPKLLIYWASTRHTGVPDRFSGSGSGTDFTL TISRLQPEDFAVYYCQQYNSYPLTFGQGTKVDIKTTTPAPRPPTPAP TIASQPLSLRPEACRPAAGGAVHTRGLDFACDIYIWAPLAGTCGVL LLSLVITLYCKRGRKKLLYIFKQPFMRPVQTTQEEDGCSCRFPEEEE GGCELRVKFSRSADAPAYKQGQNQLYNELNLGRREEYDVLDKRR GRDPEMGGKPRRKNPQEGLYNELQKDKMAEAYSEIGMKGERRRG KGHDGLYQGLSTATKDTYDALHMQALPPR |
| 88 hJ591VHVK.BBZ | ATGGCCCTGCCTGTGACAGCCCTGCTGCTGCTCTGGCTCTGCT GCTGCACGCGCCAGACCTGGAGAGGTCCAGTCTGTGCAGTCT GGAGCTGAGTGAAGAAGCCTGGGCCTCAGTGAAGGTCTCCT GCAAGGCTTCTGGATACACATTCACTGAATACACCATCCACTGG GTGAGGCAGGCCCCTGGAAAGGCCTTGAGTGGATTGGAAACA TTAATCCTAACAATGTGGTACTACCACAGCAAGAAGTTCGAG GACAGAGTCACAATCACTGTAGACAAGTCCACCAGCACAGCCT ACATGGAGCTCAGCAGCCTGAGATCTGAAGATACTGCAGTCTA TTACTGTGCAGCTGGTTGGAACTTTGACTACTGGGGCCAAGGCA CCACGGTCACCGTCTCCTCAGGAGGCGGAGGATCTGGCGCGG |

TABLE 2-continued

Sequences used in the invention

| SEQ ID NO: Name | Amino Acid/Nucleotide Sequence |
|---|---|
| | AGGAAGTTCTGGCGAGGCAGCGACATTCAGATGACCCAGTCT |
| | CCCAGCCACCCTGTCCGCATCAGTAGGAGACAGGGTCACCATCA |
| | CTTGCAAGGCCAGTCAGGATGTGGGTACTGCTGTAGACTGGTAT |
| | CAACAGAAACCAGGGCAAGCTCCTAAACTACTGATTTACTGGG |
| | CATCCACCCGGCACACTGGAGTCCCTGATCGCTTCAGCGCAGT |
| | GGATCTGGGACAGATTTCACTCTCACCATCAGCAGACTGCAGCC |
| | TGAAGACTTTGCAGTTTATTACTGTCAGCAATATAACAGCTATC |
| | CTCTCACGTTCGGCCAGGGGACCAAGGTGGATATCAAAACCAC |
| | GACGCCAGCGCCGCGACCACCAACACCGGCGCCACCATCGCG |
| | TCGCAGCCCCTGTCCCTGCGCCCCGAGGCGTGCCGGCCAGCGC |
| | CGGGGGCGCAGTGCACACGAGGGGGCTGGACTTCGCCTGTGA |
| | TATCTACATCTGGGCGCCCTTGGCCGGGACTTGTGGGGTCCTTC |
| | TCCTGTCACTGGTTATCACCCTTTACTGCAAACGGGGCAGAAAG |
| | AAACTCCTGTATATATTCAAACAACCATTTATGAGACCAGTACA |
| | AACTACTCAAGAGGAGGATGTGAACTGAGAGTTCAGAGTT |
| | GAAGAAGAAGGACCCCCGTACAAGCAGGGCCAGAACCAGCTCT |
| | AGCCCAGACGCCCCCGTACAAGCAGGGCCAGAACCAGCTCT |
| | ATAACGAGCTCAATCTAGGACGAAGAGAGAGTACGACGTTTT |
| | GGACAAGAGACGTGGCCGGGACCCTGAGATGGGGGGAAAGCC |
| | GAGAAGGAAGAACCCTCAGGAAGGCCTGTACAACGAACTGCAG |
| | AAAGATAAGATGGCCGAGGCCTACAGTGAGATTGGGATGAAAG |
| | GCGACGCCGGAGGGCAAGGGCACACCTACGACGCCTTTACCAGGG |
| | TCTCAGTACGCCACCAAGGACACACCTACGACGCGCCCTTCACATGC |
| | AGGCCCTGCCCCCTCGC |
| 89 hJ591VKVH.BBZ | MALPVTALLLPLALLLHAARPGDIQMTQSPSTLSASVGDRVTITCK |
| | ASQDVGTAVDWYQQKPGQAPKLLIYWASTRHTGVPDRFSGSGSG |
| | TDFTLTISRLQPEDFAVYYCQQYNSYPLTFGQGTKVDIKGGGSGG |
| | GGSSGGGSEVQLVQSGAEVKKPGASVKVSCKASGYTFTEYTIHWV |
| | RQAPGKGLEWIGNINPNNGTTYNQKFEDRVTITVDKSTSTAYME |
| | LSSLRSEDTAVYYCAAGWNFDYWGQGTTVTVSSTTITPAPRPPTPA |
| | PTIASQPLSLRPEACRPAAGGAVHTRGLDFACDIYIWAPLAGTCGV |
| | LLLSLVITLYCKRGRKKLLYIFKQPFMRPVQTTQEEDGCSCRFPEEE |
| | EGGCELRVKFSRSADAPAYKQGQNQLYNELNLGREEYDVLDKR |
| | RGRDPEMGGKPRRKNPQEGLYNELQKDKMAEAYSEIGMKGERRR |
| | GKGHDGLYQGLSTATKDTYDALHMQALPPR |
| 90 hJ591VKVH.BBZ | ATGGCCCTGCCTGTGACAGCCCTGCTGCTCTGCTCTCTGCT |
| | GCTGCACGCCGCCAGACCTGGACAGATCCAGATGACCCAGTCT |
| | CCCAGCACCCTGTCCGCATCAGTAGGAGACAGGGTCACCATCA |
| | CTTGCAAGGCCAGTCAGGATGTGGGTACTGCTGTAGACTGGTAT |
| | CAACAGAAACCAGGGCAAGCTCCTAAACTACTGATTTACTGGG |
| | CATCCACCCGGCACACTGGAGTCCCTGATCGCTTCAGCGCAGT |
| | GGATCTGGGACAGATTTCACTCTCACCATCAGCAGACTGCAGCC |
| | TGAAGACTTTGCAGTTTATTACTGTCAGCAATATAACAGCTATC |
| | CTCTCACGTTCGGCCAGGGGACCAAGGTGGATATCAAAGGAGG |
| | CGGAGGATCTGGCGGCGGAGGAAGTTCTGGCGAGGCGGAG |

TABLE 2-continued

Sequences used in the invention

| SEQ ID NO: Name | Amino Acid/Nucleotide Sequence |
|---|---|
|  | GTCCAGCTGTGTGCAGTCTGGAGCTGAGGTGAAGAAGCCTGGGG |
|  | CCTCAGTGAAGGTCTCCTGCAAGGCTTCTGGATACACATTCACT |
|  | GAATACACCATCCACTGGGTGAGGCAGGCCCCTGGAAAGGGCC |
|  | TTGAGTGGATTGGAAACATTAATCCTAACAATGGTGACTACC |
|  | TACAACCAGAAGTTCGAGGACAGAGTCACAATCACTGTAGACA |
|  | AGTCCACCAGCACAGCCTACATGGAGCTCAGCAGCCTGAGATC |
|  | TGAGGATACTGCAGTCTATTACTGTGCAGCTGGTTGGAACTTTG |
|  | ACTACTGGGGCCAAGGCACCACGGTCACCGTCTCCTCAACCAC |
|  | GACGCCAGCGCCGCGACCACCAACAGCGCCCACCATCGCG |
|  | TCGCAGCCCCTGTCCCTGCGCCCAGAGGCGTGCCGGCCAGCG |
|  | CGGGGGGCGCAGTGCACACGAGGGGGCTGACTTCGCCTGTGA |
|  | TATCTACATCTGGGCGCCCTTGGCCGGACTTGTGGGGTCCTTC |
|  | TCCTGTCACTGGTTATCACCCTTTACTGCAAACGGGGCAGAAAG |
|  | AAACTCCTGTATATATTCAAACAACCATTTATGACACCAGTACA |
|  | AACTACTCCAAGAGGAAGACGCTGTAGCTGAAGTGAAGTTCAGCAGG |
|  | GAAGAAGAAGGAGGATGAACTGAACTGAGAGTCAGATAA |
|  | AGCCAGAGACCCCCCGGTACAAGCAGGGCCAGAACCAGCTCT |
|  | ATAACGAGCTCAATCTAGGACGAAGAGAGAGTACGACGTTTT |
|  | GGACAAGAGACGTGGCCGGGACCCTGAGATGGGGGGAAAGCC |
|  | GAGAAGGAAGAACCCTCAGGAAGGCCTGTACAACGAACTGCAG |
|  | AAAGATAAGATGGCCGAGGCCTACAGTGAGATTGGGATGAAAG |
|  | GCGACGCCGGAGGGCAAGGGCACACGCGCCTTTACCAGGG |
|  | TCTCAGTAGCCACCAAGGACACACCTACGACGCCCTTCACATGC |
|  | AGGCCCTGCCCCCTCGC |
| 91 hJ591VKVH.ICOS BBZ | MALPVTALLLPLALLLHAARPGDIQMTQSPSTLSASVGDRVTITCK ASQDVGTAVDWYQQKPGQAPKLLIYWASTRHTGVPDRFSGSGSG TDFTLTISRLQPEDFAVYYCQQYNSYPLTFGQGTKVDIKGGGSSG GGSSGGGSEVQLVQSGAEVKKPGASVKVSCKASGYTFTEYTIHWV RQAPGKGLEWIGNINPNNGTTYNQKFEDRVTITVDKSTSTAYME LSSLRSEDTAVYYCAAGWNFDYWGQGTTVTVSSTTTPAPRPPTPA PTIASQPLSLRPEACRPAAGGAVHTRGLDFACDFWLPIGCAAFVVV CILGCILICWLTKKKYSSSVHDPNGEYMFMRAVNTAKKSRLTDVT LKRGRKKLLYIFKQPFMRPVQTTQEDGCSCRFPEEEEGCELRVK FSRSADAPAYKQGQNQLYNELNLGRREEYDVLDKRRGRDPEMGG KPRRKNPQEGLYNELQKDKMAEAYSEIGMKGERRRGKGHDGLYQ GLSTATKDTYDALHMQALPPR |
| 92 hJ591VKVH.ICOS BBZ | ATGGCCCTGCCTGTGACAGCCCTGCTGCTGCCTCTGGCTCTGCT GCTCCACGCCGCCAGACCTGGAGACATTCAGATGACCCAGTCT CCCAGCACCCTGTCCGCATCAGTAGGAGACAGGGTCACCATCA CTTGCAAGGCCAGTCAGGATGTGGGTACTGCTGTAGACTGGTAT CAACAGAAACCAGGGCAAGCTCCTAAACTACTGATTTACTGGG CATCCACCCGGACACAGGGAGTCCCTGATCGCTTCAGCGGCAGT GGATCTGGGACAGATTTCACTCTCACCATCAGCAGACTGCAGCC TGAAGACTTTGCAGTTTATTACTGTCAGCAATATAACAGCTATC CTCTCACGTTCGGCCAGGGACCAAGGTGGATATCAAAGGAGG |

TABLE 2-continued

Sequences used in the invention

| SEQ ID NO: Name | Amino Acid/Nucleotide Sequence |
|---|---|
| | CGGAGGATCTGGCGCGGAGGAAGTTCTGCGCGAGGCAGCGAG<br>GTCCAGCTGTGCAGTCTGGAGCTGAGGTGAAGAAGCCTGGGG<br>CCTCAGTGAAGGTCTCCTGCAAGGCTTCTGGATACACATTCACT<br>GAATACACCATCCACTGGGTGAGGCAGGCCCCTGGAAAGGGCC<br>TTGAGTGGATTGGAAACATTAATCCTAACAATGGTGGTACTACC<br>TACAACCAGAAGTTCGAGGACAGAGTCACAATCACTGTAGACA<br>AGTCCACCAGCACAGCCTACATGGAGCTCAGCAGCCTGAGATC<br>TGAGGATACTGCAGTCTATTACTGTGCAGCTGGTTGGAACTTTG<br>ACTACTGGGGCCAAGGCACCACTGTCACCGTCTCCTCAACCAC<br>GACGCCAGCCGCGCCACCACCACACCGGCCGCCCACCATCGCG<br>TCGCAGCCCCTGTCCCTGCGCCCAGAGGCGTGCCGGCCAGCGG<br>CGGGGGGCCAGTGCACACAGGGGCTGGACTTCGCCTGTGA<br>TTTCTGGTTACCCATAGAGATGTGCAGCCTTTGTTGTAGTCGCAT<br>TTTGGATGCATATTATTTGTTGCTTACAGACCTAAACGTGAATACATGTTCATGAGA<br>CATCCAGTGTGCACAGCCAAAAAATCCAGACTCACAGATGTGACCC<br>GCAGTGAACACAGCCAAAAAGAAACTCCTGTATATATTCAAACAACC<br>TAAAACGGGCAGAGAAGAACTCTATAACGAGCTCAATCTAGGACGAAGA<br>ATTTATGAGACCAGTACAAACTACTCAAGAGGAAGATGGCTGT<br>AGCTGCCGATTTCAGAAGAAGAAGATAAGCGCCCCGCGTACAAG<br>GAGTGAAGTTCAGCAGGAGCGCAGACGCCCGGAGGGCCAAGGGCA<br>GGGCCAGAACCAGCTCTATAACGAGCTCAATCTAGGACGAAGA<br>GAGGAGTACGACGTTTTGCACAAGAACGTGGCCGGACCCTG<br>AGATGGGGGAAAGCCGAAGGAAGAACCCTCAGGAAGGCC<br>TGTACAACGAACTGCAGAAAGAAGATAGAGTGCGGAGGCCTACAG<br>CGACGCCTTTACCAGGGTCTCAGTACAGCCACCAAGGACACC<br>TACGACGCCCTTCACATGCAGGCCCTGCCCCTCGC |
| 93 hJ591VKVH.ICOS<br>BBZYMNM | MALPVTALLLPLALLLHAARPGDIQMTQSPSTLSASVGDRVTIITCK<br>ASQDVGTAVDWYQQKPGQAPKLLIYWASTRHTGVPDRFSGSGSG<br>TDFTLTISRLQPEDFAVYYCQQYNSYPLITPGQGTKVDIKGGGGSGG<br>GGSGGGGSEVQLVQSGAEVKKPGASVKVSCKASGYTFTEYTIHWV<br>RQAPGKGLEWIGNINPNNGGTTYNQKFEDRVTITVDKSTSTAYME<br>LSSLRSEDTAVYYCAAGWNFDYWGQGTTVTVSSTTTPAPRPPTPA<br>PTIASQPLSLRPEACRPAAGGAVHTRGLLDFACDFWLPIGCAAFVVV<br>CILGCILICWLTKKKYSSSVHDPNGEYMNMRAVNTAKKSRLTDVT<br>LKRGRKKLLYIFKQPFMRPVQTTQEDGCSCRFPEEEEGCELRVK<br>FSRSADAPAYKQGQNQLYNELNLGRREEYDVLDKKRRGRDPEMGG<br>KPRRKNPQEGLYNELQKDKMAEAYSEIGMKGERRRGKGHDGLYQ<br>GLSTATKDTYDALHMQALPPR |
| 94 hJ591VKVH.ICOS<br>BBZYMNM | ATGGCCCTCCTGTGACAGCCCTGCTGCCCTGGCCTCTGCT<br>GCTGCACGCCCGCCAGACCTGGAGACATTCAGATGACCCAGTCT<br>CCCAGCACCCTGTCCGCATCAGTGGAGACAGGGTCACCATCA<br>CTTGCAAGGCCAGTCAGGATGTGGGTACTGCTGTAGACTGGTAT<br>CAACAGAAACCAGGCCAAGCTCCTAAACTACTGATTTACTGGG<br>CATCCACCCGGCACACTGGAGTCCCTGACCGCTTCAGCGGCAGT |

TABLE 2-continued

Sequences used in the invention

| SEQ ID NO: Name | Amino Acid/Nucleotide Sequence |
|---|---|
| | GGATCTGGGACAGAGATTTCACTCTCACCATCAGCAGACTGCAGCC |
| | TGAAGACTTTGCAGTTTATTACTGTCAGCAATATAACAGCTATC |
| | CTCTCACGTTCGGCCAGGGGACCAAGGTGGATATCAAAGGAGG |
| | CGGAGGATCTGGCGGCGGAGGAAGTTCTGGCGGAGGCAGCGAG |
| | GTCCAGCTGGTGCAGTCTGGAGCTGAGGTGAAGAAGCCTGGGG |
| | CCTCAGTGAAGGTCTCCTGCAAGGCTTCTGGATACACATTCACT |
| | GAATACACCATCCACTGGGTGAGGCAGGCCCCTGAAAGGCC |
| | TTGAGTGGATTGGAAACATTAATCCTAACAATGGTGTACTACC |
| | TACAACCAGAAGTTCGAGGACAGAGTCACAATCACTGTAGACA |
| | AGTCCACCAGCACAGCCTACATGGAGCTCAGCAGCCTGAGATC |
| | TGAGGATACTGCAGTCTATTACTGTGCAGCTGGTTGGAACTTTG |
| | ACTACTGGGGCCAAGGCACCACCGTCACCGTCTCCTCAACCAC |
| | GACGCCAGCGCCGCACCCACCAAACCGGCGCCCACCATCGCG |
| | TCGCAGCCCCTGTCCCTGCGCCCAGAGGCTGCCCGGCCAGCG |
| | CGGGGGGCGCAGTGCACACGAGGGGGGCTGACTTCGCCTGTGA |
| | TTTCTGGTTACCCATAGGATGTGCAGCCTTTGTTGTTAGTCTGCAT |
| | TTTGGGATGCATACTATTTGTTGCTTACAAAAGAAGTATT |
| | CATCCAGTGTGCACGACCCTAACGGTGAATACATGAACATGAG |
| | AGCAGTGAACACAGCCAGAAATCCAGACTCAAGATGTGACC |
| | CTAAAACGGGCAGAAGGAACTCCTGTATATATTCAAACAAC |
| | CATTTATGAGACCCAGTACAAACTACTCAAGAGGAAGATGGCTG |
| | TAGCTGCCGATTTCCAGAAGAAGAAGGATGTGAACTG |
| | AGAGTGAAGTTCAGCAGGAGCGCAGAACGCCAATCTAGGACGAG |
| | AGGGCCAGAACCAGTCTATAACAAGCTGGTCAATCTAGGACGAAG |
| | AGAGGAGTACGACGTTTTGACAAGAGACGTGGCCGGACCCT |
| | GAGATGGGGGAAAGCCGAGAAGGAAGAACCCTCAGGAGGC |
| | CTGTACAACGAACTCAGAAAGATAAGATGGCGAGGCCTACA |
| | GTGAGATTGGGATGAAAGGCGAGCGCCGAGGGGCAAGGGGC |
| | ACGACGGCCTTTACCAGGTCTCAGTACGACCCAAGAGACAC |
| | CTACGACGCCCTTCACATGCAGGCCCTGCCCCCTCGC |
| 95 hJ591VKVH.ICOSZ | MALPVTALLLPLALLLHAARPGDIQMTQSPSTLSASVGDRVTITCK |
| | ASQDVGTAVDWYQQKPGQAPKLLIYWASTRHTGVPDRFSGSGSG |
| | TDFTLTISRLQPEDFAVYYCQQYNSYPLTFGQGTKVDIKGGGSGG |
| | GGSSGGGGSEVQLVQ SGAEVKKPGASVKVSCKASGYTFTEYTIHWV |
| | RQAPGKGLEWIGNINPNNGGTTYNQKFEDRVTITVDKSTSTAYME |
| | LSSLRSEDTAVYYCAAGWNFDYWGQGTTVTVSSTTTPAPRPPTPA |
| | PTIASQPLSLRPEACRPAAGGAVHTRGLDFACDFWLPIGCAAFVVV |
| | CILGCILICWLTKKKYSSSVHDPNGEYMFMRAVNTAKKSRLTDVT |
| | LRVKFSRSADAPAYKQGQNQLYNELNLGRREEYDVLDKRRGRDP |
| | EMGGKPRRKNPQEGLYNELQKDKMAEAYSEIGMKGERRRGKGH |
| | DGLYQGLSTATKDTYDALHMQALPPR |
| 96 hJ591VKVH.ICOSZ | ATGGCCCTGCCTGTGACAGCCCTGCTGCTGCCTCTGGCTCTGCT |
| | GCTGCACGCCCGCCAGGACCTGGAGACATTCAGATGACCCAGTCT |
| | CCCAGCACCCTGTCCGCATCAGTAGGAGACAGGGTCACCATCA |
| | CTTGCAAGGCCAGTCAGGATGTGGGTACTGCTGTAGACTGTAT |

TABLE 2-continued

Sequences used in the invention

| SEQ ID NO: Name | Amino Acid/Nucleotide Sequence |
|---|---|
| | CAACAGAAACCAGGGCAAGTCCTAAACTACTGATTTACTGGG CATCCACCCGGCACACTGGAGTCCCTGATCGCTTCAGCGCAGT GGATCTGGGACAGATTTCACTCTCACCATCAGCAGACTGCAGCC TGAAGACTTTGCAGTTTATTACTGTCAGCAATATAACAGCTATC CTCTCACGTTCGGCCAGGGGACCAAGGTGGATATCAAAGAGG CGGAGGATCTGGCCGCGGAGGAAGTTCTGGCGAGGCAGCGAG GTCCAGCTGTGTGCAGTCTGGAGCTGAGGTGAAGAAGCCTGGGG CCTCAGTGAAGGTCTCCTGCAAGGCTTCTGGATACACATTCACT GAATACACCATCCACTGGGTGAGGCAGGCCCCTGAAAGGGCC TTGAGTGGATTGGAAACATTAATCCTAACAATGGTACTACC TACAACCAGAAGTTCGAGGACAGAGTCACAATCACTGTAGACA AGTCCACCAGCACAGCCTACATGGAGCTCAGCAGCCTGAGATC TGAGGATACTGCAGTCTATTACTGTGCAGCTGGTTGGAACTTTG ACTACTGGGGCCAAGGCACCACTGTCACCGTCTCCTCAACCAC GACGCCAGCGCCGCGACCACCACAACCGGCGCCCACCATCGCG TCGCAGCCCCTGTCCCTGCGCCCAGAGGCGTGCCGGCCAGCGG CGGGGGCGCCAGTGCACACAGAGGGGCTGGACTTCGCCTGTGA TTTCTGGTTACCCATAGGATGTGCAGCCTTTGTTGTAGTCTGCAT TTTGGGATGCATACTTATTTGTTGGCTTACAAAAAGAAGTATT CATCCAGTGTGCACGACCCTAACGGTGAATACATGTTCATGAGA GCAGTGAACACAGCCAAAAATCCAGACTCACAGATGTGACCC TAAGAGTGAAGTTCAGCAGCGCCAGACACCCCCCGCGTACAA GCAGGGCCAGAACCAGCTCTATAACGAGCTCAATCTAGAGCGA AGAGGAGTACGACGTTTTGGACAAGAGACGTGCCGGGACC CTGAGATGGGGGAAGCCCGAGAAGATAAGATGGCGAGGCCTA GCCTTACAACGTGCAGAAAGGCGAGCCGGCGAGGGGCAAGGG CAGTGAGATTGGGATGAAAGGCGAGCGGCGAGGCCACCAAGGAC GCACGACGCCCTTTACCAGGGTCTCAGTACAGCCACCAAGGAC ACCTACGACCCCTTCACATGCAGGCCCTGCCCCCTGC |
| 97 hJ591VkVH.ICOSZ YMNM | MALPVTALLLPLALLLHAARPGDIQMTQSPSTLSASVGDRVTITCK ASQDVGTAVDWYQQKPGQAPKLLIYWASTRHTGVPDRFSGSGSG TDFTLTISRLQPEDFAVYYCQQYNSYPLTFGQGTKVDIKGGGGSGG GGSSGGGSEVQLVQSGAEVKKPGASVKVSCKASGYTFTEYTIHWV RQAPGKGLEWIGNINPNNGGTTYNQKFEDRVTITVDKSTSTAYME LSSLRSEDTAVYYCAAGWNFDYWGQGTTVTVSSTTTPAPRPPTPA PTIASQPLSLRPEACRPAAGGAVHTRGLDFACDFWLPIGCAAFVVV CILGCILIGWLTKKKYSSSVHDPNGEYMNMRAVNTAKKSRLTDVT LRVKFSRSADAPAYKQGQNQLYNELNLGRREEYDVLDKRRGRDP EMGGKPRRKNPQEGLYNELQKDKMAEAYSEIGMKGERRRGKGH DGLYQGLSTATKDTYDALHMQALPPR |
| 98 hJ591VkVH.ICOSZ YMNM | ATGGCCCTGCCTGTGACAGCCCTGCTGCTCCTCGGCTCTGCT GCTCACGCCCGCCAGACCTGGAGACATTCAGATGACCCAGTCT CCCAGCACCCTGTCCGCATCAGTAGGAGACAGGGTCACCATCA CTTGCAAGGCCAGTCAGGATGTGGGTACTGCTGTAGACTGGTAT CAACAGAAACCAGGGCAAGTCCTAAACTACTGATTTACTGGG |

TABLE 2-continued

Sequences used in the invention

| SEQ ID NO: Name | Amino Acid/Nucleotide Sequence |
|---|---|
|  | CATCCACCCGGCACACTGGAGTCCCTGATGCTTCAGCGCAGT<br>GGATCTGGGACAGATTTCACTCTCCACCATCAGCAGACTGCAGCC<br>TGAAGACTTTGCAGTTTATTACTGTCAGCAATATAACAGCTATC<br>CTCTCACGTTCGGCCAGGGGACCAAGGTGGATATCAAAGGAGG<br>CGGAGGATCTGGCGGCGGAGGAAGTTCTGGCGGCAGCGAG<br>GTCCAGCTGGTGCAGTCTGGAGCTGAGGTGAAGAAGCCTGGGG<br>CCTCAGTGAAGGTCTCCTGCAAGGCTTCTGGATACACATTCACT<br>GAATACACCATCCACTGGGTGAGGCAGGCCCCTGAAAGGGCC<br>TTGAGTGGATGGAAACATTAATCTAACAATGGTGGTACTACC<br>TACAACCAGAAGTTCGAGGACAGAGTCACACTCACTGTAGACA<br>AGTCCACCAGCACAGCCTACATGGAGCTCAGCAGCCTGAGATC<br>TGAGGATACTGCAGTCTATTACTGTGCAGCTGGTTGGAACTTTG<br>ACTACTGGGGCCAAGGCACCACTGTCACCGTCTCCTCAACCAC<br>GACGCCAGCCGCCGCGACCACAACACCGGCCGCCATCGCG<br>TCGCAGCCCCTGTCCTGCGCCCAGAGGCGTGCCGCCAGCGG<br>CGGGGGGCCAGTGCACACGAGGGGCCTGGACTTCGCCTGTGA<br>TTTCTGGTTACCCATAGGATGTGCAGCCTTTGTTGTTGTAGTCTGCAT<br>TTTGGGATGCATACTTATTGTTGGCTTACAAAAAAGAAGTATT<br>CATCCAGTGTGCACGACCCTAACGTGAATACATCAGAGATGAG<br>AGCAGTGAACACAGCCAAAAAATCCAGATCACAGATGTGACC<br>CTAAGAGTGAAGTTCAGCAGGACGCCAGGACGCCCGCGTACA<br>AGCAGGGCCAGAACCAGCTCTATAACGAGTCAATCTAGACG<br>AAGAGGAGTACACGTTTTGGACAAGAGACTGGCCGGAC<br>CCTGAGATGGGGAAAGCCGAGAAGGAAGAACCCTCAGGA<br>GGCCTGTACAACGAACTGCAGAAAGATAAGATGGCGGAGGCCT<br>ACAGTGAGATTGGGATGAAAGGCGAGCGCCGAGGGCAAGG<br>GGCACGACCGGCCTTTACCAGGGTCTCAGTACAGCCACCAAGGA<br>CACCTACGACGCCCTTCACATGCAGGCCTCGCCCCTCGC |
| 79 2B3-hJ591.BBZ | atggcccctgcctgtcgacagcccctgcctctggctctgtcgacgcgccagacctggaGcca<br>ccatggcgtaccggtgaccgcactccctgctgcactcgccctcccacgcgcccgccgatat<br>ccagctgacccaatcaccgtcgtccctgctgcctccgtgggcaacccgggtgacgatcaccctgatgtcct<br>cgagcagtgtacggttcatccactggtaccaacagaaagcccggcaaggcaccaaagcggctgatctacg<br>acaccagcaagctcgcttctcggagtgcccagcaggttcctcggggaagtggcacagacttcaactct<br>caccatcagttcactccagcgaggacttgccacctactattgccagcagtggtcctcgtccccttac<br>cttcggccaggggaccaaaggtgaaattaaggttcgacctcggagggggctcctggtgggctccg<br>gcggggggtcctcatcggaggttcagctgtggaagcgccggccggtgtgcacgcccggga<br>gtctgcggtcctgtgccctgccgcccaagccggcttcaacatcaaggtacactactactcactggtgggcaagc<br>cccaggcaaggtctggagtgggtggttgatgtgacccctgaaaacggcgacactgagttcgtgccaaa<br>attccaggggggcgggcgacatctccgcgacacctccaagaatacggcctacctgcagatgaactccct<br>gcgcgccgaagaacacagccggtctactactgcaagacaggggtctcggcagggcaccccgtga<br>ccgtttcgaatgccgcggcGgagtggtgaggtggatccGACATTCAGATGACCCAGTCT<br>CCCAGCACCCTGTCCGCATCAGTAGGAGACAGGGTCACCATCA<br>CTTGCAAGGCCAGTCAGGATGTGGGTACTGCTGTAGACTGGTAT<br>CAACAGAAACCAGGGCAAGCTCCTAAACTACTGATTTACTGGG<br>CATCCACCCGGCACAGATTTCACTCTCACCATCAGCAGACTGCAGGC<br>GGATCTGGGACAGATTTCACTCTCACCATCAGCAGACTGAGGC |

TABLE 2-continued

Sequences used in the invention

| SEQ ID NO: Name | Amino Acid/Nucleotide Sequence |
|---|---|
| | TGAAGACTTTGCAGTTTATTACTGTCAGCAATATAACAGCTATC |
| | CTCTCACGTTCGGCCAGGGGACCAAGGTGGATATCAAAGaggcg |
| | gaggatctggcggcggcggaagttctggcggcggcggctccagtGGTCCAGTGGTGCAG |
| | TCTGGAGCTGAGGTGAAGAAGCCTGGGGCCTCAGTGAAGGTCT |
| | CCTGCAAGGCTTCTGGATACACATTCACTGAATACACCATCCAC |
| | TGGGTGAGGCAGGCCCCTGGAAAGGGCTTGAGTGGATTGGAA |
| | ACATTAATCCTAACAATGGTGGTACTACCTACAACCAGAAGTTC |
| | GAGGACAGAGTCACAATCACTGTAGACAAGTCCACCAGACAG |
| | CCTACATGGAGCTCAGCCTGAGATCTGAGGATACTGCAGT |
| | CTATTACTGTGCAGCTGGTTGGAACTTTGACTACTGGGGCCAAG |
| | GCACCACGGTCACCGTCTCCTCAaACcacgacgccagccgcgaccaccaac |
| | accggcgcccaccatgctgctgcaccccctgtccctggccgcccagagcgtgccgccagcgcgggg |
| | ggccagtgcacacgagggggctgactcgctgatctacaatctggccgcccttggccgggact |
| | tgtgggtccttcctgctcctgtcactggttatcacccttactgcAaacgggcagaagaactccctatatat |
| | tcaaacaaccatttatgagaccagtaacaccactccaaggagaagacggtagctgccccccgcgtacaag |
| | gaagaaggaggatgtgaactgAgagtgaagttcagcagggcgcagaagctacgacgttttggacaag |
| | cagggccagaaccagctcttataacgagctcaatctaggacgaagaggaagtacgacgttttggacaag |
| | agactggcgggaacctgagatgggggaaagcaatcaggcctacagtgagttgaagaggcctacgcc |
| | aacgaactcagaaagataagatgcgaggctacaggttcagtacagcagcaaggacacctacgccccct |
| | gggccaagggcacgacgccttaccaggtcagtacagcagcaaggacacctacgccgacgcccctt |
| | ccatgcaggccctgccccctgc |
| 80 2B3-hJ591.BBZ | MALPVTALLLPLALLLHAARPGATMALPVTALLLPLALLLHAARP |
| | DIQLTQSPSSLSASVGDRVTITCSASSSVRFIHWYQQKPGKAPKRLI |
| | YDTSKLASGVPSRFSGSGSGTDFTLTISSLQPEDFATYYCQQWSSSP |
| | FTFGQGTKVEIKGSTSGSGGSGGGSEVQLVESGGGLVQPG |
| | GSLRLSCAASGFNIKDYYIHWVRQAPGKGLEWVAWIDPENGDTEF |
| | VPKFQGRATISADTSKNTAYLQMNSLRAEDTAVYYCKTGFWGQ |
| | GTLVTVSSAAGGGGSGGGGSDIQMTQSPSTLSASVGDRVTITCKASQDV |
| | GTAVDWYQQKPGQAPKLLIYWASTRHTGVPDRFSGSGSGTDFTLT |
| | ISRLQPEDFAVYYCQQYNSYPLTFGQGTKVDIKGGGGSGGGGSG |
| | GGSEVQLVQSGAEVKKPGASVKVSCKASGYTFTEYTIHWVRQAP |
| | GKGLEWIGNINPNNGGTTYNQKFEDRVTITVDKSTSTAYMELSSLR |
| | SEDTAYYYCAAGWNFDYWQQGTTVTVSSNHDASAATTNTGAHH |
| | ASQPLSLRPEACRPAAGAVHTRGLDFACDIYIWAPLAGTCGVLLL |
| | SLVITLYCKRGRKKLLYIFKQPFMRPVQTTQEEDGCSCRFPEEEEG |
| | GCELRVKFSRSADAPAYKQQONQLYNELNLGRREEYDVLDKRRG |
| | RDPEMGGKPRKNPQEGLYNELQKDKMAEAYSEIGMKGERRRGK |
| | GHDGLYQGLSTATKDTVDALHMQALPPR |
| 81 2B3-hJ591.BRZ | MALPVTALLLPLALLLHAARPGATMALPVTALLLPLALLLHAARP |
| | DIQLTQSPSSLSASVGDRVTITCSASSSVRFIHWYQQKPGKAPKRLI |
| | YDTSKLASGVPSRFSGSGSGTDFTLTISSLQPEDFATYYCQQWSSSP |
| | FTFGQGTKVEIKGSTSGSGGSGGGSSEVQLVESGGGLVQPG |
| | GSLRLSCAASGFNIKDYYIHWVRQAPGKGLEWVAWIDPENGDTEF |
| | VPKFQGRATISADTSKNTAYLQMNSLRAEDTAVYYCKTGFWGQ |
| | GTLVTVSSAAGGGGSGGGGSDIQMTQSPSTLSASVGDRVTITCKASQDV |

TABLE 2-continued

Sequences used in the invention

| SEQ ID NO: Name | Amino Acid/Nucleotide Sequence |
|---|---|
| | GTAVDWYQQKPGQAPKLLIYWASTRHTGVPDRFSGSGSGTDFTLT ISRLQPEDFAVYYCQQYNSYPLTFGQGTKVDIKGGGSGGGGSGG GSEVQLVQSGAEVKKPGASVKVSCKASGYTFTEYTIHWVRQAP GKGLEWIGNINPNNGGTTYNQKFEDRVTITVDKSTSTAYMELSSLR SEDTAVYYCAAGWNFDYWGQGTTVTVSSHTTPAPRPPTPAPTIAS QPLSLRPEACRPAAGGAVHTRGLDFACDIYIWAPLAGTCGVLLLSL VITLYCKRGRKKLLYIFKQPFMRPVQTTQEEDGCSCRFPEEEEGC ELRVKFSRSADAPAYKQGQNQLYNELNLGRREEYDVLDKRRGRD PEMGGKPRRKNPQEGLYNELQKDKMAEAYSEIGMKGERRRGKGH DGLYQGLSTATKDTYDALHMQALPPR |
| 82 2B3-hJ591.BBZ | MALPVTALLLPLALLLHAARPGATMALPVTALLLPLALLLHAARP DIQLTQSPSSLSASVGDRVTITCSASSSVRFIHWYQQKPGKAPKRLI YDTSKLASGVPSRFSGSGSGTDFTLTISSLQPEDFATYYCQQWSSSP FTFGQGTKVEIKGSTSGGGSGGGSGGGSSEVQLVESGGGLVQPG GSLRLSCAASGFNIKDYYIHWVRQAPGKGLEWVAWIDPENGDTEF VPKFQGRATISADTSKNTAYLQMNSLRAEDTAVYYCKTGFWGQ GTLVTVSSAAGGGGSDIQMTQSPSTLSASVGDRVTITCKASQDV GTAVDWYQQKPGQAPKLLIYWASTRHTGVPDRFSGSGSGTDFTLT ISRLQPEDFAVYYCQQYNSYPLTFGQGTKVDIKGGGSGGGGSGG GSEVQLVQSGAEVKKPGASVKVSCKASGYTFTEYTIHWVRQAP GKGLEWIGNINPNNGGTTYNQKFEDRVTITVDKSTSTAYMELSSLR SEDTAVYYCAAGWNFDYWGQGTTVTVSSTTTPAPRPPTPAPTIAS QPLSLRPEACRPAAGGAVHTRGLDFACDIYIWAPLAGTCGVLLLSL VITLYCKRGRKKLLYIFKQPFMRPVQTTQEEDGCSCRFPEEEEGC ELRVKFSRSADAPAYKQGQNQLYNELNLGRREEYDVLDKRRGRD PEMGGKPRRKNPQEGLYNELQKDKMAEAYSEIGMKGERRRGKGH DGLYQGLSTATKDTYDALHMQALPPR |

C. Nucleic Acids and Expression Vectors

The present disclosure provides a nucleic acid encoding a CAR. The nucleic acid of the present disclosure may comprises a polynucleotide sequence encoding any one of the CARs (including the bispecific CARs) disclosed herein.

In certain aspects, the invention includes a nucleic acid comprising a polynucleotide sequence encoding a chimeric antigen receptor (CAR) capable of binding prostate stem cell antigen (PSCA), comprising an antigen binding domain, a transmembrane domain, and an intracellular domain. In certain embodiments, the antigen-binding domain comprises: a heavy chain variable region that comprises three heavy chain complementarity determining regions (HCDRs), wherein HCDR1 comprises the amino acid sequence DYYI (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6).

In certain embodiments, the antigen binding domain comprises a heavy chain variable region encoded by a polynucleotide sequence at least 60%, 65%, 70%, 75%, 80%, 85%, 90%, 95%, 96%, 97%, 98%, 99%, or 100% identical to SEQ ID NO: 43 and/or a light chain variable region encoded by a polynucleotide sequence at least 60%, 65%, 70%, 75%, 80%, 85%, 90%, 95%, 96%, 97%, 98%, 99%, or 100% identical to SEQ ID NO: 44.

In certain embodiments, the antigen binding domain is a single-chain variable fragment (scFv) encoded by a polynucleotide sequence at least 60%, 65%, 70%, 75%, 80%, 85%, 90%, 95%, 96%, 97%, 98%, 99%, or 100% identical to SEQ ID NO: 45.

Also provided is a nucleic acid comprising a polynucleotide sequence encoding a chimeric antigen receptor (CAR) capable of binding prostate stem cell antigen (PSCA), comprising an antigen-binding domain, a transmembrane domain, and an intracellular domain, wherein the antigen-binding domain comprises a heavy chain variable region comprising an amino acid sequence at least 60%, 65%, 70%, 75%, 80%, 85%, 90%, 95%, 96%, 97%, 98%, 99%, or 100% identical to SEQ ID NO: 7; and/or a light chain variable region comprising an amino acid sequence at least 60%, 65%, 70%, 75%, 80%, 85%, 90%, 95%, 96%, 97%, 98%, 99%, or 100% identical to SEQ ID NO: 8.

Also provided is a nucleic acid comprising a polynucleotide sequence encoding a chimeric antigen receptor (CAR) capable of binding prostate stem cell antigen (PSCA), comprising a polynucleotide sequence at least 60%, 65%, 70%, 75%, 80%, 85%, 90%, 95%, 96%, 97%, 98%, 99%, or 100% identical to SEQ ID NO: 20.

The invention also provides a nucleic acid comprising a polynucleotide sequence encoding a chimeric antigen receptor (CAR) capable of binding prostate stem cell antigen (PSCA), comprising a polynucleotide sequence at least 60%, 65%, 70%, 75%, 80%, 85%, 90%, 95%, 96%, 97%, 98%, 99%, or 100% identical to SEQ ID NO: 20, 22, 24, or 26.

The invention also provides a nucleic acid comprising a polynucleotide sequence encoding a chimeric antigen receptor (CAR) capable of binding prostate specific membrane antigen (PSMA), wherein the PSMA-CAR comprises an amino acid sequence at least 60%, 65%, 70%, 75%, 80%, 85%, 90%, 95%, 96%, 97%, 98%, 99%, or 100% identical to the amino acid sequence set forth in SEQ ID NO: 67, 87, 89, 91, 93, 95, or 97. In certain embodiments, the PSMA-CAR is encoded by a polynucleotide sequence at least 60%, 65%, 70%, 75%, 80%, 85%, 90%, 95%, 96%, 97%, 98%, 99%, or 100% identical to SEQ ID NO: 88, 90, 92, 94, 96, or 98.

Also provided is a nucleic acid comprising a polynucleotide sequence encoding a bispecific chimeric antigen receptor (CAR) capable of binding prostate stem cell antigen (PSCA) and prostate specific membrane antigen (PSMA), wherein the bispecific CAR comprises an extracellular domain comprising an antigen-binding domain capable of PSCA and an antigen-binding domain capable of binding PSMA, a transmembrane domain, and an intracellular domain.

In certain embodiments, the extracellular domain comprises an antigen binding domain capable of binding PSCA and an antigen binding domain capable of binding PSMA. The antigen binding domain capable of binding PSCA comprises a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The antigen binding domain capable of binding PSMA comprises a second heavy chain variable region that comprises three heavy chain complementarity determining regions (HCDRs), wherein HCDR1 comprises the amino acid sequence SNWIG (SEQ ID NO: 28), HCDR2 comprises the amino acid sequence IIYPGDSDTRYSPSFQG (SEQ ID NO: 29), and HCDR3 comprises the amino acid sequence QTGFLWSFDL (SEQ ID NO: 30); and a second light chain variable region that comprises three light chain complementarity determining regions (LCDRs), wherein LCDR1 comprises the amino acid sequence RASQDISSALA (SEQ ID NO: 31), LCDR2 comprises the amino acid sequence DASSLES (SEQ ID NO: 32), and LCDR3 comprises the amino acid sequence QQFNSYPLT (SEQ ID NO: 33).

In certain embodiments, the extracellular domain comprises an antigen binding domain capable of binding PSCA and an antigen binding domain capable of binding PSMA wherein the antigen binding domain capable of binding PSCA comprises a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The antigen binding domain capable of binding PSMA comprises a second heavy chain variable region that comprises three heavy chain complementarity determining regions (HCDRs), wherein HCDR1 comprises the amino acid sequence EYTIH (SEQ ID NO: 68), HCDR2 comprises the amino acid sequence NINPNNGGTTYNQKFED (SEQ ID NO: 69), and HCDR3 comprises the amino acid sequence GWNFDY (SEQ ID NO: 70); and a second light chain variable region that comprises three light chain complementarity determining regions (LCDRs), wherein LCDR1 comprises the amino acid sequence KASQDVGTAVD (SEQ ID NO: 71), LCDR2 comprises the amino acid sequence WASTRHT (SEQ ID NO: 72), and LCDR3 comprises the amino acid sequence QQYNSYPLT (SEQ ID NO: 73).

In certain embodiments, the first heavy chain variable region (capable of binding PSCA) is encoded by a polynucleotide sequence at least 60%, 65%, 70%, 75%, 80%, 85%, 90%, 95%, 96%, 97%, 98%, 99%, or 100% identical to SEQ ID NO: 43; and the first light chain variable region (capable of binding PSCA) is encoded by a polynucleotide sequence at least 60%, 65%, 70%, 75%, 80%, 85%, 90%, 95%, 96%, 97%, 98%, 99%, or 100% identical to SEQ ID NO: 44 and/or the second heavy chain variable region (capable of binding PSMA) is encoded by a polynucleotide sequence at least 60%, 65%, 70%, 75%, 80%, 85%, 90%, 95%, 96%, 97%, 98%, 99%, or 100% identical to SEQ ID NO: 46 or 74; and the second light chain variable region (capable of binding PSMA) is encoded by a polynucleotide sequence at least 60%, 65%, 70%, 75%, 80%, 85%, 90%, 95%, 96%, 97%, 98%, 99%, or 100% identical to SEQ ID NO: 47 or 76.

In certain embodiments, the antigen binding domain capable of binding PSCA comprises an scFv encoded by a polynucleotide sequence at least 60%, 65%, 70%, 75%, 80%, 85%, 90%, 95%, 96%, 97%, 98%, 99%, or 100% identical to SEQ ID NO: 45. In certain embodiments, the antigen binding domain capable of binding PSMA comprises an scFv encoded by a polynucleotide sequence at least 60%, 65%, 70%, 75%, 80%, 85%, 90%, 95%, 96%, 97%, 98%, 99%, or 100% identical to SEQ ID NO: 48, 83, or 86.

In certain embodiments, the extracellular domain is encoded by a polynucleotide sequence comprising a nucleic acid sequence set forth in SEQ ID NO: 49 or 51.

In certain embodiments, the CAR (including the bispecific CAR) further comprises a hinge sequence comprising the amino acid sequence set forth in SEQ ID NO: 10, 99, or 100. In certain embodiments, the transmembrane domain of the CAR or bispecific CAR comprises a transmembrane domain of CD8 alpha comprising the amino acid sequence set forth in SEQ ID NO: 11. In certain embodiments, the transmembrane domain comprises a transmembrane domain of CD28 comprising the amino acid sequence set forth in SEQ ID NO: 12. In certain embodiments, the transmembrane domain comprises a transmembrane domain of ICOS comprising the amino acid sequence set forth in SEQ ID NO: 13.

In certain embodiments, the intracellular domain comprises a costimulatory signaling domain and an intracellular signaling domain. In certain embodiments, the costimulatory signaling domain comprises a costimulatory domain of 4-1BB comprising the amino acid sequence set forth in SEQ ID NO: 14. In certain embodiments, the costimulatory signaling domain comprises a costimulatory domain of CD28 comprising the amino acid sequence set forth in SEQ ID NO: 15. In certain embodiments, the costimulatory signaling domain comprises a costimulatory domain of ICOS comprising the amino acid sequence set forth in SEQ ID NO: 16. In certain embodiments, the costimulatory signaling domain comprises a costimulatory domain of ICOS(YMNM) comprising the amino acid sequence set forth in SEQ ID NO: 17. In certain embodiments, the intracellular signaling domain comprises an intracellular domain of CD3ζ or a variant thereof, wherein the intracellular domain of CD3ζ comprises the amino acid sequence set forth in SEQ ID NO: 18 or 19.

In certain embodiments, the bispecific CAR is encoded by a polynucleotide sequence at least 60%, 65%, 70%, 75%, 80%, 85%, 90%, 95%, 96%, 97%, 98%, 99%, or 100% identical to SEQ ID NO: 39, 41, or 79.

Another aspect of the invention includes a nucleic acid comprising a first polynucleotide sequence encoding a chimeric antigen receptor (CAR) capable of binding prostate stem cell antigen (PSCA-CAR), and a second polynucleotide sequence encoding a dominant negative receptor, wherein the CAR comprises an antigen binding domain, a transmembrane domain, and an intracellular domain.

In certain embodiments, the dominant negative receptor is a truncated variant of a wild-type protein associated with a negative signal. In certain embodiments, the truncated variant of a wild-type protein associated with a negative signal comprises an amino acid sequence sequence at least 80%, 85%, 90%, 95%, 96%, 97%, 98%, 99%, or 100% identical to SEQ ID NO: 56 and/or is encoded by a polynucleotide sequence at least 80%, 85%, 90%, 95%, 96%, 97%, 98%, 99%, or 100% identical to SEQ ID NO: 55.

Also provided is a nucleic acid comprising a first polynucleotide sequence encoding a chimeric antigen receptor (CAR) capable of binding prostate stem cell antigen (PSCA-CAR), and a second polynucleotide sequence encoding a switch receptor, wherein the CAR comprises an antigen-binding domain, a transmembrane domain, and an intracellular domain.

In certain embodiments, the switch receptor comprises a first domain derived from a first switch polypeptide that is associated with a negative signal; and a second domain derived from a second switch polypeptide that is associated with a positive signal. In certain embodiments, the first domain comprises at least a portion of the extracellular domain of the first switch polypeptide that is associated with a negative signal, and the second domain comprises at least a portion of the intracellular domain of the second switch polypeptide that is associated with a positive signal.

In certain embodiments, the switch receptor further comprises a switch receptor transmembrane domain. In certain embodiments, the switch receptor transmembrane domain comprises: the transmembrane domain of the first switch polypeptide that is associated with a negative signal; or the transmembrane domain of the second switch polypeptide that is associated with a positive signal.

In certain embodiments, the first switch polypeptide that is associated with a negative signal is selected from the group consisting of CTLA4, PD-1, PD-L1, BTLA, TIM-3, an IFNγR, and a TGFPR. In certain embodiments, wherein the switch polypeptide that is associated with a positive signal is selected from the group consisting of CD28, ICOS, and an IL-12R.

In certain embodiments, the switch receptor comprises a first domain comprising at least a portion of the extracellular domain of PD1; a switch receptor transmembrane domain comprising at least a portion of the transmembrane domain of CD28; and a second domain comprising at least a portion of the intracellular domain of CD28. PD1-CD28 switch receptors are described in Liu X, et al. (2016) *Cancer research,* 76(6), 1578-1590, contents of which are incorporated by reference in their entirety herein. In certain embodiments, the switch receptor is encoded by a polynucleotide sequence at least 80%, 85%, 90%, 95%, 96%, 97%, 98%, 99%, or 100% identical to SEQ ID NO: 57 and/or comprises an amino acid sequence at least 80%, 85%, 90%, 95%, 96%, 97%, 98%, 99%, or 100% identical to SEQ ID NO: 58.

In certain embodiments, the switch receptor comprises a first domain comprising at least a portion of the extracellular domain of an IFNγR; and a second domain comprising at least a portion of the intracellular domain of IL12Rβ1. In certain embodiments, the switch receptor is encoded by a polynucleotide sequence at least 80%, 85%, 90%, 95%, 96%, 97%, 98%, 99%, or 100% identical to the nucleotide sequence set forth in SEQ ID NO: 59 and/or comprises an amino acid sequence at least 80%, 85%, 90%, 95%, 96%, 97%, 98%, 99%, or 100% identical to SEQ ID NO: 60.

In certain embodiments, the switch receptor comprises a first domain comprising at least a portion of the extracellular domain of an IFNγR; and a second domain comprising at least a portion of the intracellular domain of IL12Rβ2. In certain embodiments, the switch receptor is encoded by a polynucleotide sequence at least 80%, 85%, 90%, 95%, 96%, 97%, 98%, 99%, or 100% identical to the sequence set forth in SEQ ID NO: 61 and/or comprises an amino acid sequence at least 80%, 85%, 90%, 95%, 96%, 97%, 98%, 99%, or 100% identical to SEQ ID NO: 62.

Additional switch receptors are described in PCT/US2019/020729, contents of which are incorporated by reference in their entirety herein.

Another aspect of the invention provides a nucleic acid comprising a first polynucleotide sequence encoding a chimeric antigen receptor (CAR) capable of binding prostate stem cell antigen (PSCA-CAR), and a second polynucleotide sequence encoding a bispecific antibody, wherein the CAR comprises an antigen-binding domain, a transmembrane domain, and an intracellular domain.

In certain embodiments, the bispecific antibody comprises a first binding domain and a second binding domain. In certain embodiments, the first binding domain binds to a negative signal selected from the group consisting of CTLA4, PD-1, PD-L1, BTLA, TIM-3, and a TGFβR. In certain embodiments, the second binding domain binds to a costimulatory molecule. In certain embodiments, the costimulatory molecule is CD28.

In certain embodiments, the bispecific antibody comprises a first binding domain capable of binding PD-L1, and a second binding domain capable of binding CD28. In certain embodiments, the bispecific antibody is encoded by a polynucleotide sequence at least 80%, 85%, 90%, 95%, 96%, 97%, 98%, 99%, or 100% identical to SEQ ID NO: 63 and/or comprises an amino acid sequence at least 80%, 85%, 90%, 95%, 96%, 97%, 98%, 99%, or 100% identical to SEQ ID NO: 64.

In certain embodiments, the bispecific antibody comprises a first binding domain capable of binding TGFβR2, and a second binding domain capable of binding CD28. In certain embodiments, the bispecific antibody is encoded by a polynucleotide sequence at least 80%, 85%, 90%, 95%, 96%, 97%, 98%, 99%, or 100% identical to SEQ ID NO: 65 and/or comprises an amino acid sequence at least 80%, 85%, 90%, 95%, 96%, 97%, 98%, 99%, or 100% identical to SEQ ID NO: 66.

In certain embodiments, a nucleic acid of the present disclosure comprises a first polynucleotide sequence and a second polynucleotide sequence. The first and second polynucleotide sequence may be separated by a linker. For example, in certain embodiments the antigen binding domain capable of binding PSCA and the antigen binding domain capable of binding PSMA are separated by a linker. In certain embodiments, the linker is encoded by a polynucleotide sequence comprising the nucleic acid sequence set forth in SEQ ID NO: 53 or 54. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a nucleic acid of the present disclosure comprising a PSCA CAR coding sequence and an PSMA CAR coding sequence, allows for the PSCA CAR and PSMA CAR to be translated as a polyprotein that is dissociated into separate CARs. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH-terminus of its consensus recognition sequence. Various furin consensus recognition sequences (or "furin cleavage sites") are known to those of skill in the art, including, without limitation, Arg-X-Lys-Arg (SEQ ID NO:143) or Arg-X1-Arg-Arg (SEQ ID NO:144), X2-Arg-X1-X3-Arg (SEQ ID NO:145) and Arg-X1-X1-Arg (SEQ ID NO:146), such as an Arg-Gln-Lys-Arg (SEQ ID NO:147), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding a Furin cleavage site and F2A, a linker comprising a nucleic acid sequence encoding a Furin cleavage site and E2A, a linker comprising a nucleic acid sequence encoding a Furin cleavage site and P2A, a linker comprising a nucleic acid sequence encoding a Furin cleavage site and T2A. Those of skill in the art would be able to select the appropriate combination for use in the present invention. In such embodiments, the linker may further comprise a spacer sequence between the Furin cleavage site and the 2A peptide. In some embodiments, the linker comprises a Furin cleavage site 5' to a 2A peptide. In some embodiments, the linker comprises a 2A peptide 5' to a Furin cleavage site. Various spacer sequences are known in the art, including, without limitation, glycine serine (GS) spacers such as (GS)n, (GSGGS)n (SEQ ID NO:119) and (GGGS)n (SEQ ID NO:120), where n represents an integer of at least 1. Exemplary spacer sequences can comprise amino acid sequences including, without limitation, GGSG (SEQ ID NO:122), GGSGG (SEQ ID NO:123), GSGSG (SEQ ID NO:124), GSGGG (SEQ ID NO:125), GGGSG (SEQ ID NO:126), GSSSG (SEQ ID NO:127), and the like. Those of skill in the art would be able to select the appropriate spacer sequence for use in the present invention.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid encoding an exogenous CAR is in operable linkage with a promoter. In certain embodiments, the promoter is a phosphoglycerate kinase-1 (PGK) promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding for a CAR. In some embodiments, the expression vector (e.g., lentiviral vector) will comprise additional elements that will aid in the functional expression of the CAR encoded therein. In some embodiments, an expression vector comprising a nucleic acid encoding for a CAR further comprises a mammalian promoter. In one embodiment, the vector further comprises an elongation-factor-i-alpha promoter (EF-la promoter). Use of an EF-la promoter may increase the efficiency in expression of downstream transgenes (e.g., a CAR encoding nucleic acid sequence). Physiologic promoters (e.g., an EF-la promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. Cancer Res. (2010) 15: 9053. Introducing RNA comprising a nucleotide sequence encoding a CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of a CAR as described herein, e.g., in a mammalian cell. In some embodiments, a nucleic acid of the present disclosure provides for amplification of the CAR-encoding nucleic acid.

D. Modified Immune Cells

The present invention provides modified immune cells or precursors thereof (e.g., T cells) comprising chimeric antigen receptors (CARs) capable of binding PSCA (e.g. human PSCA). Also provided are modified immune cells or precursors thereof comprising bispecific CARs (e.g. PSCA & PSMA), PSCA CARs with a dominant negative receptor (e.g., TGFbRDN), PSCA CARs with a switch receptor (e.g., PD1/CD28 or TGFbR/IL12R), and PSCA CARs in combination with bispecific antibodies (e.g., PD-L1/CD28). The invention also includes modified immune cells or precursors thereof comprising any of the nucleic acids disclosed herein or any of the vectors disclosed herein.

In one aspect, the invention includes a modified immune cell or precursor cell thereof, comprising a CAR comprising an antigen-binding domain capable of binding PSCA, a transmembrane domain, and an intracellular domain.

In certain exemplary embodiments, the antigen binding domain comprises three heavy chain complementarity determining regions (HCDRs), wherein HCDR1 comprises the amino acid sequence DYYIH (SEQ ID NO: 1), HCDR2 comprises the amino acid sequence WIDPENGDT EFVPKFQG (SEQ ID NO: 2), and HCDR3 comprises the amino acid sequence TGGF (SEQ ID NO: 3); and a light chain variable region that comprises three light chain complementarity determining regions (LCDRs), wherein LCDR1 comprises the amino acid sequence SASSSV-RFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6).

In another aspect, the instant disclosure provides a modified immune cell or precursor cell thereof, comprising a chimeric antigen receptor (CAR) capable of binding prostate stem cell antigen (PSCA), comprising an antigen binding domain, a transmembrane domain, and an intracellular domain, wherein the antigen-binding domain comprises: a heavy chain variable region comprising an amino acid sequence at least 80%, 85%, 90%, 95%, 96%, 97%, 98%, 99%, or 100% identical to SEQ ID NO: 7; and a light chain variable region comprising an amino acid sequence at least 80%, 85%, 90%, 95%, 96%, 97%, 98%, 99%, or 100% identical to SEQ ID NO: 8.

In another aspect, the instant disclosure provides a modified immune cell or precursor cell thereof, comprising a chimeric antigen receptor (CAR) capable of binding prostate stem cell antigen (PSCA), comprising an amino acid sequence at least 80%, 85%, 90%, 95%, 96%, 97%, 98%, 99%, or 100% identical to SEQ ID NO: 9.

In certain exemplary embodiments, the transmembrane domain comprises a transmembrane domain of CD8 alpha.

In certain exemplary embodiments, the intracellular domain comprises a costimulatory signaling domain and an intracellular signaling domain. In certain exemplary embodiments, the costimulatory signaling domain comprises a costimulatory domain of 4-1BB. In certain exemplary embodiments, the costimulatory signaling domain comprises a costimulatory domain of CD28. In certain exemplary embodiments, the costimulatory signaling domain comprises a costimulatory domain of ICOS. In certain exemplary embodiments, the costimulatory signaling domain comprises a costimulatory domain of ICOS (YMNM). In certain exemplary embodiments, the intracellular signaling domain comprises an intracellular domain of CD3ζ or a variant thereof.

In another aspect, the instant disclosure provides a modified immune cell or precursor cell thereof, comprising a chimeric antigen receptor (CAR) capable of binding prostate stem cell antigen (PSCA), comprising an amino acid sequence at least 80%, 85%, 90%, 95%, 96%, 97%, 98%, 99%, or 100% identical to SEQ ID NO: 21, 23, 25 or 27.

In certain exemplary embodiments, the modified cell further comprises a PSMA-CAR, wherein the PSMA-CAR comprises an antigen-binding domain, a transmembrane domain, and an intracellular domain.

In one aspect, the invention includes a modified immune cell or precursor cell thereof comprising a bispecific chimeric antigen receptor (CAR) comprising an extracellular domain comprising an antigen-binding domain capable of binding prostate stem cell antigen (PSCA) and an antigen-binding domain capable of binding prostate specific membrane antigen (PSMA).

In certain embodiments, the extracellular domain of the bispecific CAR comprises an antigen binding domain capable of binding PSCA comprising: a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The extracellular domain also comprises an antigen binding domain capable of binding PSMA comprising: a second heavy chain variable region that comprises three heavy chain complementarity determining regions (HCDRs), wherein HCDR1 comprises the amino acid sequence SNWIG (SEQ ID NO: 28), HCDR2 comprises the amino acid sequence IIYPGDSDTRYSPSFQG (SEQ ID NO: 29), and HCDR3 comprises the amino acid sequence QTGFLWSFDL (SEQ ID NO: 30); and a second light chain variable region that comprises three light chain complementarity determining regions (LCDRs), wherein LCDR1 comprises the amino acid sequence RASQDISSALA (SEQ ID NO: 31), LCDR2 comprises the amino acid sequence DASSLES (SEQ ID NO: 32), and LCDR3 comprises the amino acid sequence QQFNSYPLT (SEQ ID NO: 33).

In certain embodiments, the extracellular domain comprises an antigen binding domain capable of binding PSCA comprising: a first heavy chain variable region comprising an amino acid sequence at least 80%, 85%, 90%, 95%, 96%, 97%, 98%, 99%, or 100% identical to SEQ ID NO: 7; and a first light chain variable region comprising an amino acid sequence at least 80%, 85%, 90%, 95%, 96%, 97%, 98%, 99%, or 100% identical to SEQ ID NO: 8 and/or the antigen binding domain capable of binding PSMA comprises: a second heavy chain variable region comprising an amino acid sequence at least 80%, 85%, 90%, 95%, 96%, 97%, 98%, 99%, or 100% identical to SEQ ID NO: 34; and a second light chain variable region comprising an amino acid sequence at least 80%, 85%, 90%, 95%, 96%, 97%, 98%, 99%, or 100% identical to SEQ ID NO: 35.

In certain embodiments, the extracellular domain of the bispecific CAR comprises an antigen binding domain capable of binding PSCA comprising: a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6) and/or the antigen binding domain capable of binding PSMA comprises: a second heavy chain variable region that comprises three heavy chain complementarity determining regions (HCDRs), wherein HCDR1 comprises the amino acid sequence EYTIH (SEQ ID NO: 68), HCDR2 comprises the amino acid sequence NINPNNGGTTYNQKFED (SEQ ID NO: 69), and HCDR3 comprises the amino acid sequence GWNFDY (SEQ ID NO: 70); and a second light chain variable region that comprises three light chain complementarity determining regions (LCDRs), wherein LCDR1 comprises the amino acid sequence KASQDVGTAVD (SEQ ID NO: 71), LCDR2 comprises the amino acid sequence WASTRHT (SEQ ID NO: 72), and LCDR3 comprises the amino acid sequence QQYNSYPLT (SEQ ID NO: 73).

In certain embodiments, the extracellular domain of the bispecific CAR comprises an antigen binding domain capable of binding PSCA comprising: a first heavy chain variable region comprising an amino acid sequence at least 80%, 85%, 90%, 95%, 96%, 97%, 98%, 99%, or 100% identical to SEQ ID NO: 7; and a first light chain variable region comprising an amino acid sequence at least 80%, 85%, 90%, 95%, 96%, 97%, 98%, 99%, or 100% identical to SEQ ID NO: 8 and/or the antigen binding domain capable of binding PSMA comprises: a second heavy chain variable region comprising an amino acid sequence at least 80%, 85%, 90%, 95%, 96%, 97%, 98%, 99%, or 100% identical to SEQ ID NO: 75; and a second light chain variable region comprising an amino acid sequence at least 80%, 85%, 90%, 95%, 96%, 97%, 98%, 99%, or 100% identical to SEQ ID NO: 77.

In certain exemplary embodiments, the bispecific CAR is capable of binding human PSCA. In certain exemplary embodiments, the bispecific CAR is capable of binding human PSMA. In certain exemplary embodiments, the bispecific CAR is capable of binding human PSCA and human PSMA.

In another aspect, the invention includes a modified immune cell or precursor cell thereof, comprising a first CAR comprising a first antigen binding domain capable of binding prostate stem cell antigen (PSCA) and a second CAR comprising a second antigen binding domain capable of binding prostate specific membrane antigen (PSMA), wherein the first and the second CAR each comprise a transmembrane domain and an intracellular domain.

In certain exemplary embodiments, the first antigen binding domain comprises: a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The second antigen binding domain comprises: a second heavy chain variable region that comprises three heavy chain complementarity determining regions (HCDRs), wherein HCDR1 comprises the amino acid sequence SNWIG (SEQ ID NO: 28), HCDR2 comprises the amino acid sequence IIYPGDSDTRYSPSFQG (SEQ ID NO: 29), and HCDR3 comprises the amino acid sequence QTGFLWSFDL (SEQ ID NO: 30); and a second light chain variable region that comprises three light chain complementarity determining regions (LCDRs), wherein LCDR1 comprises the amino acid sequence RASQDISSALA (SEQ ID NO: 31), LCDR2 comprises the amino acid sequence DASSLES (SEQ ID NO: 32), and LCDR3 comprises the amino acid sequence QQFNSYPLT (SEQ ID NO: 33).

In certain exemplary embodiments, the first heavy chain variable region comprises an amino acid sequence at least 80%, 85%, 90%, 95%, 96%, 97%, 98%, 99%, or 100% identical to SEQ ID NO: 7; and/or the first light chain variable region comprises an amino acid sequence at least 80%, 85%, 90%, 95%, 96%, 97%, 98%, 99%, or 100% identical to SEQ ID NO: 8; and/or the second heavy chain variable region comprises an amino acid sequence at least 80%, 85%, 90%, 95%, 96%, 97%, 98%, 99%, or 100% identical to SEQ ID NO: 34; and/or the second light chain variable region comprises an amino acid sequence at least 80%, 85%, 90%, 95%, 96%, 97%, 98%, 99%, or 100% identical to SEQ ID NO: 35.

In certain exemplary embodiments, the first antigen binding domain comprises: a first heavy chain variable region that comprises three heavy chain complementarity determining regions (HCDRs), wherein HCDR1 comprises the amino acid sequence DYYIH (SEQ ID NO: 1), HCDR2 comprises the amino acid sequence WIDPENGDTEFVPKFQG (SEQ ID NO: 2), and HCDR3 comprises the amino acid sequence TGGF (SEQ ID NO: 3); and a first light chain variable region that comprises three light chain complementarity determining regions (LCDRs), wherein LCDR1 comprises the amino acid sequence SASSSVRFIHW (SEQ ID NO: 4), LCDR2 comprises the amino acid sequence DTSKLAS (SEQ ID NO: 5), and LCDR3 comprises the amino acid sequence QQWSSSPFT (SEQ ID NO: 6). The second antigen binding domain comprises: a second heavy chain variable region that comprises three heavy chain complementarity determining regions (HCDRs), wherein HCDR1 comprises the amino acid sequence EYTIH (SEQ ID NO: 68), HCDR2 comprises the amino acid sequence NINPNNGGTTYNQKFED (SEQ ID NO: 69), and HCDR3 comprises the amino acid sequence GWNFDY (SEQ ID NO: 70); and a second light chain variable region that comprises three light chain complementarity determining regions (LCDRs), wherein LCDR1 comprises the amino acid sequence KASQDVGTAVD (SEQ ID NO: 71), LCDR2 comprises the amino acid sequence WASTRHT (SEQ ID NO: 72), and LCDR3 comprises the amino acid sequence QQYNSYPLT (SEQ ID NO: 73).

In certain exemplary embodiments, the first heavy chain variable region comprises an amino acid sequence at least 80%, 85%, 90%, 95%, 96%, 97%, 98%, 99%, or 100% identical to SEQ ID NO: 7; and/or the first light chain variable region comprises an amino acid sequence at least 80%, 85%, 90%, 95%, 96%, 97%, 98%, 99%, or 100% identical to SEQ ID NO: 8; and/or the second heavy chain variable region comprises an amino acid sequence at least 80%, 85%, 90%, 95%, 96%, 97%, 98%, 99%, or 100% identical to SEQ ID NO: 75; and/or the second light chain variable region comprises an amino acid sequence at least 80%, 85%, 90%, 95%, 96%, 97%, 98%, 99%, or 100% identical to SEQ ID NO: 77.

In certain exemplary embodiments, the first CAR and the second CAR each comprise a transmembrane domain selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), ICOS, and CD154, or a transmembrane domain derived from a killer immunoglobulin-like receptor (KR). In certain exemplary embodiments, the first CAR and the second CAR each comprise a transmembrane domain of CD8 alpha.

In certain exemplary embodiments, the intracellular domain of the first CAR and the second CAR each comprise a costimulatory signaling domain and an intracellular signaling domain.

In certain exemplary embodiments, the intracellular domain of the first CAR and the second CAR each comprise a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3 (CD276), or a variant thereof, or an intracellular domain derived from a killer immunoglobulin-like receptor (KIR). In certain exemplary embodiments, the intracellular domain of the first CAR and the second CAR each comprise a costimulatory domain of 4-1BB.

In certain exemplary embodiments, the intracellular signaling domain of the first CAR and the second CAR each comprise an intracellular domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In certain exemplary embodiments, the intracellular signaling domain of the first CAR and the second CAR each comprise an intracellular domain of CD3 or a variant thereof.

In certain exemplary embodiments, the first CAR comprises an amino acid sequence at least 80%, 85%, 90%, 95%, 96%, 97%, 98%, 99%, or 100% identical to SEQ ID NO: 21 and/or the second CAR comprises an amino acid sequence at least 80%, 85%, 90%, 95%, 96%, 97%, 98%, 99%, or 100% identical to SEQ ID NO: 67, 87, 89, 91, 93, 95, or 97.

In certain embodiments, the modified cell further comprises a dominant negative receptor. In certain embodiments, the dominant negative receptor is a truncated variant of a wild-type protein associated with a negative signal. In certain exemplary embodiments, the truncated variant of a wild-type protein associated with a negative signal comprises an amino acid sequence at least 80%, 85%, 90%, 95%, 96%, 97%, 98%, 99%, or 100% identical to SEQ ID NO: 56.

In certain embodiments, the modified cell further comprises a switch receptor. In certain embodiments, the switch receptor comprises a first domain derived from a first switch polypeptide that is associated with a negative signal; and a second domain derived from a second switch polypeptide that is associated with a positive signal. In certain exemplary embodiments, the switch receptor comprises an amino acid sequence at least 80%, 85%, 90%, 95%, 96%, 97%, 98%, 99%, or 100% identical to SEQ ID NO: 58, 60, or 62.

Accordingly, in certain embodiments, the invention includes a modified immune cell or precursor cell thereof, comprising a CAR comprising an antigen-binding domain capable of binding PSCA, a transmembrane domain, and an intracellular domain, wherein the cell further comprises a dominant negative receptor (e.g., TGFbRDN).

Accordingly, in certain embodiments, the invention includes a modified immune cell or precursor cell thereof, comprising a CAR comprising an antigen-binding domain capable of binding PSCA, a transmembrane domain, and an intracellular domain, wherein the cell further comprises a switch receptor (e.g., a PD1/CD28 switch receptor).

Also provided is a modified immune cell or precursor cell thereof, comprising a CAR capable of binding prostate stem cell antigen (PSCA-CAR), and a bispecific antibody, wherein the CAR comprises an antigen-binding domain, a transmembrane domain, and an intracellular domain, and wherein the modified cell secretes the bispecific antibody.

In certain embodiments, the modified cell further comprises a bispecific antibody, wherein the cell secretes the bispecific antibody. In certain embodiments, the bispecific antibody comprises an amino acid sequence at least 80%, 85%, 90%, 95%, 96%, 97%, 98%, 99%, or 100% identical to SEQ ID NO: 64 or 66.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

E. Sources of Immune Cells

In certain embodiments, a source of immune cells (e.g. T cells) is obtained from a subject for ex vivo manipulation. Sources of immune cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker −) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the T cell is comprised within a population of cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

F. Methods of Treatment

The modified immune cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method of treating a disease or condition in a subject comprising administering to a subject in need thereof an effective amount of a modified cell (e.g. T cell) of the present invention. In another aspect, the invention includes a method of treating a disease or condition in a subject comprising administering to a subject in need thereof a pharmaceutical compositon comprising an effective amount of a modified cell (e.g. T cell) of the present invention. In another aspect, the invention includes a method for adoptive cell transfer therapy comprising administering to a subject in need thereof an effective amount of a modified cell (e.g. T cell) of the present invention.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases). In certain embodiments, the cancer is an astrocytoma. In certain embodiments, the cancer is a high-grade astrocytoma. In certain embodiments, the cancer is prostate cancer. In certain embodiments, the cancer is metastatic castrate resistant prostate cancer.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4+ to CD8+ cells, and/or is based on a desired fixed or minimum dose of CD4+ and/or CD8+ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1 \times 10^5$ cells/kg to about $1 \times 10^{11}$ cells/kg $10^4$ and at or about $10^{11}$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1 \times 10^5$ T cells/kg, $1.5 \times 10^5$ T cells/kg, $2 \times 10^5$ T cells/kg, or $1 \times 10^6$ T cells/kg body weight. In other exemplary embodiments, a suitable dosage range of modified cells for use in a method of the present disclosure includes, without limitation, from about $1 \times 10^5$ cells/kg to about $1 \times 10^6$ cells/kg, from about $1 \times 10^6$ cells/kg to about $1 \times 10^7$ cells/kg, from about $1 \times 10^7$ cells/kg about $1 \times 10^8$ cells/kg, from about $1 \times 10^8$ cells/kg about $1 \times 10^9$ cells/kg, from about $1 \times 10^9$ cells/kg about $1 \times 10^{10}$ cells/kg, from about $1 \times 10^{10}$ cells/kg about $1 \times 10^{11}$ cells/kg. In an exemplary embodiment, a suitable dosage for use in a method of the present disclosure is about $1 \times 10^8$ cells/kg. In an exemplary embodiment, a suitable dosage for use in a method of the present disclosure is about $1 \times 10^7$ cells/kg. In other embodiments, a suitable dosage is from about $1 \times 10^7$ total cells to about $5 \times 10^7$ total cells. In some embodiments, a suitable dosage is from about $1 \times 10^8$ total cells to about $5 \times 10^8$ total cells. In some embodiments, a suitable dosage is from about $1.4 \times 10^7$ total cells to about $1.1 \times 10^9$ total cells. In an exemplary embodiment, a suitable dosage for use in a method of the present disclosure is about $7 \times 10^9$ total cells.

In some embodiments, the cells are administered at or within a certain range of error of between at or about $10^4$ and at or about $10^9$ CD4+ and/or CD8+ cells/kilograms (kg) body weight, such as between $10^5$ and $10^6$ CD4+ and/or CD8+ cells/kg body weight, for example, at or about $1 \times 10^5$ CD4$^+$ and/or CD8$^+$ cells/kg, $1.5 \times 10^5$ CD4$^+$ and/or CD8$^+$ cells/kg, $2 \times 10^5$ CD4$^+$ and/or CD8+ cells/kg, or $1 \times 10^6$ CD4+ and/or CD8+ cells/kg body weight. In some embodiments, the cells are administered at or within a certain range of error of, greater than, and/or at least about $1 \times 10^6$, about $2.5 \times 10^6$, about $5 \times 10^6$, about $7.5 \times 10^6$, or about $9 \times 10^6$ CD4+ cells, and/or at least about $1 \times 10^6$, about $2.5 \times 10^6$, about $5 \times 10^6$, about $7.5 \times 10^6$, or about $9 \times 10^6$ CD8+ cells, and/or at least about $1 \times 10^6$, about $2.5 \times 10^6$, about $5 \times 10^6$, about $7.5 \times 10^6$, or about $9 \times 10^6$ T cells. In some embodiments, the cells are administered at or within a certain range of error of between about $10^8$ and $10^{12}$ or between about $10^{10}$ and $10^{11}$ T cells, between about 108 and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an inhibitor of an immune checkpoint. Examples of immune checkpoints include but are not limited to CTLA-4, PD-1, and TIM-3. Antibodies may be used to inhibit an immune checkpoint (e.g., an anti-PDi, anti-CTLA-4, or anti-TIM-3 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-LI antibody or antigen-binding fragment thereof. Examples of anti-PD-LI antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) Biol Blood Marrow Transplant, doi.org/10.1016/j.bbmt.2018.12.758; Neelapu et al. (2018) Nat Rev Clin Oncology, 15:47; Teachey et al. (2016) Cancer Discov, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

The modified immune cells comprising CAR of the present invention may be used in a method of treatment as described herein. In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

One aspect of the invention provides a method of treating prostate cancer in a subject in need thereof, comprising administering to the subject an effective amount of a modified T cell comprising a chimeric antigen receptor (CAR) capable of binding prostate stem cell antigen (PSCA-CAR).

In another aspect, the invention provides a method of treating prostate cancer in a subject in need thereof, comprising administering to the subject an effective amount of a modified T cell comprising a first chimeric antigen receptor (CAR) capable of binding prostate stem cell antigen (PSCA-CAR), and a second chimeric antigen receptor (CAR) capable of binding prostate specific membrane antigen (PSMA-CAR), wherein the first CAR and the second CAR each comprise an antigen-binding domain, a transmembrane domain, and an intracellular domain.

Another aspect of the invention provides a method of treating prostate cancer in a subject in need thereof, comprising administering to the subject an effective amount of a modified T cell comprising a bispecific chimeric antigen receptor (CAR) comprising an extracellular domain comprising an antigen-binding domain capable of binding prostate stem cell antigen (PSCA) and an antigen-binding domain capable of binding prostate specific membrane antigen (PSMA), a transmembrane domain, and an intracellular domain.

Another aspect of the invention provides a method of treating prostate cancer in a subject in need thereof, comprising administering to the subject an effective amount of any of the modified T cells contemplated herein.

Yet another aspect includes a method of treating metastatic castrate resistant prostate cancer in a subject in need thereof, comprising administering to the subject an effective amount of a modified T cell comprising a first chimeric antigen receptor (CAR) capable of binding prostate stem cell antigen (PSCA-CAR), and a second chimeric antigen receptor (CAR) capable of binding prostate specific membrane antigen (PSMA-CAR), wherein the first CAR and the second CAR each comprise an antigen-binding domain, a transmembrane domain, and an intracellular domain.

Also provided is a method of treating metastatic castrate resistant prostate cancer in a subject in need thereof, comprising administering to the subject an effective amount of a modified T cell comprising a bispecific chimeric antigen receptor (CAR) comprising an extracellular domain comprising an antigen-binding domain capable of binding prostate stem cell antigen (PSCA) and an antigen-binding domain capable of binding prostate specific membrane antigen (PSMA), a transmembrane domain, and an intracellular domain.

In another aspect, the invention provides a method of treating metastatic castrate resistant prostate cancer in a subject in need thereof, comprising administering to the subject an effective amount of a modified T cell comprising a chimeric antigen receptor (CAR) capable of binding prostate stem cell antigen (PSCA-CAR), and a dominant negative receptor.

In another aspect, the invention provides a method of treating metastatic castrate resistant prostate cancer in a subject in need thereof, comprising administering to the subject an effective amount of a modified T cell comprising a chimeric antigen receptor (CAR) capable of binding prostate stem cell antigen (PSCA-CAR), and a switch receptor.

In another aspect, the invention provides a method of treating metastatic castrate resistant prostate cancer in a subject in need thereof, comprising administering to the subject an effective amount of a modified T cell comprising a chimeric antigen receptor (CAR) capable of binding prostate stem cell antigen (PSCA-CAR), and a bispecific antibody, wherein the modified T cell secretes the bispecific antibody.

G. Expansion of Immune Cells

Whether prior to or after modification of cells to express a CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

H. Methods of Producing Modified Immune Cells

The present disclosure provides methods for producing or generating a modified immune cell or precursor thereof (e.g., a T cell) of the invention for tumor immunotherapy, e.g., adoptive immunotherapy.

In some embodiments, the CAR is introduced into a cell by an expression vector. Expression vectors comprising a nucleic acid sequence encoding a CAR of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

In certain embodiments, the nucleic acid encoding a CAR is introduced into the cell via viral transduction. In certain embodiments, the viral transduction comprises contacting the immune or precursor cell with a viral vector comprising the nucleic acid encoding a CAR. In certain embodiments, the viral vector is an adeno-associated viral (AAV) vector. In certain embodiments, the AAV vector comprises a 5' ITR and a 3'ITR derived from AAV6. In certain embodiments, the AAV vector comprises a Woodchuck Hepatitis Virus post-transcriptional regulatory element (WPRE). In certain embodiments, the AAV vector comprises a polyadenylation (polyA) sequence. In certain embodiments, the polyA sequence is a bovine growth hormone (BGH) polyA sequence.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR in the host cell. In some embodiments, the adenovirus genome is a 36 kb, linear, double stranded DNA, where a foreign DNA sequence (e.g., a nucleic acid encoding a CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding a CAR) into the viral genome at certain locations to produce a virus that is replication defective. Though the retroviral vectors are able to infect a broad variety of cell types, integration and stable expression of the CAR requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a CAR of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In certain embodiments, the genetically engineered cells are autologous cells. In certain embodiments, the modified cell is resistant to T cell exhaustion.

Modified cells (e.g., comprising a CAR) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a CAR of the present disclosure will be RNA, e.g., in vitro synthesized RNA. Methods for in vitro synthesis of RNA are known in the art; any known method can be used to synthesize RNA comprising a sequence encoding a CAR. Methods for introducing RNA into a host cell are known in the art. See, e.g., Zhao et al. Cancer Res. (2010) 15: 9053. Introducing RNA comprising a nucleotide sequence encoding a CAR into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/

0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

I. Pharmaceutical Compositions and Formulations

In another aspect, the instant disclosure provides a pharmaceutical composition comprising a therapeutically effective amount of any of the modified cells contemplated herein. Also provided are populations of immune cells of the invention, compositions containing such cells and/or enriched for such cells, such as in which cells expressing the CAR make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Cell lines and primary human T lymphocyte cultures: Primary human CD4 and CD8 T cells were isolated from healthy volunteer donors following leukapheresis by negative selection using RosetteSep Kits (Stem Cell Technologies). All specimens were collected under a University Institutional Review Board-approved protocol, and written informed consent was obtained from each donor. Mixed primary human CD4 and CD8 T cells (1:1) were stimulated with anti-CD3/CD28 Dynabeads (Life Technologies).

CAR constructs and lentiviral transduction: A PSCA CAR comprised of an scFv from a humanized anti-PSCA Ab (2B3) was constructed and cloned into retroviral vector MSGV. The scFv domain against PSCA was synthesized and/or amplified by PCR, linked to CD8 transmembrane domain and 4-1BB, CD28, ICOS or ICOS.YMNM, and CD3 zeta intracellular signaling domains, and subcloned into pTRPE lentiviral vectors. T cells were transduced with lentiviral vectors at an MOI of 5.

Flow cytometry: Flow cytometry was used to determine the transduction efficiency of transduced cells following staining with biotin-labeled polyclonal anti-mouse F(ab)2 antibody (Jackson Immunoresearch). The following antibodies were used in flow cytometry experiments: PE conjugated Streptavidin. Data acquisition was performed on FACSCalibur (BC Biosciences) and analyzed via FlowJo.

CD107a assay: Cells were plated at an E:T of 1:2 (1×105 effectors: 2×105) in 160 μL of R10 medium in a 96-well plate. Of note, 20 μL of phycoerythrin-labeled anti-CD107a Ab was added and the plate was incubated at 37° C. for 1 hour before adding Golgi Stop (2 mL Golgi Stop in 3 mL R10 medium, 20 mL/well; BD Biosciences, 51-2092 KZ) and incubating for another 2.5 hours. Then 5 mL FITC-anti-CD8 and 5 mL streptavidin-allophycocyanin (APC)-anti-CD3 were added and incubated at 37° C. for 30 minutes. After incubation, the samples were washed with FACS buffer and analyzed by flow cytometry.

Enzyme-linked immunosorbent assay (ELISA): Target cells were washed and suspended at $1 \times 10^6$ cells/mL in R10 medium. Of note, 100 μL each target cell type were added in triplicate to a 96-well round bottom plate (Corning). Effector T cells were washed and resuspended at $1 \times 10^6$ cells/mL in R10 cells and then 100 μL of T cells were combined with target cells in the indicated wells. The plates were incubated at 37° C. for 18 to 24 hours. After the incubation, supernatant was harvested and subjected to an ELISA assay (eBioscience).

Luciferase-based cytolytic T-cell (CTL) assay: Briefly, Click beetle green luciferase (CBG)-T2A-eGFP was *lenti*virally transduced into PSCA tumor cells and sorted for GFP expression. Tumor cells were incubated with different ratios of T cells 8 hours at 37° C. Of note, 100 mL of the mixture was transferred to a 96-well white luminometer plate, 100 mL of substrate was added, and the luminescence was immediately determined. Results are reported as percent killing based on luciferase activity in wells with tumor, but no T cells. (% killing=100−((RLU from well with effector and target cell coculture)/(RLU from well with target cells)× 100).

Example 1

Various prostate stem cell antigen (PSCA) specific CARs were generated herein. The antigen binding domain was derived from a humanized anti-PSCA antibody (2B3) (U.S. Patent Publication No. US2010/0297004, the contents of which is hereby incorporated by reference in its entirety) (FIG. 1). The 2B3 scFv was used in combination with various intracellular domains including 4-1BB and CD3 zeta (2B3.BBZ CAR), CD28 and CD3 zeta (2B3.28Z CAR), ICOS and CD3 zeta (2B3.ICOSZ CAR), and a mutated ICOS (ICOS.YMNM CAR) and CD3 zeta (2B3.ICOS.YMNM CAR). PSCA CARs comprising PD1-CD28 switch receptors, TGFbR/IL12R switch receptors, and a dominant negative receptor (TGFbRDN) were also generated. Dual CARs comprising specificity for PSCA and PSMA were also developed. PSCA CARs were also used in combination with bispecific antibodies (e.g. aPD-L1/CD28 or aTGFbRII-CD28).

CAR expression was measured in T cells co-electroporated with in vitro transcribed RNA of a PSCA CAR (2B3.BBZ) and a PMSA CAR (J591.BBZ) (FIG. 2 upper panel). PD-L1-Fc staining of a PSCA CAR co-electroporated with a bispecific antibody 10A5-1412 (an aPDL1-aCD28 bispecific Ab) or TGFB3-1412 (an aTGFbRII-aCD28 bispecific Ab) is shown in FIG. 2, lower panel.

Figure 3:
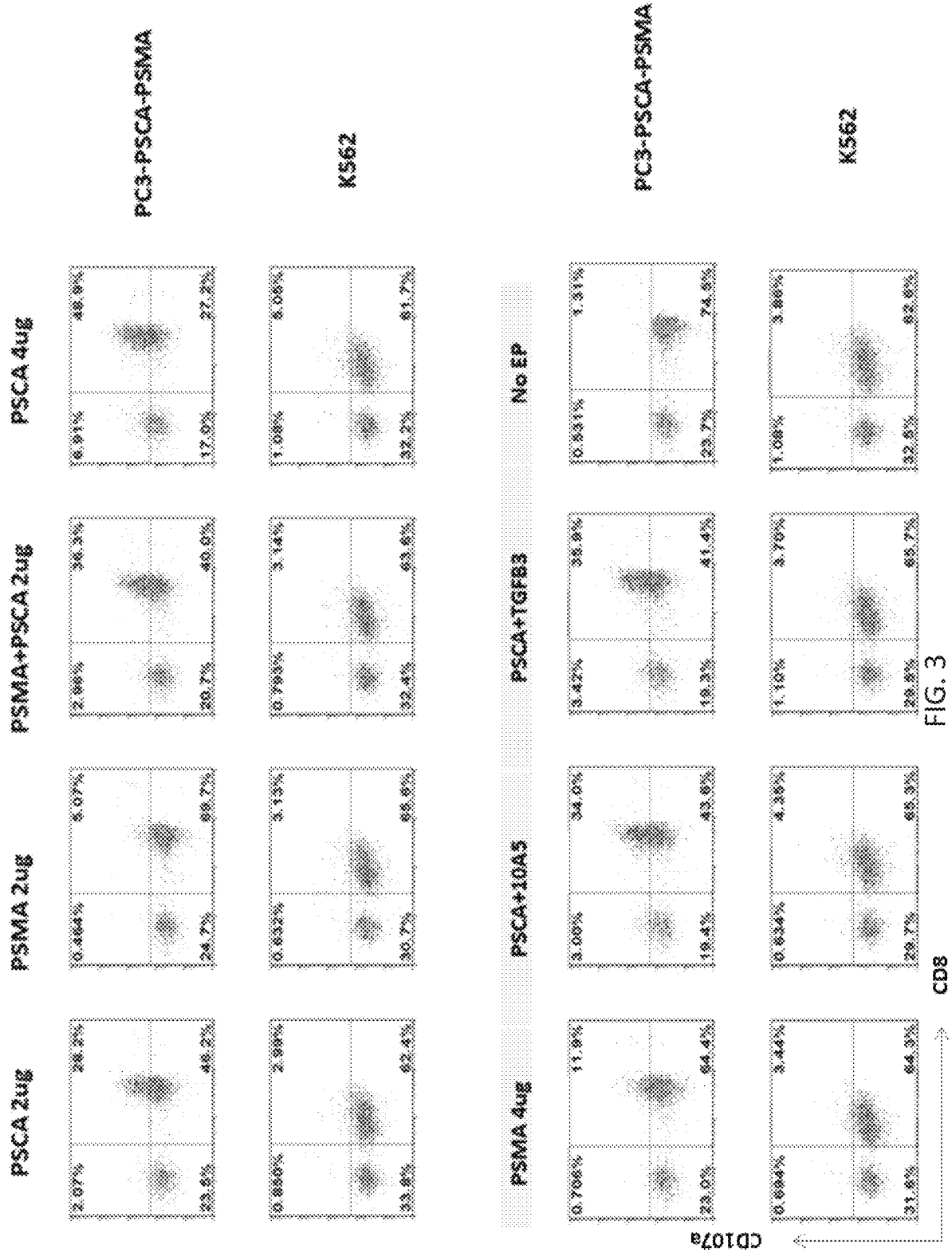
FIG. 3 illustrates CD107a expression of RNA co-electroporated T cells stimulated with PC3-PSCA-PSMA or K562. T cells were electroporated with a PSCA CAR with 4-1BB and CD3z domains (2B3.BBZ) and/or a PSMA CAR with 4-1BB and CD3z domains (J591.BBZ), as indicated.

CD107a was measured in RNA co-electroporated T cells stimulated with PC3-PSCA-PSMA or K562 (FIG. 3).

Figure 4:
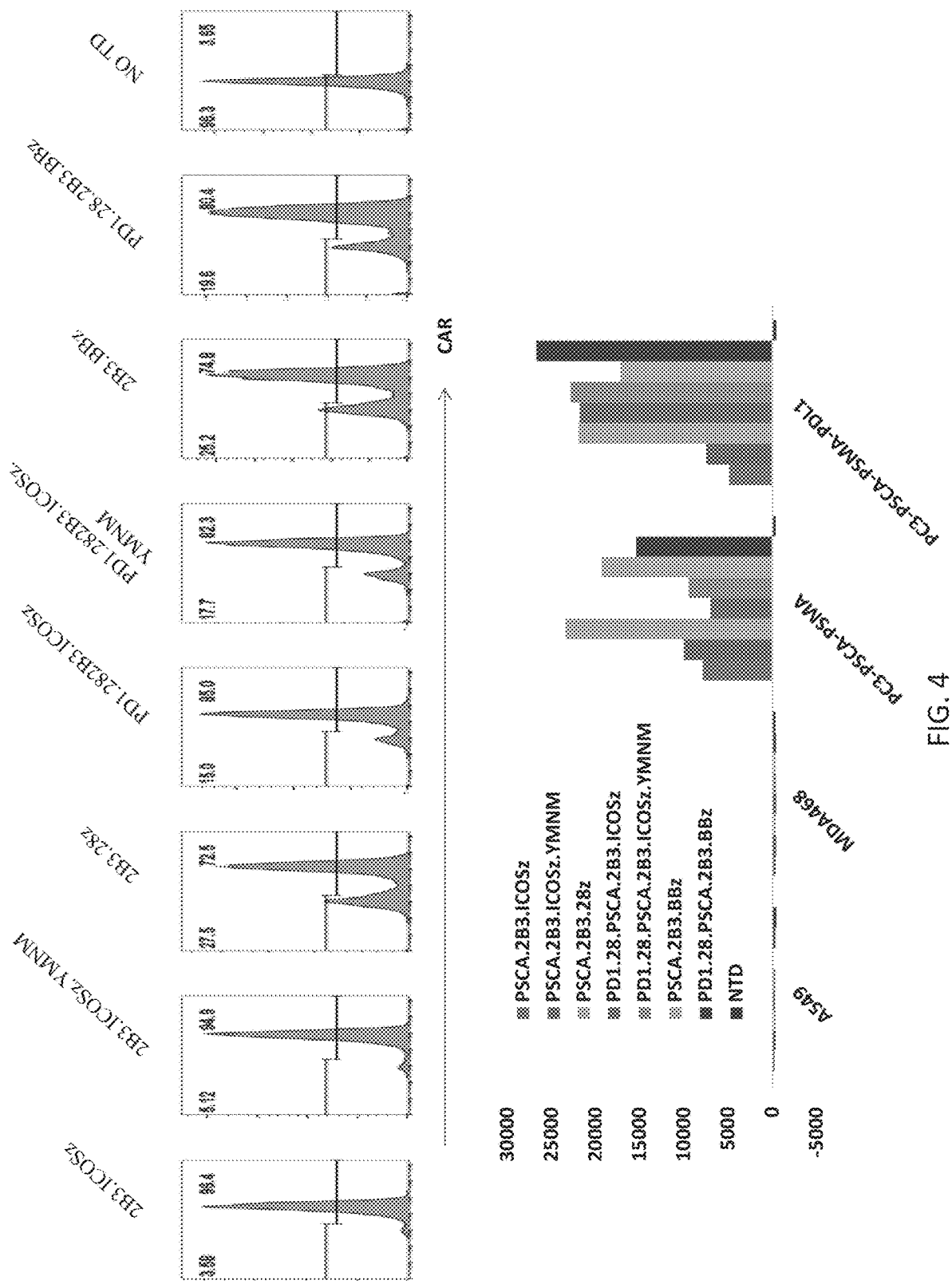
FIG. 4 illustrates T cells lentivirally transduced with a PSCA (2B3) CAR with a mutated ICOS signaling domain (ICOS.YMNM) showed improved lytic capability, decreased cytokine production in vitro and equivalent in vivo antitumor activities as a 4-1BB signaling PSCA CAR. PSCA CARs with either ICOS or ICOS.YMNM signaling domain were constructed and cloned into a lentiviral vector. The CAR expression levels were comparable with either 4-1BB or CD28 signaling domain CARs (upper). CAR-T cells were stimulated with PSCA positive cell lines PC3.PSCA.PSMA.CBG or PC3.PSCA.PSMA.CBG.PD-L1 and examined for cytokine (IL-2 and IFN-gamma) production (lower panel). Human lung cancer cell line A549 and human breast cancer cell line MDA468 were also used. Abbreviations: PSCA (2B3) CAR with ICOS and CD3z domains (2B3.ICOSz or PSCA.2B3.ICOSz); PSCA (2B3) CAR with variant ICOS (YMNM) and CD3z domains (2B3.ICOSz.YMNM or PSCA.2B3.ICOSz.YMNM); PSCA (2B3) CAR with CD28 and CD3z domains (2B3.28z or PSCA.2B3.28z); PSCA (2B3) CAR with ICOS and CD3z domain co-expressed with a PD1-CD28 switch receptor (PD1.282B3.ICOSz or PD1.28.PSCA.2B3.ICOSz); PSCA (2B3) CAR with variant ICOS (YMNM) and CD3z domain co-expressed with a PD1-CD28 switch receptor (PD1.282B3.ICOSz.YMNNM or PD1.28.PSCA.2B3. ICOSz.YMNM); PSCA (2B3) CAR with 4-1BB and CD3z domains (2B3.BBz or PSCA.2B3.BBz); PSCA (2B3) CAR with 4-1BB and CD3z domains (2B3.BBz) co-expressed with a PD1-CD28 switch receptor (PD1.28.2B3.BBz or PD1.28.PSCA.2B3.BBz); and non-transduced (NO TD or NTD).
Figure 6:
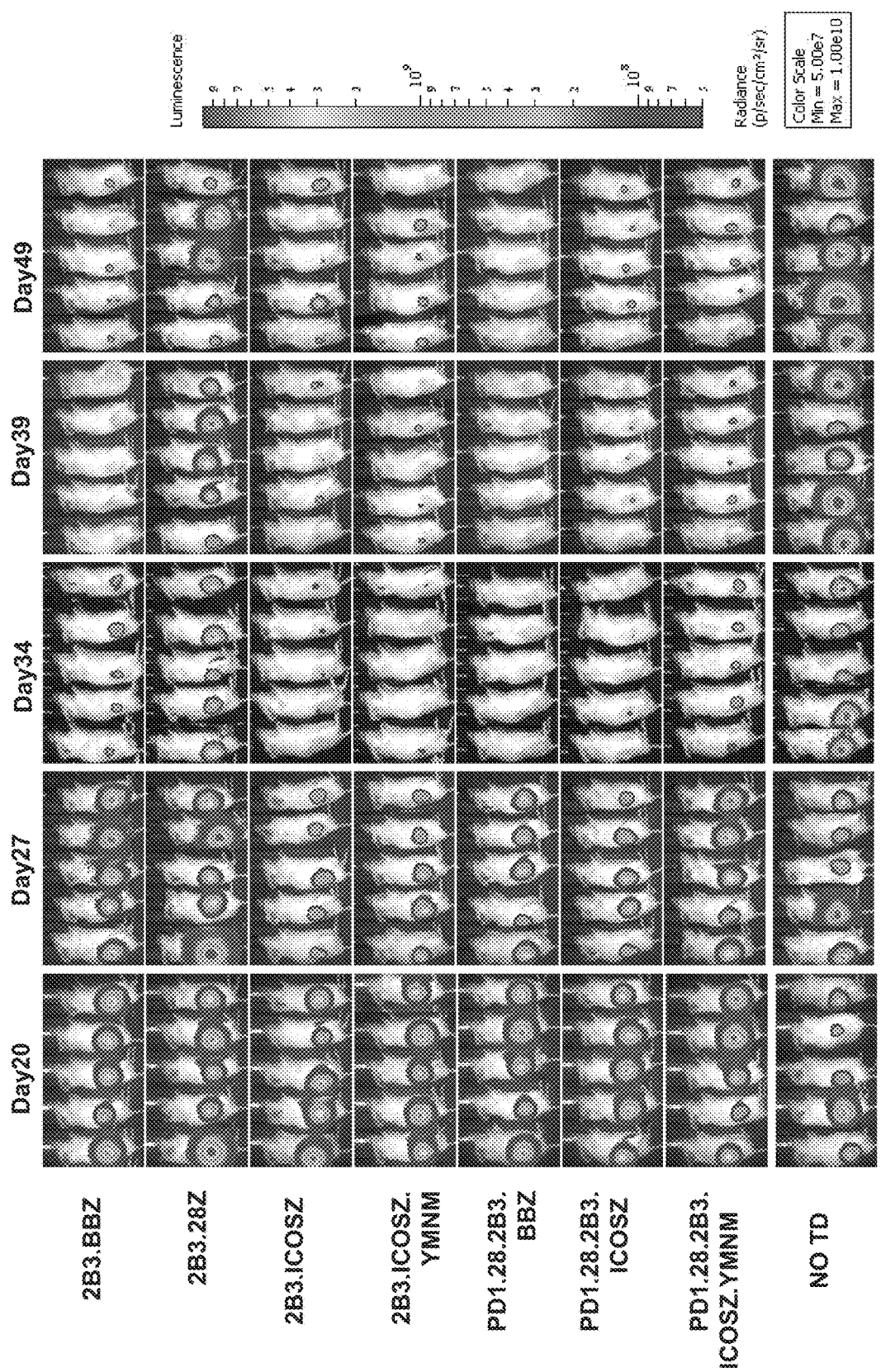
FIG. 6 illustrates results from experiments using a PC3-PSCA-CBG-PDL1 tumor model. For lentiviral transduced (LVV TD) T cells, $1e^6$ cells per mouse were i.v. (intravenous) injected at day 21 days post tumor inoculation. 5 mice were tested in each group. Abbreviations used in FIG. 7 are the same as those in FIG. 4.

T cells lentivirally transduced with a PSCA (2B3) CAR with mutated ICOS signaling domain (ICOS.YMNM) showed improved lytic capability, decreased cytokine production in vitro and equivalent in vivo antitumor activities as a 4-1BB signaling PSCA CAR (FIG. 4 and FIG. 6). PSCA CARs with either ICOS or ICOS.YMNM signaling domain were constructed and cloned into a lentiviral vector. The CAR expression levels were comparable with either 4-1BB or CD28 signaling domain CARs (FIG. 4 upper). Following stimulation with PSCA positive cell lines PC3.PSCA.PMSA.CBG or PC3.PSCA.PMSA.CBG.PD-L1, cytokine production (IFN-gamma) was measured (FIG. 4 lower panel).

Figure 5A:
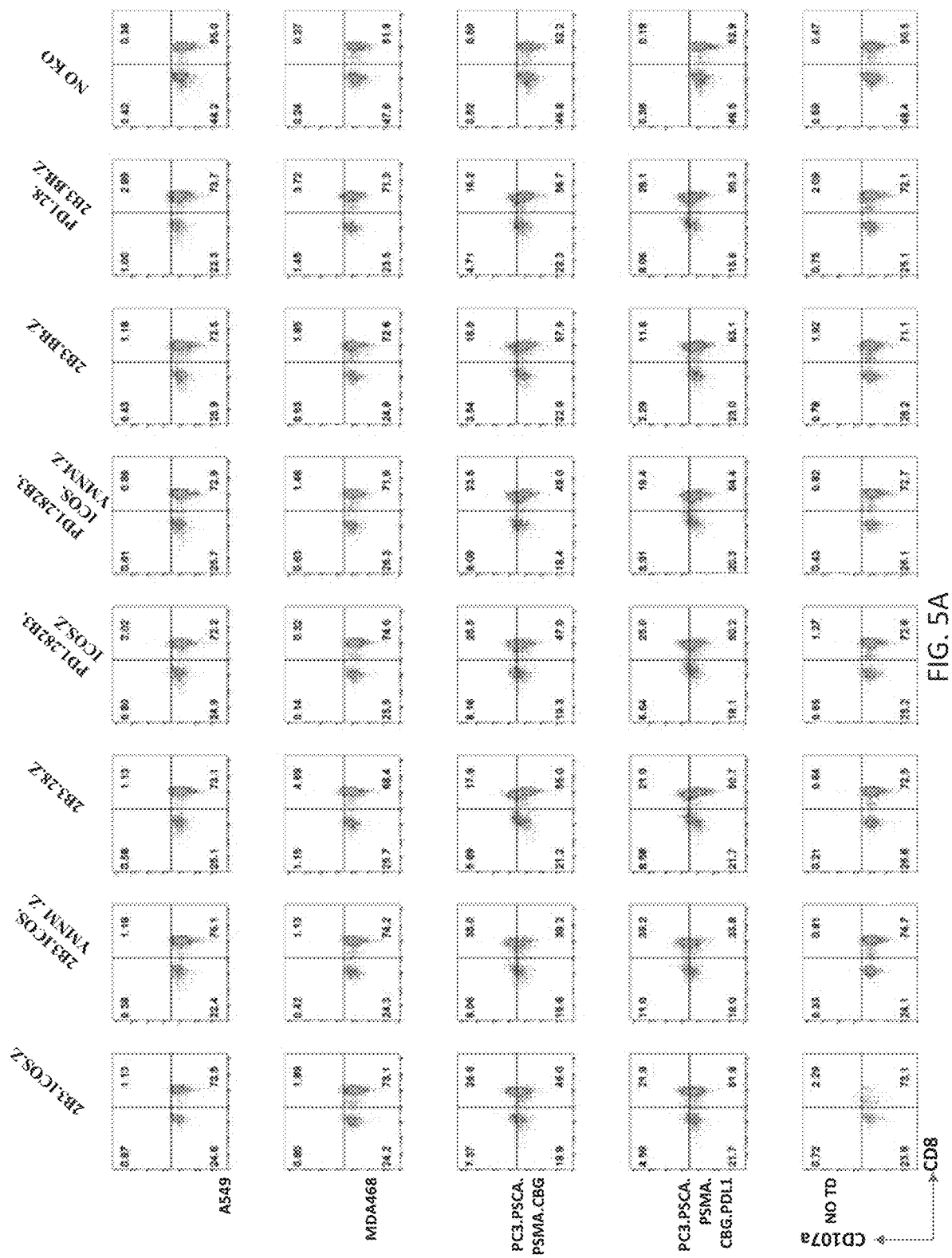
FIG. 5A illustrates results from a CD107a assay of T cells expressing PSCA CARs with either an ICOS or ICOS.YMNNM signaling domain. Abbreviations used in FIG. 5A are the same as those in FIG. 4.
Figure 5B:
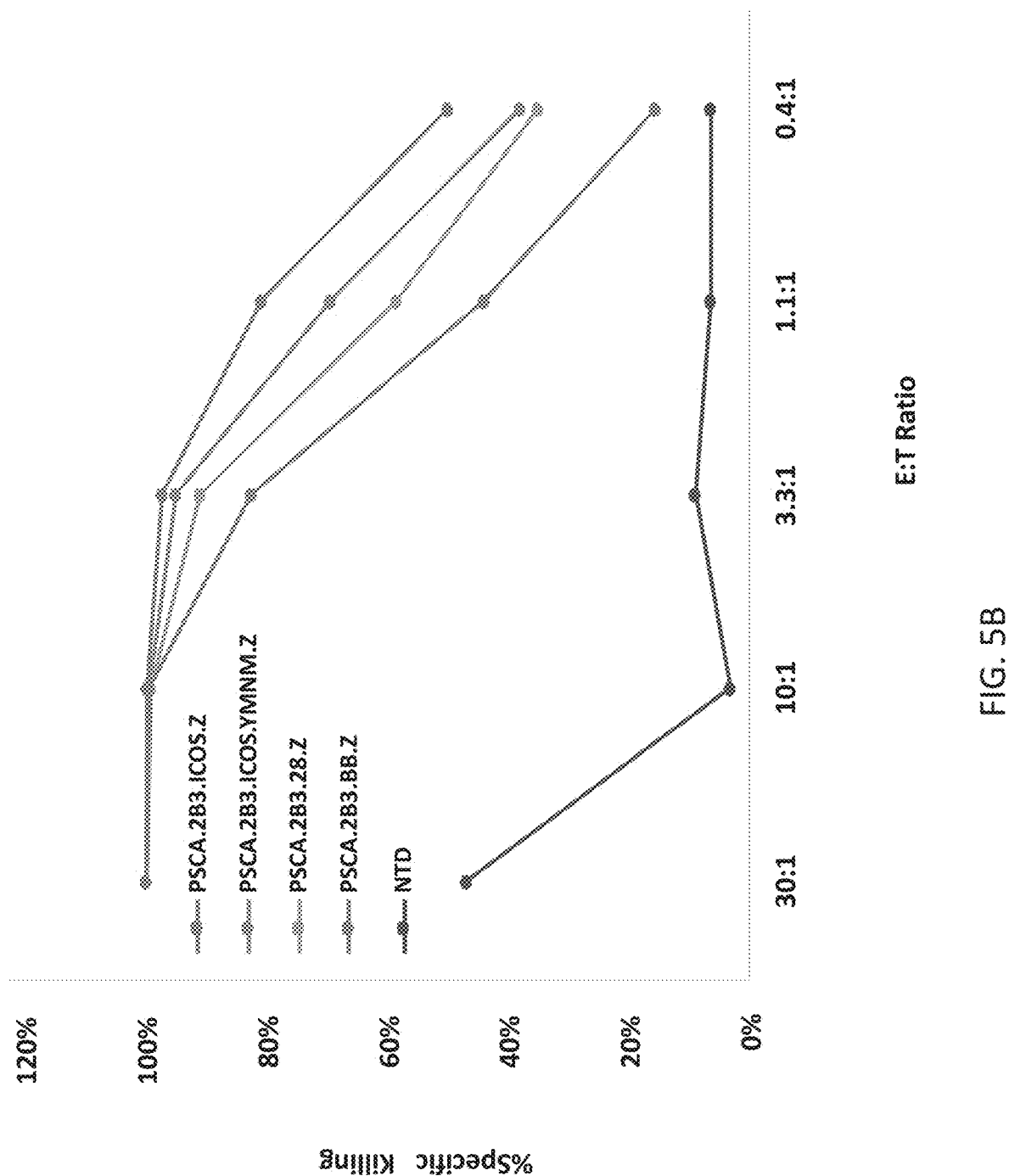
FIG. 5B illustrates results from a killing assay for T cells expressing PSCA CARs with either an ICOS or ICOS.YMNM signaling domain. Abbreviations used in FIG. 5B are the same as those in FIG. 4.

Results from a CD107a assay for T cells expressing PSCA CARs with either ICOS or ICOS.YMNM signaling domain are shown in FIG. 5A. FIG. 5B illustrates results from a killing assay for T cells expressing PSCA CARs with either ICOS or ICOS.YMNNM signaling domain against tumor line PC3-PSCA.

Figure 7:
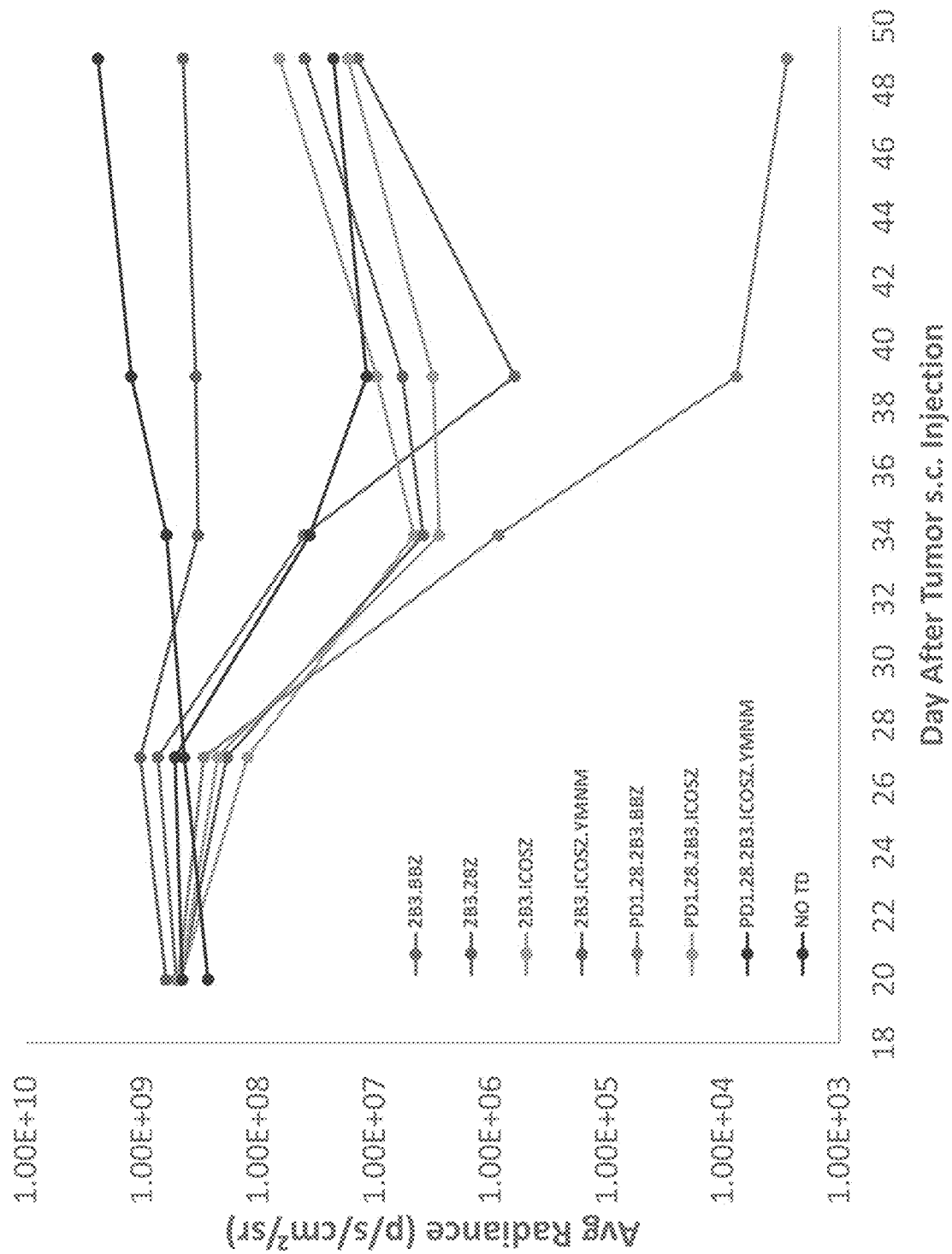
FIG. 7 illustrates the average radiance of tumors after subcutaneous injection with various PSCA CARs. Abbreviations used in FIG. 7 are the same as those in FIG. 4.
Figure 8:
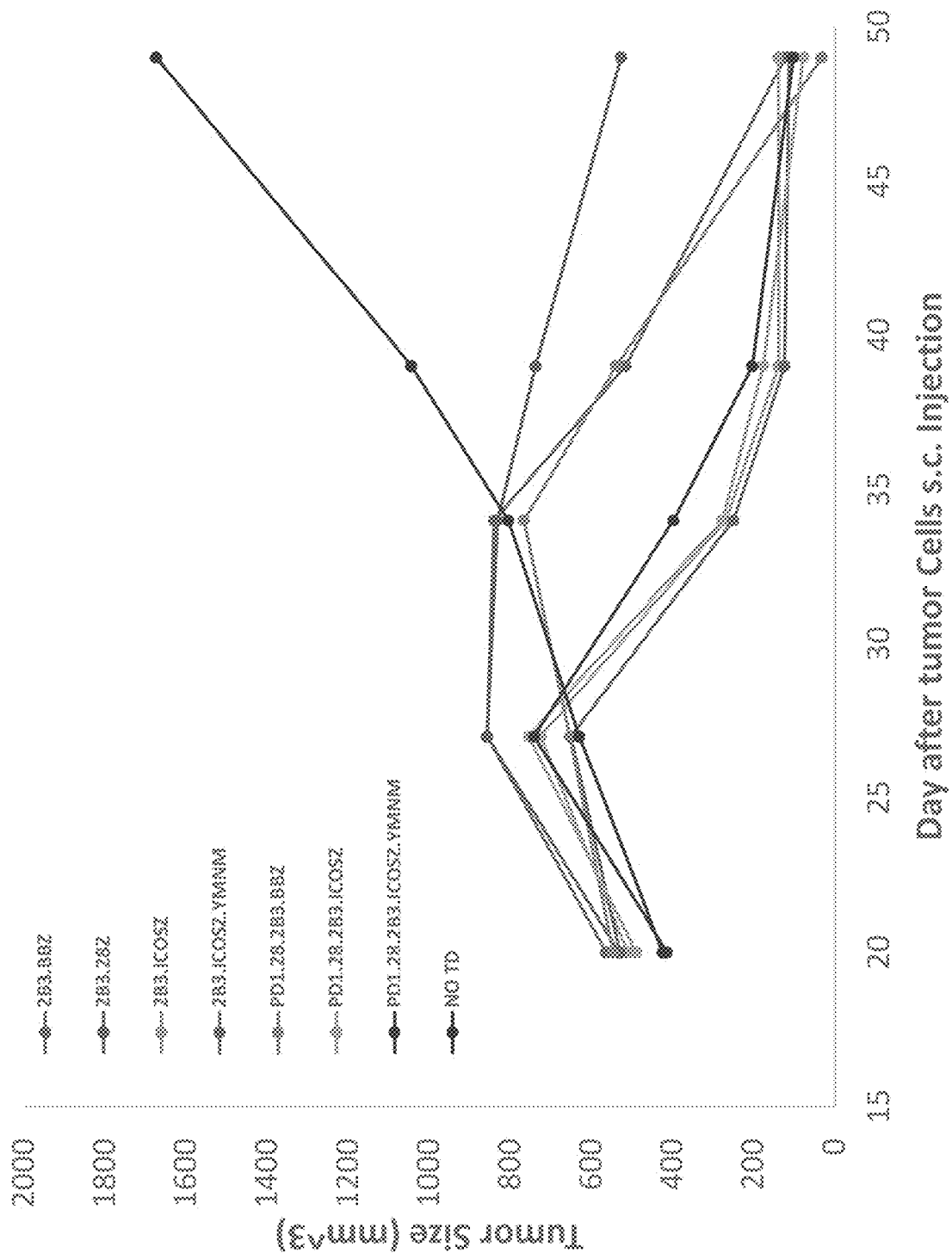
FIG. 8 illustrates tumor sizes after subcutaneous injection with various PSCA CARs. Abbreviations used in FIG. 8 are the same as those in FIG. 4.

FIG. 6 illustrates BLI results from a PC3-PSCA-CBG-PDL1 tumor model. For lentivirally transduced (LVV TD) T cells, $1e^6$ cells were transduced per mouse, intravenously (i.v.) at day 21 post tumor inoculation. BLI (the average radiace) of tumors (FIG. 7) and tumor sizes (FIG. 8) were measured after subcutaneous injection with various PSCA CARs.

Figure 9D:
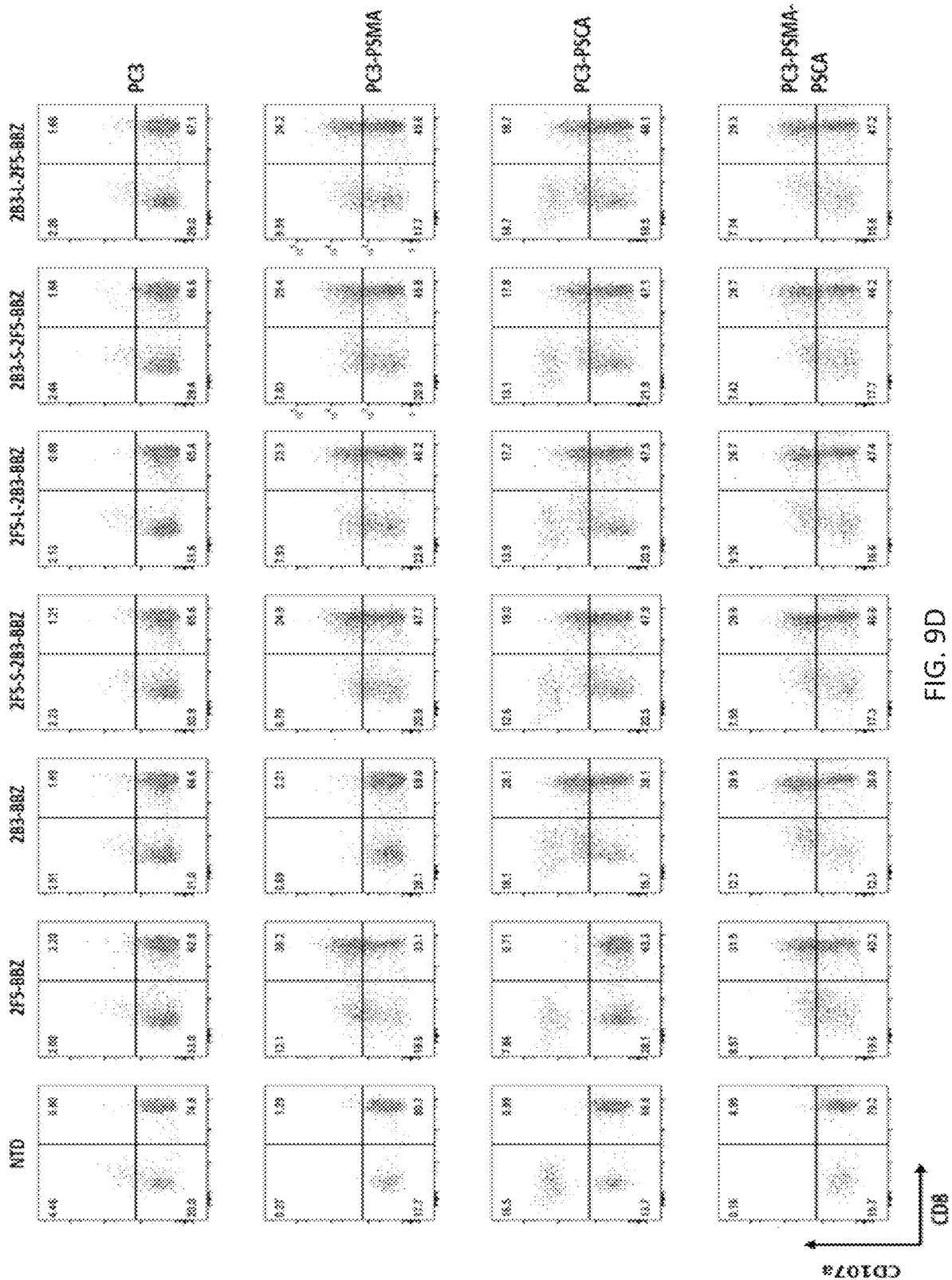
FIG. 9D illustrates CAR T cells comprising the indicated CAR were co-cultured with targets for 4 hours and the percentage CD107a expression was quantified on CD8 positive cells.

Bi-specific CARs were also generated herein. Vectors used for studies encoding the PSMA (2F5 scFv) and PSCA-targeted CARs, linked with a Gly4Ser element are depicted in FIG. 9A. Surface expression of the CARs on lentivirus transduced CAR T cells at the end of the primary expansion is depicted in FIG. 9B. The percentage of lentivirus transduced CAR T cells that express the PSMA or PSCA-CAR or bispecific CAR was measured by staining with human recombinant PSMA-Fc and PSCA-His protein and analyzed by flow cytometry (FIG. 9C). CAR T cells expressing the indicated scFv were co-cultured with targets for 4 hours and the percentage CD107a expression was quantified on CD8 positive cells (FIG. 9D).

Figure 10B:
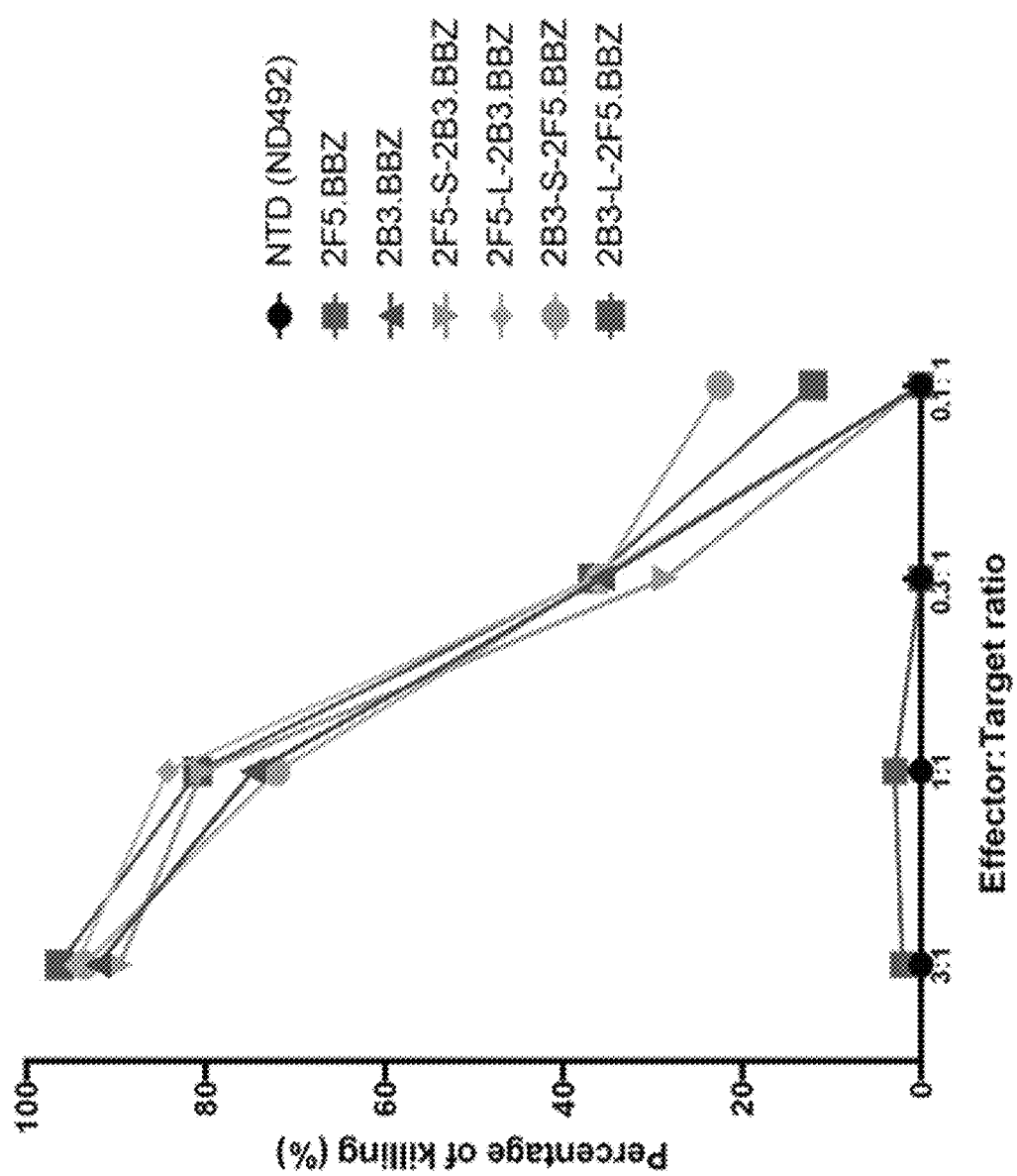
FIG. 10B illustrates results from T cells tested for their cytolytic activity at indicated E:T ratios for 8 hours against PC3-PSCA cells.
Figure 10C:
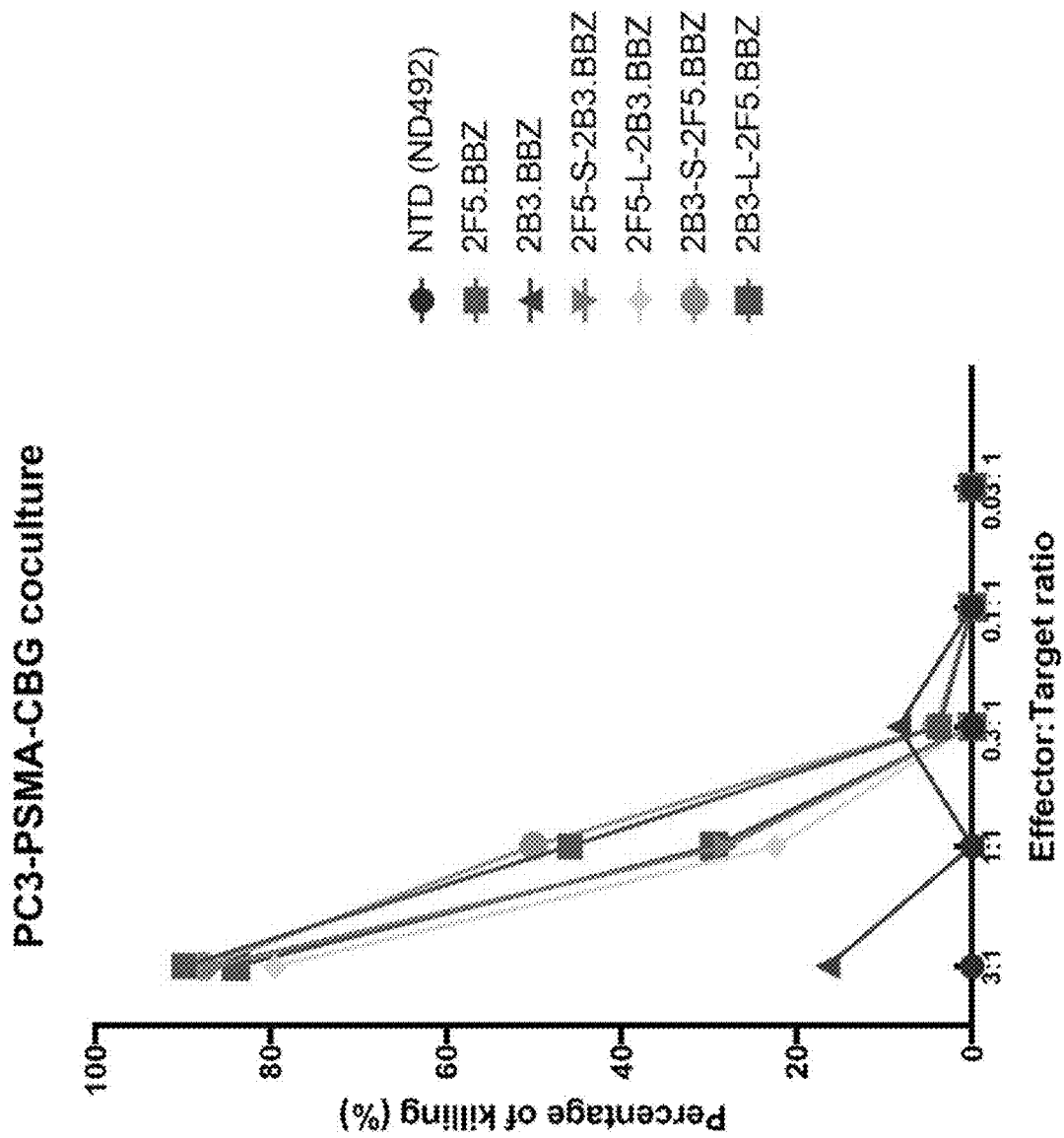
FIG. 10C illustrates results from CAR T cells co-cultured with PC3-PSMA cells (Effector:Target ratio=1:1). Supernatants were obtained 24 hours after co-culture, and cytokine production was analyzed by ELISA.

Bi-specific CAR T cells were co-cultured with PC3-PSCA cells (Effect:Target=1:1). Supernatants were obtained 24 hours after co-culture, and cytokine production was analyzed by ELISA (FIG. 10A). Bi-specific CAR T cells were tested for their cytolytic activity at various E:T ratios for 8 hours against PC3-PSCA cells (FIG. 10B). Bi-specific CAR T cells were co-cultured with PC3-PSMA cells (Effect: Target=1:1). Supernatants were obtained 24 hours after co-culture, and cytokine production was analyzed by ELISA (FIG. 10C). Bi-specific CAR T cells were tested for their cytolytic activity at various E:T ratios for 8 hours against PC3-PSMA cells (FIG. 10D).

Figure 11B:
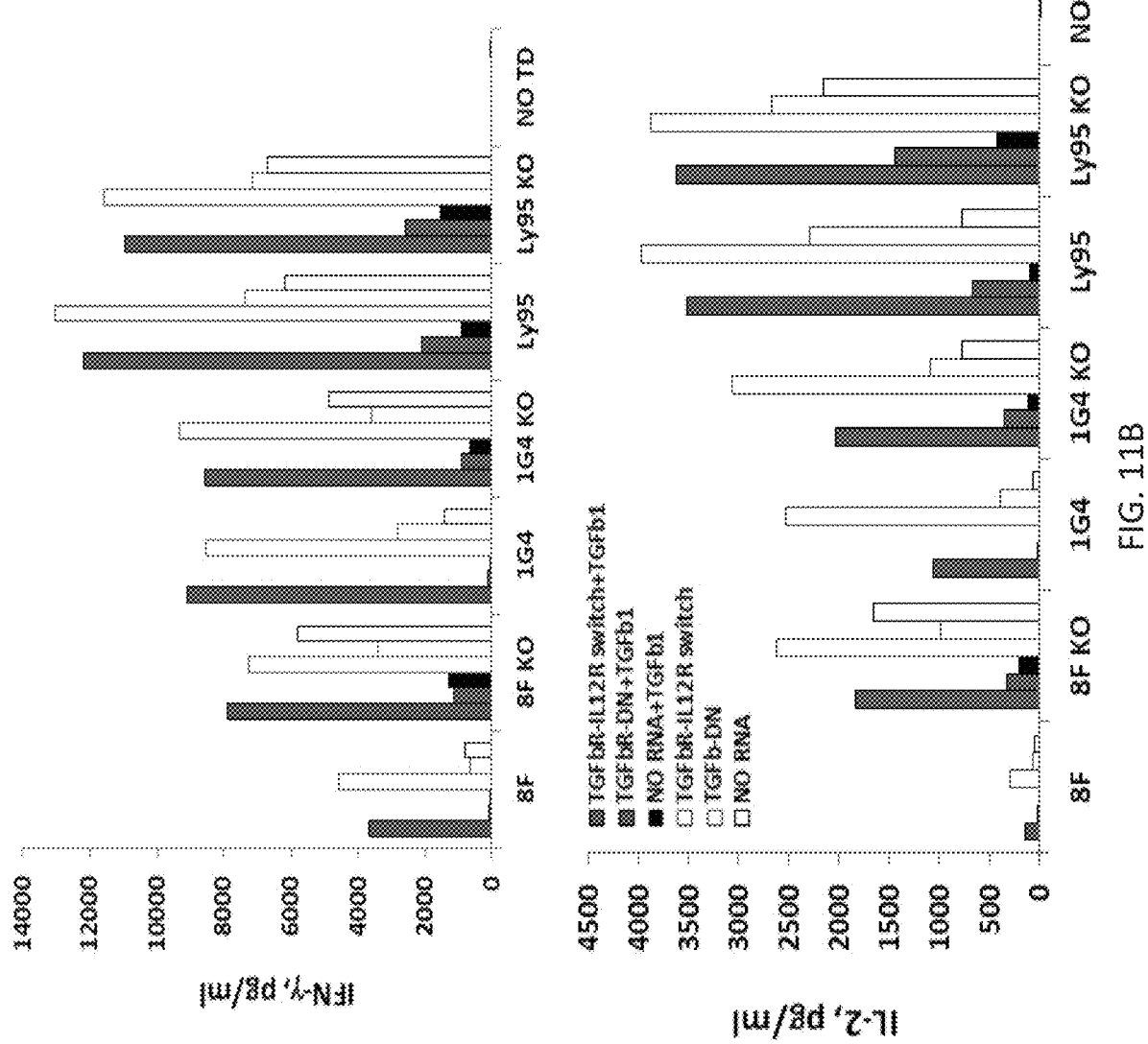

FIGS. 11A-11B illustrate the finding that TGFbR-IL12R switch receptors can boost T cell function. FIG. 11A, upper right panel, shows IFN-gamma production of NK cells transferred with TGFbR-IL12R co-cultured with K562, with or without TGFb1 in the cultures. FIG. 11A, lower right panel, shows pSmad staining of T cells transferred with TGFbR-IL12R switch receptors after stimulation with TGF beta. FIG. 11B shows cytokine production of NY-ESO-1 positive tumors stimulated NY-ESO-1 TCR transduced T cells, co-transferred with TGFbR-IL12R switch receptors.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A modified immune cell or precursor cell thereof, comprising a chimeric antigen receptor (CAR) comprising an antigen binding domain capable of binding prostate stem cell antigen (PSCA), a transmembrane domain, and an intracellular domain, wherein the CAR comprises the amino acid sequence of SEQ ID NO: 21, 23, 25, or 27.

2. The modified immune cell or precursor cell thereof according to claim 1, wherein:
   (a) the modified immune cell or precursor cell thereof further comprises a CAR capable of binding prostate specific membrane antigen (PSMA);
   (b) the PSMA-CAR comprises an antigen-binding domain, a transmembrane domain, and an intracellular domain; and
   (c) the antigen binding domain of the PSMA-CAR comprises:
      (i) a heavy chain complementarity determining region (HCDR) 1 comprising the amino acid sequence of SEQ ID NO: 28, HCDR 2 comprising the amino acid sequence of SEQ ID NO: 29, and HCDR 3 comprising the amino acid sequence of SEQ ID NO: 30; and a light chain complementarity determining region (LCDR) 1 comprising the amino acid sequence of SEQ ID NO: 31, LCDR 2 comprising the amino acid sequence of SEQ ID NO: 32, and LCDR 3 comprising the amino acid sequence of SEQ ID NO: 33; or
      (ii) a heavy chain complementarity determining region (HCDR) 1 comprising the amino acid sequence of SEQ ID NO: 68, HCDR 2 comprising the amino acid sequence of SEQ ID NO: 69, and HCDR 3 comprising the amino acid sequence of SEQ ID NO: 70; and a light chain complementarity determining region (LCDR) 1 comprising the amino acid sequence of SEQ ID NO: 71, LCDR 2 comprising the amino acid sequence of SEQ ID NO: 72, and LCDR 3 comprising the amino acid sequence of SEQ ID NO: 73.

3. The modified immune cell or precursor cell thereof according to claim 2, wherein the PSMA-CAR comprises an amino acid sequence at least about 90% identical to SEQ ID NO: 67, 87, 89, 91, 93, 95, or 97.

4. A pharmaceutical composition comprising a therapeutically effective amount of the modified immune cell or precursor cell thereof of claim 2.

5. The modified immune cell or precursor cell thereof according to claim 2, wherein the PSMA-CAR is encoded by the polynucleotide sequence of SEQ ID NO: 88, 90, 92, 94, 96, or 98.

6. The modified immune cell or precursor cell thereof according to claim 2, wherein:
   (a) the PSCA-CAR comprises the amino acid sequence of SEQ ID NO: 21; and
   (b) the PSMA-CAR comprises an amino acid sequence at least about 90% identical to SEQ ID NO: 67.

7. The modified immune cell or precursor cell thereof according to claim 2, wherein:
   (a) the PSCA-CAR comprises the amino acid sequence of SEQ ID NO: 21; and
   (b) the PSMA-CAR comprises an amino acid sequence at least about 90% identical to SEQ ID NO: 87.

8. The modified immune cell or precursor cell thereof according to claim 2, wherein the intracellular domain of the PSMA-CAR comprises:
   (a) a 4-1BB intracellular domain; or
   (b) CD28 intracellular domain; or
   (c) an ICOS intracellular domain; or
   (d) an ICOS(YMNM); and
   (e) a CD3 zeta intracellular domain.

9. The modified immune cell or precursor cell thereof according to claim 2, wherein the intracellular domain of the PSCA-CAR is different from the intracellular domain of the PSMA-CAR.

10. The modified immune cell or precursor cell thereof according to claim 2, wherein the modified cell or precursor cell thereof comprises a vector comprising the polynucleotide sequence of SEQ ID NO: 39, 41, or 79.

11. The modified immune cell or precursor cell thereof according to claim 2, wherein the modified cell or precursor cell thereof comprises the amino acid sequence of SEQ ID NO: 40, 42, 80, 81, or 82.

12. A pharmaceutical composition comprising a therapeutically effective amount of the modified immune cell or precursor cell thereof of claim 1.

13. The modified immune cell or precursor cell thereof according to claim 1, wherein the CAR comprises the amino acid sequence of SEQ ID NO: 21.

14. A modified immune cell or precursor cell thereof, comprising a vector comprising a nucleic acid sequence encoding a chimeric antigen receptor (CAR) comprising an antigen binding domain capable of binding prostate stem cell antigen (PSCA), a transmembrane domain, and an intracellular domain, wherein the CAR comprises the amino acid sequence of SEQ ID NO: 21, 23, 25, or 27.

15. The modified immune cell or precursor cell thereof according to claim 14, wherein the nucleic acid sequence comprises the polynucleotide sequence of SEQ ID NO: 20, 22, 24, or 26.

16. The modified immune cell or precursor cell thereof according to claim 14, wherein the modified cell or precursor cell thereof further comprises a vector comprising the polynucleotide sequence of SEQ ID NO: 88, 90, 92, 94, 96, or 98.

* * * * *

UNITED STATES PATENT AND TRADEMARK OFFICE
CERTIFICATE OF CORRECTION

| | | |
|---|---|---|
| PATENT NO. | : 11,766,453 B2 | Page 1 of 1 |
| APPLICATION NO. | : 17/017238 | |
| DATED | : September 26, 2023 | |
| INVENTOR(S) | : Zhao | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this
Fifth Day of August, 2025

Coke Morgan Stewart
*Acting Director of the United States Patent and Trademark Office*